US009834778B2

(12) United States Patent
Loyall et al.

(10) Patent No.: US 9,834,778 B2
(45) Date of Patent: Dec. 5, 2017

(54) SYNTHETIC ARCELIN-5 PROMOTER AND METHODS OF USE THEREOF

(75) Inventors: Linda Patricia Loyall, Limburgerhof (DE); Josef Martin Kuhn, Ludwigshafen (DE); Malte Siebert, Heidelberg (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 209 days.

(21) Appl. No.: 13/991,566

(22) PCT Filed: Dec. 1, 2011

(86) PCT No.: PCT/IB2011/055412
§ 371 (c)(1),
(2), (4) Date: Jun. 4, 2013

(87) PCT Pub. No.: WO2012/077020
PCT Pub. Date: Jun. 14, 2012

(65) Prior Publication Data
US 2013/0263330 A1    Oct. 3, 2013

Related U.S. Application Data

(60) Provisional application No. 61/419,895, filed on Dec. 6, 2010.

(30) Foreign Application Priority Data

Dec. 6, 2010 (EP) .................................. 10193800

(51) Int. Cl.
C12N 15/82 (2006.01)
C12N 15/113 (2010.01)
C12N 15/63 (2006.01)

(52) U.S. Cl.
CPC ........ *C12N 15/8234* (2013.01); *C12N 15/113* (2013.01); *C12N 15/63* (2013.01); *C12N 15/82* (2013.01); *C12N 15/8201* (2013.01); *C12N 15/8216* (2013.01); *C12N 15/8241* (2013.01)

(58) Field of Classification Search
None
See application file for complete search history.

(56) References Cited

U.S. PATENT DOCUMENTS 6,927,321 B2    8/2005  Wang et al.
2010/0199365 A1  8/2010  Senger et al.

FOREIGN PATENT DOCUMENTS

| CA | 2721879 | 10/2009 |
|---|---|---|
| CN | 1489631 | 4/2004 |
| WO | WO 0250295 | 6/2002 |
| WO | WO 2006131490 | 12/2006 |
| WO | WO 2009016202 | 2/2009 |
| WO | WO 2009117417 | 9/2009 |
| WO | WO 2009133145 | 11/2009 |
| WO | WO 2010127969 | 11/2010 |

OTHER PUBLICATIONS

Kramvis et a. The core promoter of hepatitis B virus. Journal of Viral Hepatitis. 1999. 6: 415-427.*
Buckwold et al. Effects of a naturally occurring mutation in the Hepatitis B Virus Basal Core Promoter on Precore gene expression and viral replication. Journal of Virology. 1996. 70(9): 5845-5851.*
Kim et al. A 20 nucleotide upstream element is essential for the nopaline synthase (nos) promoter activity. Plant Molecular Biology. 1994. 24: 105-117.*
Donald et al. Mutation of either G box or I box sequences profoundly affects expression from the Arabidopsis rbcS-1A promoter. The EMBO Journal. 1990. 9(6): 1717-1726.*
Ito et al. A novel cis-acting element in promoters of plant b-type cyclin genes activates M phase-specific transcription. The Plant Cell. 1998. 10: 331-341.*
Kutach et al. The downstream promoter element DPE appears to be as widely used as the TATA box in *Drosphila* core promoters. Molecular and Cellular Biology. 2000. 4754-4764.*
Goossens et al. The arcelin-5 Gene of Phaseolus vulgarisDirects High Seed-Specific Expression in TransgenicPhaseolus acutifolius and Arabidopsis Plants. Molecular Genetis and Genomics. 1999. 120(4): 1095-1103.*
Rombauts et al. PlantCARE, a plant cis-acting regulatory element database. Nucleic Acids Research. 1999. 27(1): 295-296.*
Ross et al. Activation of the Oryza sativa non-symbiotic haemoglobin-2 promoter by the cytokinin-regulated transcription factor, ARR1. Journal of Experimental Biology. 2004. 55(403): 1721-1731.*
Extended European Search Report, issued in co-assigned application No. 11846949.3, dated Apr. 23, 2014.
Goossens et al., "The arcelin-5 Gene of *Phaseolus vulgaris* Directs High Seed-Specific Expression in Transgenic *Phaseolus acutifolius* and Arabidopsis Plants," Plant Physiology, vol. 120, (1999), pp. 1095-1104.
Konishi and Yanagisawa, "Identification of a Nitrate-Responsive cis-Element in the Arabidopsis NIR1 Promoter Defines the Presence of Multiple cis-Regulatory Elements for Nitrogen Response," The Plant Journal, vol. 62, (2010), pp. 269-282.
Roychoudhury et al., "Trans-acting Factor Designated OSBZ8 Interacts with Both Typical Abscisic Acid Responsive Elements as well as Abscisic Acid Responsive Element-Like Sequences in the Vegetative Tissues of Indica Rice Cultivars," Plant Cell Rep., vol. 27, (2008), pp. 779-794.
Baek et al., "Human Mediator Enhances Basal Transcription by Facilitating Recruitment of Transcription Factor IIB During Preinitiation Complex Assembly," Journal of Biological Chemistry, vol. 281, (2006), pp. 15172-15181.
Cartharius et al., "MatInspector and Beyond: Promoter Analysis Based on Transcription Factor Biding Sites," Bioinformatics, vol. 21, No. 13, (2005), pp. 2933-2942.

(Continued)

*Primary Examiner* — Ashley K Buran
(74) *Attorney, Agent, or Firm* — Marshall, Gerstein & Borun LLP

(57) ABSTRACT

The present invention relates to methods for the design and production of synthetic promoters with a defined specificity and promoters produced with these methods.

9 Claims, 3 Drawing Sheets

(56) References Cited

OTHER PUBLICATIONS

Figure 1:
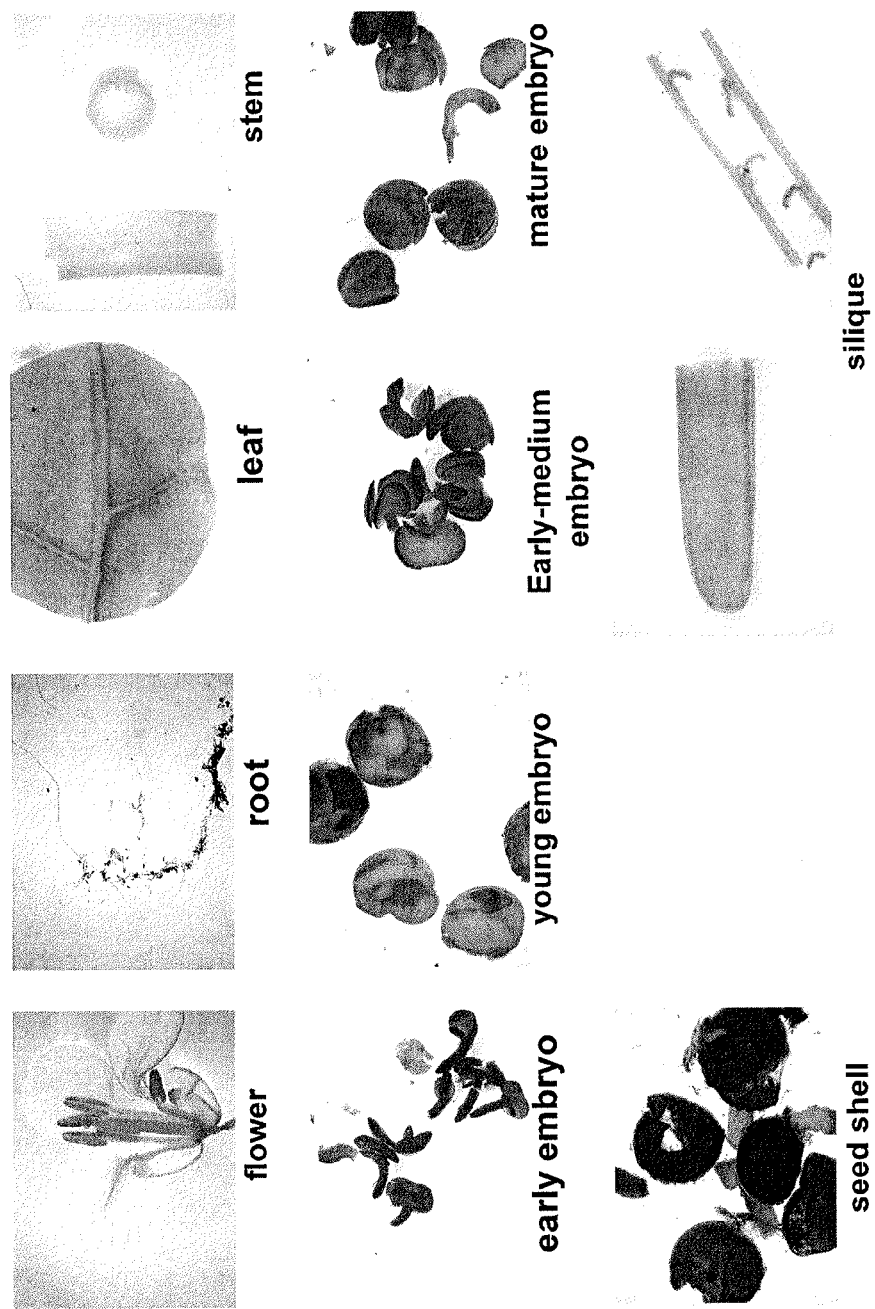

Cartharius, "MatInspector: Analysing Promoters for Transcription Factor Binding Sites," Analytical Tools for DNA, Genes and Genomes, (2005), pp. 161-184.
Dare et al., "Identification of a Cis-Regulatory Element by Transient Analysis of Co-ordinately Regulated Genes," Plant Methods, vol. 4, No. 17, (2008).
DePater et al., "The Promoter of the Rice Gene GOS2 is Active in Various Different Monocot Tissues and Binds Rice Nuclear Factor ASF-1," Plant Journal, vol. 2, No. 6, (1992), pp. 837-844.
Hamilton et al., "A Monocot Pollen-Specific Promoter Contains Separable Pollen-Specific and Quantitative Elements," Plant Molecular Biology, vol. 38, No. 4, (1998), pp. 663-669.
Hehl and Wingender, "Database-Assisted Promoter Analysis," Trends in Plant Science, vol. 6, No. 6, (2001), pp. 251-255.
Hehl and Bulow, "Internet Resources for Gene Expression Analysis in *Arabidopsis thaliana*," Current Genomics, vol. 9, No. 6, (2008), pp. 375-380.
International Preliminary Report on Patentability, issued in PCT/IB2011/055412, dated Jun. 20, 2013.
International Search Report, issued in PCT/IB2011/055412, dated Apr. 12, 2012.
Jensen et al., "The Sequence of Spacers Between the Consensus Sequences Modulates the Strength of Prokaryotic Promoters," Applied and Environmental Microbiology, vol. 64, No. 1, (1998), pp. 82-87, Search Report.
Kaplan et al., "Rapid Transcriptome Changes Induced by Cytosolic $Ca^{2+}$ Transients Reveal ABRE-Related Sequences as $CA^{2+}$-Responsive cis Elements in *Arabidopsis*," Plant Cell, vol. 18, No. 10, (2006), pp. 2733-2748.
Matys et al., "TRANSFAC®: Transcriptional Regulation, from Patterns to Profiles," Nucleic Acids Research, vol. 31, No. 1, (2003), pp. 374-378.
Montgomery et al., "Positive and Negative Regulatory Regions Control the Spatial-Distribution of Polygalacturonase Transcription in Tomato Fruit Pericarp," Plant Cell, vol. 5, No. 9, (1993), pp. 1049-1062.
Quandt et al., "MatInd and MatInspector: New Fast and Versatile Tools for Detection of Consensus Matches in Nucleotide Sequence Data," Nucleic Acids Research, vol. 23, (1995), pp. 4878-4884.
Que and Jorgensen, "Homology-Based Control of Gene Expression Patterns in Transgenic Petunia Flowers," Developmental Genetics, vol. 22, No. 1, (1998), pp. 100-109.
Roeder, "The Role of General Initiation Factors in Transcription by RNA Polymerase II," Trends in Biochemical Science, vol. 21, No. 9, (1996), pp. 327-335.
Rossi et al., "Biological Expression of an *Escherichia coli* Consensus Sequence Promoter and Some Mutant Derivatives," Proc. Natl. Acad. Sci. USA, vol. 80, (1983), pp. 3203-3207, Search Report.
Wu et al., "Quantitative Nature of the Prolamin-box, ACGT and AACA Motifs in a Rice Glutelin Gene Promoter: Minimal cis-Element Requirements for Endosperm-Specific Gene Expression," The Plant Journal, vol. 23, No. 3, (2000), pp. 415-421, Search Report.

* cited by examiner

SEQUENCE LISTING

```
<160> NUMBER OF SEQ ID NOS: 15

<210> SEQ ID NO 1
<211> LENGTH: 1151
<212> TYPE: DNA
<213> ORGANISM: Phaseolus vulgaris
<220> FEATURE:
<221> NAME/KEY: Promoter
<222> LOCATION: (1)..(1151)
<223> OTHER INFORMATION: p-PvArc

<400> SEQUENCE: 1
ttctatagaa aatgtgttat ttcctcatca ccagacaaag gggcaacagt taacaaaaca      60
aatttatgtt tcatttgaga ttaaggaagg taaggaagaa aaaagattaa aaaaaatgtc     120
cttatctctt tgtttctgta ataataatat aagagactta aactttttaat ataataattg     180 taattaggtt ttctagtcat gagcaccact cagagacaag atttcaagaa aacaattttg     240
ttaaacatct tattagaaac ttttagttaa gtcttgaagt tagaattaaa caaaaaaaag     300
tacacacgag aaacacaata aacccactac cgtcaggtta tcataaggat gaaatgtttt     360
gatatcatta aatataacac acacaaaaat acatctaatt ataacaatat atgttataca     420
tatatttttg taaaaactta gagttttca aaacattcta atacatgatt agagtttata     480
gaaatacaaa tatttaaaaa atataatttt aaaaaaacat tctaaagtca ttcagatcct     540
ctcacacctg tgtgatcatt tagtcatgta tgtagtacaa tcattgtagt tcacaacaga     600
gtaaaataaa taaggataaa ctagggaata tatataatat atacaattaa ataaaaaagg     660
gaaaatcaaa ttagaatttt agattcccca catgacacaa ctcaccatgc acgctgccac     720
```

```
ctcagctccc tcctctccac acatgtctca tgtcactttc gactttggtt tttcactat    780 gacacaactc gccatgcatg ttgccacgtg agctccttcc tcttcccatg atgacaccac    840
tgggcatgca tgctgccacc tcagctccca cctcttctca ttatgagcct actggccatg    900
cacactgcca cctcagcact cctctcactt cccattgcta cctgccaaac cgcttctctc    960
cataaatatc tatttaaatt taaactaatt atttcatata ctttttgat gacgtggatg   1020 cattgccatc gttgtttaat aattgttaat ttggagttga ataataaat gaaagaaaaa   1080 agttggaaag attttgcatt tgttgttgta taaatagaga agagagtgat ggttaatgca   1140
tgaatgcatg a                                                        1151

<210> SEQ ID NO 2
<211> LENGTH: 1151
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(1151)
<223> OTHER INFORMATION: p-PvArc-perm

<400> SEQUENCE: 2
tactatagaa aatgtgttat atcgacatga ccagacaaag gggcaacagt taacaaaaca     60
attaattctt tcatttgaga ttaaggaagg taaggtacta aaaagattaa aaaaaatgag    120
cttatctctt tgtttctgta ataataatat aagtgtgata aactttaat ataataattg    180 taattaggtt ttctacagat gagcaccact cagagacaag ataagaagaa acaattttg    240 ttaaacatga ttatagaaac ttttagttaa gtcttgaagt atcaatataa caaaaaaag    300 tacacacgac tatgacaata aacccactac cgtcaggtta tcatttcgat gaaatgtttt    360
gatatcatta aatataacag tcacaaaaaa tcatctaatt ataacaatat aacttataca    420
tatatttaac taaaaactta gagttttgt aatgattcta attgatgatt agagtttata    480
gaaatacaat taaataaaa atataatttt aaaaaaacat agtaaagtca atgagatcct    540
ctctgacctc agtgatcatt tagtcatgta tgtacaacaa tcattgttca tcacatgact    600
gtaaaataaa taaggataaa cttgggaata tatataatat attgtattaa ataaaaaagg    660
gaaatacaaa tatcaattt agattcccga gttgacacaa ctcaccatgc acgctgccac    720
ctcagctccc agctctcgtc acatgtctca tgtcagttag gtctttggtt tttagtcttt    780
gacacaactc gccatgcatg ttgccacgtg agctcgttcc tcttcccatg atctcaccac    840
tgggcatgca tgctgccacc tcagctggca cctcttctct atatgtccct agaggccatg    900
cacagtgcca cctcagcact cctctcagaa cccatacgta cctgccaatc ggcttctctc    960
cataaatatc tatttaaatt ataactaatt atttcatata cttaattgat gacgtggatg   1020
cattgccatc gttgtttaat aattgttaat tacgacatga taaataaat gaaagtaaaa   1080 agtacgaaag attttccatt tgttgttgta taaatagaga agtgagtgat gcataatgca   1140
tgaatgcatg a                                                        1151

<210> SEQ ID NO 3
<211> LENGTH: 1799
<212> TYPE: DNA
<213> ORGANISM: Vicia faba
<220> FEATURE:
<221> NAME/KEY: Promoter
<222> LOCATION: (1)..(1799)
<223> OTHER INFORMATION: p-VfSBP
```

<400> SEQUENCE: 3

```
tcgacggccc ggactgtatc caacttctga tctttgaatc tctctgttcc aacatgttct      60
gaaggagttc taagactttt cagaaagctt gtaacatgct ttgtagactt tctttgaatt     120
actcttgcaa actctgattg aacctacgtg aaaactgctc cagaagttct aaccaaattc     180
cgtcttggga aggcccaaaa tttattgagt acttcagttt catggacgtg tcttcaaaga     240
tttataactt gaaatcccat cattttaag agaagttctg ttccgcaatg tcttagatct      300
cattgaaatc tacaactctt gtgtcagaag ttcttccaga atcaacttgc atcatggtga     360
aaatctggcc agaagttctg aacttgtcat atttcttaac agttagaaaa atttctaagt     420
gtttagaatt ttgacttttc caaagcaaac ttgacttttg actttcttaa taaaacaaac     480
ttcatattct aacatgtctt gatgaaatgt gattcttgaa atttgatgtt gatgcaaaag     540
tcaaagtttg acttttcagt gtgcaattga ccattttgct cttgtgccaa ttccaaacct     600
aaattgatgt atcagtgctg caaacttgat gtcatggaag atcttatgag aaaattcttg     660
aagactgaga ggaaaaattt tgtagtacaa cacaaagaat cctgttttc atagtcggac      720
tagacacatt aacataaaac accacttcat tcgaagagtg attgaagaag gaaatgtgca     780
gttacctttc tgcagttcat aagagcaact tacagacact tttactaaaa tactacaaag     840
aggaagattt taacaactta gagaagtaat gggagttaaa gagcaacaca ttaagggga     900
gtgttaaaat taatgtgttg taaccaccac tacctttagt aagtattata agaaaattgt     960
aatcatcaca ttataattat tgtccttatt taaaattatg ataaagttgt atcattaaga    1020
ttgagaaaac caaatagtcc tcgtcttgat ttttgaatta ttgttttcta tgttactttt    1080
cttcaagcct atataaaaac tttgtaatgc taaattgtat gctggaaaaa aatgtgtaat    1140
gaattgaata gaaattatgg tatttcaaag tccaaaatcc atcaatagaa atttagtaca    1200
aaacgtaact caaaaatatt ctcttatttt aaatttaca acaatataaa atattctct      1260
tattttaaat tttacaataa tataatttat cacctgtcac ctttagaata ccaccaacaa    1320
tattaatact tagatatttt attcttaata attttgagat ctctcaatat atctgatatt    1380
tattttatat ttgtgtcata ttttcttatg ttttagagtt aacccttata tcttggtcaa    1440
actagtaatt caatatatga gtttgtgaag gacacattga catcttgaaa cattggtttt    1500
aaccttgttg gaatgttaaa ggtaataaaa cattcagaat tatgaccatc tattaatata    1560
cttcctttgt cttttaaaaa agtgtgcatg aaaatgctct atggtaagct agagtgtctt    1620
gctggcctgt gtatatcaat tccatttcca gatggtagaa actgccacta cgaataatta    1680
gtcataagac acgtatgtta acacacgtcc ccttgcatgt ttttgccat atattccgtc     1740
tctttctttt tcttcacgta taaaacaatg aactaattaa tagagcgatc aagctgaac     1799
```

<210> SEQ ID NO 4
<211> LENGTH: 1799
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(1799)
<223> OTHER INFORMATION: p-VfSBP-perm

<400> SEQUENCE: 4

```
tgctcggccc ggactgtatc caacttgaga tctttgaatc tctctgttcc ttgatgttct      60
```

-continued

| | |
|---|---|
| gaaggagttc taagtgtaat cagaaagctt gtaacatgct ttgtagactt tctttgatat | 120 |
| actcttgcaa tgactgattg aacctacgtg aaaactgctg gtcaagttct aaccaaattc | 180 |
| cgtctacgga aggcccaaaa tttattgaca tcttcagttt catggacgtg tcttcaaagt | 240 |
| tttataactt cttatcccat cattttttaag tctagttctg ttccgcatag tcttagatct | 300 |
| caaacaaatc tacaactctt gtgtcagttc ttcttccaga atcaacttgc tacatggtga | 360 |
| aaatctggcg tcaagttctg aacttgtcaa ttttcttaac agttagaaaa taatctaagt | 420 |
| gtttagaata ttgactttc caaagcaaag aagactttg actttcttaa taaaacaaac | 480 |
| ttctaattct aacatgtctt gatgaaatgt cttcttgaa atttgatcaa gatgcaaaag | 540 |
| tcaaagtttg actttcaga ctgcaattga ccattttgca gaagtgccaa ttccaaacca | 600 |
| aaattgatga tacagtgctg caaacttgat gtcatggaag atcttaacag aaaattcttg | 660 |
| aagactgaga gcaaaaattt tcatgtacaa cacaaacttt cctgtttttc atagtcgctg | 720 |
| tagacacatt aacataaaac acctgatcat tcgaagagtg attcttgaag gaaatgtgca | 780 |
| gttacctttg tgcagaactt aagagcaact tacagactca tttactaaaa tactacaatc | 840 |
| aggaagattt taacaactta cagaagtatt cggagttaaa gagcaacaca ttaagggcga | 900 |
| cagttaaaat taatgtgttg taaccaccac tacgaatagt aagtattata agttaaatgt | 960 |
| aatcatcaca ttataattat tgtccttata attaattatg ataaacatgt atcattaaga | 1020 |
| ttgtcataac caaatagtcc tcgacttgat tttttgaatta ttgtattcta tgttactttt | 1080 |
| cttgtagcct atataaaaac tttgtaaagc ataattgtat gctggaaaaa atactgtaat | 1140 |
| gaattgaata gaaattatgg tatttcattc tccaaaatcc atcaatagaa atttagtaca | 1200 |
| aatcgaaaga caaaaatatt gacttatttt aaatttttaca acaatataaa atattgact | 1260 |
| tatttttaaat tttacaataa tataaatttt cacctgtcac ctttagaaat ccaccaacaa | 1320 |
| tattaattct tagataaatt attcttaata attttgagat ctctgtaatt atctgatatt | 1380 |
| tattttatat ttgtcagtta ttttcttatg ttttactgtt aacccttata tcttggtcaa | 1440 |
| actagaataa gtaaatatga gtttgtgaag gacacattga caagatgaaa cattggtttt | 1500 |
| ttccttcttc gaatgttaaa ggtaataaaa cattcagaat attgacctac tattaatata | 1560 |
| gatcctttgt cttttaaaaa agtgtgcatg aaaatgctct taggtaagct agtgtctctt | 1620 |
| gcagggctgt gtatatcaat tccatttcca gatggttgta actgccacta cctataatta | 1680 |
| gtcataagac acgtatgtta acacacgtcc ccatgcatgt ttttgccat atattcccac | 1740 |
| actttctttt tcttcacgta taaaacattg aactaattaa tagtccgatc aagctgaac | 1799 |

<210> SEQ ID NO 5
<211> LENGTH: 1138
<212> TYPE: DNA
<213> ORGANISM: Vicia faba
<220> FEATURE:
<221> NAME/KEY: Promoter
<222> LOCATION: (1)..(1138)
<223> OTHER INFORMATION: p-VfNapin

<400> SEQUENCE: 5

| | |
|---|---|
| tcttcatcgg tgattgattc ctttaaagac ttatgtttct tatcttgctt ctgaggcaag | 60 |
| tattcagtta ccagttacca cttatattct ggactttctg actgcatcct cattttccca | 120 |
| acattttaaa tttcactatt ggctgaatgc ttcttctttg aggaagaaac aattcagatg | 180 |
| gcagaaatgt atcaaccaat gcatatatac aaatgtacct cttgttctca aaacatctat | 240 |
| cggatggttc catttgcttt gtcatccaat tagtgactac tttatattat tcactcctct | 300 |

```
ttattactat tttcatgcga ggttgccatg tacattatat ttgtaaggat tgacgctatt      360
gagcgttttt cttcaatttt ctttatttta gacatgggta tgaaatgtgt gttagagttg      420
ggttgaatga gatatacgtt caagtgaatg gcataccgtt ctcgagtaag gatgacctac      480
ccattcttga gacaaatgtt acattttagt atcagagtaa aatgtgtacc tataactcaa      540
attcgattga catgtatcca ttcaacataa aattaaacca gcctgcacct gcatccacat      600
ttcaagtatt ttcaaaccgt tcggctccta tccaccgggt gtaacaagac ggattccgaa      660
tttggaagat tttgactcaa attcccaatt tatattgacc gtgactaaat caactttaac      720
ttctataatt ctgattaagc tcccaattta tattcccaac ggcactacct ccaaaattta      780
tagactctca tcccctttta aaccaactta gtaaacgttt ttttttttaa ttttatgaag      840
ttaagttttt accttgtttt taaaaagaat cgttcataag atgccatgcc agaacattag      900
ctacacgtta cacatagcat gcagccgcgg agaattgttt tcttcgcca cttgtcactc       960
ccttcaaaca cctaagagct tctctctcac agcacacaca tacaatcaca tgcgtgcatg     1020
cattattaca cgtgatcgcc atgcaaatct cctttatagc ctataaatta actcatccgc     1080
ttcactcttt actcaaacca aaactcatca atacaaacaa gattaaaaac atacacga      1138

<210> SEQ ID NO 6
<211> LENGTH: 990
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(990)
<223> OTHER INFORMATION: p-VfNapin-perm

<400> SEQUENCE: 6
cccggggata tcaagcttaa acaatacagg tggctgaaat atataaacca attcatgtct       60
acaaatgtac cctttgcact taaaaaattt atcggaggga tccactcgca ttggaagtca      120
atcaaggact attggttatt agtctgtccg ttatttgaat atgataacgc aaggtttccg      180
tgtacaatat atgtgcatgg aatgccgctg ttgagcgttt aacctgaatt ttcatgattt      240
gaggcatggg gctgtattgc ttgttagcgt tggggtgaat gaaatttagc ttcaacctaa      300
tgagatacag ttcccgggtc aggatgatct aatcattcct catacaaatg tctcattttt      360
caattagagt aatatgtgtc catatgtctc gatttcgatt gacttacatc cattcaagat      420
aaaattgcgc aatcttgcac ttcccttaac attttcataa gttcatacc tatcactacc       480
tatacacccg ggataacaca tcgtgttcgg gtgttggaag attttgactc aaattcctaa      540
tttacattgc tcctaactat attagcttta acttctgtac tgctggtaaa gctgccaacc      600
gttatcacca taggccatac ttccatcggt tatagactct catccccttt tagaccagct      660
tagtcaacgt tctgtctttt aattctaaga cgttatgaac ttagatggtt ttcaaaaaaa      720
atcgtgatga gaatgccttg ccaggacatt agctacacgt tacacatacc atgcaatcca      780
ggagaatatt atttcttcgc cacttgtcac tcccttcaaa cacctaagac cttatctctc      840
acatcagccg catacattca catgcgtgca tgcattatta cacgtgatcg ccatgcaaat      900
cttcattaaa gtgtataaaa gtacccatcc gattcaggct tgaatctacc gatacctgag      960
caacacaaac acggtcaaaa acatacacga                                       990

<210> SEQ ID NO 7
```

<211> LENGTH: 14944
<212> TYPE: DNA
<213> ORGANISM: Artificial Sequence
<220> FEATURE:
<223> OTHER INFORMATION: Transformation Vector

<400> SEQUENCE: 7

| | | | | | |
|---|---|---|---|---|---|
| tggcaggata | tattgtggtg | taaacaaatt | gacgcttaga | caacttaata | acacattgcg | 60 |
| gacgtcttta | atgtactgaa | tttagttact | gatcactgat | taagtactgc | gatcgcctcg | 120 |
| acatattgtt | tttgtttcac | ataaatgtcg | ttttggatta | ttcatgtaat | attttaaact | 180 |
| aaagtacaat | ttttgactac | tttagtttac | tagttaagct | tttatttttt | tgactaacca | 240 |
| ttgaatgatg | aagagatcaa | cgcatcatat | ttacaactta | catagtcttt | tggaagtgta | 300 |
| aattgctaat | actacctaaa | atatatctat | aattaactaa | tatttttcg | tcaattataa | 360 |
| tagatcaatt | aaaaggctat | caaaaggaaa | aaatgaaat | ccacatcctg | ccatcataac | 420 |
| ctcatgctgg | aaaagaaat | gaaaaatat | aaaaaattc | ttttgtttat | taaatttaca | 480 |
| actttaatac | tagtttcttt | tctattttt | aaaagctttt | gtcacttact | taaaaaaaaa | 540 |
| aaacttttg | aaatattcct | acttccaatg | tctgattagt | gcttctggat | ttccttttg | 600 |
| gatcatgtga | atcctaaatc | agaaaaattc | atataatacc | caattcagta | tattttcata | 660 |
| cttcaattta | caagagttct | ctatgttttt | agcttctttc | ttttaagcca | aatgtttaa | 720 |
| gcatctttta | tacattaaaa | taattagtg | ttgagttgag | attttttttt | tttttttg | 780 |
| gatttacttg | ttcaaaatct | gaaaaatgt | ttacagaagg | ttaaaatgaa | ccaaaaggca | 840 |
| tatcaagcta | gattttgaat | taccctattt | catcgtatac | acaaaactga | taatgtggac | 900 |
| acagttgatt | ttacttctcg | atgacatcgt | agttttattt | aatttggaaa | ccacggccca | 960 |
| tatgagcaca | tttcaattaa | aaaccaatgg | taagagcatt | ttccatgcaa | gattcgagag | 1020 |
| atattaaccc | agtgactgtt | aaaacagctt | agaaccctaa | taacgaattt | caattactca | 1080 |
| atttaccatt | cgcatttcgc | aataaccaaa | ctgagccagt | cacaaggagt | aaaccgaacc | 1140 |
| ggattattta | tttataaaat | gaaagaaagg | aaaccaaaca | acaacagcag | tagtagtctg | 1200 |
| acgtaaacca | aaaagcaggc | agatcaacaa | ctaaaagaaa | ctcaaattac | caaaacaaac | 1260 |
| aggaaattgc | aaactaagtt | ttttaccat | atgcatacaa | agaccataaa | aggttctgat | 1320 |
| aatcaccggt | ttcatctcgt | cgagattacc | ctgttatccc | tatcagtatt | taatccggcc | 1380 |
| atctccttcc | gttatgacat | cgttgaaagt | gccaccattc | gggatcatcg | gcaacacatg | 1440 |
| ttcttggtgc | ggacaaatca | catccaacag | gtaaggtcct | ggtgtatcca | gcattgtctg | 1500 |
| aatagcttct | cggagatctg | ctttctttgt | caccctcgcc | gctggaatcc | cgcaagctgc | 1560 |
| tgcaaacagc | aacatgttcg | ggaatatctc | gtcctcctga | gccggatccc | cgagaaatgt | 1620 |
| gtgagctcgg | ttagctttgt | agaaccgatc | ttcccattgc | ataaccatgc | caagatgctg | 1680 |
| gttgtttaat | aaaagtacct | tcactggaag | attctctaca | cgaatagtgg | ctagctcttg | 1740 |
| cacattcatt | ataaagcttc | catctccgtc | aatatccaca | actatcgcat | cagggttagc | 1800 |
| aacagacgct | ccaatcgcag | caggaagtcc | aaatcccata | gctccaaggc | ctcctgatga | 1860 |
| tagccactgc | cttggtttct | tgtaattgta | gaactgcgcc | gcccacattt | gatgttgccc | 1920 |
| gacaccagta | cttattatgg | cttttccatc | agtcaactca | tcaaggacct | taatcgcata | 1980 |
| ctgtggagga | atagcttccc | caaacgtctt | aaagctcaac | ggaaacttct | gtttctgtac | 2040 |
| gttcaactca | ttcctccaaa | ctccaaaatc | aagcttaagc | tcctccgctc | ggttctcaag | 2100 |
| aaccttattc | atcccttgca | aagccagctt | aacatcacca | cacacagaca | catgaggagt | 2160 |

```
cttattcttc ccaatctcag ccgagtcaat atcaatatga acaatcttag ccctactagc    2220
aaaagcctca agcttacccg tgacacgatc atcaaacctt accccaaacg ccaacaacaa    2280
atcactatgc tccacagcgt aatttgcata cacagtccca tgcattccaa gcatatgtaa    2340
cgacaactca tcatcacaag gataagatcc cagccccatc aacgtactcg caacagggat    2400
ccccgtaagc tcaacaaacc tacccaattc atcgctagaa ttcaaacaac caccaccaac    2460
atacaacaca ggcttcttag actcagaaat caacctaaca atctgctcca aatgagaatc    2520
ttccggaggt ttaggcatcc tagacatata accaggtaat ctcatagcct gttcccaatt    2580
aggaatcgca agctgttgtt gaatatcttt aggaacatca accaaaacag gtccaggtct    2640
accagaagta gctaaaaaga aagcttcctc aataatccta gggatatctt caacatccat    2700
cacaagatag ttatgcttcg taatcgaacg cgttacctca acaatcggag tctcttgaaa    2760
cgcatctgta ccaatcatac gacgagggac ttgtcctgtg attgctacaa gaggaacact    2820
atctaacaac gcatcggcta atccgctaac gagatttgta gctccgggac ctgaagtggc    2880
tatacagata cctggtttac ctgaggatcg agcgtatcct tctgctgcga atacacctcc    2940
ttgttcgtga cgaggaagga cgttacggat tgaggaagag cgggttaagg cttggtgaat    3000
ctccattgat gtacctccag ggtaagcgaa tacggtttct acgccttgac gttctaaagc    3060
ttcgacgagg atatcagcgc ctttgcgggg ttgatctgga gcgaatcggg agatgaatgt    3120
ttcgggtttg gtaggtttgg ttggagaggg agtggttgtg acattggtgg ttgtgttgag    3180
cacggcggag atggaggagg gagagctgga tttgataccg cggcggcggg aggaggagga    3240
tgatttgttg gggtttaggg agaatgggag ggagaatctg gagattggta atggtgattt    3300
ggaggaggaa ggagatggtt tggtggagaa ggagatcgaa aagatgttg ttgttgttgt     3360 tgttgccgcc gccatggttc agctgcacat acataacata tcaagatcag aacacacata    3420
tacacacaca aatacaatca agtcaacaac tccaaaaagt ccagatctac atatatacat    3480
acgtaaataa caaaatcatg taaataatca caatcatgta atccagatct atgcacatat    3540
atatatacac aattaataaa aaaaatgata taacagatct atatctatgt atgtaacaac    3600
acaatcagat gagagaagtg atgttttcag atctgtatac atacaaacac aaacagatga    3660
acaattgata cgtagatcca tatgtatacg tacaattagc tacacgatta aatgaaaaaa    3720
atcaacgatt tcggattggt acacacaaac gcaacaatat gaagaaattc atatctgatt    3780
agatataaac ataaccacgt gtagatacac agtcaaatca acaaatttat agcttctaaa    3840
cggatgagat gaacaagata aagatattca cataaggcat acataagata agcagattaa    3900
caaactagca ataatacata cctaattaaa acaaggaata acagagagag agagagagag    3960
agagatttac cttgaaaatg aagaggagaa gagaggattt cttaaaattg ggggtagaga    4020
aagaaagatg atgaattgtg agaaaggaga gatagaaggg ggggttgtat atataggctg    4080
tagaagatta tttttgtgtt tgaggcggtg aaggaagagg ggatctgact atgacacgtt    4140
tgcggttacg tatttcgata ggagtctttc aacgcttaac gccgttactc tatatgaccg    4200
tttgggccgt aacggggccg tttgttaacg ctgatgttga ttcttttctt tctttctttc    4260
ttcctttttt aaagaagcaa ttgtacaatc gttgctagct gtcaaacgga taattcggat    4320
acggatatgc ctatattcat atccgtaatt tttggattcg aattttcccc tctagggata    4380
acagggtaat ggatctatat tgttttgtt tcacataaat gtcgttttgg attattcatg     4440
taatatttta aactaaagta caattttga ctactttagt ttactagtta agcttttatt     4500
```

```
tttttgacta accattgaat gatgaagaga tcaacgcatc atatttacaa cttacatagt    4560
cttttggaag tgtaaattgc taatactacc taaaatatat ctataattaa ctaatatttt    4620
ttcgtcaatt ataatagatc aattaaaagg ctatcaaaag gaaaaaaatg aaatccacat    4680
cctgccatca taacctcatg ctggaaaaag aaatgaaaaa ataaaaaaa tttcttttgt     4740 ttattaaatt tacaacttta atactagttt cttttctatt ttttaaaagc ttttgtcact    4800
tacttaaaaa aaaaaaactt tttgaaatat tcctacttcc aatgtctgat tagtgcttct    4860
ggatttcctt tttggatcat gtgaatccta aatcagaaaa attcatataa tacccaattc    4920
agtatatttt catacttcaa tttacaagag ttctctatgt ttttagcttc tttcttttaa    4980
gccaaatgtt ttaagcatct tttatacatt aaaataattt agtgttgagt tgagattttt    5040
tttttttttt tttggattta cttgttcaaa atctgaaaaa atgtttacag aaggttaaaa    5100
tgaaccaaaa ggcatatcaa gctagatttt gaattaccct atttcatcgt atacacaaaa    5160
ctgataatgt ggacacagtt gattttactt ctcgatgaca tcgtagtttt atttaatttg    5220 gaaccacgg cccatatgag cacatttcaa ttaaaaacca atggtaagag cattttccat     5280
gcaagattcg agagatatta acccagtgac tgttaaaaca gcttagaacc ctaataacga    5340
atttcaatta ctcaatttac cattcgcatt tcgcaataac caaactgagc cagtcacaag    5400
gagtaaaccg aaccggatta tttatttata aaatgaaaga aaggaaacca aacaacaaca    5460
gcagtagtag tctgacgtaa accaaaaagc aggcagatca acaactaaaa gaaactcaaa    5520
ttaccaaaac aaacaggaaa ttgcaaacta agttttttta ccatatgcat acaaagacca    5580
taaaaggttc tgataatcac cggtttcatc tcagatccgc gatcgccaat tgacgcgtac    5640
tagtgtacaa gcttgcggcc gcgaattcgg tacatccggc cagtgaatta tcaactatgt    5700
ataataaagt tgggtaccgg cctattaggc acggtccgt acagtgttta aacgattgac     5760
ctgcaggata caagtgcgca cagactagcg gccgctaatc ccgggaatta ccggtagtag    5820
gcgcctactt tggccggcct agtagattta aattggcctt agtggccaag cttgcgtaa     5880 tcatggccac tttgtacaag aaagctgggt ggtaccggcc tattaggcca cggtccgtac    5940
agtgtttaaa cgattgacct gcaggataca agtgcgcaca gactagcggc cgctaatccc    6000
gggaattacc ggtagtaggc gcctactttg gccggcctag tagatttaaa ttggccttag    6060
tggccaagct tggcgtaatc atggagcctg ctttttttgta caaacttggg taccggccta    6120
ttaggccacg gtccgtacag tgtttaaacg attgacctgc aggatacaag tgcgcacaga    6180
ctagcggccg ctaatcccgg gaattaccgg tagtaggcgc cttgttttag actgaatata    6240
acacaacgat tatatagccg ctgtctttgt ttgaagagaa tggactacat gctgaaaaat    6300
agtgatacaa gaatcgttgt tttaatgcta aaatgaccat ctcgtgattt aacttttctg    6360
gaccaatgat tgtaaagttt tttttagaga ggtggtgata acatatatt gattttgaa      6420 atgaatagag ttagaaagta agaaaaatac aataaaaatg ttaataatg ttgtagaaat     6480 agaaatggaa gagaagtgta aagaaattta aataaaaatt agatgggaga gtaagttagt    6540
ttatattgat ttgttttgtg gttagtttat ctatgttata cttttaactt ataataatcc    6600
tttccatcat taagcaattt ttaaaaatga cataatttta aaattatgaa gtaataattg    6660
gcatggtgaa taatagacag tgtaaatggt gtaaatatat gagctcccat tttatttatt    6720
gctcccattt tatttatttt agtttgtgtg acagatgaac attattagga ggaaaggtat    6780
aagcagggtt taactgtcac agggaaggtg gttttgggag tcttagttaa ttaatcattg    6840
tttgcctccc tgctgcggtt tttcaccgaa gttcatgcca gtccagcgtt tttgcagcag    6900
```

```
aaaagccgcc gacttcggtt tgcggtcgcg agtgaagatc cctttcttgt taccgccaac    6960
gcgcaatatg ccttgcgagg tcgcaaaatc ggcgaaattc catacctgtt caccgacgac    7020
ggcgctgacg cgatcaaaga cgcggtgata catatccagc catgcacact gatactcttc    7080
actccacatg tcggtgtaca ttgagtgcag cccggctaac gtatccacgc cgtattcggt    7140
gatgataatc ggctgatgca gtttctcctg ccaggccaga agttctttt ccagtacctt     7200 ctctgccgtt tccaaatcgc cgctttggac ataccatccg taataacggt tcaggcacag    7260
cacatcaaag agatcgctga tggtatcggt gtgagcgtcg cagaacatta cattgacgca    7320
ggtgatcgga cgcgtcgggt cgagtttacg cgttgcttcc gccagtggcg cgaaatattc    7380
ccgtgcacct tgcggacggg tatccggttc gttggcaata ctccacatca ccacgcttgg    7440 gtggttttg tcacgcgcta tcagctcttt aatcgcctgt aagtgcgctt gctgagtttc     7500
cccgttgact gcctcttcgc tgtacagttc tttcggcttg ttgcccgctt cgaaaccaat    7560
gcctaaagag aggttaaagc cgacagcagc agtttcatca atcaccacga tgccatgttc    7620
atctgcccag tcgagcatct cttcagcgta agggtaatgc gaggtacggt aggagttggc    7680
cccaatccag tccattaatg cgtggtcgtg caccatcagc acgttatcga atcctttgcc    7740
acgcaagtcc gcatcttcat gacgaccaaa gccagtaaag tagaacggtt tgtggttaat    7800
caggaactgt tcgcccttca ctgccactga ccggatgccg acgcgaagcg ggtagatatc    7860
acactctgtc tggcttttgg ctgtgacgca cagttcatag agataacctt caccggttg     7920 ccagaggtgc ggattcacca cttgcaaagt cccgctagtg ccttgtccag ttgcaaccac    7980
ctgttgatcc gcatcacgca gttcaacgct gacatcacca ttggccacca cctgccagtc    8040
aacagacgcg tggttacagt cttgcgcgac atgcgtcacc acggtgatat cgtccaccca    8100
ggtgttcggc gtggtgtaga gcattacgct gcgatggatt ccggcatagt taaagaaatc    8160
atggaagtaa gactgctttt tcttgccgtt ttcgtcggta atcaccattc ccggcgggat    8220
agtctgccag ttcagttcgt tgttcacaca acggtgata cctgcacatc aacaaatttt     8280
ggtcatatat tagaaaagtt ataaattaaa atatacacac ttataaacta cagaaaagca    8340
attgctatat actacattct tttattttga aaaaaatatt tgaaatatta tattactact    8400
aattaatgat aattattata tatatatcaa aggtagaagc agaaacttac gtacactttt    8460
cccggcaata acatacggcg tgacatcggc ttcaaatggc gtatagccgc cctgatgctc    8520
catcacttcc tgattattga cccacacttt gccgtaatga gtgaccgcat cgaaacgcag    8580
cacgatacgc tggcctgccc aacctttcgg tataaagact tcgcgctgat accagacgtt    8640
gcccgcataa ttacgaatat ctgcatcggc gaactgatcg ttaaaactgc ctggcacagc    8700
aattgcccgg ctttcttgta acgcgctttc ccaccaacgc tgaccaattc cacagttttc    8760
gcgatccaga ctgaatgccc acaggccgtc gagttttttg atttcacggg ttggggtttc    8820
tacaggacgt accatggtca tgcattcatg cattatgcat cactcacttc tctatttata    8880
caacaacaaa tggaaaatct ttcgtacttt ttactttcat tttatttatc atgtcgtaat    8940
taacaattat taaacaacga tggcaatgca tccacgtcat caattaagta tatgaaataa    9000
ttagttataa tttaaataga tatttatgga gagaagccga ttggcaggta cgtatgggtt    9060
ctgagaggag tgctgaggtg gcactgtgca tggcctctag ggacatatag agaagaggtg    9120
ccagctgagg tggcagcatg catgcccagt ggtgagatca tgggaagagg aacgagctca    9180
cgtggcaaca tgcatggcga gttgtgtcaa agactaaaaa ccaaagacct aactgacatg    9240
```

```
agacatgtga cgagagctgg gagctgaggt ggcagcgtgc atggtgagtt gtgtcaactc    9300
gggaatctaa aattgatatt tgtatttccc ttttttattt aatacaatat attatatata    9360
ttcccaagtt tatccttatt tattttacag tcatgtgatg aacaatgatt gttgtacata    9420
catgactaaa tgatcactga ggtcagagag gatctcattg actttactat gttttttaa     9480 aattatattt tttatttaat tgtatttcta taaactctaa tcatcaatta gaatcattac    9540
aaaaactcta agttttagt taaatatatg tataagttat attgttataa ttagatgatt     9600
ttttgtgact gttatattta atgatatcaa aacatttcat cgaaatgata acctgacggt    9660
agtgggttta ttgtcatagt cgtgtgtact ttttttgtt atattgatac ttcaagactt     9720
aactaaaagt ttctataatc atgtttaaca aaattgtttt cttcttatct tgtctctgag    9780
tggtgctcat ctgtagaaaa cctaattaca attattat taaaagttta tcacacttat      9840
attattatta cagaaacaaa gagataagct cattttttt aatctttta gtaccttacc      9900 ttccttaatc tcaaatgaaa gaattaattg ttttgttaac tgttgcccct ttgtctggtc    9960
atgtcgatat aacacatttt ctatagtagg ccggcctagt agatttaaat tggccttagt   10020
ggccaagctt ggcgtaatca tggcaacttt tctatacaaa gttgatagct tggcgtaatc   10080
gatgtaccga tatcaattta aattggccgg ccgagctccc tgcaggggc ccggcgcgcc    10140 tctagattaa ttaaaggcct tagttactaa tcagtgatca gattgtcgtt tcccgccttc   10200
agtttaaact atcagtgttt gacaggatat attggcgggt aaacctaaga gaaagagcg    10260 tttattagaa taatcggata tttaaagggg cgtgaaaagg tttatccgtt cgtccatttg   10320
tatgtcaata tccatgataa gtcgcgctgt atgtgtttgt ttgaatattc atggaacgca   10380
gtggcggttt tcatggcttg ttatgactgt ttttttgggg tacagtctat gcctcgggca   10440
tccaagcagc aagcgcgtta cgccgtgggt cgatgtttga tgttatggag cagcaacgat   10500
gttacgcagc agggcagtcg ccctaaaaca aagttaaaca tcatgggtga agcggtcatc   10560
gccgaggtgt ccacccagct gtcggaagtc gtgggtgtca tcgagcgcca cctcgaaccg   10620
accctcctcg ccgtgcatct gtatggtagc gccgttgacg gcggccttaa gccccattcg   10680
gacatcgacc tgcttgtcac cgttaccgtc cgtctcgacg agaccacgcg ccgcgcgctt   10740
atcaacgacc ttctggaaac gtccgcctcc cccggcgaga gcgaaatcct gcgcgcggtt   10800
gaggtgacga ttgtggtgca cgatgacatc atccccctgg cgctatccggc caaacgcgaa   10860 ctccagttcg gcgaatggca gcgtaatgat attctggcgg gtatctttga accggccacc   10920
atcgacattg atctggcgat cctgctcacc aaggcccggg agcatagcgt ggccctcgtc   10980
ggccccgcgg ccgaggaact tttcgacccg gtgccggaac aggatctgtt cgaagcactg   11040
aacgagacgc tgaccctgtg gaactccccg ccggattggg cggcgatga gcgcaatgtg    11100 gtccttacgc tgagccggat ttggtactcg gcggttaccg gcaagatcgc gccgaaggat   11160
gtcgccgccg actgggcgat ggagcgcctt ccggcgcaat accagcccgt gatcctcgaa   11220
gcgcgccaag cctatctggg ccaagaagaa gaccgtctcg cgtcccgggc cgaccagctc   11280
gaagaatttg tccactatgt caagggcgag atcacgaagg tcgttggcaa ataatgtcta   11340
gctagaaatt cgttcaagcc gacgccgctt cgcggcgcgg cttaactcaa gcgttagatg   11400
cactaagcac ataattgctc acagccaaac tatcgatgag ttgaaggacc ccgtagaaaa   11460
gatcaaagga tcttcttgag atccttttt tctgcgcgta atctgctgct tgcaaacaaa    11520
aaaaccaccg ctaccagcgg tggtttgttt gccggatcaa gagctaccaa ctctttttcc   11580
gaaggtaact ggcttcagca gagcgcagat accaaatact gtccttctag tgtagccgta   11640
```

```
gttaggccac cacttcaaga actctgtagc accgcctaca tacctcgctc tgctaatcct   11700
gttaccagtg gctgctgcca gtggcgataa gtcgtgtctt accgggttgg actcaagacg   11760
atagttaccg gataaggcgc agcggtcggg ctgaacgggg ggttcgtgca cacagcccag   11820
cttggagcga acgacctaca ccgaactgag atacctacag cgtgagctat gagaaagcgc   11880
cacgcttccc gaagggagaa aggcggacag gtatccggta agcggcaggg tcggaacagg   11940
agagcgcacg agggagcttc cagggggaaa cgcctggtat ctttatagtc ctgtcgggtt   12000
tcgccacctc tgacttgagc gtcgattttt gtgatgctcg tcagggggc ggagcctatg   12060
gaaaaacgcc agcaacgcgg ccttttacg gttcctggcc ttttgctggc cttttgctca   12120
catgttcttt cctgcgttat ccctgattc tgtggataac cgtattaccg cctttgagtg   12180
agctgatacc gctcgccgca gccgaacgac cgagcgcagc gagtcagtga gcgaggaagc   12240
ggaagagcgc ctgatgcggt attttctcct tacgcatctg tgcggtattt cacaccgcat   12300
aggccgcgat aggccgacgc gaagcggcgg ggcgtaggga gcgcagcgac cgaagggtag   12360
gcgcttttg cagctcttcg gctgtgcgct ggccagacag ttatgcacag gccaggcggg   12420
ttttaagagt tttaataagt tttaaagagt tttaggcgga aaaatcgcct tttttctctt   12480
ttatatcagt cacttacatg tgtgaccggt tcccaatgta cggctttggg ttcccaatgt   12540
acgggttccg gttcccaatg tacggctttg ggttcccaat gtacgtgcta ccacaggaa   12600
agagaccttt tcgaccttt tcccctgcta gggcaatttg ccctagcatc tgctccgtac   12660
attaggaacc ggcggatgct tcgccctcga tcaggttgcg gtagcgcatg actaggatcg   12720
ggccagcctg ccccgcctcc tccttcaaat cgtactccgg caggtcattt gacccgatca   12780
gcttgcgcac ggtgaaacag aacttcttga actctccggc gctgccactg cgttcgtaga   12840
tcgtcttgaa caaccatctg gcttctgcct tgcctgcggc gcggcgtgcc aggcggtaga   12900
gaaaacggcc gatgccgggg tcgatcaaaa agtaatcggg gtgaaccgtc agcacgtccg   12960
ggttcttgcc ttctgtgatc tcgcggtaca tccaatcagc aagctcgatc tcgatgtact   13020
ccggccgccc ggtttcgctc tttacgatct tgtagcggct aatcaaggct tcaccctcgg   13080
ataccgtcac caggcggccg ttcttggcct tcttggtacg ctgcatggca acgtgcgtgg   13140
tgtttaaccg aatgcaggtt tctaccaggt cgtctttctg ctttccgcca tcggctcgcc   13200
ggcagaactt gagtacgtcc gcaacgtgtg gacggaacac gcggccgggc ttgtctccct   13260
tcccttcccg gtatcggttc atggattcgg ttagatggga aaccgccatc agtaccaggt   13320
cgtaatccca cacactggcc atgccggcgg ggcctgcgga aacctctacg tgcccgtctg   13380
gaagctcgta gcggatcacc tcgccagctc gtcggtcacg cttcgacaga cggaaaacgg   13440
ccacgtccat gatgctgcga ctatcgcggg tgcccacgtc atagagcatc ggaacgaaaa   13500
aatctggttg ctcgtcgccc ttgggcggct tcctaatcga cggcgcaccg gctgccggcg   13560
gttgccggga ttctttgcgg attcgatcag cggcccttg ccacgattca ccggggcgtg   13620
cttctgcctc gatgcgttgc cgctgggcgg cctgcgcggc cttcaacttc tccaccaggt   13680
catcacccag cgccgcgccg atttgtaccg ggcggatgg tttgcgaccg ctcacgccga   13740
ttcctcgggc ttgggggttc cagtgccatt gcagggccgg cagacaaccc agccgcttac   13800
gcctggccaa ccgcccgttc ctccacacat ggggcattcc acggcgtcgg tgcctggttg   13860
ttcttgattt tccatgccgc ctcctttagc cgctaaaatt catctactca tttattcatt   13920
tgctcattta ctctggtagc tgcgcgatgt attcagatag cagctcggta atggtcttgc   13980
```

```
cttggcgtac cgcgtacatc ttcagcttgg tgtgatcctc cgccggcaac tgaaagttga    14040
cccgcttcat ggctggcgtg tctgccaggc tggccaacgt tgcagccttg ctgctgcgtg    14100
cgctcggacg gccggcactt agcgtgtttg tgcttttgct cattttctct ttacctcatt    14160
aactcaaatg agttttgatt taatttcagc ggccagcgcc tggacctcgc gggcagcgtc    14220
gccctcgggt tctgattcaa gaacggttgt gccggcggcg gcagtgcctg ggtagctcac    14280
gcgctgcgtg atacgggact caagaatggg cagctcgtac ccggccagcg cctcggcaac    14340
ctcaccgccg atgcgcgtgc ctttgatcgc ccgcgacacg acaaaggccg cttgtagcct    14400
tccatccgtg acctcaatgc gctgcttaac cagctccacc aggtcggcgg tggcccaaat    14460
gtcgtaaggg cttggctgca ccggaatcag cacgaagtcg gctgccttga tcgcggacac    14520
agccaagtcc gccgcctggg gcgctccgtc gatcactacg aagtcgcgcc ggccgatggc    14580
cttcacgtcg cggtcaatcg tcgggcggtc gatgccgaca acggttagcg gttgatcttc    14640
ccgcacggcc gcccaatcgc gggcactgcc ctggggatcg gaatcgacta acagaacatc    14700
ggccccggcg agttgcaggg cgcgggctag atggggttgcg atggtcgtct tgcctgaccc    14760
gcctttctgg ttaagtacag cgataacctt catgcgttcc ccttgcgtat tgtttatttt    14820
actcatcgca tcatatacgc agcgaccgca tgacgcaagc tgttttactc aaatacacat    14880 cacctttttat gatgatcagt gattttgtgc cgagctgccg gtcggggagc tgttggctgg    14940
ctgg                                                                14944

<210> SEQ ID NO 8
<211> LENGTH: 15242
<212> TYPE: DNA
<213> ORGANISM: Artificial Sequence
<220> FEATURE:
<223> OTHER INFORMATION: Transformation vector

<400> SEQUENCE: 8
tggcaggata tattgtggtg taaacaaatt gacgcttaga caacttaata acacattgcg      60 gacgtctttta atgtactgaa tttagttact gatcactgat taagtactgc gatcgcctcg     120
acatattgtt tttgtttcac ataaatgtcg ttttggatta ttcatgtaat attttaaact     180
aaagtacaat ttttgactac tttagtttac tagttaagct tttatttttt tgactaacca     240
ttgaatgatg aagagatcaa cgcatcatat ttacaactta catagtcttt tggaagtgta     300
aattgctaat actacctaaa atatatctat aattaactaa tatttttttcg tcaattataa     360 tagatcaatt aaaaggctat caaaaggaaa aaaatgaaat ccacatcctg ccatcataac     420
ctcatgctgg aaaaagaaat gaaaaaatat aaaaaatttc ttttgtttat taaatttaca     480
actttaatac tagtttctttt tctattttttt aaaagcttttt gtcacttact taaaaaaaaa     540 aaacttttttg aaatattcct acttccaatg tctgattagt gcttctggat ttccttttttg     600 gatcatgtga atcctaaatc agaaaaattc atataatacc caattcagta tattttcata     660
cttcaattta caagagttct ctatgttttt agcttctttc ttttaagcca aatgtttttaa     720 gcatctttta tacattaaaa taatttagtg ttgagttgag attttttttt ttttttttttg     780 gatttacttg ttcaaaatct gaaaaaatgt ttacagaagg ttaaaatgaa ccaaaaggca     840
tatcaagcta gattttgaat taccctatt tcatcgtatac acaaaactga aatgtggac      900 acagttgatt ttacttctcg atgacatcgt agtttttattt aatttggaaa ccacggccca     960
tatgagcaca tttcaattaa aaaccaatgg taagagcatt ttccatgcaa gattcgagag    1020
atattaaccc agtgactgtt aaaacagctt agaaccctaa taacgaattt caattactca    1080
```

```
atttaccatt cgcatttcgc aataaccaaa ctgagccagt cacaaggagt aaaccgaacc    1140
ggattattta tttataaaat gaaagaaagg aaaccaaaca acaacagcag tagtagtctg    1200
acgtaaacca aaaagcaggc agatcaacaa ctaaagaaa ctcaaattac caaaacaaac     1260
aggaaattgc aaactaagtt ttttaccat atgcatacaa agaccataaa aggttctgat    1320
aatcaccggt ttcatctcgt cgagattacc ctgttatccc tatcagtatt taatccggcc   1380
atctccttcc gttatgacat cgttgaaagt gccaccattc gggatcatcg gcaacacatg   1440
ttcttggtgc ggacaaatca catccaacag gtaaggtcct ggtgtatcca gcattgtctg   1500
aatagcttct cggagatctg ctttctttgt caccctcgcc gctggaatcc cgcaagctgc   1560
tgcaaacagc aacatgttcg ggaatatctc gtcctcctga gccggatccc cgagaaatgt   1620
gtgagctcgg ttagctttgt agaaccgatc ttcccattgc ataaccatgc caagatgctg   1680
gttgtttaat aaaagtacct tcactggaag attctctaca cgaatagtgg ctagctcttg   1740
cacattcatt ataaagcttc catctccgtc aatatccaca actatcgcat cagggttagc   1800
aacagacgct ccaatcgcag caggaagtcc aaatcccata gctccaaggc ctcctgatga   1860
tagccactgc cttggtttct tgtaattgta gaactgcgcc gcccacattt gatgttgccc   1920
gacaccagta cttattatgg cttttccatc agtcaactca tcaaggacct taatcgcata   1980
ctgtggagga atagcttccc caaacgtctt aaagctcaac ggaaacttct gtttctgtac   2040
gttcaactca ttcctccaaa ctccaaaatc aagcttaagc tcctccgctc ggttctcaag   2100
aaccttattc atcccttgca agccagctt aacatcacca cacacagaca catgaggagt    2160
cttattcttc ccaatctcag ccgagtcaat atcaatatga acaatcttag ccctactagc   2220
aaaagcctca agcttacccg tgacacgatc atcaaaccttt accccaaacg ccaacaacaa   2280
atcactatgc tccacagcgt aatttgcata cacagtccca tgcattccaa gcatatgtaa   2340
cgacaactca tcatcacaag gataagatcc cagccccatc aacgtactcg caacagggat   2400
ccccgtaagc tcaacaaacc tacccaattc atcgctagaa ttcaaacaac caccaccaac   2460
atacaacaca ggcttcttag actcagaaat caacctaaca atctgctcca atgagaatc    2520 ttccggaggt ttaggcatcc tagacatata accaggtaat ctcatagcct gttcccaatt   2580
aggaatcgca agctgttgtt gaatatcttt aggaacatca accaaaacag gtccaggtct   2640
accagaagta gctaaaaaga aagcttcctc aataatccta gggatatctt caacatccat   2700
cacaagatag ttatgcttcg taatcgaacg cgttacctca acaatcggag tctcttgaaa   2760
cgcatctgta ccaatcatac gacgagggac ttgtcctgtg attgctacaa gaggaacact   2820
atctaacaac gcatcggcta atccgctaac gagatttgta gctccgggac ctgaagtggc   2880
tatacagata cctggtttac ctgaggatcg agcgtatcct tctgctgcga atacacctcc   2940
ttgttcgtga cgaggaagga cgttacggat tgaggaagag cgggttaagg cttggtgaat   3000
ctccattgat gtacctccag ggtaagcgaa tacggtttct acgccttgac gttctaaagc   3060
ttcgacgagg atatcagcgc ctttgcgggg ttgatctgga gcgaatcggg agatgaatgt   3120
ttcgggtttg gtaggtttgg ttggagaggg agtggttgtg acattggtgg ttgtgttgag   3180
cacggcggag atggaggagg gagagctgga tttgataccg cggcggcggg aggaggagga   3240
tgatttgttg gggtttaggg agaatgggag ggagaatctg gagattggta atggtgattt   3300
ggaggaggaa ggagatggtt tggtggagaa ggagatcgaa gaagatgttg ttgttgttgt   3360
tgttgccgcc gccatggttc agctgcacat acataacata tcaagatcag aacacacata   3420
```

```
tacacacaca aatacaatca agtcaacaac tccaaaaagt ccagatctac atatatacat    3480
acgtaaataa caaaatcatg taaataatca caatcatgta atccagatct atgcacatat    3540
atatatacac aattaataaa aaaaatgata taacagatct atatctatgt atgtaacaac    3600
acaatcagat gagagaagtg atgttttcag atctgtatac atacaaacac aaacagatga    3660
acaattgata cgtagatcca tatgtatacg tacaattagc tacacgatta aatgaaaaaa    3720
atcaacgatt tcggattggt acacacaaac gcaacaatat gaagaaattc atatctgatt    3780
agatataaac ataaccacgt gtagatacac agtcaaatca acaaatttat agcttctaaa    3840
cggatgagat gaacaagata aagatattca cataaggcat acataagata agcagattaa    3900
caaactagca ataatacata cctaattaaa acaaggaata acagagagag agagagagag    3960
agagatttac cttgaaaatg aagaggagaa gagaggattt cttaaaattg ggggtagaga    4020
aagaaagatg atgaattgtg agaaaggaga gatagaaggg ggggttgtat ataggctg     4080 tagaagatta ttttttgtgtt tgaggcggtg aaggaagagg ggatctgact atgcacgtt    4140 tgcggttacg tatttcgata ggagtctttc aacgcttaac gccgttactc tatatgaccg    4200
tttgggccgt aacggggccg tttgttaacg ctgatgttga ttcttttctt tctttctttc    4260 ttccttttttt aaagaagcaa ttgtacaatc gttgctagct gtcaaacgga taattcggat    4320
acggatatgc ctatattcat atccgtaatt tttggattcg aatttttcccc tctagggata    4380 acagggtaat ggatctatat tgttttttgtt tcacataaat gtcgttttgg attattcatg    4440
taatatttta aactaaagta caattttttga ctactttagt ttactagtta agcttttatt    4500
tttttgacta accattgaat gatgaagaga tcaacgcatc atatttacaa cttacatagt    4560
cttttggaag tgtaaattgc taatactacc taaaatatat ctataattaa ctaatatttt    4620
ttcgtcaatt ataatagatc aattaaaagg ctatcaaaag gaaaaaaatg aaatccacat    4680
cctgccatca taacctcatg ctggaaaaag aaatgaaaaa atataaaaaa tttcttttgt    4740
ttattaaatt tacaacttta atactagttt cttttctatt tttttaaagc ttttgtcact    4800
tacttaaaaa aaaaaaactt tttgaaatat tcctacttcc aatgtctgat tagtgcttct    4860
ggatttcctt tttggatcat gtgaatccta aatcagaaaa attcatataa tacccaattc    4920
agtatatttt catacttcaa tttacaagag ttctctatgt ttttagcttc tttctttttaa    4980 gccaaatgtt ttaagcatct tttatacatt aaaataattt agtgttgagt tgagattttt    5040
tttttttttt tttggattta cttgttcaaa atctgaaaaa atgtttacag aaggttaaaa    5100
tgaaccaaaa ggcatatcaa gctagattt gaattaccct atttcatcgt atacacaaaa     5160
ctgataatgt ggacacagtt gattttactt ctcgatgaca tcgtagttttt atttaatttg    5220 gaaaccacgg cccatatgag cacatttcaa ttaaaaacca atggtaagag cattttccat    5280
gcaagattcg agagatatta acccagtgac tgttaaaaca gcttagaacc ctaataacga    5340
atttcaatta ctcaatttac cattcgcatt tcgcaataac caaactgagc cagtcacaag    5400
gagtaaaccg aaccggatta tttatttata aaatgaaaga aaggaaacca aacaacaaca    5460
gcagtagtag tctgacgtaa accaaaaagc aggcagatca acaactaaaa gaaactcaaa    5520
ttaccaaaac aaacaggaaa ttgcaaacta agttttttta ccatatgcat acaaagacca    5580
taaaaggttc tgataatcac cggtttcatc tcagatccgc gatcgccaat tgacgcgtac    5640
tagtgtacaa gcttgcggcc gcgaattcgg tacatccggc cagtgaatta tcaactatgt    5700
ataataaagt tgggtaccgg cctattaggc cacggtccgt acagtgttta aacgattgac    5760
ctgcaggata caagtgcgca cagactagcg gccgctaatc ccgggaatta ccggtagtag    5820
```

```
gcgcctactt tggccggcct agtagattta aattggcctt agtggccaag cttggcgtaa    5880
tcatggccac tttgtacaag aaagctgggt ggtaccggcc tattaggcca cggtccgtac    5940
agtgtttaaa cgattgacct gcaggataca agtgcgcaca gactagcggc cgctaatccc    6000
gggaattacc ggtagtaggc gccccccact ccgccctaca ctcgtatata tatgcctaaa    6060
cctgccccgt tcctcatatg tgatattatt atttcattat taggtataag atagtaaacg    6120
ataaggaaag acaatttatt gagaaagcca tgctaaaata tagatagata taccttagca    6180
ggtgtttatt ttacaacata acataacata gtagctagcc agcaggcagg ctaaaacata    6240
gtatagtcta tctgcagggg gtacggtcga ggcggcctta attaatcatt gtttgcctcc    6300
ctgctgcggt ttttcaccga agttcatgcc agtccagcgt ttttgcagca gaaaagccgc    6360
cgacttcggt tgcggtcgc gagtgaagat ccctttcttg ttaccgccaa cgcgcaatat    6420
gccttgcgag gtcgcaaaat cggcgaaatt ccatacctgt tcaccgacga cggcgctgac    6480
gcgatcaaag acgcggtgat acatatccag ccatgcacac tgatactctt cactccacat    6540
gtcggtgtac attgagtgca gcccggctaa cgtatccacg ccgtattcgg tgatgataat    6600
cggctgatgc agtttctcct gccaggccag aagttctttt tccagtacct tctctgccgt    6660
ttccaaatcg ccgctttgga cataccatcc gtaataacgg ttcaggcaca gcacatcaaa    6720
gagatcgctg atggtatcgg tgtgagcgtc gcagaacatt acattgacgc aggtgatcgg    6780
acgcgtcggg tcgagtttac gcgttgcttc cgccagtggc gcgaaatatt cccgtgcacc    6840
ttgcggacgg gtatccggtt cgttggcaat actccacatc accacgcttg ggtggttttt    6900
gtcacgcgct atcagctctt taatcgcctg taagtgcgct tgctgagttt ccccgttgac    6960
tgcctcttcg ctgtacagtt ctttcggctt gttgcccgct tcgaaaccaa tgcctaaaga    7020
gaggttaaag ccgacagcag cagtttcatc aatcaccacg atgccatgtt catctgccca    7080
gtcgagcatc tcttcagcgt aagggtaatg cgaggtacgg taggagttgg ccccaatcca    7140
gtccattaat gcgtggtcgt gcaccatcag cacgttatcg aatcctttgc cacgcaagtc    7200
cgcatcttca tgacgaccaa agccagtaaa gtagaacggt ttgtggttaa tcaggaactg    7260
ttcgcccttc actgccactg accggatgcc gacgcgaagc gggtagatat cacactctgt    7320
ctggcttttg gctgtgacgc acagttcata gagataacct tcacccggtt gccagaggtg    7380
cggattcacc acttgcaaag tcccgctagt gccttgtcca gttgcaacca cctgttgatc    7440
cgcatcacgc agttcaacgc tgacatcacc attggccacc acctgccagt caacagacgc    7500
gtggttacag tcttgcgcga catgcgtcac cacggtgata tcgtccaccc aggtgttcgg    7560
cgtggtgtag agcattacgc tgcgatggat tccggcatag ttaaagaaat catggaagta    7620
agactgcttt ttcttgccgt tttcgtcggt aatcaccatt cccggcggga tagtctgcca    7680
gttcagttcg ttgttcacac aaacggtgat acctgcacat caacaaattt tggtcatata    7740
ttagaaaagt tataaattaa aatatacaca cttataaact acagaaaagc aattgctata    7800
tactacattc ttttattttg aaaaaaatat ttgaaatatt atattactac taattaatga    7860
taattattat atatatatca aaggtagaag cagaaactta cgtacacttt tcccggcaat    7920
aacatacggc gtgacatcgg cttcaaatgg cgtatagccg ccctgatgct ccatcacttc    7980
ctgattattg acccacactt tgccgtaatg agtgaccgca tcgaaacgca gcacgatacg    8040
ctggcctgcc caacctttcg gtataaagac ttcgcgctga taccagacgt tgcccgcata    8100
attacgaata tctgcatcgg cgaactgatc gttaaaactg cctggcacag caattgcccg    8160
```

```
gctttcttgt aacgcgcttt cccaccaacg ctgaccaatt ccacagttttt cgcgatccag    8220 actgaatgcc cacaggccgt cgagttttttt gatttcacgg gttggggttt ctacaggacg    8280
taccatggtg ttcagcttga tcggactatt aattagttca atgtttttata cgtgaagaaa    8340 aagaaagtgt gggaatatat ggcaaaaaac atgcatgggg acgtgtgtta acatacgtgt    8400
cttatgacta attataggta gtggcagtta caaccatctg gaaatggaat tgatatacac    8460
agccctgcaa gagacactag cttacctaag agcattttca tgcacacttt tttaaaagac    8520
aaaggatcta tattaatagt aggtcaatat tctgaatgtt ttattacctt taacattcga    8580
agaaggaaaa aaccaatgtt tcatcttgtc aatgtgtcct tcacaaactc atatttactt    8640
attctagttt gaccaagata taagggttaa cagtaaaaca taagaaaata actgacaaat    8700
ataaaataaa tatcagataa ttacagagat ctcaaaatta ttaagaataa tttatctaag    8760
aattaatatt gttggtggat ttctaaaggt gacaggtgaa aatttatatt attgtaaaat    8820
ttaaataaag tcaatatttt tatattgttg taaaatttaa aataagtcaa tattttttgtc    8880 tttcgatttg tactaaattt ctattgatgg attttggaga atgaaatacc ataatttcta    8940
ttcaattcat tacagtattt tttccagcat acaattatgc tttacaaagt tttttatatag    9000 gctacaagaa aagtaaacata gaatacaata attcaaaaat caagtcgagg actatttggt    9060
tatgacaatc ttaatgatac atgtttatca taattaatta taaggacaat aattataatg    9120
tgatgattac atttaactta taatacttac tattcgtagt ggtggttaca acacattaat    9180
tttaactgtc gcccttaatg tgttgctctt taactccgaa tacttctgta agttgttaaa    9240
atcttcctga ttgtagtatt ttagtaaatg agtctgtaag ttgctcttaa gttctgcaca    9300
aaggtaactg cacatttcct tcaagaatca ctcttcgaat gatcaggtgt tttatgttaa    9360
tgtgtctaca gcgactatga aaacaggaa agtttgtgtt gtacatgaaa attttttgctc    9420 tcagtcttca agaattttct gttaagatct tccatgacat caagtttgca gcactgtatc    9480
atcaattttg gttggaatt ggcacttctg caaaatggtc aattgcagtc tgaaaagtca    9540
aactttgact tttgcatctt gatcaaattt caagaaagac atttcatcaa gacatgttag    9600
aattagaagt ttgttttatt aagaaagtca aagtcttct ttgctttgga aaagtcaata    9660
ttctaaacac ttagattatt ttctaactgt taagaaaatt gacaagttca gaacttgacg    9720
ccagattttc accatgtagc aagttgattc tggaagaaga actgacacaa gagttgtaga    9780
tttgtttgag atctaagact atgcggaaca gaactagact taaaaatgat gggataagaa    9840
gttataaaac tttgaagaca cgtccatgaa actgaagatg tcaataaatt ttgggccttc    9900
cgtagacgga atttggttag aacttgacca gcagttttca cgtaggttca atcagtcatt    9960
gcaagagtat atcaaagaaa gtctacaaag catgttacaa gctttctgat tacacttaga   10020
actccttcag aacatcaagg aacagagaga ttcaaagatc tcaagttgga tacagtccgg   10080
gccgagcagg ccggcctagt agatttaaat tggccttagt ggccaagctt ggcgtaatca   10140
tggagcctgc ttttttgtac aaacttgggt accggcctat taggccacgg tccgtacagt   10200
gtttaaacga ttgacctgca ggatacaagt gcgcacagac tagcggccgc taatcccggg   10260
aattaccggg agtaggcgcc tactttggcc ggcctagtag atttaaattg gccttagtgg   10320
ccaagcttgg cgtaatcatg gcaacttttc tatacaaagt tgatagcttg gcgtaatcga   10380
tgtaccgata tcaatttaaa ttggccggcc gagctccctg caggggggccc ggcgcgcctc   10440 tagattaatt aaaggcctta gttactaatc agtgatcaga ttgtcgtttc ccgccttcag   10500
tttaaactat cagtgtttga caggatatat tggcgggtaa acctaagaga aaagagcgtt   10560
```

```
tattagaata atcggatatt taaaagggcg tgaaaaggtt tatccgttcg tccatttgta    10620
tgtcaatatc catgataagt cgcgctgtat gtgtttgttt gaatattcat ggaacgcagt    10680
ggcggttttc atggcttgtt atgactgttt ttttggggta cagtctatgc ctcgggcatc    10740
caagcagcaa gcgcgttacg ccgtgggtcg atgtttgatg ttatggagca gcaacgatgt    10800
tacgcagcag ggcagtcgcc ctaaaacaaa gttaaacatc atgggtgaag cggtcatcgc    10860
cgaggtgtcc acccagctgt cggaagtcgt gggtgtcatc gagcgccacc tcgaaccgac    10920
cctcctcgcc gtgcatctgt atggtagcgc cgttgacggc ggccttaagc cccattcgga    10980
catcgacctg cttgtcaccg ttaccgtccg tctcgacgag accacgcgcc gcgcgcttat    11040
caacgacctt ctggaaacgt ccgcctcccc cggcgagagc gaaatcctgc gcgcggttga    11100
ggtgacgatt gtggtgcacg atgacatcat cccctggcgc tatccggcca aacgcgaact    11160
ccagttcggc gaatggcagc gtaatgatat tctggcgggt atctttgaac cggccaccat    11220
cgacattgat ctggcgatcc tgctcaccaa ggcccgggag catagcgtgg ccctcgtcgg    11280
ccccgcggcc gaggaacttt tcgacccggt gccggaacag gatctgttcg aagcactgaa    11340
cgagacgctg accctgtgga actccccgcc ggattgggcg ggcgatgagc gcaatgtggt    11400
ccttacgctg agccggattt ggtactcggc ggttaccggc aagatcgcgc cgaaggatgt    11460
cgccgccgac tggcgatgg agcgccttcc ggcgcaatac cagcccgtga tcctcgaagc    11520
gcgccaagcc tatctgggcc aagaagaaga ccgtctcgcg tcccgggccg accagctcga    11580
agaatttgtc cactatgtca agggcgagat cacgaaggtc gttggcaaat aatgtctagc    11640
tagaaattcg ttcaagccga cgccgcttcg cggcgcggct taactcaagc gttagatgca    11700
ctaagcacat aattgctcac agccaaacta tcgatgagtt gaaggacccc gtagaaaaga    11760
tcaaaggatc ttcttgagat cctttttttc tgcgcgtaat ctgctgcttg caaacaaaaa    11820
aaccaccgct accagcggtg gtttgtttgc cggatcaaga gctaccaact cttttttccga   11880
aggtaactgg cttcagcaga gcgcagatac caaatactgt ccttctagtg tagccgtagt    11940
taggccacca cttcaagaac tctgtagcac cgcctacata cctcgctctg ctaatcctgt    12000
taccagtggc tgctgccagt ggcgataagt cgtgtcttac cgggttggac tcaagacgat    12060
agttaccgga taaggcgcag cggtcgggct gaacggggggtt cgtgcaca cagcccagct    12120
tggagcgaac gacctacacc gaactgagat acctacagcg tgagctatga gaaagcgcca    12180
cgcttcccga agggagaaag gcggacaggt atccggtaag cggcagggtc ggaacaggag    12240
agcgcacgag ggagcttcca gggggaaacg cctggtatct ttatagtcct gtcgggtttc    12300
gccacctctg acttgagcgt cgatttttgt gatgctcgtc agggggcgg agcctatgga    12360
aaaacgccag caacgcggcc tttttacggt tcctggcctt ttgctggcct tttgctcaca    12420
tgttctttcc tgcgttatcc cctgattctg tggataaccg tattaccgcc tttgagtgag    12480
ctgataccgc tcgccgcagc cgaacgaccg agcgcagcga gtcagtgagc gaggaagcgg    12540
aagagcgcct gatgcggtat tttctcctta cgcatctgtg cggtatttca caccgcatag    12600
gccgcgatag gccgacgcga gcggcgggg cgtagggagc gcagcgaccg aagggtaggc    12660
gcttttgca gctcttcggc tgtgcgctgg ccagacagtt atgcacaggc caggcgggtt    12720
ttaagagttt taataagttt taaagagttt taggcggaaa aatcgccttt tttctctttt    12780
atatcagtca cttacatgtg tgaccggttc ccaatgtacg gctttgggtt cccaatgtac    12840
gggttccggt tcccaatgta cggctttggg ttcccaatgt acgtgctatc cacaggaaag    12900
```

-continued

```
agaccttttc gacctttttc ccctgctagg gcaatttgcc ctagcatctg ctccgtacat    12960
taggaaccgg cggatgcttc gccctcgatc aggttgcggt agcgcatgac taggatcggg    13020
ccagcctgcc ccgcctcctc cttcaaatcg tactccggca ggtcatttga cccgatcagc    13080
ttgcgcacgg tgaaacagaa cttcttgaac tctccggcgc tgccactgcg ttcgtagatc    13140
gtcttgaaca accatctggc ttctgccttg cctgcggcgc ggcgtgccag gcggtagaga    13200
aaacggccga tgccggggtc gatcaaaaag taatcggggt gaaccgtcag cacgtccggg    13260
ttcttgcctt ctgtgatctc gcggtacatc caatcagcaa gctcgatctc gatgtactcc    13320
ggccgcccgg tttcgctctt tacgatcttg tagcggctaa tcaaggcttc accctcggat    13380
accgtcacca ggcggccgtt cttggccttc ttggtacgct gcatggcaac gtgcgtggtg    13440
tttaaccgaa tgcaggtttc taccaggtcg tctttctgct ttccgccatc ggctcgccgg    13500
cagaacttga gtacgtccgc aacgtgtgga cggaacacgc ggccgggctt gtctcccttc    13560
ccttcccggt atcggttcat ggattcggtt agatgggaaa ccgccatcag taccaggtcg    13620
taatcccaca cactggccat gccggcgggg cctgcgaaa cctctacgtg cccgtctgga     13680
agctcgtagc ggatcacctc gccagctcgt cggtcacgct tcgacagacg aaaacggcc    13740 acgtccatga tgctgcgact atcgcgggtg cccacgtcat agagcatcgg aacgaaaaaa    13800
tctggttgct cgtcgccctt gggcggcttc ctaatcgacg gcgcaccggc tgccggcggt    13860
tgccgggatt ctttgcggat tcgatcagcg gccccttgcc acgattcacc ggggcgtgct    13920
tctgcctcga tgcgttgccg ctgggcggcc tgcgcggcct tcaacttctc caccaggtca    13980
tcacccagcg ccgcgccgat ttgtaccggg ccggatggtt tgcgaccgct cacgccgatt    14040
cctcgggctt gggggttcca gtgccattgc agggccggca gacaacccag ccgcttacgc    14100
ctggccaacc gcccgttcct ccacacatgg ggcattccac ggcgtcggtg cctggttgtt    14160
cttgattttc catgccgcct cctttagccg ctaaaattca tctactcatt tattcatttg    14220
ctcatttact ctggtagctg cgcgatgtat tcagatagca gctcggtaat ggtcttgcct    14280
tggcgtaccg cgtacatctt cagcttggtg tgatcctccg ccggcaactg aaagttgacc    14340
cgcttcatgg ctgcgtgtc tgccaggctg gccaacgttg cagccttgct gctgcgtgcg    14400
ctcggacggc cggcacttag cgtgtttgtg cttttgctca tttcctcttt acctcattaa    14460
ctcaaatgag ttttgattta atttcagcgg ccagcgcctg gacctcgcgg gcagcgtcgc    14520
cctcgggttc tgattcaaga acggttgtgc cggcggcggc agtgcctggg tagctcacgc    14580
gctgcgtgat acgggactca agaatgggca gctcgtaccc ggccagcgcc tcggcaacct    14640
caccgccgat gcgcgtgcct ttgatcgccc gcgacacgac aaaggccgct tgtagccttc    14700
catccgtgac ctcaatgcgc tgcttaacca gctccaccag gtcggcggtg gcccaaatgt    14760
cgtaagggct tggctgcacc ggaatcagca cgaagtcggc tgccttgatc gcggacacag    14820
ccaagtccgc cgcctgggc gctccgtcga tcactacgaa gtcgcgccgg ccgatggcct    14880
tcacgtcgcg gtcaatcgtc gggcggtcga tgccgacaac ggttagcggt tgatcttccc    14940
gcacggccgc ccaatcgcgg gcactgccct ggggatcgga atcgactaac agaacatcgg    15000
ccccggcgag ttgcagggcg cgggctagat gggttgcgat ggtcgtcttg cctgacccgc    15060 cttctggtt aagtacagcg ataaccttca tgcgttcccc ttgcgtattt gtttatttac     15120
tcatcgcatc atatacgcag cgaccgcatg acgcaagctg ttttactcaa atacacatca    15180
cctttttaga tgatcagtga ttttgtgccg agctgccggt cggggagctg ttggctggct    15240
gg                                                                    15242
```

<210> SEQ ID NO 9
<211> LENGTH: 15405
<212> TYPE: DNA
<213> ORGANISM: Artificial Sequence
<220> FEATURE:
<223> OTHER INFORMATION: Transformation vector

<400> SEQUENCE: 9

| | | | | | |
|---|---|---|---|---|---|
| gacatacaaa | tggacgaacg | gataaacctt | ttcacgccct | tttaaatatc | cgattattct | 60 |
| aataaacgct | cttttctctt | aggtttaccc | gccaatatat | cctgtcaaac | actgatagtt | 120 |
| taaactgaag | gcgggaaacg | acaatcagat | ctagtaggaa | acagctatga | ccatgattac | 180 |
| gccaagctat | cgattacgcc | aagctatcaa | ctttgtatag | aaaagttggg | taccccgggg | 240 |
| gatatcaagc | ttaaacaata | caggtggctg | aaatatataa | accaattcat | gtctacaaat | 300 |
| gtacccttg | cacttaaaaa | atttatcgga | gggatccact | cgcattggaa | gtcaatcaag | 360 |
| gactattggt | tattagtctg | tccgttattt | gaatatgata | acgcaaggtt | tccgtgtaca | 420 |
| atatatgtgc | atggaatgcc | gctgttgagc | gtttaacctg | aattttcatg | atttgaggca | 480 |
| tggggctgta | ttgcttgtta | gcgttggggt | gaatgaaatt | tagcttcaac | ctaatgagat | 540 |
| acagttcccg | ggtcaggatg | atctaatcat | tcctcataca | aatgtctcat | ttttcaatta | 600 |
| gagtaatatg | tgtccatatg | tctcgatttc | gattgactta | catccattca | agataaaatt | 660 |
| gcgcaatctt | gcacttccct | taacattttc | ataagtttca | tacctatcac | tacctataca | 720 |
| cccgggataa | cacatcgtgt | tcgggtgttg | gaagattttg | actcaaattc | ctaatttaca | 780 |
| ttgctcctaa | ctatattagc | tttaacttct | gtactgctgg | taaagctgcc | aaccgttatc | 840 |
| accataggcc | atacttccat | cggttataga | ctctcatccc | cttttagacc | agcttagtca | 900 |
| acgttctgtc | ttttaattct | aagacgttat | gaacttagat | ggttttcaaa | aaaaatcgtg | 960 |
| atgagaatgc | cttgccagga | cattagctac | acgttacaca | taccatgcaa | tccaggagaa | 1020 |
| tattatttct | tcgccacttg | tcactccctt | caaacaccta | agaccttatc | tctcacatca | 1080 |
| gccgcataca | ttcacatgcg | tgcatgcatt | attacacgtg | atcgccatgc | aaatcttcat | 1140 |
| taaagtgtat | aaaagtaccc | atccgattca | ggcttgaatc | taccgatacc | tgagcaacac | 1200 |
| aaacacggtc | aaaaacatac | acgaaccatg | gtacgtcctg | tagaaacccc | aacccgtgaa | 1260 |
| atcaaaaaac | tcgacggcct | gtgggcattc | agtctggatc | gcgaaaactg | tggaattggt | 1320 |
| cagcgttggt | gggaaagcgc | gttacaagaa | agccgggcaa | ttgctgtgcc | aggcagtttt | 1380 |
| aacgatcagt | tcgccgatgc | agatattcgt | aattatgcgg | gcaacgtctg | gtatcagcgc | 1440 |
| gaagtcttta | taccgaaagg | ttgggcaggc | cagcgtatcg | tgctgcgttt | cgatgcggtc | 1500 |
| actcattacg | gcaaagtgtg | ggtcaataat | caggaagtga | tggagcatca | gggcggctat | 1560 |
| acgccatttg | aagccgatgt | cacgccgtat | gttattgccg | ggaaaagtgt | acgtaagttt | 1620 |
| ctgcttctac | ctttgatata | tatataataa | ttatcattaa | ttagtagtaa | tataatattt | 1680 |
| caaatatttt | tttcaaaata | aaagaatgta | gtatatagca | attgcttttc | tgtagtttat | 1740 |
| aagtgtgtat | attttaattt | ataacttttc | taatatatga | ccaaaatttg | ttgatgtgca | 1800 |
| ggtatcaccg | tttgtgtgaa | caacgaactg | aactggcaga | ctatcccgcc | gggaatggtg | 1860 |
| attaccgacg | aaaacggcaa | gaaaaagcag | tcttacttcc | atgatttctt | taactatgcc | 1920 |
| ggaatccatc | gcagcgtaat | gctctacacc | acgccgaaca | cctgggtgga | cgatatcacc | 1980 |
| gtggtgacgc | atgtcgcgca | agactgtaac | cacgcgtctg | ttgactggca | ggtggtggcc | 2040 |

```
aatggtgatg tcagcgttga actgcgtgat gcggatcaac aggtggttgc aactggacaa    2100
ggcactagcg ggactttgca agtggtgaat ccgcacctct ggcaaccggg tgaaggttat    2160
ctctatgaac tgtgcgtcac agccaaaagc cagacagagt gtgatatcta cccgcttcgc    2220
gtcggcatcc ggtcagtggc agtgaagggc gaacagttcc tgattaacca caaaccgttc    2280
tactttactg gctttggtcg tcatgaagat gcggacttgc gtggcaaagg attcgataac    2340
gtgctgatgt tgcacgacca cgcattaatg gactggattg gggccaactc ctaccgtacc    2400
tcgcattacc cttacgctga agagatgctc gactgggcag atgaacatgg catcgtggtg    2460
attgatgaaa ctgctgctgt cggctttaac ctctctttag gcattggttt cgaagcgggc    2520
aacaagccga agaactgta cagcgaagag gcagtcaacg gggaaactca gcaagcgcac    2580
ttacaggcga ttaaagagct gatagcgcgt gacaaaaacc acccaagcgt ggtgatgtgg    2640
agtattgcca acgaaccgga tacccgtccg caaggtgcac gggaatattt cgcgccactg    2700
gcggaagcaa cgcgtaaact cgacccgacg cgtccgatca cctgcgtcaa tgtaatgttc    2760
tgcgacgctc acaccgatac catcagcgat ctctttgatg tgctgtgcct gaaccgttat    2820
tacggatggt atgtccaaag cggcgatttg gaaacggcag agaaggtact ggaaaaagaa    2880
cttctggcct ggcaggagaa actgcatcag ccgattatca tcaccgaata cggcgtggat    2940
acgttagccg ggctgcactc aatgtacacc gacatgtgga gtgaagagta tcagtgtgca    3000
tggctggata tgtatcaccg cgtctttgat cgcgtcagcg ccgtcgtcgg tgaacaggta    3060
tggaatttcg ccgatttgc gacctcgcaa ggcatattgc gcgttggcgg taacaagaaa    3120
gggatcttca ctcgcgaccg caaaccgaag tcggcggctt ttctgctgca aaaacgctgg    3180
actggcatga acttcggtga aaaaccgcag cagggaggca acaatgaat caacaactct    3240 cctggcgcac catcgtcggc tacagcctcg ggaattgcta ccgagtaagg ccgcctcgag    3300
catatgggct cgaatttccc cgatcgttca aacatttggc aataaagttt cttaagattg    3360
aatcctgttg ccggtcttgc gatgattatc atataatttc tgttgaatta cgttaagcat    3420
gtaataatta acatgtaatg catgacgtta tttatgagat gggttttat gattagagtc    3480 ccgcaattat acatttaata cgcgatagaa aacaaaatat agcgcgcaaa ctaggataaa    3540
ttatcgcgcg cggtgtcatc tatgttacta gatcgggaat tcaagcttgg cgtaatcatg    3600
gcaagtttgt acaaaaaagc aggctggtac ccggggatcc tctaggtcga ccagatctga    3660
tatctgcggc cgcctcgagc atatgggcat gcaagcttgg cgtaatcatg acccagctt    3720 tcttgtacaa agtggggtac caattcgaat ccaaaaatta cggatatgaa ataggcata    3780 tccgtatccg aattatccgt ttgacagcta gcaacgattg tacaattgct tctttaaaaa    3840
aggaagaaag aaagaaagaa aagaatcaac atcagcgtta acaaacggcc ccgttacggc    3900
ccaaacggtc atatagagta acggcgttaa gcgttgaaag actcctatcg aaatacgtaa    3960
ccgcaaacgt gtcatagtca gatccctct tccttcaccg cctcaaacac aaaataatc    4020 ttctacagcc tatatataca acccccccctt ctatctctcc tttctcacaa ttcatcatct    4080
ttctttctct accccaatt ttaagaaatc ctctcttctc ctcttcattt tcaaggtaaa    4140
tctctctctc tctctctctc tctgttattc cttgttttaa ttaggtatgt attattgcta    4200
gtttgttaat ctgcttatct tatgtatgcc ttatgtgaat atctttatct tgttcatctc    4260
atccgtttag aagctataaa tttgttgatt tgactgtgta tctacacgtg gttatgttta    4320
tatctaatca gatatgaatt tcttcatatt gttgcgtttg tgtgtaccaa tccgaaatcg    4380
ttgatttttt tcatttaatc gtgtagctaa ttgtacgtat acatatggat ctacgtatca    4440
```

```
attgttcatc tgtttgtgtt tgtatgtata cagatctgaa acatcactt ctctcatctg    4500 attgtgttgt tacatacata gatatagatc tgttatatca ttttttttat taattgtgta    4560
tatatatatg tgcatagatc tggattacat gattgtgatt atttacatga ttttgttatt    4620
tacgtatgta tatatgtaga tctggacttt ttggagttgt tgacttgatt gtatttgtgt    4680
gtgtatatgt gtgttctgat cttgatatgt tatgtatgtg cagctgaacc atggcggcgg    4740
caacaacaac aacaacaaca tcttcttcga tctccttctc caccaaacca tctccttcct    4800
cctccaaatc accattacca atctccagat tctccctccc attctcccta aaccccaaca    4860
aatcatcctc ctcctcccgc cgccgcggta tcaaatccag ctctccctcc tccatctccg    4920
ccgtgctcaa cacaaccacc aatgtcacaa ccactccctc tccaaccaaa cctaccaaac    4980
ccgaaacatt catctcccga ttcgctccag atcaaccccg caaaggcgct gatatcctcg    5040
tcgaagcttt agaacgtcaa ggcgtagaaa ccgtattcgc ttaccctgga ggtacatcaa    5100
tggagattca ccaagcctta acccgctctt cctcaatccg taacgtcctt cctcgtcacg    5160
aacaaggagg tgtattcgca gcagaaggat acgctcgatc ctcaggtaaa ccaggtatct    5220
gtatagccac ttcaggtccc ggagctacaa atctcgttag cggattagcc gatgcgttgt    5280
tagatagtgt tcctcttgta gcaatcacag acaagtccc tcgtcgtatg attggtacag    5340
atgcgtttca agagactccg attgttgagg taacgcgttc gattacgaag cataactatc    5400
ttgtgatgga tgttgaagat atccctagga ttattgagga agctttcttt ttagctactt    5460
ctggtagacc tggacctgtt ttggttgatg ttcctaaaga tattcaacaa cagcttgcga    5520
ttcctaattg ggaacaggct atgagattac ctggttatat gtctaggatg cctaaacctc    5580
cggaagattc tcatttggag cagattgtta ggttgatttc tgagtctaag aagcctgtgt    5640
tgtatgttgg tggtggttgt ttgaattcta gcgatgaatt gggtaggttt gttgagctta    5700
cggggatccc tgttgcgagt acgttgatgg ggctgggatc ttatccttgt gatgatgagt    5760
tgtcgttaca tatgcttgga atgcatggga ctgtgtatgc aaattacgct gtggagcata    5820
gtgatttgtt gttggcgttt ggggtaaggt ttgatgatcg tgtcacgggt aagcttgagg    5880
cttttgctag tagggctaag attgttcata ttgatattga ctcggctgag attgggaaga    5940
ataagactcc tcatgtgtct gtgtgtggtg atgttaagct ggctttgcaa gggatgaata    6000
aggttcttga gaaccgagcg gaggagctta agcttgattt tggagtttgg aggaatgagt    6060
tgaacgtaca gaaacagaag tttccgttga gctttaagac gtttggggaa gctattcctc    6120
cacagtatgc gattaaggtc cttgatgagt tgactgatgg aaaagccata ataagtactg    6180
gtgtcgggca acatcaaatg tgggcggcgc agttctacaa ttacaagaaa ccaaggcagt    6240
ggctatcatc aggaggcctt ggagctatgg gatttggact tcctgctgcg attggagcgt    6300
ctgttgctaa ccctgatgcg atagttgtgg atattgacgg agatggaagc tttataatga    6360
atgtgcaaga gctagccact attcgtgtag agaatcttcc agtgaaggta cttttattaa    6420
acaaccagca tcttggcatg gttatgcaat gggaagatcg gttctacaaa gctaaccgag    6480
ctcacacatt tctcggggat ccggctcagg aggacgagat attcccgaac atgttgctgt    6540
ttgcagcagc ttgcgggatt ccagcggcga gggtgacaaa gaaagcagat ctccgagaag    6600
ctattcagac aatgctggat acaccaggac cttacctgtt ggatgtgatt tgtccgcacc    6660
aagaacatgt gttgccgatg atcccgaatg gtggcacttt caacgatgtc ataacggaag    6720
gagatggccg gattaaatac tgagagatga aaccggtgat tatcagaacc ttttatggtc    6780
```

```
tttgtatgca tatggtaaaa aaacttagtt tgcaatttcc tgtttgtttt ggtaatttga    6840
gtttctttta gttgttgatc tgcctgcttt ttggtttacg tcagactact actgctgttg    6900
ttgtttggtt tcctttcttt cattttataa ataaataatc cggttcggtt tactccttgt    6960
gactggctca gtttggttat tgcgaaatgc gaatggtaaa ttgagtaatt gaaattcgtt    7020
attagggttc taagctgttt taacagtcac tgggttaata tctctcgaat cttgcatgga    7080
aaatgctctt accattggtt tttaattgaa atgtgctcat atgggccgtg gtttccaaat    7140
taaataaaac tacgatgtca tcgagaagta aaatcaactg tgtccacatt atcagttttg    7200
tgtatacgat gaaatagggt aattcaaaat ctagcttgat atgccttttg gttcatttta    7260
accttctgta aacatttttt cagattttga acaagtaaat ccaaaaaaaa aaaaaaaaa    7320
tctcaactca acactaaatt attttaatgt ataaagatg cttaaaacat ttggcttaaa    7380
agaaagaagc taaaaacata gagaactctt gtaaattgaa gtatgaaaat atactgaatt    7440
gggtattata tgaattttc tgatttagga ttcacatgat ccaaaaagga aatccagaag    7500
cactaatcag acattggaag taggaatatt tcaaaaagtt ttttttttt aagtaagtga    7560
caaaagcttt taaaaatag aaagaaact agtattaaag ttgtaaattt aataaacaaa    7620
agaattttt tatatttttt catttctttt tccagcatga ggttatgatg gcaggatgtg    7680
gatttcattt ttttcctttt gatagccttt taattgatct attataattg acgaaaaaat    7740
attagttaat tatagatata ttttaggtag tattagcaat ttacacttcc aaaagactat    7800
gtaagttgta aatatgatgc gttgatctct tcatcattca atggttagtc aaaaaaataa    7860
aagcttaact agtaaactaa agtagtcaaa aattgtactt tagtttaaaa tattacatga    7920
ataatccaaa acgacattta tgtgaaacaa aaacaatatc tagagtcgac ttaattaaac    7980
tagtggcgcg ccaattgact agtaggccta tcgattaatt aaggccgcct cgagcatatg    8040
ggcatgcaag cttggcgtaa tcatggcaac tttattatac atagttgata attcactggc    8100
cggataattc actggccgtc gttttacaac gactcaggat cctgtcaaac actgatagtt    8160
taaactgaag gcgggaaacg acaatctgat catgagcgga gaattaaggg agtcacgtta    8220
tgaccccgc cgatgacgcg ggacaagccg ttttacgttt ggaactgaca gaaccgcaac    8280
gttgaaggag ccactcagcc gcgggtttct ggagtttaat gagctaagca catacgtcag    8340
aaaccattat tgcgcgttca aaagtcgcct aaggtcacta tcagctagca aatatttctt    8400
gtcaaaaatg ctccactgac gttccataaa ttcccctcgg tatccaatta gagtctcata    8460
ttcactctca atccaaataa tctgcaccgg atctggatcg tttcgcatga ttgaacaaga    8520
tggattgcac gcaggttctc cggccgcttg ggtggagagg ctattcggct atgactgggc    8580
acaacagaca atcggctgct ctgatgccgc cgtgttccgg ctgtcagcgc aggggcgccc    8640
ggttcttttt gtcaagaccg acctgtccgg tgccctgaat gaactgcagg acgaggcagc    8700
gcggctatcg tggctggcca cgacgggcgt tccttgcgca gctgtgctcg acgttgtcac    8760
tgaagcggga agggactggc tgctattggg cgaagtgccg gggcaggatc tcctgtcatc    8820
tcaccttgct cctgccgaga agtatccat catggctgat gcaatgcggc ggctgcatac    8880
gcttgatccg gctacctgcc cattcgacca ccaagcgaaa catcgcatcg agcgagcacg    8940
tactcggatg gaagccggtc ttgtcgatca ggatgatctg gacgaagagc atcagggct    9000
cgcgccagcc gaactgttcg ccaggctcaa ggcgcgcatg cccgacggcg aggatctcgt    9060
cgtgacccat ggcgatgcct gcttgccgaa tatcatggtg gaaaatggcc gcttttctgg    9120
attcatcgac tgtggccggc tgggtgtggc ggaccgctat caggacatag cgttggctac    9180
```

```
ccgtgatatt gctgaagagc ttggcggcga atgggctgac cgcttcctcg tgctttacgg   9240
tatcgccgct cccgattcgc agcgcatcgc cttctatcgc cttcttgacg agttcttctg   9300
agcgggaccc aagctctaga tcttgctgcg ttcggatatt ttcgtggagt tcccgccaca   9360
gacccggatg atccccgatc gttcaaacat ttggcaataa agtttcttaa gattgaatcc   9420
tgttgccggt cttgcgatga ttatcatata atttctgttg aattacgtta agcatgtaat   9480
aattaacatg taatgcatga cgttatttat gagatgggtt tttatgatta gagtcccgca   9540
attatacatt taatacgcga tagaaaacaa atatagcgc gcaaactagg ataaattatc   9600
gcgcgcggtg tcatctatgt tactagatcg ggcctcctgt caagctctgc ttggtaataa   9660
ttgtcattag attgttttta tgcatagatg cactcgaaat cagccaattt tagacaagta   9720
tcaaacggat gttaattcag tacattaaag acgtccgcaa tgtgttatta agttgtctaa   9780
gcgtcaattt gtttacacca caatatatcc tgccaccagc cagccaacag ctccccgacc   9840
ggcagctcgg cacaaaatca ccacgcgtta ccaccacgcc ggccggccgc atggtgttga   9900
ccgtgttcgc cggcattgcc gagttcgagc gttccctaat catcgaccgc acccggagcg   9960
ggcgcgaggc cgccaaggcc cgaggcgtga agtttggccc ccgccctacc ctcaccccgg  10020
cacagatcgc gcacgcccgc gagctgatcg accaggaagg ccgcaccgtg aaagaggcgg  10080
ctgcactgct tggcgtgcat cgctcgaccc tgtaccgcgc acttgagcgc agcgaggaag  10140
tgacgcccac cgaggccagg cggcgcggtg ccttccgtga ggacgcattg accgaggccg  10200
acgccctggc ggccgccgag aatgaacgcc aagaggaaca agcatgaaac cgcaccagga  10260
cggccaggac gaaccgtttt tcattaccga agagatcgag gcggagatga tcgcggccgg  10320
gtacgtgttc gagccgcccg cgcacgtctc aaccgtgcgg ctgcatgaaa tcctggccgg  10380
tttgtctgat gccaagctgg cggcctggcc ggccagcttg gccgctgaag aaaccgagcg  10440
ccgccgtcta aaaggtgat gtgtatttga gtaaaacagc ttgcgtcatg cggtcgctgc  10500
gtatatgatg cgatgagtaa ataaacaaat acgcaagggg aacgcatgaa ggttatcgct  10560
gtacttaacc agaaaggcgg gtcaggcaag acgaccatcg caacccatct agcccgcgcc  10620
ctgcaactcg ccggggccga tgttctgtta gtcgattccg atcccagggg cagtgccgc  10680 gattgggcgg ccgtgcggga agatcaaccg ctaaccgttg tcggcatcga ccgcccgacg  10740
attgaccgcg acgtgaaggc catcggccgg cgcgacttcg tagtgatcga cggagcgccc  10800
caggcggcgg acttggctgt gtccgcgatc aaggcagccg acttcgtgct gattccggtg  10860
cagccaagcc cttacgacat atgggccacc gccgacctgg tggagctggt taagcagcgc  10920
attgaggtca cggatggaag gctacaagcg gcctttgtcg tgtcgcgggc gatcaaaggc  10980
acgcgcatcg gcgtgaggt tgccgaggcg ctggccgggt acgagctgcc cattcttgag  11040
tcccgtatca cgcagcgcgt gagctaccca ggcactgccg ccgccggcac aaccgttctt  11100
gaatcagaac ccgagggcga cgctgcccgc gaggtccagg cgctggccgc tgaaattaaa  11160
tcaaaactca tttgagttaa tgaggtaaag agaaaatgag caaaagcaca aacacgctaa  11220
gtgccggccg tccgagcgca cgcagcagca aggctgcaac gttggccagc ctggcagaca  11280
cgccagccat gaagcgggtc aactttcagt tgccggcgga ggatcacacc aagctgaaga  11340
tgtacgcggt acgccaaggc aagaccatta ccgagctgct atctgaatac atcgcgcagc  11400
taccagagta aatgagcaaa tgaataaatg agtagatgaa ttttagcggc taaaggaggc  11460
ggcatggaaa atcaagaaca accaggcacc gacgccgtgg aatgccccat gtgtggagga  11520
```

```
acgggcggtt ggccaggcgt aagcggctgg gttgtctgcc ggccctgcaa tggcactgga    11580 accccccaagc ccgaggaatc ggcgtgagcg gtcgcaaacc atccggcccg gtacaaatcg   11640
gcgcggcgct gggtgatgac ctggtggaga agttgaaggc cgcgcaggcc gcccagcggc    11700
aacgcatcga ggcagaagca cgccccggtg aatcgtggca agcggccgct gatcgaatcc    11760
gcaaagaatc ccggcaaccg ccggcagccg gtgcgccgtc gattaggaag ccgcccaagg    11820
gcgacgagca accagatttt ttcgttccga tgctctatga cgtgggcacc cgcgatagtc    11880
gcagcatcat ggacgtggcc gttttccgtc tgtcgaagcg tgaccgacga gctggcgagg    11940
tgatccgcta cgagcttcca gacgggcacg tagaggtttc gcagggccg gccggcatgg     12000 ccagtgtgtg ggattacgac ctggtactga tggcggtttc ccatctaacc gaatccatga    12060
accgataccg ggaagggaag ggagacaagc ccggccgcgt gttccgtcca cacgttgcgg    12120
acgtactcaa gttctgccgg cgagccgatg gcggaaagca gaaagacgac ctggtagaaa    12180
cctgcattcg gttaaacacc acgcacgttg ccatgcagcg tacgaagaag gccaagaacg    12240
gccgcctggt gacggtatcc gagggtgaag ccttgattag ccgctacaag atcgtaaaga    12300
gcgaaaccgg gcggccggag tacatcgaga tcgagctagc tgattggatg taccgcgaga    12360
tcacagaagg caagaacccg gacgtgctga cggttcaccc cgattacttt ttgatcgatc    12420
ccggcatcgg ccgttttctc taccgcctgg cacgccgcgc cgcaggcaag gcagaagcca    12480
gatggttgtt caagacgatc tacgaacgca gtggcagcgc cggagagttc aagaagttct    12540
gtttcaccgt gcgcaagctg atcgggtcaa atgacctgcc ggagtacgat ttgaaggagg    12600
aggcggggca ggctggcccg atcctagtca tgcgctaccg caacctgatc gagggcgaag    12660
catccgccgg ttcctaatgt acggagcaga tgctagggca aattgcccta gcaggggaaa    12720
aaggtcgaaa aggtctcttt cctgtggata gcacgtacat tgggaaccca aagccgtaca    12780
ttgggaaccg gaacccgtac attgggaacc caaagccgta cattgggaac cggtcacaca    12840
tgtaagtgac tgatataaaa gagaaaaaag gcgattttc cgcctaaaac tctttaaaac     12900
ttattaaaac tcttaaaacc cgcctggcct gtgcataact gtctggccag cgcacagccg    12960
aagagctgca aaaagcgcct acccttcggt cgctgcgctc cctacgcccc gccgcttcgc    13020
gtcggcctat cgcggccgct ggccgctcaa aaatggctgg cctacggcca ggcaatctac    13080
cagggcgcgg acaagccgcg ccgtcgccac tcgaccgccg cgcccacat caaggcaccc     13140 tgcctcgcgc gtttcggtga tgacggtgaa aacctctgac acatgcagct cccggagacg    13200
gtcacagctt gtctgtaagc ggatgccggg agcagacaag cccgtcaggg cgcgtcagcg    13260
ggtgttggcg ggtgtcgggg cgcagccatg acccagtcac gtagcgatag cggagtgtat    13320
actggcttaa ctatgcggca tcagagcaga ttgtactgag agtgcaccat atgcggtgtg    13380
aaataccgca cagatgcgta aggagaaaat accgcatcag gcgctcttcc gcttcctcgc    13440
tcactgactc gctgcgctcg gtcgttcggc tgcggcgagc ggtatcagct cactcaaagg    13500
cggtaatacg gttatccaca gaatcagggg ataacgcagg aaagaacatg tgagcaaaag    13560
gccagcaaaa ggccaggaac cgtaaaaagg ccgcgttgct ggcgtttttc cataggctcc    13620
gcccccctga cgagcatcac aaaaatcgac gctcaagtca gaggtggcga acccgacag     13680 gactataaag ataccaggcg tttccccctg gaagctccct cgtgcgctct cctgttccga    13740
ccctgccgct taccggatac ctgtccgcct ttctcccttc gggaagcgtg gcgctttctc    13800
atagctcacg ctgtaggtat ctcagttcgg tgtaggtcgt tcgctccaag ctgggctgtg    13860
tgcacgaacc ccccgttcag cccgaccgct gcgccttatc cggtaactat cgtcttgagt    13920
```

```
ccaacccggt aagacacgac ttatcgccac tggcagcagc cactggtaac aggattagca   13980
gagcgaggta tgtaggcggt gctacagagt tcttgaagtg gtggcctaac tacggctaca   14040
ctagaaggac agtatttggt atctgcgctc tgctgaagcc agttaccttc ggaaaaagag   14100
ttggtagctc ttgatccggc aaacaaacca ccgctggtag cggtggtttt tttgtttgca   14160
agcagcagat tacgcgcaga aaaaaaggat ctcaagaaga tcctttgatc ttttctacgg   14220
ggtctgacgc tcagtggaac gaaaactcac gttaagggat tttggtcatg catgatatat   14280
ctcccaattt gtgtagggct tattatgcac gcttaaaaat aataaaagca gacttgacct   14340
gatagtttgg ctgtgagcaa ttatgtgctt agtgcatcta acgcttgagt taagccgcgc   14400
cgcgaagcgg cgtcggcttg aacgaatttc tagctagaca ttatttgccg actaccttgg   14460
tgatctcgcc tttcacgtag tggacaaatt cttccaactg atctgcgcgc gaggccaagc   14520
gatcttcttc ttgtccaaga taagcctgtc tagcttcaag tatgacgggc tgatactggg   14580
ccggcaggcg ctccattgcc cagtcggcag cgacatcctt cggcgcgatt ttgccggtta   14640
ctgcgctgta ccaaatgcgg gacaacgtaa gcactacatt tcgctcatcg ccagcccagt   14700
cgggcggcga gttccatagc gttaaggttt catttagcgc ctcaaataga tcctgttcag   14760
gaaccggatc aaagagttcc tccgccgctg gacctaccaa ggcaacgcta tgttctcttg   14820
cttttgtcag caagatagcc agatcaatgt cgatcgtggc tggctcgaag atacctgcaa   14880
gaatgtcatt gcgctgccat tctccaaatt gcagttcgcg cttagctgga taacgccacg   14940
gaatgatgtc gtcgtgcaca acaatggtga cttctacagc gcggagaatc tcgctctctc   15000
caggggaagc cgaagtttcc aaaaggtcgt tgatcaaagc tcgccgcgtt gtttcatcaa   15060
gccttacggt caccgtaacc agcaaatcaa tatcactgtg tggcttcagg ccgccatcca   15120
ctgcggagcc gtacaaatgt acggccagca acgtcggttc gagatggcgc tcgatgacgc   15180
caactacctc tgatagttga gtcgatactt cggcgatcac cgcttccccc atgatgttta   15240
actttgtttt agggcgactg ccctgctgcg taacatcgtt gctgctccat aacatcaaac   15300
atcgacccac ggcgtaacgc gcttgctgct tggatgcccg aggcatagac tgtaccccaa   15360
aaaaacagtc ataacaagcc atgaaaaccg ccactgcgtt ccatg                   15405
```

<210> SEQ ID NO 10
<211> LENGTH: 15552
<212> TYPE: DNA
<213> ORGANISM: Artificial Sequence
<220> FEATURE:
<223> OTHER INFORMATION: Transformation vector

<400> SEQUENCE: 10

```
ggacatacaa atggacgaac ggataaacct tttcacgccc ttttaaatat ccgattattc     60
taataaacgc tctttctct taggtttacc cgccaatata tcctgtcaaa cactgatagt    120
ttaaactgaa ggcgggaaac gacaatcaga tctagtagga aacagctatg accatgatta    180
cgccaagcta tcgattacgc caagctatca actttgtata gaaaagttgg gtacctcttc    240
atcggtgatt gattccttta aagacttatg tttcttatct tgcttctgag gcaagtattc    300
agttaccagt taccacttat attctggact ttctgactgc atcctcattt ttccaacatt    360
ttaaatttca ctattggctg aatgcttctt ctttgaggaa gaaacaattc agatggcaga    420
aatgtatcaa ccaatgcata tatacaaatg tacctcttgt tctcaaaaca tctatcggat    480
ggttccattt gctttgtcat ccaattagtg actactttat attattcact cctctttatt    540
```

-continued

| | |
|---|---|
| actattttca tgcgaggttg ccatgtacat tatatttgta aggattgacg ctattgagcg | 600 |
| tttttcttca attttcttta ttttagacat gggtatgaaa tgtgtgttag agttgggttg | 660 |
| aatgagatat acgttcaagt gaatggcata ccgttctcga gtaaggatga cctacccatt | 720 |
| cttgagacaa atgttacatt ttagtatcag agtaaaatgt gtacctataa ctcaaattcg | 780 |
| attgacatgt atccattcaa cataaaatta aaccagcctg cacctgcatc cacatttcaa | 840 |
| gtattttcaa accgttcggc tcctatccac cgggtgtaac aagacggatt ccgaatttgg | 900 |
| aagattttga ctcaaattcc caatttatat tgaccgtgac taaatcaact ttaacttcta | 960 |
| taattctgat taagctccca atttatattc ccaacggcac tacctccaaa atttatagac | 1020 |
| tctcatcccc ttttaaacca acttagtaaa cgtttttttt tttaatttta tgaagttaag | 1080 |
| ttttaccttt gttttttaaaa agaatcgttc ataagatgcc atgccagaac attagctaca | 1140 |
| cgttacacat agcatgcagc cgcggagaat tgttttctt cgccacttgt cactcccttc | 1200 |
| aaacacctaa gagcttctct ctcacagcac acacatacaa tcacatgcgt gcatgcatta | 1260 |
| ttacacgtga tcgccatgca aatctccttt atagcctata aattaactca tccgcttcac | 1320 |
| tctttactca aaccaaaact catcaataca aacaagatta aaaacataca cgaccatggt | 1380 |
| acgtcctgta gaaaccccaa cccgtgaaat caaaaaactc gacggcctgt gggcattcag | 1440 |
| tctggatcgc gaaaactgtg gaattggtca gcgttggtgg gaaagcgcgt tacaagaaag | 1500 |
| ccgggcaatt gctgtgccag gcagttttaa cgatcagttc gccgatgcag atattcgtaa | 1560 |
| ttatgcgggc aacgtctggt atcagcgcga agtctttata ccgaaaggtt gggcaggcca | 1620 |
| gcgtatcgtg ctgcgtttcg atgcggtcac tcattacggc aaagtgtggg tcaataatca | 1680 |
| ggaagtgatg gagcatcagg gcggctatac gccatttgaa gccgatgtca cgccgtatgt | 1740 |
| tattgccggg aaaagtgtac gtaagtttct gcttctacct ttgatatata tataataatt | 1800 |
| atcattaatt agtagtaata taatatttca aatattttt tcaaaataaa agaatgtagt | 1860 |
| atatagcaat tgcttttctg tagtttataa gtgtgtatat tttaattttat aacttttcta | 1920 |
| atatatgacc aaaatttgtt gatgtgcagg tatcaccgtt tgtgtgaaca acgaactgaa | 1980 |
| ctggcagact atcccgccgg gaatggtgat taccgacgaa aacggcaaga aaaagcagtc | 2040 |
| ttacttccat gatttcttta actatgccgg aatccatcgc agcgtaatgc tctacaccac | 2100 |
| gccgaacacc tgggtggacg atatcaccgt ggtgacgcat gtcgcgcaag actgtaacca | 2160 |
| cgcgtctgtt gactggcagg tggtggccaa tggtgatgtc agcgttgaac tgcgtgatgc | 2220 |
| ggatcaacag gtggttgcaa ctggacaagg cactagcggg actttgcaag tggtgaatcc | 2280 |
| gcacctctgg caaccgggtg aaggttatct ctatgaactg tgcgtcacag ccaaaagcca | 2340 |
| gacagagtgt gatatctacc cgcttcgcgt cggcatccgg tcagtggcag tgaagggcga | 2400 |
| acagttcctg attaaccaca aaccgttcta ctttactggc tttggtcgtc atgaagatgc | 2460 |
| ggacttgcgt ggcaaaggat tcgataacgt gctgatggtg cacgaccacg cattaatgga | 2520 |
| ctggattggg gccaactcct accgtacctc gcattaccct tacgctgaag atgctcga | 2580 |
| ctgggcagat gaacatggca tcgtggtgat tgatgaaact gctgctgtcg gctttaacct | 2640 |
| ctctttaggc attggtttcg aagcgggcaa caagccgaaa gaactgtaca gcgaagaggc | 2700 |
| agtcaacggg gaaactcagc aagcgcactt acaggcgatt aaagagctga tagcgcgtga | 2760 |
| caaaaaccac ccaagcgtgg tgatgtggag tattgccaac gaaccggata cccgtccgca | 2820 |
| aggtgcacgg gaatatttcg cgccactggc ggaagcaacg cgtaaactcg acccgacgcg | 2880 |
| tccgatcacc tgcgtcaatg taatgttctg cgacgctcac accgatacca tcagcgatct | 2940 |

```
ctttgatgtg ctgtgcctga accgttatta cggatggtat gtccaaagcg gcgatttgga    3000
aacggcagag aaggtactgg aaaaagaact tctggcctgg caggagaaac tgcatcagcc    3060
gattatcatc accgaatacg gcgtggatac gttagccggg ctgcactcaa tgtacaccga    3120
catgtggagt gaagagtatc agtgtgcatg gctggatatg tatcaccgcg tctttgatcg    3180
cgtcagcgcc gtcgtcggtg aacaggtatg gaatttcgcc gattttgcga cctcgcaagg    3240
catattgcgc gttggcggta acaagaaagg gatcttcact cgcgaccgca aaccgaagtc    3300
ggcggctttt ctgctgcaaa aacgctggac tggcatgaac ttcggtgaaa accgcagca    3360 gggaggcaaa caatgaatca acaactctcc tggcgcacca tcgtcggcta cagcctcggg    3420
aattgctacc gagtaaggcc gcctcgagca tatgggctcg aatttccccg atcgttcaaa    3480
catttggcaa taaagtttct taagattgaa tcctgttgcc ggtcttgcga tgattatcat    3540
ataatttctg ttgaattacg ttaagcatgt aataattaac atgtaatgca tgacgttatt    3600
tatgagatgg gttttttatga ttagagtccc gcaattatac atttaatacg cgatagaaaa    3660
caaaatatag cgcgcaaact aggataaatt atcgcgcgcg gtgtcatcta tgttactaga    3720
tcgggaattc aagcttggcg taatcatggc aagtttgtac aaaaaagcag gctggtaccc    3780
ggggatcctc taggtcgacc agatctgata tctgcggccg cctcgagcat atgggcatgc    3840
aagcttggcg taatcatgga cccagctttc ttgtacaaag tggggtacca attcgaatcc    3900
aaaaattacg gatatgaata taggcatatc cgtatccgaa ttatccgttt gacagctagc    3960
aacgattgta caattgcttc tttaaaaaag gaagaaagaa agaaagaaaa gaatcaacat    4020
cagcgttaac aaacggcccc gttacggccc aaacggtcat atagagtaac ggcgttaagc    4080
gttgaaagac tcctatcgaa atacgtaacc gcaaacgtgt catagtcaga tcccctcttc    4140
cttcaccgcc tcaaacacaa aaataatctt ctacagccta tatatacaac ccccccttct    4200
atctctcctt tctcacaatt catcatcttt ctttctctac ccccaatttt aagaaatcct    4260
ctcttctcct cttcattttc aaggtaaatc tctctctctc tctctctctc tgttattcct    4320
tgttttaatt aggtatgtat tattgctagt ttgttaatct gcttatctta tgtatgcctt    4380
atgtgaatat ctttatcttg ttcatctcat ccgtttagaa gctataaatt tgttgatttg    4440
actgtgtatc tacacgtggt tatgtttata tctaatcaga tatgaatttc ttcatattgt    4500
tgcgtttgtg tgtaccaatc cgaaatcgtt gattttttc atttaatcgt gtagctaatt    4560
gtacgtatac atatggatct acgtatcaat tgttcatctg tttgtgtttg tatgtataca    4620
gatctgaaaa catcacttct ctcatctgat tgtgttgtta catacataga tatagatctg    4680
ttatatcatt ttttttatta attgtgtata tatatgtg catagatctg gattacatga    4740
ttgtgattat ttacatgatt ttgttattta cgtatgtata tatgtagatc tggactttt    4800 ggagttgttg acttgattgt atttgtgtgt gtatatgtgt gttctgatct tgatatgtta    4860
tgtatgtgca gctgaaccat ggcggcggca acaacaacaa caacaacatc ttcttcgatc    4920
tccttctcca ccaaaccatc tccttcctcc tccaaatcac cattaccaat ctccagattc    4980
tccctcccat tctccctaaa ccccaacaaa tcatcctcct cctcccgccg ccgcggtatc    5040
aaatccagct ctccctcctc catctccgcc gtgctcaaca caaccaccaa tgtcacaacc    5100
actccctctc caaccaaacc taccaaaccc gaaacattca tctcccgatt cgctccagat    5160
caaccccgca aaggcgctga tatcctcgtc gaagctttag aacgtcaagg cgtagaaacc    5220
gtattcgctt accctggagg tacatcaatg gagattcacc aagccttaac ccgctcttcc    5280
```

```
tcaatccgta acgtccttcc tcgtcacgaa caaggaggtg tattcgcagc agaaggatac    5340
gctcgatcct caggtaaacc aggtatctgt atagccactt caggtcccgg agctacaaat    5400
ctcgttagcg gattagccga tgcgttgtta gatagtgttc ctcttgtagc aatcacagga    5460
caagtccctc gtcgtatgat tggtacagat gcgtttcaag agactccgat tgttgaggta    5520
acgcgttcga ttacgaagca taactatctt gtgatggatg ttgaagatat ccctaggatt    5580
attgaggaag cttcttttt agctacttct ggtagacctg gacctgtttt ggttgatgtt    5640
cctaaagata ttcaacaaca gcttgcgatt cctaattggg aacaggctat gagattacct    5700
ggttatatgt ctaggatgcc taaacctccg gaagattctc atttggagca gattgttagg    5760
ttgatttctg agtctaagaa gcctgtgttg tatgttggtg gtggttgttt gaattctagc    5820
gatgaattgg gtaggtttgt tgagcttacg gggatccctg ttgcgagtac gttgatgggg    5880
ctgggatctt atccttgtga tgatgagttg tcgttacata tgcttggaat gcatgggact    5940
gtgtatgcaa attacgctgt ggagcatagt gatttgttgt tggcgtttgg ggtaaggttt    6000
gatgatcgtg tcacgggtaa gcttgaggct tttgctagta gggctaagat tgttcatatt    6060
gatattgact cggctgagat tgggaagaat aagactcctc atgtgtctgt gtgtggtgat    6120
gttaagctgg ctttgcaagg gatgaataag gttcttgaga accgagcgga ggagcttaag    6180
cttgattttg gagtttggag gaatgagttg aacgtacaga aacagaagtt tccgttgagc    6240
tttaagacgt ttggggaagc tattcctcca cagtatgcga ttaaggtcct tgatgagttg    6300
actgatggaa aagccataat aagtactggt gtcgggcaac atcaaatgtg ggcggcgcag    6360
ttctacaatt acaagaaacc aaggcagtgg ctatcatcag gaggccttgg agctatggga    6420
tttggacttc ctgctgcgat tggagcgtct gttgctaacc ctgatgcgat agttgtggat    6480
attgacggag atggaagctt tataatgaat gtgcaagagc tagccactat tcgtgtagag    6540
aatcttccag tgaaggtact tttattaaac aaccagcatc ttggcatggt tatgcaatgg    6600
gaagatcggt tctacaaagc taaccgagct cacacatttc tcggggatcc ggctcaggag    6660
gacgagatat tcccgaacat gttgctgttt gcagcagctt gcgggattcc agcggcgagg    6720
gtgacaaaga aagcagatct ccgagaagct attcagacaa tgctggatac accaggacct    6780
tacctgttgg atgtgatttg tccgcaccaa gaacatgtgt tgccgatgat cccgaatggt    6840
ggcactttca acgatgtcat aacgaaagga gatggccgga ttaaatactg agagatgaaa    6900
ccggtgatta tcagaacctt ttatggtctt tgtatgcata tggtaaaaaa acttagtttg    6960
caatttcctg tttgtttgg taatttgagt ttcttttagt tgttgatctg cctgcttttt    7020
ggtttacgtc agactactac tgctgttgtt gtttggtttc ctttctttca ttttataaat    7080
aaataatccg gttcggttta ctccttgtga ctggctcagt ttggttattg cgaaatgcga    7140
atggtaaatt gagtaattga aattcgttat tagggttcta agctgttta acagtcactg    7200 ggttaatatc tctcgaatct tgcatggaaa atgctcttac cattggtttt taattgaaat    7260
gtgctcatat gggccgtggt ttccaaatta aataaaacta cgatgtcatc gagaagtaaa    7320
atcaactgtg tccacattat cagttttgtg tatacgatga aatagggtaa ttcaaaatct    7380
agcttgatat gccttttggt tcattttaac ccttctgtaaa catttttca gattttgaac    7440 aagtaaatcc aaaaaaaaa aaaaaaatc tcaactcaac actaaattat tttaatgtat    7500 aaagatgct taaacatttt ggcttaaaag aaagaagcta aaacataga gaactcttgt    7560 aaattgaagt atgaaaatat actgaattgg gtattatatg aattttttctg atttaggatt    7620 cacatgatcc aaaaaggaaa tccagaagca ctaatcagac attggaagta ggaatatttc    7680
```

```
aaaaagttttt ttttttttaa gtaagtgaca aaagctttta aaaaatagaa aagaaactag    7740
tattaaagtt gtaaatttaa taaacaaaag aaattttta tatttttttca tttcttttc     7800 cagcatgagg ttatgatggc aggatgtgga tttcattttt ttccttttga tagccttta    7860 attgatctat tataattgac gaaaaaatat tagttaatta tagatatatt ttaggtagta    7920
ttagcaattt acacttccaa aagactatgt aagttgtaaa tatgatgcgt tgatctcttc    7980
atcattcaat ggttagtcaa aaaaataaaa gcttaactag taaactaaag tagtcaaaaa    8040
ttgtacttta gtttaaaata ttacatgaat aatccaaaac gacatttatg tgaaacaaaa    8100
acaatatcta gagtcgactt aattaaacta gtggcgcgcc aattgactag taggcctatc    8160
gattaattaa ggccgcctcg agcatatggg catgcaagct tggcgtaatc atggcaactt    8220
tattatacat agttgataat tcactggccg gataattcac tggccgtcgt tttacaacga    8280
ctcaggatcc tgtcaaacac tgatagttta aactgaaggc gggaaacgac aatctgatca    8340
tgagcggaga attaagggag tcacgttatg acccccgccg atgacgcggg acaagccgtt    8400
ttacgtttgg aactgacaga accgcaacgt tgaaggagcc actcagccgc gggtttctgg    8460
agtttaatga gctaagcaca tacgtcagaa accattattg cgcgttcaaa agtcgcctaa    8520
ggtcactatc agctagcaaa tatttcttgt caaaaatgct ccactgacgt tccataaatt    8580
cccctcggta tccaattaga gtctcatatt cactctcaat ccaaataatc tgcaccggat    8640
ctggatcgtt tcgcatgatt gaacaagatg gattgcacgc aggttctccg gccgcttggg    8700
tggagaggct attcggctat gactgggcac aacagacaat cggctgctct gatgccgccg    8760
tgttccggct gtcagcgcag gggcgcccgg ttcttttgt caagaccgac ctgtccggtg    8820
ccctgaatga actgcaggac gaggcagcgc ggctatcgtg gctggccacg acgggcgttc    8880
cttgcgcagc tgtgctcgac gttgtcactg aagcgggaag ggactggctg ctattgggcg    8940
aagtgccggg gcaggatctc ctgtcatctc accttgctcc tgccgagaaa gtatccatca    9000
tggctgatgc aatgcggcgg ctgcatacgc ttgatccggc tacctgccca ttcgaccacc    9060
aagcgaaaca tcgcatcgag cgagcacgta ctcggatgga agccggtctt gtcgatcagg    9120
atgatctgga cgaagagcat caggggctcg cgccagccga actgttcgcc aggctcaagg    9180
cgcgcatgcc cgacggcgag gatctcgtcg tgacccatgg cgatgcctgc ttgccgaata    9240
tcatggtgga aaatggccgc ttttctggat tcatcgactg tggccggctg ggtgtggcgg    9300
accgctatca ggacatagcg ttggctaccc gtgatattgc tgaagagctt ggcggcgaat    9360
gggctgaccg cttcctcgtg ctttacggta tcgccgctcc cgattcgcag cgcatcgcct    9420
tctatcgcct tcttgacgag ttcttctgag cgggacccaa gctctagatc ttgctgcgtt    9480
cggatatttt cgtggagttc ccgccacaga cccggatgat cccgatcgt tcaaacattt    9540 ggcaataaag tttcttaaga ttgaatcctg ttgccggtct tgcgatgatt atcatataat    9600
ttctgttgaa ttacgttaag catgtaataa ttaacatgta atgcatgacg ttatttatga    9660
gatgggtttt tatgattaga gtcccgcaat tatacattta atacgcgata gaaaacaaaa    9720
tatagcgcgc aaactaggat aaattatcgc gcgcggtgtc atctatgtta ctagatcggg    9780
cctcctgtca agctctgctt ggtaataatt gtcattagat tgtttttatg catagatgca    9840
ctcgaaatca gccaattta gacaagtatc aaacggatgt taattcagta cattaaagac    9900
gtccgcaatg tgttattaag ttgtctaagc gtcaatttgt ttacaccaca atatatcctg    9960
ccaccagcca gccaacagct ccccgaccgg cagctcggca caaaatcacc acgcgttacc    10020
```

```
accacgccgg ccggccgcat ggtgttgacc gtgttcgccg gcattgccga gttcgagcgt   10080
tccctaatca tcgaccgcac ccggagcggg cgcgaggccg ccaaggcccg aggcgtgaag   10140
tttggccccc gccctaccct cacccggca cagatcgcgc acgcccgcga gctgatcgac    10200
caggaaggcc gcaccgtgaa agaggcggct gcactgcttg gcgtgcatcg ctcgaccctg   10260
taccgcgcac ttgagcgcag cgaggaagtg acgcccaccg aggccaggcg gcgcggtgcc   10320
ttccgtgagg acgcattgac cgaggccgac gccctggcgg ccgccgagaa tgaacgccaa   10380
gaggaacaag catgaaaccg caccaggacg gccaggacga accgtttttc attaccgaag   10440
agatcgaggc ggagatgatc gcggccgggt acgtgttcga gccgcccgcg cacgtctcaa   10500
ccgtgcggct gcatgaaatc ctggccggtt tgtctgatgc caagctggcg gcctggccgg   10560
ccagcttggc cgctgaagaa accgagcgcc gccgtctaaa aggtgatgt gtatttgagt    10620 aaaacagctt gcgtcatgcg gtcgctgcgt atatgatgcg atgagtaaat aaacaaatac   10680
gcaaggggaa cgcatgaagg ttatcgctgt acttaaccag aaaggcgggt caggcaagac   10740
gaccatcgca acccatctag cccgcgccct gcaactcgcc ggggccgatg ttctgttagt   10800
cgattccgat ccccagggca gtgcccgcga ttgggcggcc gtgcgggaag atcaaccgct   10860
aaccgttgtc ggcatcgacc gcccgacgat tgaccgcgac gtgaaggcca tcggccggcg   10920
cgacttcgta gtgatcgacg gagcgcccca ggcggcggac ttggctgtgt ccgcgatcaa   10980
ggcagccgac ttcgtgctga ttccggtgca gccaagccct tacgacatat gggccaccgc   11040
cgacctggtg gagctggtta agcagcgcat tgaggtcacg gatggaaggc tacaagcggc   11100
ctttgtcgtg tcgcgggcga tcaaaggcac gcgcatcggc ggtgaggttg ccgaggcgct   11160
ggccgggtac gagctgccca ttcttgagtc ccgtatcacg cagcgcgtga gctacccagg   11220
cactgccgcc gccggcacaa ccgttcttga atcagaaccc gagggcgacg ctgcccgcga   11280
ggtccaggcg ctggccgctg aaattaaatc aaaactcatt tgagttaatg aggtaaagag   11340
aaaatgagca aaagcacaaa cacgctaagt gccggccgtc cgagcgcacg cagcagcaag   11400
gctgcaacgt tggccagcct ggcagacacg ccagccatga agcgggtcaa ctttcagttg   11460
ccggcggagg atcacaccaa gctgaagatg tacgcggtac gccaaggcaa gaccattacc   11520
gagctgctat ctgaatacat cgcgcagcta ccagagtaaa tgagcaaatg aataaatgag   11580
tagatgaatt ttagcggcta aggaggcgg catggaaaat caagaacaac caggcaccga   11640
cgccgtggaa tgccccatgt gtggaggaac gggcggttgg ccaggcgtaa gcggctgggt   11700
tgtctgccgg ccctgcaatg gcactggaac ccccaagccc gaggaatcgg cgtgagcggt   11760
cgcaaaccat ccggcccggt acaaatcggc gcggcgctgg gtgatgacct ggtggagaag   11820
ttgaaggccg cgcaggccgc ccagcggcaa cgcatcgagg cagaagcacg ccccggtgaa   11880
tcgtggcaag cggccgctga tcgaatccgc aaagaatccc ggcaaccgcc ggcagccggt   11940
gcgccgtcga ttaggaagcc gcccaagggc gacgagcaac cagattttttt cgttccgatg  12000 ctctatgacg tgggcacccg cgatagtcgc agcatcatgg acgtggccgt tttcgtctg   12060 tcgaagcgtg accgacgagc tggcgaggtg atccgctacg agcttccaga cgggcacgta   12120
gaggtttccg cagggccggc cggcatggcc agtgtgtggg attacgacct ggtactgatg   12180
gcggtttccc atctaaccga atccatgaac cgataccggg aagggaaggg agacaagccc   12240
ggccgcgtgt tccgtccaca cgttgcggac gtactcaagt tctgccggcg agccgatggc   12300
ggaaagcaga aagacgacct ggtagaaacc tgcattcggt taaacaccac gcacgttgcc   12360
atgcagcgta cgaagaaggc caagaacggc cgcctggtga cggtatccga gggtgaagcc   12420
```

```
ttgattagcc gctacaagat cgtaaagagc gaaaccgggc ggccggagta catcgagatc   12480
gagctagctg attggatgta ccgcgagatc acagaaggca agaacccgga cgtgctgacg   12540
gttcaccccg attacttttt gatcgatccc ggcatcggcc gttttctcta ccgcctggca   12600
cgccgcgccg caggcaaggc agaagccaga tggttgttca agacgatcta cgaacgcagt   12660
ggcagcgccg gagagttcaa gaagttctgt ttcaccgtgc gcaagctgat cgggtcaaat   12720
gacctgccgg agtacgattt gaaggaggag gcggggcagg ctggcccgat cctagtcatg   12780
cgctaccgca acctgatcga gggcgaagca tccgccggtt cctaatgtac ggagcagatg   12840
ctagggcaaa ttgccctagc aggggaaaaa ggtcgaaaag gtctctttcc tgtggatagc   12900
acgtacattg ggaacccaaa gccgtacatt gggaaccgga acccgtacat tgggaaccca   12960
aagccgtaca ttgggaaccg gtcacacatg taagtgactg atataaaaga gaaaaaggc    13020 gattttccg cctaaaactc tttaaaactt attaaaactc ttaaacccg cctggcctgt     13080 gcataactgt ctggccagcg cacagccgaa gagctgcaaa aagcgcctac ccttcggtcg   13140
ctgcgctccc tacgccccgc cgcttcgcgt cggcctatcg cggccgctgg ccgctcaaaa   13200
atggctggcc tacggccagg caatctacca gggcgcggac aagccgcgcc gtcgccactc   13260
gaccgccggc gcccacatca aggcaccctg cctcgcgcgt ttcggtgatg acggtgaaaa   13320
cctctgacac atgcagctcc cggagacggt cacagcttgt ctgtaagcgg atgccgggag   13380
cagacaagcc cgtcagggcg cgtcagcggg tgttggcggg tgtcggggcg cagccatgac   13440
ccagtcacgt agcgatagcg gagtgtatac tggcttaact atgcggcatc agagcagatt   13500
gtactgagag tgcaccatat gcggtgtgaa ataccgcaca gatgcgtaag gagaaaatac   13560
cgcatcaggc gctcttccgc ttcctcgctc actgactcgc tgcgctcggt cgttcggctg   13620
cggcgagcgg tatcagctca ctcaaaggcg gtaatacggt tatccacaga atcagggggat  13680 aacgcaggaa agaacatgtg agcaaaaggc cagcaaaagg ccaggaaccg taaaaaggcc   13740
gcgttgctgg cgttttttcca taggctccgc cccctgacg agcatcacaa aaatcgacgc   13800
tcaagtcaga ggtggcgaaa cccgacagga ctataaagat accaggcgtt tccccctgga   13860
agctccctcg tgcgctctcc tgttccgacc ctgccgctta ccggatacct gtccgccttt   13920
ctcccttcgg gaagcgtggc gctttctcat agctcacgct gtaggtatct cagttcggtg   13980
taggtcgttc gctccaagct gggctgtgtg cacgaacccc ccgttcagcc cgaccgctgc   14040
gccttatccg gtaactatcg tcttgagtcc aacccggtaa gacacgactt atcgccactg   14100
gcagcagcca ctggtaacag gattagcaga gcgaggtatg taggcggtgc tacagagttc   14160
ttgaagtggt ggcctaacta cggctacact agaaggacag tatttggtat ctgcgctctg   14220
ctgaagccag ttaccttcgg aaaaagagtt ggtagctctt gatccggcaa acaaaccacc   14280
gctggtagcg gtggtttttt tgtttgcaag cagcagatta cgcgcagaaa aaaggatct    14340 caagaagatc ctttgatctt ttctacgggg tctgacgctc agtggaacga aaactcacgt   14400
taagggattt tggtcatgca tgatatatct cccaatttgt gtagggctta ttatgcacgc   14460
ttaaaaataa taaagcaga cttgacctga tagtttggct gtgagcaatt atgtgcttag    14520
tgcatctaac gcttgagtta agccgcgccg cgaagcggcg tcggcttgaa cgaatttcta   14580
gctagacatt atttgccgac taccttggtg atctcgcctt tcacgtagtg acaaattct    14640 tccaactgat ctgcgcgcga ggccaagcga tcttcttctt gtccaagata agcctgtcta   14700
gcttcaagta tgacgggctg atactgggcc ggcaggcgct ccattgccca gtcggcagcg   14760
```

-continued

| | |
|---|---|
| acatccttcg gcgcgatttt gccggttact gcgctgtacc aaatgcggga caacgtaagc | 14820 |
| actacatttc gctcatcgcc agcccagtcg ggcggcgagt tccatagcgt taaggtttca | 14880 |
| tttagcgcct caaatagatc ctgttcagga accggatcaa agagttcctc cgccgctgga | 14940 |
| cctaccaagg caacgctatg ttctcttgct tttgtcagca agatagccag atcaatgtcg | 15000 |
| atcgtggctg gctcgaagat acctgcaaga atgtcattgc gctgccattc tccaaattgc | 15060 |
| agttcgcgct tagctggata acgccacgga atgatgtcgt cgtgcacaac aatggtgact | 15120 |
| tctacagcgc ggagaatctc gctctctcca ggggaagccg aagtttccaa aaggtcgttg | 15180 |
| atcaaagctc gccgcgttgt tcatcaagc cttacggtca ccgtaaccag caaatcaata | 15240 |
| tcactgtgtg gcttcaggcc gccatccact gcggagccgt acaaatgtac ggccagcaac | 15300 |
| gtcggttcga gatggcgctc gatgacgcca actacctctg atagttgagt cgatacttcg | 15360 |
| gcgatcaccg cttcccccat gatgtttaac tttgttttag ggcgactgcc ctgctgcgta | 15420 |
| acatcgttgc tgctccataa catcaaacat cgacccacgg cgtaacgcgc ttgctgcttg | 15480 |
| gatgcccgag gcatagactg taccccaaaa aacagtcat aacaagccat gaaaaccgcc | 15540 |
| actgcgttcc at | 15552 |

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11

| | |
|---|---|
| gatataggta cctcttcatc ggtgattgat tcct | 34 |

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12

| | |
|---|---|
| gatataccat ggtcgtgtat gtttttaatc ttgtttg | 37 |

<210> SEQ ID NO 13
<211> LENGTH: 2194
<212> TYPE: DNA
<213> ORGANISM: Oryza sativa
<220> FEATURE:
<221> NAME/KEY: Promoter
<222> LOCATION: (1)..(2194)
<223> OTHER INFORMATION: p-GOS2

<400> SEQUENCE: 13

| | |
|---|---|
| aatccgaaaa gtttctgcac cgttttcacc ccctaactaa caatataggg aacgtgtgct | 60 |
| aaatataaaa tgagaccctta tatatgtagc gctgataact agaactatgc aagaaaaact | 120 |
| catccaccta ctttagtggc aatcgggcta ataaaaaag agtcgctaca ctagtttcgt | 180 |
| tttccttagt aattaagtgg gaaaatgaaa tcattattgc ttagaatata cgttcacatc | 240 |
| tctgtcatga agttaaatta ttcgaggtag ccataattgt catcaaactc ttcttgaata | 300 |
| aaaaaatctt tctagctgaa ctcaatgggt aaagagagag attttttta aaaaaataga | 360 |
| atgaagatat tctgaacgta ttggcaaaga tttaaacata taattatata attttatagt | 420 |
| ttgtgcattc gtcatatcgc acatcattaa ggacatgtct tactccatcc caatttttat | 480 |

```
ttagtaatta aagacaattg acttattttt attatttatc tttttcgat tagatgcaag      540 gtacttacgc acacactttg tgctcatgtg catgtgtgag tgcacctcct caatacacgt      600
tcaactagca acacatctct aatatcactc gcctatttaa tacatttagg tagcaatatc      660
tgaattcaag cactccacca tcaccagacc acttttaata atatctaaaa tacaaaaaat      720
aattttacag aatagcatga aaagtatgaa acgaactatt taggttttc acatacaaaa       780 aaaaaagaa ttttgctcgt gcgcgagcgc caatctccca tattgggcac acaggcaaca       840
acagagtggc tgcccacaga acaacccaca aaaacgatg atctaacgga ggacagcaag       900
tccgcaacaa ccttttaaca gcaggctttg cggccaggag agaggaggag aggcaaagaa      960
aaccaagcat cctccttctc ccatctataa attcctcccc ccttttcccc tctctatata     1020
ggaggcatcc aagccaagaa gagggagagc accaaggaca cgcgactagc agaagccgag     1080
cgaccgcctt ctcgatccat atcttccggt cgagttcttg gtcgatctct ccctcctcc      1140 acctcctcct cacagggtat gtgcctccct tcggttgttc ttggatttat tgttctaggt     1200
tgtgtagtac gggcgttgat gttaggaaag gggatctgta tctgtgatga ttcctgttct     1260
tggatttggg atagaggggt tcttgatgtt gcatgttatc ggttcggttt gattagtagt     1320
atggttttca atcgtctgga gagctctatg gaaatgaaat ggtttaggga tcggaatctt     1380
gcgattttgt gagtaccttt tgtttgaggt aaaatcagag caccggtgat tttgcttggt     1440
gtaataaagt acggttgttt ggtcctcgat tctggtagtg atgcttctcg atttgacgaa     1500
gctatccttt gtttattccc tattgaacaa aaataatcca actttgaaga cggtcccgtt     1560
gatgagattg aatgattgat tcttaagcct gtccaaaatt tcgcagctgg cttgtttaga     1620
tacagtagtc cccatcacga aattcatgga aacagttata atcctcagga acagggatt      1680 ccctgttctt ccgatttgct ttagtcccag aattttttt cccaaatatc ttaaaaagtc      1740
actttctggt tcagttcaat gaattgattg ctacaaataa tgcttttata gcgttatcct     1800
agctgtagtt cagttaatag gtaataccc tatagtttag tcaggagaag aacttatccg      1860
atttctgatc tccattttta attatatgaa atgaactgta gcataagcag tattcatttg     1920 gattatttt tttattagct ctcacccctt cattattctg agctgaaagt ctggcatgaa      1980
ctgtcctcaa ttttgttttc aaattcacat cgattatcta tgcattatcc tcttgtatct     2040
acctgtgaaa gttctttttt ggttattcct tgactgcttg attacagaaa gaaatttatg     2100
aagctgtaat cgggatagtt atactgcttg ttcttatgat tcatttcctt tgtgcagttc     2160
ttggtgtagc ttgccacttt caccagcaaa gttc                                 2194
```

<210> SEQ ID NO 14
<211> LENGTH: 2194
<212> TYPE: DNA
<213> ORGANISM: Artificial Sequence
<220> FEATURE:
<223> OTHER INFORMATION: Promoter
<220> FEATURE:
<221> NAME/KEY: Promoter
<222> LOCATION: (1)..(2194)
<223> OTHER INFORMATION: p-GOS2_perm1

<400> SEQUENCE: 14

```
aatccgaaaa gtttctgcac cgttttcact ccctaactaa caatataggg aacgtgtgct       60
gaatataaaa tgagagctta tatatgtagc gctgataact agaactatga aagaaaaact      120
catccaccta ctttagtggc aacagggcta aataaaaag agtcgcaaca ctagtttcgt       180
```

```
tttccttagt aaataagtgg gaaaacgaaa tcattattgc ttagaatata cgtccacatc    240
tctgtcatga agttaaatta ttcgaggcag ccataattgt catcaaactc ttcttgaata    300
ataaaatctt tctagctgaa ctcaatgggt caagagagag attttttta aaaaaataga    360 atggagatat tctgaacgta ttggcaaagt tttaaacata taattatata attttatagg    420
ttgtgcattc gtcatattgc acatcattaa ggacatgtct tactccatcc cgatttttat    480
ttagtaatta agacaattg acttcttttt attatttatc tttttcgat tagatgcagg      540 gtacttacgc acacactttg tgctcatgtg catctgtgag tgcacctcct caatacacgt    600
tcaactatca acacatctct aatatcactc gcctatttaa ttcatttagg tagcaatatc    660
tgaattcaag cactcgacca tcaccagacc acttttaata atatctaaac tacaaaaaat    720
aattttacag aatagcatga aaaatatgaa acgaactatt taggttttc acatacacaa     780 aaaaaagaa ttttgctcgt gcgcgagcgc taatctccca tattgggcac acaggcaaaa     840
acagagtggc tgcccacaga acaacccaca taaaacgatg atctaacgga ggacagtaag    900
tccgcaacaa ccttttaaca gcaggctgtg cggccaggag agaggaggag aacgaaagaa    960
aaccaagcat cctccttctc cgatctataa attcctcctc ccttttcccc tctctatata   1020
ggaaacatcc aagccaagaa gagggagagg accatggaca cgcgactagc agaagccgag   1080
cgaccgccct ctcgatccat atcttccggt cgagttcttg gtcgctctct tccttcctcc   1140
acctcctcct cacagggtat gtgcctcgct tcggttgttc ttggatttat tgttctggtt   1200
tgtgtagtac gggcgttgat gttaagaaag gggatctgta tctgtgatga ttgctgttct   1260
tggatttggg atagagcggt tcttgatgtt gcatgttatc ggctcgattt gattagtagt   1320
atggttttca atactctgga gagctctatg gaaatgaaat agtttaggga tcggaatctt   1380
gcgattttgt gagttccttt tgtttgaggt aaaatcagag caccgctgat tttgcttgga   1440
ctaataaagt acggttgttt ggccctcgat tctggttgtg atgcttctcg atttgaccag   1500
gctatccttt gtttattccc tgttaacaa aaataatcca actttgaaga gcttcccgtt    1560
gatgagattg aatgattgaa tcttaagcct gtccaaaact tcgcagctgg cttgtttaga   1620
tacagtagtc gccatcacga aagtcatgga aacagttata atcctctgga acagggggatt  1680 ccgagttctt ccgatttgct ttagtccaag aatttttttt cccaaatatc ttaaaaaatc   1740
actttctggt tcagttcaat gaattgattg ctccaaataa tgcttttata gcgttatcct   1800
aggtgtagtt cagttaatag gtaataccc tatagtctag tcaggagaag aacttatccg   1860
atttctgatg accatttta attatatgaa atgaactgta gcatgagcag tattcatttg   1920
gattattttt tttattagcc ctcacccctt cattattctg agctgaaagt ctcgcatgaa   1980
ctgtcctcaa ttttgttttc aaactcacat ggtttatcta tgcattatcc tcttgtatct   2040
accactagaa gtttctttt ggttattcct tgactccttg attacagaaa gaaatttatg    2100
aagctgtatt cgggatagtt atactgcctg ttcttatgat tcattacctt tgtgcagttc   2160
ttggtgtagc atcccaattt caccagcaaa gttc                               2194
```

<210> SEQ ID NO 15
<211> LENGTH: 2194
<212> TYPE: DNA
<213> ORGANISM: Artificial
<220> FEATURE:
<223> OTHER INFORMATION: Promoter
<220> FEATURE:
<221> NAME/KEY: Promoter
<222> LOCATION: (1)..(2194)
<223> OTHER INFORMATION: p-GOS2_perm2

```
<400> SEQUENCE: 15
actccgaaaa gtttctgcac cgttttcacc cgctaactaa caatataggg aacgtgtgtt      60
aaatataaaa tgagagctta tatatgtagc gctgaaaact agaactatac aagaaaaact     120
catccaccta ctttagtggc aataaggcta aataaaaaag agtcgctaca ccagtttcgt     180
tttccttagt aattaagggg gaaaatgaaa tcattattgc ttagcatata cgttcacagc     240
tctgtcatga agttaaatta ttcgaggtag ccttaattgt catcaaactc ttcttgaatc     300
aaaaaatctt tctagctgaa ctcaatgggt acagagagag attttttta aaaaaataga     360
atcaagatat tctgaacgta ttggcagaga tttaaacata taattatata attttatagt     420
tcgtgcattc gtcatatcgc agatcattaa ggacatgtct tactccatcc cagttttat     480
ttagtaatta aagacaattg acttgttttt attacttatc tttttcgat tagatgcaag      540
gtacttacgc ccacactttg tgctcatgtg catgtgtgag cgcacctcct caatacacgt     600
tcaactagcc acacatctct aatatcactc gccgatttaa tacatttagg cagcaatatc     660
tgaattcaag cactccaaca tcaccagacc acttttaata atatctaaaa tagaaaaaat     720
aattttacag aatagcatga aaagtctgaa acgaactatt taggttttc acatacaaat      780
aaaaaaagaa tttgctcgt gcgcgagcgg caatctccca tattgggcac acaggcacca     840
acagagtggc tgcccacaga acaacccaaa aaaaacgatg atctaacgga ggacagccag     900
tccgcaacaa ccttttaaca gcaggctatg cggccaggag agaggaggag aggcaaagaa     960
atccaagcat cctccttctc ccatctataa atacctcccc ccttttcccc tctctatata    1020
ggaggcctcc aagccaagaa gagggagagc accaaagaca cgcgactagc agaagccgag    1080
cgaccgcctt ttcgatccct atcttccggt cgagttcttg gtcgatctct tgcctcctcc    1140
acctcctcct cacagggtat gtgcctctct tcggttgttc ttggatttat tgttctagtt    1200
tgtgtagtac gggcgttgat gttaggaatg gggatctgta tctctgatga ttcctgttct    1260
tggatttggg atagaggcgt tcttgatgtt gcatgttatc gcatcggttt gattagttgt    1320
atggttttca atcgtctgga gaactctatg gaaatgaaat ggtttaggga tcgtaatctt    1380
gcgattttgt gagtaccttt tgtttcaggt aaaatcagag caccggtgat tttgcttgga    1440
gtaataaagt acggttgttt ggtcctcgat tctgatagtg atgcttctcg atttgacgaa    1500
ggtatccttt gtttattccc cattgaacaa aaataatcca actttgaaga cgggcccgtt    1560
gatgagattg aatgattgat tcttaagctt gtccaaaatt tcgcagctag cttgtttaga    1620
tacagtagtc cccatcacga aactcatgga aacagttata atcctcagga acagggaatt    1680
ccctgttctt ccgatttgct ttagtcctag aatttttttt cccaaatatc tcaaaaagtc    1740
actttctggt tcagttcagt gaattgattg cttcaaataa tgcttttata gcgttatcct    1800
agctgtactt cagttaatag gtaataccc tatagtatag tcaggagaag aacttatccg     1860
atttctgatc gccattttta attatatgaa atgaactgta gcagaagcag tattcatttg    1920
gattatttt tttattaact ctcaccccctt cattattctg agctgaaagt caggcatgaa    1980
ctgtcttcaa ttttgttttc aaattcacat cgattatctc tgcattatcc tcttgtatct    2040
acctgaagaa gtttctttt ggttattcct tgacttcttg attacagaaa gaaatttatg     2100
aagctataat cgggatagtt atactacttg ttcttatgat tcattccctt tgtgcagttc    2160
ttggtgtagc ttgtcacttt caccagcaaa gttc                               2194
```

SYNTHETIC ARCELIN-5 PROMOTER AND METHODS OF USE THEREOF

This application is a National Stage application of International Application No. PCT/IB2011/055412, filed Dec. 1, 2011, which claims the benefit of U.S. Provisional Application No. 61/419,895, filed Dec. 6, 2010. This application also claims priority under 35 U.S.C. §119 to European Patent Application No. 10193800.9, filed Dec. 6, 2010.

FIELD OF THE INVENTION

The present invention relates to methods for the design and production of synthetic promoters with a defined specificity and promoters produced with these methods.

BACKGROUND OF THE INVENTION

Manipulation of plants to alter and/or improve phenotypic characteristics such as productivity or quality requires expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

Advanced traits often require the coordinated expression of more than one gene in a transgenic plant. For example, to achieve the production of polyunsaturated fatty acids such as archachidonic acid in a plant requires expression of at least 5 genes. There is also increasing demand of trait stacking which requires the combination of more than one gene in transgenic plants.

The availability of suitable promoters for such coordinated expression is limited. Promoters would often need to have the same tissue and/or developmental specificity and preferably comparable expression strength. One solution has been to use the same promoter for the expression of several genes. Expression constructs comprising more than one expression cassette with tandem or inverted sequence repeats of for example a promoter cause various problems. When located on one vector, handling of the vector in bacteria for cloning, amplification and transformation is difficult due to recombination events which lead to the loss and/or rearrangement of part of the expression construct. Moreover, sequence verification of constructs comprising repeated sequences is difficult and sometimes impossible. A further problem of such expression constructs comprising repeats of the same promoter sequence is that recombination may also occur after introduction into the genome of the target organism such as a plant.

Additionally it is well known that repeated promoter sequences in the genome of organisms such as a plant may induce silencing of expression derived from these promoters, for example by methylation of the promoter or increase of chromatin density at the site of the promoters which makes the promoter inaccessible for transcription factors.

The use of different promoters in expression constructs comprising more than one expression cassette is one possibility to circumvent these problems. Isolation and analysis of promoters is laborious and time consuming. It is unpredictable what expression pattern and expression strength an isolated promoter will have and hence a high number of promoters need to be tested in order to find at least two promoters with comparable expression pattern and optionally comparable expression strength.

There is, therefore, a great need in the art for the availability of new sequences that may be used for expression of selected transgenes in economically important plants. It is thus an objective of the present invention to provide new methods for the production of synthetic promoters with identical and/or overlapping expression pattern or expression specificity and optionally similar expression strength. This objective is solved by the present invention.

DETAILED DESCRIPTION OF THE INVENTION

A first embodiment of the invention is a method for the production of one or more synthetic regulatory nucleic acid molecules of a defined specificity comprising the steps of
a) identifying at least one naturally occurring nucleic acid molecule of the defined specificity (starting molecule) and
b) identifying conserved motives in the at least one nucleic acid sequence (starting sequence) of the starting molecule of the defined specificity as defined in a) and
c) mutating the starting sequence while
  i) leaving at least 70%, preferably 80%, 85%, 90%, more preferably at least 95%, even more preferably at least 98% or at least 99% for example 100% of the motives unaltered known to be involved in regulation of the respective defined specificity (also called preferentially associated motives) and
  ii) leaving at least 80%, preferably at least 90%, 95% for example 100% of the motives unaltered involved in transcription initiation (also called essential motives) and
  iii) leaving at least 10%, preferably at least 20%, 30%, 40% or 50%, more preferably at least 60%, 70% or 80%, even more preferably at least 90% or 95% of other identified motives (also called non exclusively associated) unaltered and
  iv) keeping the arrangement of the identified motives substantially unchanged and
  v) avoiding the introduction of new motives known to influence expression with another specificity than said defined specificity and
  vi) avoiding identical stretches of more than 50 basepairs, preferably 45 basepairs, more preferably 40 basepairs, most preferably 35 basepairs, for example 30 basepairs between each of the starting sequence and the one or more mutated sequences and
d) producing a nucleic acid molecule comprising the mutated sequence and
e) optionally testing the specificity of the mutated sequence in the respective organism.

In one embodiment of the invention, additional preferably associated motives may be introduced into the sequence of the synthetic nucleic acid molecule.

Production of the nucleic acid molecule comprising the mutated sequence could for example be done by chemical synthesis or by oligo ligation whereby smaller oligos comprising parts of the sequence of the invention are stepwise annealed and ligated to form the nucleic acid molecule of the invention.

In a preferred embodiment of the invention, the synthetic regulatory nucleic acid molecule is a synthetic promoter, in a more preferred embodiment the synthetic regulatory nucleic acid molecule is a synthetic promoter functional in a plant, plant tissue or plant cell.

The at least one starting molecule comprising the starting sequence may for example be identified by searches in literature or internet resources such as sequence and/or gene expression data bases. The at least one starting molecule comprising the starting sequence may in another example be identified by isolation and characterization of a natural occurring promoter from the respective organism, for example plants, algae, fungi, animals and the like. Such methods are well known to a person skilled in the art and for example described in Back et al., 1991, Keddie et al., 1992, Keddie et al., 1994.

Motives in a series of nucleic acid molecules may be identified by a variety of bioinformatic tools available in the art. For example see Hehl and Wingender, 2001, Hehl and Bulow, 2002, Cartharius et al., 2005, Kaplan et al., 2006, Dare at al., 2008.

In addition, there are various databases available specialized in promoter analysis and motif prediction in any given sequence. For example as reviewed in Hehl and Wingender, 2001.

It is also possible to identify motives necessary for regulation of expression of the defined specificity with experimental methods known to a skilled person. Such methods are for example deletion or mutation analysis of the respective starting sequence as for example described in Montgomery et al., 1993.

Essential motives known to be involved in transcription initiation for example by being bound by general initiation factors and/or RNA polymerases as described above under ii) are for example the TATA box, the CCAAT box, the GC box or other functional similar motives as for example identified in Roeder (1996, Trends in Biochemical Science, 21(9)) or Baek et al. (2006, Journal of Biological Chemistry, 281). These motives allow a certain degree of degeneration or variation of their sequence without changing or destroying their functionality in initiation of transcription. The skilled person is aware of such sequence variations that leave the respective motives functional. Such variations are for example given in the Transfac database as described by Matys et al, ((2003) NAR 31 (1)) and literature given therein. The Transfac database may for example be accessed via ftp://ftp.ebi.ac.uk/pub/databases/transfac/transfac32.tar.Z. Hence it is to be understood that the term "leaving motives unaltered involved in transcription initiation" means that the respective motives may be mutated, hence altered in their sequence as long as their respective function which is enabling initiation of transcription is not altered, hence as long as the essential motives are functional. In another embodiment of the invention the first 49, preferably 44, more preferably 39, even more preferably 34, most preferably 29 bp directly upstream of the transcription initiation site are kept unaltered.

The term "keeping the arrangement of the motives unchanged" as used above under iv) means, that the order of the motives and/or the distance between the motives are kept substantially unchanged, preferably unchanged. Substantially unchanged means, that the distance between two motives in the starting sequence does not differ from the distance between these motives in the synthetic regulatory nucleic acid sequence, hence the distance between said motives is not longer or shorter, by more than 100%, for example 90%, 80% or 70%, preferably 60%, 50% or 40%, more preferably not more than 30% or 20%, most preferably not more than 10% in the synthetic regulatory nucleic acid sequence as compared to the starting sequence. Preferably the distance between two motives in the starting sequence differs by not more than 10, preferably 9, more preferably 8 or 7 or 6 or 5 or 4, even more preferably not more than 3 or 2, most preferably not more than 1 basepairs from the distance in the permutated sequence.

Inverted and/or direct stretches of repeated sequences may lead to the formation of secondary structures in plasmids or genomic DNA. Repeated sequences may lead to recombination, deletion and/or rearrangement in the plasmid both in *E. coli* and *Agrobacterium*. In eukaryotic organisms, for example plants, repeated sequences also tend to be silenced by methylation. Recombination events which lead to deletions or rearrangements of one or more expression cassettes and/or T-DNAs are likely to lead to loss of function for example loss of expression of such constructs in the transgenic plant (Que and Jorgensen, 1998, Hamilton et al., 1998). It is therefore a critical feature of the invention at hand to avoid identical stretches of 50 basepairs, preferably 45 basepairs, more preferably 40 basepairs, most preferably 35 basepairs, for example 30 basepairs between each of the starting sequence and the one or more permutated sequences. In case of the production of more than one permutated sequences said identical stretches must be avoided between the starting sequence and each of the permutated sequences in a pair wise comparison. In another embodiment, such identical stretches must be avoided between all permutated sequences and the starting sequence; hence none of the permutated and starting sequences shares such identical stretches with any of the other sequences.

The skilled person is aware that regulatory nucleic acids may comprise promoters and functionally linked to said promoters 5'UTR the latter may comprise at least one intron. It has been shown, that introns may be lead to increased expression levels derived from the promoter to which the 5'UTR comprising the intron is functionally linked. The 5' UTR and the intron may be altered in their sequence as described, wherein the splice sites and putative branching point are not altered in order to ensure correct splicing of the intron after permutation. No nucleotide exchanges are introduced into sequences at least 2, preferably at least 3, more preferably at least 5, even more preferably at least 10 bases up- and downstream of the splice sites (5' GT; 3' CAG) are kept unchanged. In addition, "CURAY" and "TNA" sequence elements being potential branching points of the intron are kept unchanged within the last 200 base pairs, preferably the last 150 base pairs, more preferably the last 100 base pairs, even more preferably the last 75 base pairs of the respective intron.

The 5'UTR may be permutated according to the rules as defined above, wherein preferably at least 25, more preferably at least 20, even more preferably at least 15, for example at least 10, most preferably at least 5 base pairs up- and downstream of the transcription start are kept unchanged. The AT content of both the 5' UTR and the intron is not changed by more than 20%, preferably not more than 15%, for example 10% or 5% compared to the AT content of the starting sequence.

A further embodiment of the invention is a synthetic regulatory nucleic acid molecule produced according to the method of the invention.

An expression construct comprising the said synthetic regulatory nucleic acid molecule is another embodiment of the invention.

A vector comprising the regulatory nucleic acid molecule or the expression construct of the invention is also comprised in this invention, as well as microorganisms, plant cells or animal cells comprising the regulatory nucleic acid molecule, the expression construct and/or the vector of the invention.

A further embodiment of the invention is a plant, plant seed, plant cell or part of a plant comprising the regulatory nucleic acid molecule, the expression construct and/or the vector of the invention.

A further embodiment of the invention are exemplary recombinant seed specific or seed preferential synthetic regulatory nucleic acid molecules produced according to the method of the invention wherein the regulatory nucleic acid molecule is comprised in the group consisting of I) a nucleic acid molecule represented by SEQ ID NO: 2, 4 or 6 and II) a nucleic acid molecule comprising at least 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 2, 4 or 6 and III) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% over a sequence of at least 250, 300, 400, 500, 600 preferably 700, more preferably 800, even more preferably 900, most preferably 1000 consecutive nucleic acid base pairs to a sequences described by SEQ ID NO: 2, 4 or 6 and IV) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% to a sequence consisting of at least 50%, 60%, 70%, 80%, 90% or 100% of any of the sequences described by SEQ ID NO: 2, 4 or 6 and V) a nucleic acid molecule hybridizing under high stringent, preferably very high stringent conditions with a nucleic acid molecule of at least 250, 300, 400, 500, 600, 700, 800, 900, 1000 or the complete consecutive base pairs of a nucleic acid molecule described by any of SEQ ID NO: 2, 4 or 6 and VI) a complement of any of the nucleic acid molecules as defined in I) to V).

Another embodiment of the invention are exemplary recombinant seed specific or seed preferential synthetic regulatory nucleic acid molecules produced according to the method of the invention wherein the regulatory nucleic acid molecule is comprised in the group consisting of i) a nucleic acid molecule represented by SEQ ID NO: 2, 4 or 6 and ii) a nucleic acid molecule comprising at least 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 2, 4 or 6 and iii) a nucleic acid molecule having an identity of at least 75% over a sequence of at least 250, 300, 400, 500, 600 preferably 700, more preferably 800, even more preferably 900, most preferably 1000 or the complete consecutive nucleic acid base pairs to a sequences described by SEQ ID NO: 6, iv) a nucleic acid molecule having an identity of at least 90% over a sequence of at least 250, 300, 400, 500, 600 preferably 700, more preferably 800, even more preferably 900, most preferably 1000 or the complete consecutive nucleic acid base pairs to a sequences described by SEQ ID NO: 2 or 4 and v) a nucleic acid molecule hybridizing under high stringent, preferably very high stringent conditions with a nucleic acid molecule of at least 250, 300, 400, 500, 600, 700, 800, 900, 1000 or the complete consecutive base pairs of a nucleic acid molecule described by any of SEQ ID NO: 2, 4 or 6 and vi) a complement of any of the nucleic acid molecules as defined in i) to v).

Further embodiments of the invention are exemplary recombinant constitutive regulatory nucleic acid molecules produced according to the method of the invention wherein the regulatory nucleic acid molecule is comprised in the group consisting of I) a nucleic acid molecule represented by SEQ ID NO: 14 or 15 and II) a nucleic acid molecule comprising at least 1750, 1500, 1250 or 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 14 or 15 and III) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% over a sequence of at least 250, 300, 400, 500, 600 preferably 700, more preferably 800, even more preferably 900, for example 1000, most preferably 1250, for example 1500 or 1750 or 2000 consecutive nucleic acid base pairs to a sequences described by SEQ ID NO: 14 or 15 and IV) a nucleic acid molecule having an identity of at least 70%, for example at least 75%, 76%, 77%, 78%, 79% preferably at least 80%, for example at least 81%, 82%, 83%, 84%, 85%, 86%, 87%, 88%, 89%, more preferably 90%, for example at least 91%, 92%, 93%, 94%, 95%, 96%, 97%, even more preferably 98% most preferably 99% to a sequence consisting of at least 50%, 60%, 70%, 80%, 90% or 100% of any of the sequences described by SEQ ID NO: 14 or 15 and V) a nucleic acid molecule hybridizing under high stringent, preferably very high stringent conditions with a nucleic acid molecule of at least 250, 300, 400, 500, 600, 700, 800, 900, 1000, 1250, 1500, 1750 or 2000 or the complete consecutive base pairs of a nucleic acid molecule described by any of SEQ ID NO: 14 or 15 and VI) a complement of any of the nucleic acid molecules as defined in I) to V).

Another embodiment of the invention are exemplary recombinant constitutive synthetic regulatory nucleic acid molecules produced according to the method of the invention wherein the regulatory nucleic acid molecule is comprised in the group consisting of i) a nucleic acid molecule represented by SEQ ID NO: 14 or 15 and ii) a nucleic acid molecule comprising at least 2000, 1750, 1500, 1250 or 1000 consecutive base pairs, for example 1000 base pairs, preferably at least 800 consecutive base pairs, for example 800 base pairs, more preferably at least 700 consecutive base pairs, for example 700 base pairs, even more preferably at least 600 consecutive base pairs, for example 600 base pairs, most preferably at least 500 consecutive base pairs, for example 500 base pairs or at least 400, at least 300, at least 250 for example 400, 300 or 250 base pairs of a sequence described by SEQ ID NO: 14 or 15 and iii) a nucleic acid molecule having an identity of at least 95%, preferably 97%, more preferably 98%, most preferably 99% over a sequence of at least 250, 300, 400, 500, 600 preferably 700, more preferably 800, even more preferably 900, fore example 1000, most preferably 1500, for example 2000 or the complete consecutive nucleic acid base pairs to a sequences described by SEQ ID NO: 14 or 15, iv) a nucleic acid molecule hybridizing under high stringent, preferably very high stringent conditions with a nucleic acid molecule of at least 250, 300, 400, 500, 600, 700, 800, 900, 1000, 1250. 1500, 1750, 2000 or the complete consecutive base pairs of a nucleic acid molecule described by any of SEQ ID NO: 14 or 15 and v) a complement of any of the nucleic acid molecules as defined in i) to v).

It is to be understood, that the group of exemplary recombinant seed specific or seed preferential or constitutive synthetic regulatory nucleic acid molecules produced according to the method of the invention as defined above under I) to V) and i) to vi) does not comprise the starting molecules as defined by SEQ ID NO: 1, 3, 5 and 13 or a complement thereof or a nucleic acid molecule having at least 250 consecutive base pairs of a sequence described by SEQ ID NO: 1, 3, 5 or 13 or a complement thereof or any other nucleic acid molecule occurring in a wild type plant as such nucleic acid molecules are molecules that are not produced according to the invention but are naturally present in wild type plants.

An expression construct comprising any of said synthetic regulatory nucleic acid molecules as defined above under I) to VI) and i) to vi) is another embodiment of the invention.

A vector comprising the regulatory nucleic acid molecule or the expression construct of the invention is also comprised in this invention, as well as microorganisms, plant cells or animal cells comprising the regulatory nucleic acid molecule, the expression construct and/or the vector of the invention.

A further embodiment of the invention is a plant, plant seed, plant cell or part of a plant comprising the regulatory nucleic acid molecule, the expression construct and/or the vector of the invention.

DEFINITIONS

Abbreviations: GFP—green fluorescence protein, GUS—beta-Glucuronidase, BAP—6-benzylaminopurine; 2,4-D—2,4-dichlorophenoxyacetic acid; MS—Murashige and Skoog medium; NAA—1-naphtaleneacetic acid; MES, 2-(N-morpholino-ethanesulfonic acid, IAA indole acetic acid; Kan: Kanamycin sulfate; GA3—Gibberellic acid; Timentin™: ticarcillin disodium/clavulanate potassium.

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Antisense: The term "antisense" refers to a nucleotide sequence that is inverted relative to its normal orientation for transcription or function and so expresses an RNA transcript that is complementary to a target gene mRNA molecule expressed within the host cell (e.g., it can hybridize to the target gene mRNA molecule or single stranded genomic DNA through Watson-Crick base pairing) or that is complementary to a target DNA molecule such as, for example genomic DNA present in the host cell.

"Box" or as synonymously used herein "motif" or "cis-element" of a promoter means a transcription factor binding sequence defined by a highly conserved core sequence of approximately 4 to 6 nucleotides surrounded by a conserved matrix sequence of in total up to 20 nucleotides within the plus or minus strand of the promoter, which is able of interacting with the DNA binding domain of a transcription factor protein. The conserved matrix sequence allows some variability in the sequence without loosing its ability to be bound by the DNA binding domain of a transcription factor protein.

One way to describe transcription factor binding sites (TFBS) is by nucleotide or position weight matrices (NWM or PWM) (for review see Stormo, 2000). A weight matrix pattern definition is superior to a simple IUPAC consensus sequence as it represents the complete nucleotide distribution for each single position. It also allows the quantification of the similarity between the weight matrix and a potential TFBS detected in the sequence (Cartharius et al. 2005).

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Conserved motives: A conserved motif as used herein means a sequence motif or box found in various promoters having the same or overlapping specificity. Overlapping specificity means the specificity of at least two promoters wherein the expression derived from one promoter is in part or completely in the same for example tissue as the other promoter, wherein the latter one may drive expression in additional tissues in which the first promoter may not drive expression. Motives may be grouped in three classes:

Essential: motives present in the promoters of most genes that are transcribed by RNA Polymerase II and which are preferentially localized close to the transcription start side. Such motives must not be made dysfunctional by mutations according to the method of the invention. Hence they must not be altered in a way that prevents them from being bound by the respective DNA binding domain of the transcription factor protein that would have bound to the unaltered sequence.

non exclusively associated: motives present in the promoters of genes that are associated with certain tissues/physiological states/treatments but not exclusively, they may be expressed also in other tissues/physiological states/treatments. According to the method of the invention, such motives should preferably not be made dysfunctional by mutations or at least only a certain percentage of such motives present in one particular promoter or starting sequence. Hence they should preferably not be altered in a way that prevents them from being bound by the respective DNA binding domain of the transcription factor protein that would have bound to the unaltered sequence.

preferentially associated: motives present in the promoters of genes that are expressed preferentially in specific tissues/physiological states/treatments. The vast majority of such motives identified in a starting sequence must not be made dysfunctional by mutations according to the method of the invention. Hence they must not be altered in a way that prevents them from being bound by the respective DNA binding domain of the transcription factor protein that would have bound to the unaltered sequence.

Defined specificity: the term "defined specificity" means any expression specificity of a promoter, preferably a plant specific promoter, which is beneficial for the expression of a distinct coding sequence or RNA. A defined specificity may for example be a tissue or developmental specificity or the expression specificity could be defined by induction or repression of expression by biotic or abiotic stimuli or a combination of any of these.

Double-stranded RNA: A "double-stranded RNA" molecule or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule.

Endogenous: An "endogenous" nucleotide sequence refers to a nucleotide sequence, which is present in the genome of the untransformed plant cell.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule. Expression may also refer to the change of the steady state level of the respective RNA in a plant or part thereof due to change of the stability of the respective RNA.

Similar expression strength: Two or more regulatory nucleic acid molecules have a similar expression strength when the expression derived from any of the regulatory nucleic acid molecule in a distinct cell, tissue or plant organ does not deviate by more than factor 2.

Expression construct: "Expression construct" as used herein mean a DNA sequence capable of directing expression of a particular nucleotide sequence in an appropriate part of a plant or plant cell, comprising a promoter functional in said part of a plant or plant cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example RNAa, siRNA, snoRNA, snRNA, microRNA, ta-siRNA or any other noncoding regulatory RNA, in the sense or antisense direction. The expression construct comprising the nucleotide sequence of interest may be chimeric, meaning that one or more of its components is heterologous with respect to one or more of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a constitutive promoter or of an inducible promoter, which initiates transcription only when the host cell is exposed to some particular external stimulus. In the case of a plant, the promoter can also be specific to a particular tissue or organ or stage of development.

Expression pattern or expression specificity of a regulatory nucleic acid molecule as used herein defines the tissue and/or developmental and/or environmentally modulated expression of a coding sequence or RNA under the control of a distinct regulatory nucleic acid molecule.

Foreign: The term "foreign" refers to any nucleic acid molecule (e.g., gene sequence) which is introduced into the genome of a cell by experimental manipulations and may include sequences found in that cell so long as the introduced sequence contains some modification (e.g., a point mutation, the presence of a selectable marker gene, etc.) and is therefore distinct relative to the naturally-occurring sequence.

Functional linkage: The term "functional linkage" or "functionally linked" is to be understood as meaning, for example, the sequential arrangement of a regulatory element (e.g. a promoter) with a nucleic acid sequence to be expressed and, if appropriate, further regulatory elements (such as e.g., a terminator or an enhancer) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form and be inserted into a plant genome, for example by transformation.

Gene: The term "gene" refers to a region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41$ (% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

Medium stringency conditions when used in reference to nucleic acid hybridization comprise conditions equivalent to binding or hybridization at 68° C. in a solution consisting of 5×SSPE (43.8 g/L NaCl, 6.9 g/L NaH2PO4.H2O and 1.85 g/L EDTA, pH adjusted to 7.4 with NaOH), 1% SDS, 5× Denhardt's reagent [50× Denhardt's contains the following per 500 mL 5 g Ficoll (Type 400, Pharmacia), 5 g BSA (Fraction V; Sigma)] and 100 µg/mL denatured salmon sperm DNA followed by washing (preferably for one times 15 minutes, more preferably two times 15 minutes, more preferably three time 15 minutes) in a solution comprising 1×SSC (1×SSC is 0.15 M NaCl plus 0.015 M sodium citrate) and 0.1% SDS at room temperature or—preferably 37° C.—when a DNA probe of preferably about 100 to about 500 nucleotides in length is employed.

High stringency conditions when used in reference to nucleic acid hybridization comprise conditions equivalent to binding or hybridization at 68° C. in a solution consisting of 5×SSPE (43.8 g/L NaCl, 6.9 g/L NaH2PO4.H2O and 1.85 g/L EDTA, pH adjusted to 7.4 with NaOH), 1% SDS, 5× Denhardt's reagent [50× Denhardt's contains the following per 500 mL 5 g Ficoll (Type 400, Pharmacia), 5 g BSA (Fraction V; Sigma)] and 100 µg/mL denatured salmon sperm DNA followed by washing (preferably for one times 15 minutes, more preferably two times 15 minutes, more preferably three time 15 minutes) in a solution comprising 0.1×SSC (1×SSC is 0.15 M NaCl plus 0.015 M sodium citrate) and 1% SDS at room temperature or—preferably 37° C.—when a DNA probe of preferably about 100 to about 500 nucleotides in length is employed.

Very high stringency conditions when used in reference to nucleic acid hybridization comprise conditions equivalent to binding or hybridization at 68° C. in a solution consisting of 5×SSPE, 1% SDS, 5× Denhardt's reagent and 100 µg/mL denatured salmon sperm DNA followed by washing (preferably for one times 15 minutes, more preferably two times 15 minutes, more preferably three time 15 minutes) in a solution comprising 0.1×SSC, and 1% SDS at 68° C., when a probe of preferably about 100 to about 500 nucleotides in length is employed.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage identity between the two sequences is a function of the number of identical positions shared by the sequences (i.e. % homology=number of identical positions/total number of positions×100). The terms "homology" and "identity" are thus to be considered as synonyms.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444 (1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show oneline descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; —W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; —P 0 for multiple hit, 1 for single hit [Integer]; default=0; —Y Effective length of the search space (use zero for the real size) [Real]; default=0; —S Query strands to search against database (for blast[nx], and tblastx); 3 is both, 1 is top, 2 is bottom [Integer]; default=3; -T Produce HTML output [T/F]; default=F; —I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; —R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. The identity is calculated on the complete length of the query sequence, for example SEQ ID NO:1.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living plant is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, is found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Minimal Promoter: promoter elements, particularly a TATA element, that are inactive or that have greatly reduced promoter activity in the absence of upstream activation. In the presence of a suitable transcription factor, the minimal promoter functions to permit transcription.

Naturally occurring as used herein means a cell or molecule, for example a plant cell or nucleic acid molecule that occurs in a plant or organism which is not manipulated by man, hence which is for example neither mutated nor genetically engineered by man.

Non-coding: The term "non-coding" refers to sequences of nucleic acid molecules that do not encode part or all of an expressed protein. Non-coding sequences include but are not limited to introns, enhancers, promoter regions, 3' untranslated regions, and 5' untranslated regions.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used interchangeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, $NH_2$, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Overlapping specificity: The term "overlapping specificity" when used herein related to expression specificity of two or more promoters means that the expression regulated by these promoters occur partly in the same plant tissues, developmental stages or conditions. For example, a promoter expressed in leaves and a promoter expressed in root and leaves have an overlap in expression specificity in the leaves of a plant.

Plant: is generally understood as meaning any eukaryotic single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, sorghum, millet, rye, triticale, or oats; the family of the Umbelliferae, especially the genus *Daucus*, very especially the species carota (carrot) and Apium, very especially the species Graveolens dulce (celery) and many others; the family of the Solanaceae, especially the genus Lycopersicon, very especially the species esculentum (tomato) and the genus *Solanum*, very especially the species tuberosum (potato) and melongena (egg plant), and many others (such as tobacco); and the genus *Capsicum*, very especially the species annuum (peppers) and many others; the family of the Leguminosae, especially the genus *Glycine*, very especially the species max (soybean), alfalfa, pea, lucerne, beans or peanut and many others; and the family of the Cruciferae (Brassicacae), especially the genus *Brassica*, very especially the species napus (oil seed rape), campestris (beet), oleracea cv Tastie (cabbage), oleracea cv Snowball Y (cauliflower) and oleracea cv Emperor (broccoli); and of the genus *Arabidopsis*, very especially the species thaliana and many others; the family of the Compositae, especially the genus *Lactuca*, very especially the species sativa (lettuce) and many others; the family of the Asteraceae such as sunflower, Tagetes, lettuce or *Calendula* and many other; the family of the Cucurbitaceae such as melon, pumpkin/squash or zucchini, and linseed. Further preferred are cotton, sugar cane, hemp, flax, chillies, and the various tree, nut and wine species.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Primary transcript: The term "primary transcript" as used herein refers to a premature RNA transcript of a gene. A "primary transcript" for example still comprises introns and/or is not yet comprising a polyA tail or a cap structure and/or is missing other modifications necessary for its correct function as transcript such as for example trimming or editing.

Promoter: The terms "promoter", or "promoter sequence" are equivalents and as used herein, refer to a DNA sequence which when ligated to a nucleotide sequence of interest is capable of controlling the transcription of the nucleotide sequence of interest into RNA. Such promoters can for example be found in the following public databases www.grassius.org/grasspromdb.html, mendel.cs.rhul.ac.uk/mendel.php?topic=plantprom, ppdb.gene.nagoya-u.ac.jp/cgi-bin/index.cgi. Promoters listed there may be addressed with the methods of the invention and are herewith included by reference. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. Said promoter comprises for example the at least 10 kb, for example 5 kb or 2 kb proximal to the transcription start site. It may also comprise the at least 1500 bp proximal to the transcriptional start site, preferably the at least 1000 bp, more preferably the at least 500 bp, even more preferably the at least 400 bp, the at least 300 bp, the at least 200 bp or the at least 100 bp. In a further preferred embodiment, the promoter comprises the at least 50 bp proximal to the transcription start site, for example, at least 25 bp. The promoter does not comprise exon and/or intron regions or 5' untranslated regions. The promoter may for example be heterologous or homologous to the respective plant. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). A plant specific promoter is a promoter suitable for regulating expression in a plant. It may be derived from a plant but also from plant pathogens or it might be a synthetic promoter designed by man. If a promoter is an inducible promoter, then the rate of transcription increases in response to an inducing agent. Also, the promoter may be regulated in a tissue-specific or tissue preferred manner such that it is only or predominantly active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining, GFP protein or immunohistochemical staining. The term "constitutive" when made in reference to a promoter or the expression derived from a promoter means that the promoter is capable of directing transcription of an operably linked nucleic acid molecule in the absence of a stimulus (e.g., heat shock, chemicals, light, etc.) in the majority of plant tissues and cells throughout substantially the entire lifespan of a plant or part of a plant. Typically, constitutive promoters are capable of directing expression of a transgene in substantially any cell and any tissue.

Promoter specificity: The term "specificity" when referring to a promoter means the pattern of expression conferred by the respective promoter. The specificity describes the tissues and/or developmental status of a plant or part thereof, in which the promoter is conferring expression of the nucleic acid molecule under the control of the respective promoter. Specificity of a promoter may also comprise the environmental conditions, under which the promoter may be activated or down-regulated such as induction or repression by biological or environmental stresses such as cold, drought, wounding or infection.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. Recombinant nucleic acid molecules as such do not exist in nature but are modified, changed, mutated or otherwise manipulated by man. A "recombinant nucleic acid molecule" is a non-naturally occurring nucleic acid molecule that differs in sequence from a naturally occurring nucleic acid molecule by at least one nucleic acid. The term "recombinant nucleic acid molecule" may also comprise a "recombinant construct" which comprises, preferably operably linked, a sequence of nucleic acid molecules, which are not naturally occurring in that order wherein each of the nucleic acid molecules may or may not be a recombinant nucleic acid molecule. Preferred methods for producing said recombinant nucleic acid molecule may comprise cloning techniques, directed or non-directed mutagenesis, synthesis or recombination techniques.

Sense: The term "sense" is understood to mean a nucleic acid molecule having a sequence which is complementary or identical to a target sequence, for example a sequence which binds to a protein transcription factor and which is involved in the expression of a given gene. According to a preferred embodiment, the nucleic acid molecule comprises a gene of interest and elements allowing the expression of the said gene of interest.

Starting sequence: The term "starting sequence" when used herein defines the sequence of a promoter of a defined specificity which is used as a reference sequence for analysis of the presence of motives. The starting sequence is referred to for the definition of the degree of identity to the sequences of the promoters of the invention. The starting sequence could be any wild-type, naturally occurring promoter sequence or any artificial promoter sequence. The sequence of a synthetic promoter sequence produced with the method of the invention may also be used as a starting sequence.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J. Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the chromosomal DNA of the host cell. Another type of vector is an episomal vector, i.e., a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences recognized by any RNA polymerase, including mitochondrial RNA polymerase, RNA pol I, RNA pol II, and RNA pol III. These vectors can be used to transcribe the desired RNA molecule in the cell according to this invention. A plant transformation vector is to be understood as a vector suitable in the process of plant transformation.

Wild-type: The term "wild-type", "natural" or "natural origin" means with respect to an organism, polypeptide, or nucleic acid sequence, that said organism is naturally occurring or available in at least one naturally occurring organism which is not changed, mutated, or otherwise manipulated by man.

EXAMPLES

Chemicals and Common Methods

Unless indicated otherwise, cloning procedures carried out for the purposes of the present invention including restriction digest, agarose gel electrophoresis, purification of nucleic acids, Ligation of nucleic acids, transformation, selection and cultivation of bacterial cells were performed as described (Sambrook et al., 1989). Sequence analyses of recombinant DNA were performed with a laser fluorescence DNA sequencer (Applied Biosystems, Foster City, Calif., USA) using the Sanger technology (Sanger et al., 1977). Unless described otherwise, chemicals and reagents were obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases were from New England Biolabs (Ipswich, Mass., USA) or Roche Diagnostics GmbH (Penzberg, Germany). Oligonucleotides were synthesized by Eurofins MWG Operon (Ebersberg, Germany).

Example 1

1.1 Directed Permutation of the Promoter Sequence

Using publicly available data, two promoters showing seed specific expression in plants were selected for analyzing the effects of sequence permutation in periodic intervals throughout the full length of the promoter DNA sequence (WO2009016202, WO2009133145). The wildtype or starting sequences of the *Phaseolus vulgaris* p-PvARC5 (SEQ ID NO 1) (with the prefix p-denoting promoter) and the *Vicia faba* p-VfSBP (SEQ ID NO 3) promoters were analyzed and annotated for the occurrence of motives, boxes, cis-regulatory elements using e.g. the GEMS Launcher Software (www.genomatix.de) with default parameters (Core similarity 0.75, matrix similarity 0.75)

The "core sequence" of a matrix is defined as the usually 4 consecutive highest conserved positions of the matrix.

The core similarity is calculated as described here and in the papers related to MatInspector (Cartharius K, et al. (2005) Bioinformatics 21; Cartharius K (2005), DNA Press; Quandt K, et al (1995) Nucleic Acids Res. 23.

The maximum core similarity of 1.0 is only reached when the highest conserved bases of a matrix match exactly in the sequence. More important than the core similarity is the matrix similarity which takes into account all bases over the whole matrix length. The matrix similarity is calculated as described here and in the MatInspector paper. A perfect match to the matrix gets a score of 1.00 (each sequence position corresponds to the highest conserved nucleotide at that position in the matrix), a "good" match to the matrix has a similarity of >0.80.

Mismatches in highly conserved positions of the matrix decrease the matrix similarity more than mismatches in less conserved regions.

Opt. gives the Optimized matrix threshold: This matrix similarity is the optimized value defined in a way that a minimum number of matches is found in non-regulatory test sequences (i.e. with this matrix similarity the number of false positive matches is minimized). This matrix similarity is used when the user checks "Optimized" as the matrix similarity threshold for MatInspector. In the following, the DNA sequences of the promoters were permutated according to the method of the invention to yield p-PvArc5_perm (SEQ ID NO 2) and p-VfSBP_perm (SEQ ID NO 4). In case of the p-PvArc5 promoter 6.6% of the motives not associated with seed specific/preferential expression and transcription initiation have been altered, in case of the p-VfSBP 7.8%. DNA permutation was conducted in a way to not affect cis regulatory elements which have been associated previously with seed specific gene expression or initiation of transcription and permutations were distributed periodically over the full promoter DNA sequence with less than 46 nucleotides between permutated nucleotide positions and within a stretch of 5 nucleotides having at least one nucleotide permutated. Permutations were carried out with the aim to keep most of the cis regulatory elements, boxes, motives present in the native promoter and to avoid creating new putative cis regulatory elements, boxes, motives.

The list of motives, boxes, cis regulatory elements in the PvARC5 promoters before and after the permutation are shown in Table 1 and 2.

The list of motives, boxes, cis regulatory elements in the VfSBP promoters before and after the permutation are shown in Table 3 and 4.

Empty lines resemble motives, boxes, cis regulatory elements not found in one sequence but present in the corresponding sequence, hence, motives, boxes, cis regulatory elements that were deleted from the starting sequence or that were introduced into the permutated sequence.

TABLE 1

Boxes and Motifs identified in the starting sequence of the PvARC5 promoter
PvARC5 promotor

| Family | Further Family Information | Matrix | Opt. | Position Position from-to | Strand | Core sim. | Matrix sim. |
|---|---|---|---|---|---|---|---|
| P$PSRE | Pollen-specific regulatory elements | P$GAAA.01 | 0.83 | 9-25 | (+) | 1 | 0.862 |
| P$IDDF | ID domain factors | P$ID1.01 | 0.92 | 36-48 | (−) | 1 | 0.922 |
| P$MYBL | MYB-like proteins | P$ATMYB77.01 | 0.87 | 47-63 | (+) | 1 | 0.887 |
| P$RAV5 | 5'-part of bipartite RAV1 binding site | P$RAV1-5.01 | 0.96 | 48-58 | (+) | 1 | 0.96 |
| P$MYBL | MYB-like proteins | P$GAMYB.01 | 0.91 | 52-68 | (−) | 1 | 0.932 |
| O$INRE | Core promoter initiator elements | O$DINR.01 | 0.94 | 75-85 | (+) | 0.97 | 0.988 |
| P$AHBP | *Arabidopsis* homeobox protein | P$WUS.01 | 0.94 | 84-94 | (−) | 1 | 0.963 |
| P$MIIG | MYB IIG-type binding sites | P$PALBOXL.01 | 0.80 | 87-101 | (+) | 0.84 | 0.806 |
| P$NCS1 | Nodulin consensus sequence 1 | P$NCS1.01 | 0.85 | 106-116 | (+) | 1 | 0.99 |
| P$GAPB | GAP-Box (light response elements) | P$GAP.01 | 0.88 | 108-122 | (+) | 0.81 | 0.884 |
| P$AHBP | *Arabidopsis* homeobox protein | P$WUS.01 | 0.94 | 110-120 | (−) | 1 | 0.963 |
| P$TEFB | TEF-box | P$TEF1.01 | 0.76 | 111-131 | (−) | 0.96 | 0.761 |
| P$CCAF | Circadian control factors | P$CCA1.01 | 0.85 | 113-127 | (+) | 0.77 | 0.856 |
| P$IBOX | Plant I-Box sites | P$GATA.01 | 0.93 | 121-137 | (−) | 1 | 0.964 |
| P$GAGA | GAGA elements | P$GAGABP.01 | 0.75 | 125-149 | (−) | 0.75 | 0.768 |
| P$NCS2 | Nodulin consensus sequence 2 | P$NCS2.01 | 0.79 | 126-140 | (+) | 1 | 0.799 |
| P$AHBP | *Arabidopsis* homeobox protein | P$HAHB4.01 | 0.87 | 144-154 | (−) | 1 | 0.923 |
| P$AHBP | *Arabidopsis* homeobox protein | P$BLR.01 | 0.90 | 147-157 | (−) | 1 | 0.928 |
| O$VTBP | Vertebrate TA-TA binding protein factor | O$LTATA.01 | 0.82 | 151-167 | (+) | 1 | 0.839 |
| P$NCS1 | Nodulin consensus sequence 1 | P$NCS1.01 | 0.85 | 164-174 | (−) | 1 | 0.898 |

TABLE 1-continued

Boxes and Motifs identified in the starting sequence of the PvARC5 promoter
PvARC5 promotor

| Family | Further Family Information | Matrix | Opt. | Position Position from-to | Strand | Core sim. | Matrix sim. |
|---|---|---|---|---|---|---|---|
| P$L1BX | L1 box, motif for L1 layer-specific expression | P$ATML1.01 | 0.82 | 175-191 | (+) | 0.75 | 0.872 |
| P$AHBP | Arabidopsis homeobox protein | P$ATHB5.01 | 0.89 | 177-187 | (+) | 0.83 | 0.902 |
| P$AHBP | Arabidopsis homeobox protein | P$ATHB5.01 | 0.89 | 177-187 | (−) | 1 | 1 |
| O$VTBP | Vertebrate TA-TA binding protein factor | O$ATATA.01 | 0.78 | 184-200 | (+) | 0.75 | 0.797 |
| P$TELO | Telo box (plant interstitial telomere motifs) | P$ATPURA.01 | 0.85 | 186-200 | (−) | 0.75 | 0.857 |
| P$NCS2 | Nodulin consensus sequence 2 | P$NCS2.01 | 0.79 | 213-227 | (−) | 1 | 0.826 |
| P$SUCB | Sucrose box | P$SUCROSE.01 | 0.81 | 233-251 | (+) | 0.75 | 0.824 |
| P$MYBL | MYB-like proteins | P$MYBPH3.02 | 0.76 | 238-254 | (+) | 0.82 | 0.798 |
| P$NCS1 | Nodulin consensus sequence 1 | P$NCS1.01 | 0.85 | 261-271 | (−) | 1 | 0.851 |
| P$MYBL | MYB-like proteins | P$MYBPH3.02 | 0.76 | 264-280 | (+) | 1 | 0.774 |
| O$VTBP | Vertebrate TA-TA binding protein factor | O$ATATA.01 | 0.78 | 267-283 | (+) | 1 | 0.872 |
| P$SPF1 | Sweet potato DNA-binding factor with two WRKY-domains | P$SP8BF.01 | 0.87 | 298-310 | (−) | 1 | 0.872 |
| P$BRRE | Brassinosteroid (BR) response element | P$BZR1.01 | 0.95 | 303-319 | (−) | 1 | 0.953 |
| P$L1BX | L1 box, motif for L1 layer-specific expression | P$ATML1.02 | 0.76 | 319-335 | (+) | 0.89 | 0.762 |
| P$GBOX | Plant G-box/C-box bZIP proteins | P$TGA1.01 | 0.90 | 327-347 | (−) | 1 | 0.909 |
| P$GTBX | GT-box elements | P$GT1.01 | 0.85 | 337-353 | (+) | 1 | 0.854 |
| P$IBOX | Plant I-Box sites | P$GATA.01 | 0.93 | 337-353 | (−) | 1 | 0.935 |
| P$OPAQ | Opaque-2 like transcriptional activators | P$O2.01 | 0.87 | 351-367 | (−) | 1 | 0.919 |
| P$GTBX | GT-box elements | P$S1F.01 | 0.79 | 362-378 | (−) | 0.75 | 0.797 |
| P$AHBP | Arabidopsis homeobox protein | P$ATHB9.01 | 0.77 | 367-377 | (−) | 1 | 0.788 |
| P$AHBP | Arabidopsis homeobox protein | P$HAHB4.01 | 0.87 | 367-377 | (+) | 1 | 0.926 |
| P$GTBX | GT-box elements | P$SBF1.01 | 0.87 | 367-383 | (+) | 1 | 0.894 |
| P$L1BX | L1 box, motif for L1 layer-specific expression | P$ATML1.01 | 0.82 | 369-385 | (+) | 1 | 0.827 |
| P$AHBP | Arabidopsis homeobox protein | P$WUS.01 | 0.94 | 371-381 | (−) | 1 | 1 |
| O$VTBP | Vertebrate TA-TA binding protein factor | O$LTATA.01 | 0.82 | 396-412 | (−) | 1 | 0.857 |
| P$LREM | Light responsive element motif, not modulated by different light qualities | P$RAP22.01 | 0.85 | 397-407 | (+) | 1 | 0.921 |
| P$AHBP | Arabidopsis homeobox protein | P$HAHB4.01 | 0.87 | 401-411 | (−) | 1 | 0.916 |
| P$MYBL | MYB-like proteins | P$WER.01 | 0.87 | 403-419 | (−) | 1 | 0.9 |
| P$MYBS | MYB proteins with single DNA binding repeat | P$OSMYBS.01 | 0.82 | 416-432 | (+) | 0.75 | 0.837 |
| P$TELO | Telo box (plant interstitial telomere motifs) | P$ATPURA.01 | 0.85 | 440-454 | (−) | 0.75 | 0.854 |
| P$SUCB | Sucrose box | P$SUCROSE.01 | 0.81 | 461-479 | (−) | 0.75 | 0.826 |

TABLE 1-continued

Boxes and Motifs identified in the starting sequence of the PvARC5 promoter
PvARC5 promotor

| Family | Further Family Information | Matrix | Opt. | Position Position from-to | Strand | Core sim. | Matrix sim. |
|---|---|---|---|---|---|---|---|
| P$AHBP | Arabidopsis homeobox protein | P$HAHB4.01 | 0.87 | 468-478 | (+) | 1 | 0.892 |
| O$VTBP | Vertebrate TA-TA binding protein factor | O$VTATA.01 | 0.90 | 473-489 | (−) | 1 | 0.913 |
| O$PTBP | Plant TATA binding protein factor | O$PTATA.01 | 0.88 | 476-490 | (−) | 1 | 0.889 |
| P$PSRE | Pollen-specific regulatory elements | P$GAAA.01 | 0.83 | 482-498 | (+) | 1 | 0.831 |
| P$HMGF | High mobility group factors | P$HMG_IY.01 | 0.89 | 499-513 | (−) | 1 | 0.91 |
| P$SUCB | Sucrose box | P$SUCROSE.01 | 0.81 | 499-517 | (−) | 1 | 0.878 |
| P$GTBX | GT-box elements | P$SBF1.01 | 0.87 | 509-525 | (−) | 1 | 0.885 |
| P$GARP | Myb-related DNA binding proteins (Golden2, ARR, Psr) | P$ARR10.01 | 0.97 | 540-548 | (+) | 1 | 0.976 |
| P$AHBP | Arabidopsis homeobox protein | P$ATHB9.01 | 0.77 | 558-568 | (−) | 1 | 0.775 |
| P$L1BX | L1 box, motif for L1 layer-specific expression | P$PDF2.01 | 0.85 | 558-574 | (−) | 1 | 0.865 |
| P$NCS1 | Nodulin consensus sequence 1 | P$NCS1.01 | 0.85 | 558-568 | (−) | 0.88 | 0.927 |
| P$EINL | Ethylen insensitive 3 like factors | P$TEIL.01 | 0.92 | 572-580 | (+) | 1 | 0.921 |
| P$AHBP | Arabidopsis homeobox protein | P$ATHB5.01 | 0.89 | 583-593 | (+) | 0.94 | 0.977 |
| P$AHBP | Arabidopsis homeobox protein | P$ATHB5.01 | 0.89 | 583-593 | (−) | 0.83 | 0.94 |
| P$L1BX | L1 box, motif for L1 layer-specific expression | P$HDG9.01 | 0.77 | 607-623 | (+) | 1 | 0.772 |
| P$IBOX | Plant I-Box sites | P$IBOX.01 | 0.81 | 610-626 | (+) | 0.75 | 0.824 |
| P$MYBS | MYB proteins with single DNA binding repeat | P$MYBST1.01 | 0.90 | 613-629 | (−) | 1 | 0.953 |
| P$IBOX | Plant I-Box sites | P$GATA.01 | 0.93 | 616-632 | (+) | 1 | 0.942 |
| P$TEFB | TEF-box | P$TEF1.01 | 0.76 | 616-636 | (+) | 0.96 | 0.778 |
| P$MYBS | MYB proteins with single DNA binding repeat | P$TAMYB80.01 | 0.83 | 625-641 | (−) | 1 | 0.859 |
| O$PTBP | Plant TATA binding protein factor | O$PTATA.02 | 0.90 | 631-645 | (+) | 1 | 0.927 |
| O$PTBP | Plant TATA binding protein factor | O$PTATA.02 | 0.90 | 632-646 | (−) | 1 | 0.929 |
| O$VTBP | Vertebrate TA-TA binding protein factor | O$ATATA.01 | 0.78 | 646-662 | (−) | 0.75 | 0.825 |
| P$L1BX | L1 box, motif for L1 layer-specific expression | P$HDG9.01 | 0.77 | 648-664 | (+) | 1 | 0.791 |
| P$HMGF | High mobility group factors | P$HMG_IY.01 | 0.89 | 649-663 | (−) | 1 | 0.902 |
| P$DOFF | DNA binding with one finger (DOF) | P$PBF.01 | 0.97 | 654-670 | (+) | 1 | 0.979 |
| P$LREM | Light responsive element motif, not modulated by different light qualities | P$RAP22.01 | 0.85 | 682-692 | (−) | 1 | 0.975 |
| P$TEFB | TEF-box | P$TEF1.01 | 0.76 | 696-716 | (−) | 0.84 | 0.78 |
| P$MYBL | MYB-like proteins | P$CARE.01 | 0.83 | 699-715 | (−) | 1 | 0.88 |

TABLE 1-continued

Boxes and Motifs identified in the starting sequence of the PvARC5 promoter
PvARC5 promotor

| Family | Further Family Information | Matrix | Opt. | Position Position from-to | Strand | Core sim. | Matrix sim. |
|---|---|---|---|---|---|---|---|
| P$LEGB | Legumin Box family | P$RY.01 | 0.87 | 704-730 | (+) | 1 | 0.94 |
| P$GBOX | Plant G-box/C-box bZIP proteins | P$BZIP910.01 | 0.77 | 716-736 | (−) | 0.75 | 0.856 |
| P$GBOX | Plant G-box/C-box bZIP proteins | P$ROM.01 | 0.85 | 717-737 | (+) | 1 | 1 |
| P$ABRE | ABA response elements | P$ABF1.03 | 0.82 | 719-735 | (−) | 0.75 | 0.857 |
| P$GBOX | Plant G-box/C-box bZIP proteins | P$BZIP910.02 | 0.84 | 722-742 | (−) | 0.75 | 0.862 |
| P$MYCL | Myc-like basic helix-loop-helix binding factors | P$MYCRS.01 | 0.93 | 739-757 | (−) | 0.86 | 0.943 |
| P$OPAQ | Opaque-2 like transcriptional activators | P$GCN4.01 | 0.81 | 745-761 | (−) | 1 | 0.85 |
| P$AREF | Auxin response element | P$ARE.01 | 0.93 | 747-759 | (+) | 1 | 0.941 |
| P$TEFB | TEF-box | P$TEF1.01 | 0.76 | 783-803 | (−) | 0.84 | 0.78 |
| P$MYBL | MYB-like proteins | P$CARE.01 | 0.83 | 786-802 | (−) | 1 | 0.876 |
| P$LEGB | Legumin Box family | P$RY.01 | 0.87 | 788-814 | (−) | 1 | 0.929 |
| P$LEGB | Legumin Box family | P$RY.01 | 0.87 | 791-817 | (+) | 1 | 0.984 |
| P$ROOT | Root hair-specific cis-elements in angiosperms | P$RHE.01 | 0.77 | 796-820 | (+) | 1 | 0.812 |
| P$GBOX | Plant G-box/C-box bZIP proteins | P$CPRF.01 | 0.95 | 803-823 | (−) | 1 | 0.989 |
| P$GBOX | Plant G-box/C-box bZIP proteins | P$CPRF.01 | 0.95 | 804-824 | (+) | 1 | 0.98 |
| P$MYCL | Myc-like basic helix-loop-helix binding factors | P$MYCRS.01 | 0.93 | 804-822 | (−) | 1 | 0.956 |
| P$ABRE | ABA response elements | P$ABRE.01 | 0.82 | 805-821 | (+) | 1 | 0.874 |
| P$MYCL | Myc-like basic helix-loop-helix binding factors | P$PIF3.01 | 0.82 | 805-823 | (+) | 1 | 0.914 |
| P$OPAQ | Opaque-2 like transcriptional activators | P$RITA1.01 | 0.95 | 805-821 | (−) | 1 | 0.992 |
| P$ABRE | ABA response elements | P$ABF1.03 | 0.82 | 806-822 | (−) | 1 | 0.977 |
| P$OPAQ | Opaque-2 like transcriptional activators | P$RITA1.01 | 0.95 | 806-822 | (+) | 1 | 0.973 |
| P$OCSE | Enhancer element first identified in the promoter of the octopine synthase gene (OCS) of the Agrobacterium tumefaciens T-DNA | P$OCSTF.01 | 0.73 | 809-829 | (−) | 0.85 | 0.747 |
| P$GTBX | GT-box elements | P$S1F.01 | 0.79 | 823-839 | (−) | 1 | 0.794 |
| P$LFYB | LFY binding site | P$LFY.01 | 0.93 | 839-851 | (−) | 0.91 | 0.935 |
| P$LEGB | Legumin Box family | P$RY.01 | 0.87 | 840-866 | (−) | 1 | 0.948 |
| P$LEGB | Legumin Box family | P$RY.01 | 0.87 | 843-869 | (+) | 1 | 0.966 |
| P$LEGB | Legumin Box family | P$IDE1.01 | 0.77 | 847-873 | (+) | 1 | 0.779 |
| P$GBOX | Plant G-box/C-box bZIP proteins | P$BZIP910.01 | 0.77 | 855-875 | (−) | 0.75 | 0.856 |
| P$GBOX | Plant G-box/C-box bZIP proteins | P$ROM.01 | 0.85 | 856-876 | (+) | 1 | 1 |
| P$ABRE | ABA response elements | P$ABF1.03 | 0.82 | 858-874 | (−) | 0.75 | 0.857 |

TABLE 1-continued

Boxes and Motifs identified in the starting sequence of the PvARC5 promoter
PvARC5 promotor

| Family | Further Family Information | Matrix | Opt. | Position Position from-to | Strand | Core sim. | Matrix sim. |
|---|---|---|---|---|---|---|---|
| P$GBOX | Plant G-box/C-box bZIP proteins | P$BZIP910.02 | 0.84 | 861-881 | (−) | 0.75 | 0.862 |
| P$SALT | Salt/drought responsive elements | P$ALFIN1.02 | 0.95 | 871-885 | (−) | 1 | 0.963 |
| P$LEGB | Legumin Box family | P$RY.01 | 0.87 | 895-921 | (+) | 1 | 0.927 |
| P$GBOX | Plant G-box/C-box bZIP proteins | P$BZIP910.01 | 0.77 | 907-927 | (−) | 0.75 | 0.856 |
| P$GBOX | Plant G-box/C-box bZIP proteins | P$ROM.01 | 0.85 | 908-928 | (+) | 1 | 0.938 |
| P$ABRE | ABA response elements | P$ABF1.03 | 0.82 | 910-926 | (−) | 0.75 | 0.857 |
| P$GBOX | Plant G-box/C-box bZIP proteins | P$BZIP910.02 | 0.84 | 913-933 | (−) | 0.75 | 0.871 |
| P$MADS | MADS box proteins | P$SQUA.01 | 0.90 | 960-980 | (−) | 1 | 0.908 |
| P$L1BX | L1 box, motif for L1 layer-specific expression | P$PDF2.01 | 0.85 | 963-979 | (+) | 1 | 0.856 |
| P$LREM | Light responsive element motif, not modulated by different light qualities | P$RAP22.01 | 0.85 | 972-982 | (+) | 1 | 0.858 |
| O$PTBP | Plant TATA binding protein factor | O$PTATA.01 | 0.88 | 974-988 | (−) | 0.83 | 0.886 |
| O$VTBP | Vertebrate TATA binding protein factor | O$ATATA.01 | 0.78 | 974-990 | (+) | 0.75 | 0.83 |
| O$VTBP | Vertebrate TATA binding protein factor | O$MTATA.01 | 0.84 | 976-992 | (+) | 1 | 0.843 |
| P$MYBL | MYB-like proteins | P$MYBPH3.02 | 0.76 | 983-999 | (−) | 1 | 0.787 |
| P$SUCB | Sucrose box | P$SUCROSE.01 | 0.81 | 984-1002 | (−) | 1 | 0.818 |
| P$AHBP | *Arabidopsis* homeobox protein | P$ATHB1.01 | 0.90 | 991-1001 | (+) | 1 | 0.989 |
| P$AHBP | *Arabidopsis* homeobox protein | P$HAHB4.01 | 0.87 | 991-1001 | (−) | 1 | 0.943 |
| P$HMGF | High mobility group factors | P$HMG_IY.01 | 0.89 | 992-1006 | (+) | 1 | 0.913 |
| P$SPF1 | Sweet potato DNA-binding factor with two WRKY-domains | P$SP8BF.01 | 0.87 | 1003-1015 | (+) | 1 | 0.881 |
| P$OCSE | Enhancer element first identified in the promoter of the octopine synthase gene (OCS) of the Agrobacterium tumefaciens T-DNA | P$OCSTF.01 | 0.73 | 1004-1024 | (+) | 1 | 0.776 |
| P$GBOX | Plant G-box/C-box bZIP proteins | P$UPRE.01 | 0.86 | 1009-1029 | (−) | 1 | 0.974 |
| P$GBOX | Plant G-box/C-box bZIP proteins | P$TGA1.01 | 0.90 | 1010-1030 | (+) | 1 | 0.991 |
| P$ABRE | ABA response elements | P$ABF1.03 | 0.82 | 1011-1027 | (+) | 1 | 0.828 |
| P$OPAQ | Opaque-2 like transcriptional activators | P$O2.01 | 0.87 | 1011-1027 | (−) | 1 | 0.99 |
| P$OPAQ | Opaque-2 like transcriptional activators | P$O2_GCN4.01 | 0.81 | 1012-1028 | (+) | 0.95 | 0.893 |

TABLE 1-continued

Boxes and Motifs identified in the starting sequence of the PvARC5 promoter
PvARC5 promotor

| Family | Further Family Information | Matrix | Opt. | Position Position from-to | Strand | Core sim. | Matrix sim. |
|---|---|---|---|---|---|---|---|
| P$ROOT | Root hair-specific cis-elements in angiosperms | P$RHE.01 | 0.77 | 1013-1037 | (−) | 1 | 0.771 |
| P$LEGB | Legumin Box family | P$LEGB.01 | 0.65 | 1025-1051 | (+) | 1 | 0.656 |
| P$AHBP | *Arabidopsis* homeobox protein | P$ATHB5.01 | 0.89 | 1042-1052 | (+) | 0.83 | 0.902 |
| P$AHBP | *Arabidopsis* homeobox protein | P$ATHB5.01 | 0.89 | 1042-1052 | (−) | 1 | 1 |
| P$GTBX | GT-box elements | P$SBF1.01 | 0.87 | 1045-1061 | (+) | 1 | 0.904 |
| O$INRE | Core promoter initiator elements | O$DINR.01 | 0.94 | 1070-1080 | (−) | 0.97 | 0.949 |
| P$CCAF | Circadian control factors | P$CCA1.01 | 0.85 | 1093-1107 | (−) | 1 | 0.952 |
| P$L1BX | L1 box, motif for L1 layer-specific expression | P$ATML1.01 | 0.82 | 1098-1114 | (−) | 0.75 | 0.843 |
| P$CARM | CA-rich motif | P$CARICH.01 | 0.78 | 1102-1120 | (−) | 1 | 0.791 |
| P$MADS | MADS box proteins | P$SQUA.01 | 0.90 | 1108-1128 | (−) | 1 | 0.928 |
| O$PTBP | Plant TATA binding protein factor | O$PTATA.01 | 0.88 | 1111-1125 | (+) | 1 | 0.961 |
| O$VTBP | Vertebrate TATA binding protein factor | O$VTATA.01 | 0.90 | 1112-1128 | (+) | 1 | 0.968 |
| P$LEGB | Legumin Box family | P$RY.01 | 0.87 | 1130-1156 | (−) | 1 | 0.922 |
| P$AHBP | *Arabidopsis* homeobox protein | P$WUS.01 | 0.94 | 1135-1145 | (+) | 1 | 1 |
| P$LEGB | Legumin Box family | P$RY.01 | 0.87 | 1138-1164 | (−) | 1 | 0.914 |
| P$ROOT | Root hair-specific cis-elements in angiosperms | P$RHE.01 | 0.77 | 1138-1162 | (+) | 0.75 | 0.794 |
| P$L1BX | L1 box, motif for L1 layer-specific expression | P$ATML1.01 | 0.82 | 1141-1157 | (+) | 0.75 | 0.833 |

TABLE 2

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.
PvARC5 promotor permutated

| Family | Further Family Information | Matrix | Opt. | Position from-to | Strand | Core sim. | Matrix sim. |
|---|---|---|---|---|---|---|---|
| P$PSRE | Pollen-specific regulatory elements | P$GAAA.01 | 0.83 | 9-25 | (+) | 1 | 0.862 |
| P$IDDF | ID domain factors | P$ID1.01 | 0.92 | 36-48 | (−) | 1 | 0.922 |
| P$MYBL | MYB-like proteins | P$ATMYB77.01 | 0.87 | 47-63 | (+) | 1 | 0.887 |
| P$RAV5 | 5'-part of bipartite RAV1 binding site | P$RAV1-5.01 | 0.96 | 48-58 | (+) | 1 | 0.96 |
| P$MYBL | MYB-like proteins | P$GAMYB.01 | 0.91 | 52-68 | (−) | 1 | 0.932 |
| P$STKM | Storekeeper motif | P$STK.01 | 0.85 | 58-72 | (+) | 0.79 | 0.894 |
| P$MYBL | MYB-like proteins | P$MYBPH3.01 | 0.80 | 59-75 | (+) | 0.75 | 0.806 |
| P$L1BX | L1 box, motif for L1 layer-specific expression | P$ATML1.02 | 0.76 | 62-78 | (+) | 0.89 | 0.791 |
| O$INRE | Core promoter initiator elements | O$DINR.01 | 0.94 | 75-85 | (+) | 0.97 | 0.988 |
| P$AHBP | *Arabidopsis* homeobox protein | P$WUS.01 | 0.94 | 84-94 | (−) | 1 | 0.963 |

TABLE 2-continued

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.
PvARC5 promotor permutated

| Family | Further Family Information | Matrix | Opt. | Position from-to | Strand | Core sim. | Matrix sim. |
|---|---|---|---|---|---|---|---|
| P$MIIG | MYB IIG-type binding sites | P$PALBOXL.01 | 0.80 | 87-101 | (+) | 0.84 | 0.806 |
| P$NCS1 | Nodulin consensus sequence 1 | P$NCS1.01 | 0.85 | 106-116 | (+) | 1 | 0.99 |
| P$GAPB | GAP-Box (light response elements) | P$GAP.01 | 0.88 | 108-122 | (+) | 0.81 | 0.884 |
| P$AHBP | *Arabidopsis* homeobox protein | P$WUS.01 | 0.94 | 110-120 | (−) | 1 | 0.963 |
| P$IBOX | Plant I-Box sites | P$GATA.01 | 0.93 | 121-137 | (−) | 1 | 0.939 |
| P$GAGA | GAGA elements | P$GAGABP.01 | 0.75 | 125-149 | (−) | 0.75 | 0.764 |
| P$NCS2 | Nodulin consensus sequence 2 | P$NCS2.01 | 0.79 | 126-140 | (+) | 1 | 0.799 |
| P$AHBP | *Arabidopsis* homeobox protein | P$HAHB4.01 | 0.87 | 144-154 | (−) | 1 | 0.923 |
| P$AHBP | *Arabidopsis* homeobox protein | P$BLR.01 | 0.90 | 147-157 | (−) | 1 | 0.928 |
| O$VTBP | Vertebrate TA-TA binding protein factor | O$ATATA.01 | 0.78 | 149-165 | (+) | 1 | 0.78 |
| O$VTBP | Vertebrate TA-TA binding protein factor | O$LTATA.01 | 0.82 | 151-167 | (+) | 1 | 0.825 |
| P$NCS1 | Nodulin consensus sequence 1 | P$NCS1.01 | 0.85 | 164-174 | (−) | 1 | 0.898 |
| P$L1BX | L1 box, motif for L1 layer-specific expression | P$ATML1.01 | 0.82 | 175-191 | (+) | 0.75 | 0.872 |
| P$AHBP | *Arabidopsis* homeobox protein | P$ATHB5.01 | 0.89 | 177-187 | (+) | 0.83 | 0.902 |
| P$AHBP | *Arabidopsis* homeobox protein | P$ATHB5.01 | 0.89 | 177-187 | (−) | 1 | 1 |
| O$VTBP | Vertebrate TA-TA binding protein factor | O$ATATA.01 | 0.78 | 184-200 | (+) | 0.75 | 0.797 |
| P$TELO | Telo box (plant interstitial telomere motifs) | P$ATPURA.01 | 0.85 | 186-200 | (−) | 0.75 | 0.857 |
| P$PSRE | Pollen-specific regulatory elements | P$GAAA.01 | 0.83 | 188-204 | (−) | 1 | 0.843 |
| P$NCS2 | Nodulin consensus sequence 2 | P$NCS2.01 | 0.79 | 213-227 | (−) | 1 | 0.826 |
| P$IBOX | Plant I-Box sites | P$GATA.01 | 0.93 | 221-237 | (+) | 1 | 1 |
| P$SUCB | Sucrose box | P$SUCROSE.01 | 0.81 | 233-251 | (+) | 0.75 | 0.824 |
| P$MYBL | MYB-like proteins | P$MYBPH3.02 | 0.76 | 238-254 | (+) | 0.82 | 0.798 |
| P$SUCB | Sucrose box | P$SUCROSE.01 | 0.81 | 243-261 | (−) | 0.75 | 0.824 |
| P$AHBP | *Arabidopsis* homeobox protein | P$HAHB4.01 | 0.87 | 250-260 | (+) | 1 | 0.892 |
| P$PSRE | Pollen-specific regulatory elements | P$GAAA.01 | 0.83 | 257-273 | (+) | 1 | 0.881 |
| P$NCS1 | Nodulin consensus sequence 1 | P$NCS1.01 | 0.85 | 261-271 | (−) | 1 | 0.851 |
| P$MYBL | MYB-like proteins | P$MYBPH3.02 | 0.76 | 264-280 | (+) | 1 | 0.774 |
| O$VTBP | Vertebrate TA-TA binding protein factor | O$ATATA.01 | 0.78 | 267-283 | (+) | 1 | 0.872 |
| P$MYBL | MYB-like proteins | P$GAMYB.01 | 0.91 | 289-305 | (−) | 1 | 0.919 |
| P$SPF1 | Sweet potato DNA-binding factor with two WRKY-domains | P$SP8BF.01 | 0.87 | 298-310 | (−) | 1 | 0.872 |
| P$BRRE | Brassinosteroid (BR) response element | P$BZR1.01 | 0.95 | 303-319 | (−) | 1 | 0.953 |
| P$GBOX | Plant G-box/C-box bZIP proteins | P$TGA1.01 | 0.90 | 327-347 | (−) | 1 | 0.909 |
| P$GTBX | GT-box elements | P$GT1.01 | 0.85 | 337-353 | (+) | 1 | 0.854 |
| P$IBOX | Plant I-Box sites | P$GATA.01 | 0.93 | 337-353 | (−) | 1 | 0.935 |

TABLE 2-continued

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.
PvARC5 promotor permutated

| Family | Further Family Information | Matrix | Opt. | Position from-to | Strand | Core sim. | Matrix sim. |
|---|---|---|---|---|---|---|---|
| P$PSRE | Pollen-specific regulatory elements | P$GAAA.01 | 0.83 | 342-358 | (−) | 1 | 0.896 |
| P$AHBP | *Arabidopsis* homeobox protein | P$ATHB9.01 | 0.77 | 343-353 | (−) | 1 | 0.869 |
| P$NCS1 | Nodulin consensus sequence 1 | P$NCS1.01 | 0.85 | 343-353 | (−) | 0.88 | 0.915 |
| P$GTBX | GT-box elements | P$S1F.01 | 0.79 | 344-360 | (−) | 0.75 | 0.827 |
| O$INRE | Core promoter initiator elements | O$DINR.01 | 0.94 | 345-355 | (+) | 0.97 | 0.945 |
| P$OPAQ | Opaque-2 like transcriptional activators | P$O2.01 | 0.87 | 351-367 | (−) | 1 | 0.919 |
| P$GTBX | GT-box elements | P$S1F.01 | 0.79 | 362-378 | (−) | 0.75 | 0.797 |
| P$AHBP | *Arabidopsis* homeobox protein | P$ATHB9.01 | 0.77 | 367-377 | (−) | 1 | 0.788 |
| P$AHBP | *Arabidopsis* homeobox protein | P$HAHB4.01 | 0.87 | 367-377 | (+) | 1 | 0.926 |
| P$GTBX | GT-box elements | P$SBF1.01 | 0.87 | 367-383 | (+) | 1 | 0.894 |
| P$L1BX | L1 box, motif for L1 layer-specific expression | P$ATML1.01 | 0.82 | 369-385 | (+) | 1 | 0.827 |
| P$AHBP | *Arabidopsis* homeobox protein | P$WUS.01 | 0.94 | 371-381 | (−) | 1 | 1 |
| P$MYBL | MYB-like proteins | P$ATMYB77.01 | 0.87 | 376-392 | (−) | 0.86 | 0.924 |
| P$CCAF | Circadian control factors | P$CCA1.01 | 0.85 | 387-401 | (+) | 1 | 0.851 |
| P$SUCB | Sucrose box | P$SUCROSE.01 | 0.81 | 392-410 | (+) | 1 | 0.864 |
| O$VTBP | Vertebrate TATA binding protein factor | O$LTATA.01 | 0.82 | 396-412 | (−) | 1 | 0.852 |
| P$LREM | Light responsive element motif, not modulated by different light qualities | P$RAP22.01 | 0.85 | 397-407 | (+) | 1 | 0.911 |
| P$AHBP | *Arabidopsis* homeobox protein | P$HAHB4.01 | 0.87 | 401-411 | (−) | 1 | 0.916 |
| P$MYBL | MYB-like proteins | P$WER.01 | 0.87 | 403-419 | (−) | 1 | 0.9 |
| P$MYBS | MYB proteins with single DNA binding repeat | P$OSMYBS.01 | 0.82 | 416-432 | (+) | 0.75 | 0.829 |
| P$L1BX | L1 box, motif for L1 layer-specific expression | P$ATML1.01 | 0.82 | 420-436 | (−) | 0.75 | 0.821 |
| O$VTBP | Vertebrate TATA binding protein factor | O$ATATA.01 | 0.78 | 426-442 | (+) | 0.75 | 0.819 |
| P$GTBX | GT-box elements | P$SBF1.01 | 0.87 | 426-442 | (−) | 1 | 0.902 |
| P$MYBL | MYB-like proteins | P$MYBPH3.02 | 0.76 | 428-444 | (−) | 1 | 0.772 |
| P$OCSE | Enhancer element first identified in the promoter of the octopine synthase gene (OCS) of the *Agrobacterium tumefaciens* T-DNA | P$OCSL.01 | 0.69 | 428-448 | (+) | 0.77 | 0.692 |
| P$TELO | Telo box (plant interstitial telomere motifs) | P$ATPURA.01 | 0.85 | 440-454 | (−) | 0.75 | 0.854 |
| P$AHBP | *Arabidopsis* homeobox protein | P$ATHB5.01 | 0.89 | 455-465 | (+) | 0.83 | 0.902 |
| P$AHBP | *Arabidopsis* homeobox protein | P$HAHB4.01 | 0.87 | 455-465 | (−) | 1 | 0.979 |
| P$SUCB | Sucrose box | P$SUCROSE.01 | 0.81 | 461-479 | (−) | 0.75 | 0.815 |
| P$AHBP | *Arabidopsis* homeobox protein | P$HAHB4.01 | 0.87 | 468-478 | (+) | 1 | 0.901 |

TABLE 2-continued

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.
PvARC5 promotor permutated

| Family | Further Family Information | Matrix | Opt. | Position from-to | Strand | Core sim. | Matrix sim. |
|---|---|---|---|---|---|---|---|
| O$VTBP | Vertebrate TA-TA binding protein factor | O$VTATA.01 | 0.90 | 473-489 | (−) | 1 | 0.913 |
| O$PTBP | Plant TATA binding protein factor | O$PTATA.01 | 0.88 | 476-490 | (−) | 1 | 0.889 |
| O$VTBP | Vertebrate TA-TA binding protein factor | O$ATATA.01 | 0.78 | 489-505 | (−) | 0.75 | 0.825 |
| P$L1BX | L1 box, motif for L1 layer-specific expression | P$HDG9.01 | 0.77 | 491-507 | (+) | 1 | 0.791 |
| P$HMGF | High mobility group factors | P$HMG_IY.01 | 0.89 | 492-506 | (−) | 1 | 0.902 |
| P$CCAF | Circadian control factors | P$CCA1.01 | 0.85 | 498-512 | (+) | 0.76 | 0.862 |
| P$HMGF | High mobility group factors | P$HMG_IY.01 | 0.89 | 499-513 | (−) | 1 | 0.909 |
| P$SUCB | Sucrose box | P$SUCROSE.01 | 0.81 | 499-517 | (−) | 1 | 0.827 |
| P$GTBX | GT-box elements | P$SBF1.01 | 0.87 | 509-525 | (−) | 1 | 0.885 |
| P$SPF1 | Sweet potato DNA-binding factor with two WRKY-domains | P$SP8BF.01 | 0.87 | 520-532 | (−) | 1 | 0.905 |
| P$WBXF | W Box family | P$WRKY.01 | 0.92 | 526-542 | (−) | 1 | 0.936 |
| P$GARP | Myb-related DNA binding proteins (Golden2, ARR, Psr) | P$ARR10.01 | 0.97 | 540-548 | (+) | 1 | 0.976 |
| P$AHBP | *Arabidopsis* homeobox protein | P$ATHB9.01 | 0.77 | 558-568 | (−) | 1 | 0.775 |
| P$L1BX | L1 box, motif for L1 layer-specific expression | P$PDF2.01 | 0.85 | 558-574 | (−) | 1 | 0.865 |
| P$NCS1 | Nodulin consensus sequence 1 | P$NCS1.01 | 0.85 | 558-568 | (−) | 0.88 | 0.927 |
| P$EINL | Ethylen insensitive 3 like factors | P$TEIL.01 | 0.92 | 572-580 | (+) | 1 | 0.921 |
| P$SBPD | SBP-domain proteins | P$SBP.01 | 0.88 | 573-589 | (+) | 1 | 0.885 |
| P$AHBP | *Arabidopsis* homeobox protein | P$ATHB5.01 | 0.89 | 583-593 | (+) | 0.94 | 0.977 |
| P$AHBP | *Arabidopsis* homeobox protein | P$ATHB5.01 | 0.89 | 583-593 | (−) | 0.83 | 0.94 |
| P$MYCL | Myc-like basic helix-loop-helix binding factors | P$MYCRS.01 | 0.93 | 591-609 | (−) | 0.86 | 0.958 |
| P$OPAQ | Opaque-2 like transcriptional activators | P$O2_GCN4.01 | 0.81 | 593-609 | (+) | 1 | 0.838 |
| O$VTBP | Vertebrate TA-TA binding protein factor | O$VTATA.02 | 0.89 | 603-619 | (+) | 1 | 0.89 |
| P$L1BX | L1 box, motif for L1 layer-specific expression | P$HDG9.01 | 0.77 | 607-623 | (+) | 1 | 0.772 |
| P$IBOX | Plant I-Box sites | P$IBOX.01 | 0.81 | 610-626 | (+) | 0.75 | 0.824 |
| P$MYBS | MYB proteins with single DNA binding repeat | P$MYBST1.01 | 0.90 | 613-629 | (−) | 1 | 0.953 |
| P$IBOX | Plant I-Box sites | P$GATA.01 | 0.93 | 616-632 | (+) | 1 | 0.942 |
| P$TEFB | TEF-box | P$TEF1.01 | 0.76 | 616-636 | (+) | 0.96 | 0.778 |
| P$MYBS | MYB proteins with single DNA binding repeat | P$TAMYB80.01 | 0.83 | 625-641 | (−) | 1 | 0.861 |

TABLE 2-continued

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.
PvARC5 promotor permutated

| Family | Further Family Information | Matrix | Opt. | Position from-to | Strand | Core sim. | Matrix sim. |
|---|---|---|---|---|---|---|---|
| O$PTBP | Plant TATA binding protein factor | O$PTATA.02 | 0.90 | 631-645 | (+) | 1 | 0.927 |
| O$PTBP | Plant TATA binding protein factor | O$PTATA.02 | 0.90 | 632-646 | (−) | 1 | 0.929 |
| P$L1BX | L1 box, motif for L1 layer-specific expression | P$HDG9.01 | 0.77 | 648-664 | (+) | 1 | 0.822 |
| P$HMGF | High mobility group factors | P$HMG_IY.01 | 0.89 | 649-663 | (−) | 1 | 0.923 |
| P$DOFF | DNA binding with one finger (DOF) | P$PBF.01 | 0.97 | 654-670 | (+) | 1 | 0.979 |
| P$LREM | Light responsive element motif, not modulated by different light qualities | P$RAP22.01 | 0.85 | 682-692 | (−) | 1 | 0.975 |
| P$MYBL | MYB-like proteins | P$CARE.01 | 0.83 | 689-705 | (+) | 1 | 0.884 |
| P$TEFB | TEF-box | P$TEF1.01 | 0.76 | 696-716 | (−) | 0.84 | 0.779 |
| P$MYBL | MYB-like proteins | P$CARE.01 | 0.83 | 699-715 | (−) | 1 | 0.88 |
| P$LEGB | Legumin Box family | P$RY.01 | 0.87 | 704-730 | (+) | 1 | 0.94 |
| P$GBOX | Plant G-box/C-box bZIP proteins | P$BZIP910.01 | 0.77 | 716-736 | (−) | 0.75 | 0.856 |
| P$GBOX | Plant G-box/C-box bZIP proteins | P$ROM.01 | 0.85 | 717-737 | (+) | 1 | 1 |
| P$ABRE | ABA response elements | P$ABF1.03 | 0.82 | 719-735 | (−) | 0.75 | 0.857 |
| P$GBOX | Plant G-box/C-box bZIP proteins | P$BZIP910.02 | 0.84 | 722-742 | (−) | 0.75 | 0.862 |
| P$GBOX | Plant G-box/C-box bZIP proteins | P$HBP1B.01 | 0.83 | 734-754 | (+) | 0.77 | 0.852 |
| P$MYCL | Myc-like basic helix-loop-helix binding factors | P$MYCRS.01 | 0.93 | 739-757 | (−) | 0.86 | 0.953 |
| P$ABRE | ABA response elements | P$ABF1.01 | 0.79 | 741-757 | (−) | 0.75 | 0.796 |
| P$OPAQ | Opque-2 like transcriptional activators | P$O2_GCN4.01 | 0.81 | 741-757 | (+) | 1 | 0.871 |
| P$OPAQ | Opaque-2 like transcriptional activators | P$GCN4.01 | 0.81 | 745-761 | (−) | 1 | 0.85 |
| P$AREF | Auxin response element | P$ARE.01 | 0.93 | 747-759 | (+) | 1 | 0.941 |
| P$MYBL | MYB-like proteins | P$GAMYB.01 | 0.91 | 754-770 | (+) | 1 | 0.933 |
| O$INRE | Core promoter initiator elements | O$DINR.01 | 0.94 | 757-767 | (+) | 1 | 0.943 |
| P$WBXF | W Box family | P$WRKY.01 | 0.92 | 780-796 | (+) | 1 | 0.942 |
| P$TEFB | TEF-box | P$TEF1.01 | 0.76 | 783-803 | (−) | 0.84 | 0.779 |
| P$MYBL | MYB-like proteins | P$CARE.01 | 0.83 | 786-802 | (−) | 1 | 0.876 |
| P$LEGB | Legumin Box family | P$RY.01 | 0.87 | 788-814 | (−) | 1 | 0.929 |
| P$LEGB | Legumin Box family | P$RY.01 | 0.87 | 791-817 | (+) | 1 | 0.984 |
| P$ROOT | Root hair-specific cis-elements in angiosperms | P$RHE.01 | 0.77 | 796-820 | (+) | 1 | 0.812 |
| P$GBOX | Plant G-box/C-box bZIP proteins | P$CPRF.01 | 0.95 | 803-823 | (−) | 1 | 0.989 |
| P$GBOX | Plant G-box/C-box bZIP proteins | P$CPRF.01 | 0.95 | 804-824 | (+) | 1 | 0.98 |
| P$MYCL | Myc-like basic helix-loop-helix binding factors | P$MYCRS.01 | 0.93 | 804-822 | (−) | 1 | 0.956 |
| P$ABRE | ABA response elements | P$ABRE.01 | 0.82 | 805-821 | (+) | 1 | 0.874 |

TABLE 2-continued

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.
PvARC5 promotor permutated

| Family | Further Family Information | Matrix | Opt. | Position from-to | Strand | Core sim. | Matrix sim. |
|---|---|---|---|---|---|---|---|
| P$MYCL | Myc-like basic helix-loop-helix binding factors | P$PIF3.01 | 0.82 | 805-823 | (+) | 1 | 0.922 |
| P$OPAQ | Opaque-2 like transcriptional activators | P$RITA1.01 | 0.95 | 805-821 | (−) | 1 | 0.992 |
| P$ABRE | ABA response elements | P$ABF1.03 | 0.82 | 806-822 | (−) | 1 | 0.977 |
| P$OPAQ | Opaque-2 like transcriptional activators | P$RITA1.01 | 0.95 | 806-822 | (+) | 1 | 0.973 |
| P$OCSE | Enhancer element first identified in the promoter of the octopine synthase gene (OCS) of the *Agrobacterium tumefaciens* T-DNA | P$OCSL.01 | 0.69 | 809-829 | (−) | 1 | 0.819 |
| P$GTBX | GT-box elements | P$S1F.01 | 0.79 | 823-839 | (−) | 1 | 0.802 |
| P$LFYB | LFY binding site | P$LFY.01 | 0.93 | 839-851 | (−) | 0.91 | 0.936 |
| P$LEGB | Legumin Box family | P$RY.01 | 0.87 | 840-866 | (−) | 1 | 0.948 |
| P$LEGB | Legumin Box family | P$RY.01 | 0.87 | 843-869 | (+) | 1 | 0.966 |
| P$LEGB | Legumin Box family | P$IDE1.01 | 0.77 | 847-873 | (+) | 1 | 0.779 |
| P$GBOX | Plant G-box/C-box bZIP proteins | P$BZIP910.01 | 0.77 | 855-875 | (−) | 0.75 | 0.856 |
| P$GBOX | Plant G-box/C-box bZIP proteins | P$ROM.01 | 0.85 | 856-876 | (+) | 1 | 1 |
| P$ABRE | ABA response elements | P$ABF1.03 | 0.82 | 858-874 | (−) | 0.75 | 0.857 |
| P$GCCF | GCC box family | P$ERE_JERE.01 | 0.85 | 870-882 | (−) | 0.81 | 0.86 |
| P$HEAT | Heat shock factors | P$HSE.01 | 0.81 | 880-894 | (−) | 1 | 0.827 |
| P$MYBS | MYB proteins with single DNA binding repeat | P$ZMMRP1.01 | 0.79 | 881-897 | (+) | 0.81 | 0.867 |
| P$LEGB | Legumin Box family | P$RY.01 | 0.87 | 895-921 | (+) | 1 | 0.924 |
| P$GBOX | Plant G-box/C-box bZIP proteins | P$BZIP910.01 | 0.77 | 907-927 | (−) | 0.75 | 0.856 |
| P$GBOX | Plant G-box/C-box bZIP proteins | P$ROM.01 | 0.85 | 908-928 | (+) | 1 | 0.938 |
| P$ABRE | ABA response elements | P$ABF1.03 | 0.82 | 910-926 | (−) | 0.75 | 0.864 |
| P$GBOX | Plant G-box/C-box bZIP proteins | P$BZIP910.02 | 0.84 | 913-933 | (−) | 0.75 | 0.871 |
| P$SBPD | SBP-domain proteins | P$SBP.01 | 0.88 | 939-955 | (+) | 1 | 0.887 |
| P$EINL | Ethylen insensitive 3 like factors | P$TEIL.01 | 0.92 | 942-950 | (+) | 0.84 | 0.922 |
| P$MADS | MADS box proteins | P$SQUA.01 | 0.90 | 960-980 | (−) | 1 | 0.908 |
| P$L1BX | L1 box, motif for L1 layer-specific expression | P$PDF2.01 | 0.85 | 963-979 | (+) | 1 | 0.856 |
| P$LREM | Light responsive element motif, not modulated by different light qualities | P$RAP22.01 | 0.85 | 972-982 | (+) | 1 | 0.858 |

TABLE 2-continued

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.
PvARC5 promotor permutated

| Family | Further Family Information | Matrix | Opt. | Position from-to | Strand | Core sim. | Matrix sim. |
|---|---|---|---|---|---|---|---|
| O$PTBP | Plant TATA binding protein factor | O$PTATA.01 | 0.88 | 974-988 | (−) | 0.83 | 0.905 |
| O$VTBP | Vertebrate TA-TA binding protein factor | O$ATATA.01 | 0.78 | 974-990 | (+) | 0.75 | 0.83 |
| O$VTBP | Vertebrate TA-TA binding protein factor | O$MTATA.01 | 0.84 | 976-992 | (+) | 1 | 0.855 |
| P$MYBL | MYB-like proteins | P$MYBPH3.02 | 0.76 | 983-999 | (−) | 1 | 0.867 |
| P$SUCB | Sucrose box | P$SUCROSE.01 | 0.81 | 984-1002 | (−) | 1 | 0.81 |
| P$AHBP | *Arabidopsis* homeobox protein | P$ATHB1.01 | 0.90 | 991-1001 | (+) | 1 | 0.989 |
| P$AHBP | *Arabidopsis* homeobox protein | P$HAHB4.01 | 0.87 | 991-1001 | (−) | 1 | 0.943 |
| P$HMGF | High mobility group factors | P$HMG_IY.01 | 0.89 | 992-1006 | (+) | 1 | 0.913 |
| P$OCSE | Enhancer element first identified in the promoter of the octopine synthase gene (OCS) of the *Agrobacterium tumefaciens* T-DNA | P$OCSL.01 | 0.69 | 1004-1024 | (+) | 1 | 0.827 |
| P$GBOX | Plant G-box/C-box bZIP proteins | P$UPRE.01 | 0.86 | 1009-1029 | (−) | 1 | 0.974 |
| P$GBOX | Plant G-box/C-box bZIP proteins | P$TGA1.01 | 0.90 | 1010-1030 | (+) | 1 | 0.991 |
| P$ABRE | ABA response elements | P$ABF1.03 | 0.82 | 1011-1027 | (+) | 1 | 0.828 |
| P$OPAQ | Opaque-2 like transcriptional activators | P$O2.01 | 0.87 | 1011-1027 | (−) | 1 | 0.99 |
| P$OPAQ | Opaque-2 like transcriptional activators | P$O2_GCN4.01 | 0.81 | 1012-1028 | (+) | 0.95 | 0.893 |
| P$ROOT | Root hair-specific cis-elements in angiosperms | P$RHE.01 | 0.77 | 1013-1037 | (−) | 1 | 0.771 |
| P$LEGB | Legumin Box family | P$LEGB.01 | 0.65 | 1025-1051 | (+) | 1 | 0.656 |
| P$AHBP | *Arabidopsis* homeobox protein | P$ATHB5.01 | 0.89 | 1042-1052 | (+) | 0.83 | 0.902 |
| P$AHBP | *Arabidopsis* homeobox protein | P$ATHB5.01 | 0.89 | 1042-1052 | (−) | 1 | 1 |
| P$GTBX | GT-box elements | P$SBF1.01 | 0.87 | 1045-1061 | (+) | 1 | 0.888 |
| P$GTBX | GT-box elements | P$SBF1.01 | 0.87 | 1046-1062 | (−) | 1 | 0.888 |
| P$IBOX | Plant I-Box sites | P$GATA.01 | 0.93 | 1060-1076 | (+) | 1 | 0.949 |
| O$INRE | Core promoter initiator elements | O$DINR.01 | 0.94 | 1070-1080 | (−) | 0.97 | 0.949 |
| P$NACF | Plant specific NAC [NAM (no apical meristem), ATAF172, CUC2 (cup-shaped cotyledons 2)] transcription factors | P$TANAC69.01 | 0.68 | 1078-1100 | (+) | 1 | 0.775 |
| P$CCAF | Circadian control factors | P$CCA1.01 | 0.85 | 1093-1107 | (−) | 1 | 0.949 |
| P$MADS | MADS box proteins | P$SQUA.01 | 0.90 | 1097-1117 | (+) | 1 | 0.908 |
| P$CARM | CA-rich motif | P$CARICH.01 | 0.78 | 1102-1120 | (−) | 1 | 0.791 |
| P$MADS | MADS box proteins | P$SQUA.01 | 0.90 | 1108-1128 | (−) | 1 | 0.928 |

TABLE 2-continued

Boxes and Motifs identified in the permutated sequence of the PvARC5 promoter.
Preferably associated boxes are annotated in line 38, 43, 116, 121, 124, 128, 129, 137, 138,
143, 145, 146, 147, 151, 152, 153, 156, 162, 165, 175, 184, 186, 188, 203 and 205 of tables 1
and 2. Essential boxes are annotated in line 83, 111, 112, 172 and 201 of tables 1 and 2.

PvARC5 promotor permutated

| Family | Further Family Information | Matrix | Opt. | Position from-to | Strand | Core sim. | Matrix sim. |
|---|---|---|---|---|---|---|---|
| O$PTBP | Plant TATA binding protein factor | O$PTATA.01 | 0.88 | 1111-1125 | (+) | 1 | 0.961 |
| O$VTBP | Vertebrate TA-TA binding protein factor | O$VTATA.01 | 0.90 | 1112-1128 | (+) | 1 | 0.968 |
| P$LEGB | Legumin Box family | P$RY.01 | 0.87 | 1130-1156 | (−) | 1 | 0.932 |
| P$LEGB | Legumin Box family | P$RY.01 | 0.87 | 1138-1164 | (−) | 1 | 0.914 |
| P$ROOT | Root hair-specific cis-elements in angiosperms | P$RHE.01 | 0.77 | 1138-1162 | (+) | 0.75 | 0.794 |
| P$L1BX | L1 box, motif for L1 layer-specific expression | P$ATML1.01 | 0.82 | 1141-1157 | (+) | 0.75 | 0.833 |

TABLE 3

Boxes and Motifs identified in the starting sequence of the VfSBP promoter p-VfSBP (nativ)

| Family | Further Family Information | Matrix | Opt. | Position from-to | Strand | Core sim. | Matrix sim. |
|---|---|---|---|---|---|---|---|
| P$MYBS | MYB proteins with single DNA binding repeat | P$MYBST1.01 | 0.90 | 12-28 | (+) | 1 | 0.918 |
| P$GAGA | GAGA elements | P$BPC.01 | 1.00 | 25-49 | (−) | 1 | 1 |
| P$LEGB | Legumin Box family | P$IDE1.01 | 0.77 | 80-106 | (−) | 1 | 0.805 |
| P$GTBX | GT-box elements | P$GT3A.01 | 0.83 | 85-101 | (−) | 1 | 0.843 |
| P$PSRE | Pollen-specific regulatory elements | P$GAAA.01 | 0.83 | 101-117 | (−) | 1 | 0.883 |
| P$SPF1 | Sweet potato DNA-binding factor with two WRKY-domains | P$SP8BF.01 | 0.87 | 118-130 | (+) | 1 | 0.897 |
| P$GBOX | Plant G-box/C-box bZIP proteins | P$HBP1B.01 | 0.83 | 138-158 | (+) | 1 | 0.834 |
| P$MYBL | MYB-like proteins | P$MYBPH3.02 | 0.76 | 165-181 | (−) | 0.78 | 0.788 |
| P$NACF | Plant specific NAC [NAM (no apical meristem), ATAF172, CUC2 (cup-shaped cotyledons 2)] transcription factors | P$TANAC69.01 | 0.68 | 173-195 | (−) | 0.81 | 0.729 |
| P$MADS | MADS box proteins | P$AGL1.01 | 0.84 | 174-194 | (−) | 0.98 | 0.862 |
| P$MADS | MADS box proteins | P$AGL1.01 | 0.84 | 175-195 | (+) | 0.98 | 0.863 |
| P$TCPF | DNA-binding proteins with the plant specific TCP-domain | P$ATTCP20.01 | 0.94 | 189-201 | (+) | 1 | 0.968 |
| P$L1BX | L1 box, motif for L1 layer-specific expression | P$ATML1.02 | 0.76 | 194-210 | (−) | 0.89 | 0.8 |
| P$AHBP | *Arabidopsis* homeobox protein | P$BLR.01 | 0.90 | 198-208 | (+) | 0.83 | 0.936 |

TABLE 3-continued

Boxes and Motifs identified in the starting sequence of the VfSBP promoter
p-VfSBP (nativ)

| Family | Further Family Information | Matrix | Opt. | Position from-to | Strand | Core sim. | Matrix sim. |
|---|---|---|---|---|---|---|---|
| O$VTBP | Vertebrate TA-TA binding protein factor | O$ATATA.01 | 0.78 | 207-223 | (+) | 0.75 | 0.811 |
| P$EINL | Ethylen insensitive 3 like factors | P$TEIL.01 | 0.92 | 215-223 | (−) | 0.96 | 0.924 |
| P$GBOX | Plant G-box/C-box bZIP proteins | P$HBP1A.01 | 0.88 | 217-237 | (−) | 1 | 0.908 |
| P$GBOX | Plant G-box/C-box bZIP proteins | P$GBF1.01 | 0.94 | 218-238 | (+) | 1 | 0.963 |
| P$GTBX | GT-box elements | P$S1F.01 | 0.79 | 218-234 | (+) | 1 | 0.821 |
| P$ABRE | ABA response elements | P$ABF1.03 | 0.82 | 219-235 | (+) | 1 | 0.825 |
| P$ROOT | Root hair-specific cis-elements in angiosperms | P$RHE.01 | 0.77 | 221-245 | (−) | 1 | 0.803 |
| P$CE1F | Coupling element 1 binding factors | P$SBOX.01 | 0.87 | 222-234 | (−) | 0.78 | 0.916 |
| O$VTBP | Vertebrate TA-TA binding protein factor | O$VTATA.01 | 0.90 | 233-249 | (−) | 1 | 0.916 |
| O$PTBP | Plant TATA binding protein factor | O$PTATA.02 | 0.90 | 236-250 | (−) | 1 | 0.9 |
| P$AHBP | *Arabidopsis* homeobox protein | P$ATHB5.01 | 0.89 | 256-266 | (+) | 0.94 | 0.896 |
| P$NCS1 | Nodulin consensus sequence 1 | P$NCS1.01 | 0.85 | 256-266 | (−) | 0.88 | 0.871 |
| P$LREM | Light responsive element motif, not modulated by different light qualities | P$RAP22.01 | 0.85 | 290-300 | (−) | 1 | 0.931 |
| P$AGP1 | Plant GATA-type zinc finger protein | P$AGP1.01 | 0.91 | 292-302 | (−) | 1 | 0.984 |
| P$LREM | Light responsive element motif, not modulated by different light qualities | P$RAP22.01 | 0.85 | 306-316 | (+) | 1 | 0.938 |
| P$MYBL | MYB-like proteins | P$CARE.01 | 0.83 | 308-324 | (−) | 1 | 0.854 |
| P$CCAF | Circadian control factors | P$CCA1.01 | 0.85 | 354-368 | (+) | 1 | 0.895 |
| P$HEAT | Heat shock factors | P$HSE.01 | 0.81 | 375-389 | (−) | 1 | 0.861 |
| P$MYBL | MYB-like proteins | P$WER.01 | 0.87 | 392-408 | (−) | 1 | 0.87 |
| P$MYBL | MYB-like proteins | P$WER.01 | 0.87 | 394-410 | (+) | 1 | 0.95 |
| P$MSAE | M-phase-specific activator elements | P$MSA.01 | 0.80 | 395-409 | (−) | 0.75 | 0.808 |
| P$HEAT | Heat shock factors | P$HSE.01 | 0.81 | 415-429 | (+) | 1 | 0.811 |
| P$SUCB | Sucrose box | P$SUCROSE.01 | 0.81 | 421-439 | (−) | 0.75 | 0.852 |
| P$WBXF | W Box family | P$WRKY.01 | 0.92 | 426-442 | (+) | 1 | 0.939 |
| P$DOFF | DNA binding with one finger (DOF) | P$PBOX.01 | 0.75 | 431-447 | (−) | 0.76 | 0.782 |
| P$WBXF | W Box family | P$WRKY.01 | 0.92 | 453-469 | (+) | 1 | 0.958 |
| P$MYBL | MYB-like proteins | P$MYBPH3.02 | 0.76 | 468-484 | (−) | 0.82 | 0.849 |
| P$OPAQ | Opaque-2 like transcriptional activators | P$O2_GCN4.01 | 0.81 | 486-502 | (+) | 1 | 0.818 |
| P$OPAQ | Opaque-2 like transcriptional activators | P$O2.01 | 0.87 | 498-514 | (−) | 1 | 0.919 |
| P$HEAT | Heat shock factors | P$HSE.01 | 0.81 | 512-526 | (−) | 1 | 0.85 |
| P$WBXF | W Box family | P$WRKY.01 | 0.92 | 533-549 | (−) | 1 | 0.966 |
| P$WBXF | W Box family | P$WRKY.01 | 0.92 | 543-559 | (+) | 1 | 0.966 |

TABLE 3-continued

Boxes and Motifs identified in the starting sequence of the VfSBP promoter
p-VfSBP (nativ)

| Family | Further Family Information | Matrix | Opt. | Position from-to | Strand | Core sim. | Matrix sim. |
|---|---|---|---|---|---|---|---|
| P$WBXF | W Box family | P$ERE.01 | 0.89 | 562-578 | (+) | 1 | 0.972 |
| P$DOFF | DNA binding with one finger (DOF) | P$PBOX.01 | 0.75 | 614-630 | (+) | 0.76 | 0.766 |
| P$GTBX | GT-box elements | P$S1F.01 | 0.79 | 630-646 | (+) | 1 | 0.819 |
| P$AGP1 | Plant GATA-type zinc finger protein | P$AGP1.01 | 0.91 | 636-646 | (−) | 1 | 0.913 |
| P$AGP1 | Plant GATA-type zinc finger protein | P$AGP1.01 | 0.91 | 637-647 | (+) | 1 | 0.915 |
| P$HEAT | Heat shock factors | P$HSE.01 | 0.81 | 649-663 | (+) | 0.78 | 0.87 |
| P$HEAT | Heat shock factors | P$HSE.01 | 0.81 | 654-668 | (−) | 1 | 0.815 |
| O$INRE | Core promoter initiator elements | O$DINR.01 | 0.94 | 660-670 | (−) | 1 | 0.944 |
| P$GAPB | GAP-Box (light response elements) | P$GAP.01 | 0.88 | 702-716 | (−) | 1 | 0.897 |
| P$GTBX | GT-box elements | P$GT1.01 | 0.85 | 723-739 | (−) | 1 | 0.925 |
| P$AHBP | *Arabidopsis* homeobox protein | P$WUS.01 | 0.94 | 726-736 | (−) | 1 | 1 |
| P$MYBL | MYB-like proteins | P$GAMYB.01 | 0.91 | 773-789 | (+) | 1 | 0.951 |
| P$GTBX | GT-box elements | P$GT3A.01 | 0.83 | 775-791 | (+) | 1 | 0.899 |
| P$MYBL | MYB-like proteins | P$CARE.01 | 0.83 | 801-817 | (−) | 1 | 0.837 |
| O$VTBP | Vertebrate TA-TA binding protein factor | O$ATATA.01 | 0.78 | 803-819 | (−) | 1 | 0.811 |
| O$VTBP | Vertebrate TA-TA binding protein factor | O$ATATA.01 | 0.78 | 819-835 | (−) | 0.75 | 0.874 |
| P$MADS | MADS box proteins | P$AGL15.01 | 0.79 | 827-847 | (−) | 0.83 | 0.791 |
| P$MADS | MADS box proteins | P$AGL15.01 | 0.79 | 828-848 | (+) | 1 | 0.895 |
| P$CCAF | Circadian control factors | P$CCA1.01 | 0.85 | 843-857 | (−) | 1 | 0.883 |
| P$GTBX | GT-box elements | P$SBF1.01 | 0.87 | 844-860 | (−) | 1 | 0.948 |
| P$CARM | CA-rich motif | P$CARICH.01 | 0.78 | 845-863 | (+) | 1 | 0.806 |
| P$PSRE | Pollen-specific regulatory elements | P$GAAA.01 | 0.83 | 858-874 | (+) | 0.75 | 0.831 |
| P$MYBL | MYB-like proteins | P$NTMYBAS1.01 | 0.96 | 867-883 | (+) | 1 | 0.963 |
| P$GTBX | GT-box elements | P$SBF1.01 | 0.87 | 869-885 | (+) | 1 | 0.883 |
| P$RAV5 | 5′-part of bipartite RAV1 binding site | P$RAV1-5.01 | 0.96 | 882-892 | (+) | 1 | 0.96 |
| P$AHBP | *Arabidopsis* homeobox protein | P$WUS.01 | 0.94 | 888-898 | (−) | 1 | 1 |
| P$GTBX | GT-box elements | P$SBF1.01 | 0.87 | 897-913 | (+) | 1 | 0.886 |
| P$AHBP | *Arabidopsis* homeobox protein | P$BLR.01 | 0.90 | 906-916 | (+) | 1 | 1 |
| P$AHBP | *Arabidopsis* homeobox protein | P$BLR.01 | 0.90 | 907-917 | (−) | 1 | 0.903 |
| P$CARM | CA-rich motif | P$CARICH.01 | 0.78 | 908-926 | (−) | 1 | 0.826 |
| P$MYBL | MYB-like proteins | P$NTMYBAS1.01 | 0.96 | 916-932 | (−) | 1 | 0.962 |
| P$MIIG | MYB IIG-type binding sites | P$PALBOXP.01 | 0.81 | 918-932 | (−) | 0.94 | 0.817 |
| P$DOFF | DNA binding with one finger (DOF) | P$DOF1.01 | 0.98 | 929-945 | (−) | 1 | 0.983 |
| P$GTBX | GT-box elements | P$GT1.01 | 0.85 | 933-949 | (+) | 0.97 | 0.854 |
| O$VTBP | Vertebrate TA-TA binding protein factor | O$LTATA.01 | 0.82 | 944-960 | (+) | 1 | 0.829 |
| P$AHBP | *Arabidopsis* homeobox protein | P$ATHB9.01 | 0.77 | 959-969 | (+) | 0.75 | 0.816 |
| P$AHBP | *Arabidopsis* homeobox protein | P$ATHB9.01 | 0.77 | 959-969 | (−) | 1 | 0.909 |
| P$AHBP | *Arabidopsis* homeobox protein | P$HAHB4.01 | 0.87 | 970-980 | (+) | 1 | 0.916 |
| P$AHBP | *Arabidopsis* homeobox protein | P$ATHB1.01 | 0.90 | 973-983 | (+) | 1 | 0.989 |
| P$AHBP | *Arabidopsis* homeobox protein | P$HAHB4.01 | 0.87 | 973-983 | (−) | 1 | 0.976 |

TABLE 3-continued

Boxes and Motifs identified in the starting sequence of the VfSBP promoter
p-VfSBP (nativ)

| Family | Further Family Information | Matrix | Opt. | Position from-to | Strand | Core sim. | Matrix sim. |
|---|---|---|---|---|---|---|---|
| P$IDDF | ID domain factors | P$ID1.01 | 0.92 | 976-988 | (+) | 1 | 0.928 |
| P$IBOX | Plant I-Box sites | P$GATA.01 | 0.93 | 995-1011 | (+) | 1 | 0.96 |
| P$AHBP | *Arabidopsis* homeobox protein | P$HAHB4.01 | 0.87 | 1008-1018 | (+) | 1 | 0.937 |
| P$AHBP | *Arabidopsis* homeobox protein | P$WUS.01 | 0.94 | 1012-1022 | (−) | 1 | 1 |
| P$SPF1 | Sweet potato DNA-binding factor with two WRKY-domains | P$SP8BF.01 | 0.87 | 1029-1041 | (−) | 0.78 | 0.879 |
| P$SUCB | Sucrose box | P$SUCROSE.01 | 0.81 | 1036-1054 | (−) | 1 | 0.822 |
| P$AHBP | *Arabidopsis* homeobox protein | P$ATHB1.01 | 0.90 | 1054-1064 | (+) | 1 | 0.99 |
| P$AHBP | *Arabidopsis* homeobox protein | P$ATHB5.01 | 0.89 | 1054-1064 | (−) | 0.83 | 0.94 |
| P$GTBX | GT-box elements | P$GT3A.01 | 0.83 | 1066-1082 | (+) | 1 | 0.889 |
| O$PTBP | Plant TATA binding protein factor | O$PTATA.02 | 0.90 | 1086-1100 | (+) | 1 | 0.94 |
| O$VTBP | Vertebrate TA-TA binding protein factor | O$VTATA.01 | 0.90 | 1087-1103 | (+) | 0.89 | 0.927 |
| O$PTBP | Plant TATA binding protein factor | O$PTATA.01 | 0.88 | 1088-1102 | (+) | 1 | 0.958 |
| O$VTBP | Vertebrate TA-TA binding protein factor | O$VTATA.01 | 0.90 | 1089-1105 | (+) | 1 | 0.971 |
| P$E2FF | E2F-homolog cell cycle regulators | P$E2F.01 | 0.82 | 1117-1131 | (−) | 1 | 0.833 |
| P$PSRE | Pollen-specific regulatory elements | P$GAAA.01 | 0.83 | 1146-1162 | (+) | 1 | 0.908 |
| P$GTBX | GT-box elements | P$S1F.01 | 0.79 | 1153-1169 | (+) | 1 | 0.8 |
| P$GTBX | GT-box elements | P$S1F.01 | 0.79 | 1170-1186 | (−) | 1 | 0.797 |
| P$SUCB | Sucrose box | P$SUCROSE.01 | 0.81 | 1173-1191 | (+) | 1 | 0.813 |
| P$MADS | MADS box proteins | P$AGL2.01 | 0.82 | 1174-1194 | (+) | 1 | 0.9 |
| P$AHBP | *Arabidopsis* homeobox protein | P$BLR.01 | 0.90 | 1189-1199 | (+) | 0.83 | 0.919 |
| P$DOFF | DNA binding with one finger (DOF) | P$PBOX.01 | 0.75 | 1229-1245 | (−) | 0.76 | 0.763 |
| P$MYBL | MYB-like proteins | P$WER.01 | 0.87 | 1234-1250 | (−) | 0.94 | 0.88 |
| O$PTBP | Plant TATA binding protein factor | O$PTATA.01 | 0.88 | 1241-1255 | (+) | 1 | 0.964 |
| O$VTBP | Vertebrate TA-TA binding protein factor | O$VTATA.01 | 0.90 | 1242-1258 | (+) | 1 | 0.967 |
| P$DOFF | DNA binding with one finger (DOF) | P$PBOX.01 | 0.75 | 1265-1281 | (−) | 0.76 | 0.762 |
| P$GTBX | GT-box elements | P$GT3A.01 | 0.83 | 1265-1281 | (+) | 0.75 | 0.839 |
| P$AHBP | *Arabidopsis* homeobox protein | P$BLR.01 | 0.90 | 1274-1284 | (−) | 1 | 0.928 |
| P$OCSE | Enhancer element first identified in the promoter of the octopine synthase gene (OCS) of the *Agrobacterium tumefaciens* T-DNA | P$OCSL.01 | 0.69 | 1278-1298 | (+) | 0.77 | 0.732 |
| P$MYCL | Myc-like basic helix-loop-helix binding factors | P$MYCRS.01 | 0.93 | 1284-1302 | (−) | 0.86 | 0.963 |

TABLE 3-continued

Boxes and Motifs identified in the starting sequence of the VfSBP promoter
p-VfSBP (nativ)

| Family | Further Family Information | Matrix | Opt. | Position from-to | Strand | Core sim. | Matrix sim. |
|---|---|---|---|---|---|---|---|
| P$TALE | TALE (3-aa acid loop extension) class homeodomain proteins | P$KN1__KIP.01 | 0.88 | 1289-1301 | (−) | 1 | 1 |
| P$AREF | Auxin response element | P$SEBF.01 | 0.96 | 1292-1304 | (+) | 1 | 0.98 |
| P$MSAE | M-phase-specific activator elements | P$MSA.01 | 0.80 | 1295-1309 | (−) | 0.75 | 0.818 |
| P$DOFF | DNA binding with one finger (DOF) | P$PBOX.01 | 0.75 | 1296-1312 | (−) | 1 | 0.776 |
| P$MYBL | MYB-like proteins | P$WER.01 | 0.87 | 1310-1326 | (−) | 0.94 | 0.876 |
| P$AHBP | *Arabidopsis* homeobox protein | P$BLR.01 | 0.90 | 1319-1329 | (+) | 1 | 0.93 |
| O$VTBP | Vertebrate TA-TA binding protein factor | O$ATATA.01 | 0.78 | 1323-1339 | (−) | 1 | 0.881 |
| P$LREM | Light responsive element motif, not modulated by different light qualities | P$RAP22.01 | 0.85 | 1327-1337 | (−) | 1 | 0.936 |
| P$GTBX | GT-box elements | P$SBF1.01 | 0.87 | 1338-1354 | (+) | 1 | 0.896 |
| P$SUCB | Sucrose box | P$SUCROSE.01 | 0.81 | 1338-1356 | (−) | 1 | 0.819 |
| P$AHBP | *Arabidopsis* homeobox protein | P$ATHB5.01 | 0.89 | 1345-1355 | (+) | 0.83 | 0.902 |
| P$AHBP | *Arabidopsis* homeobox protein | P$BLR.01 | 0.90 | 1345-1355 | (−) | 1 | 0.998 |
| P$AGP1 | Plant GATA-type zinc finger protein | P$AGP1.01 | 0.91 | 1354-1364 | (−) | 1 | 0.916 |
| O$VTBP | Vertebrate TA-TA binding protein factor | O$VTATA.01 | 0.90 | 1376-1392 | (−) | 1 | 0.949 |
| P$HMGF | High mobility group factors | P$HMG__IY.01 | 0.89 | 1377-1391 | (+) | 1 | 0.952 |
| O$PTBP | Plant TATA binding protein factor | O$PTATA.01 | 0.88 | 1379-1393 | (−) | 1 | 0.883 |
| P$IBOX | Plant I-Box sites | P$IBOX.01 | 0.81 | 1399-1415 | (−) | 0.75 | 0.822 |
| O$VTBP | Vertebrate TA-TA binding protein factor | O$LTATA.01 | 0.82 | 1417-1433 | (−) | 1 | 0.86 |
| P$IBOX | Plant I-Box sites | P$IBOX.01 | 0.81 | 1419-1435 | (−) | 0.75 | 0.824 |
| P$WBXF | W Box family | P$WRKY.01 | 0.92 | 1429-1445 | (−) | 1 | 0.958 |
| P$MYBL | MYB-like proteins | P$MYBPH3.02 | 0.76 | 1457-1473 | (+) | 0.82 | 0.798 |
| P$ROOT | Root hair-specific cis-elements in angiosperms | P$RHE.02 | 0.77 | 1458-1482 | (+) | 0.75 | 0.786 |
| P$LFYB | LFY binding site | P$LFY.01 | 0.93 | 1486-1498 | (−) | 0.91 | 0.987 |
| P$CAAT | CCAAT binding factors | P$CAAT.01 | 0.97 | 1490-1498 | (−) | 1 | 0.982 |
| P$HEAT | Heat shock factors | P$HSE.01 | 0.81 | 1526-1540 | (+) | 1 | 0.833 |
| P$AHBP | *Arabidopsis* homeobox protein | P$BLR.01 | 0.90 | 1550-1560 | (−) | 1 | 0.93 |
| P$IDDF | ID domain factors | P$ID1.01 | 0.92 | 1563-1575 | (+) | 1 | 0.952 |
| P$NCS2 | Nodulin consensus sequence 2 | P$NCS2.01 | 0.79 | 1565-1579 | (+) | 0.75 | 0.845 |
| O$VTBP | Vertebrate TA-TA binding protein factor | O$MTATA.01 | 0.84 | 1570-1586 | (+) | 1 | 0.846 |
| P$DOFF | DNA binding with one finger (DOF) | P$PBF.01 | 0.97 | 1571-1587 | (+) | 1 | 0.988 |
| P$LEGB | Legumin Box family | P$RY.01 | 0.87 | 1572-1598 | (−) | 1 | 0.898 |

TABLE 3-continued

Boxes and Motifs identified in the starting sequence of the VfSBP promoter
p-VfSBP (nativ)

| Family | Further Family Information | Matrix | Opt. | Position from-to | Strand | Core sim. | Matrix sim. |
|---|---|---|---|---|---|---|---|
| P$MADS | MADS box proteins | P$AGL3.01 | 0.83 | 1637-1657 | (+) | 1 | 0.851 |
| P$MYBL | MYB-like proteins | P$ATMYB77.01 | 0.87 | 1654-1670 | (−) | 1 | 0.909 |
| P$URNA | Upstream sequence element of U-snRNA genes | P$USE.01 | 0.75 | 1659-1675 | (+) | 1 | 0.758 |
| P$AHBP | *Arabidopsis* homeobox protein | P$ATHB1.01 | 0.90 | 1671-1681 | (−) | 1 | 0.989 |
| P$AHBP | *Arabidopsis* homeobox protein | P$HAHB4.01 | 0.87 | 1671-1681 | (+) | 1 | 0.955 |
| P$OCSE | Enhancer element first identified in the promoter of the octopine synthase gene (OCS) of the *Agrobacterium tumefaciens* T-DNA | P$OCSL.01 | 0.69 | 1677-1697 | (+) | 1 | 0.763 |
| P$GBOX | Plant G-box/C-box bZIP proteins | P$GBF1.01 | 0.94 | 1682-1702 | (−) | 1 | 0.968 |
| P$ABRE | ABA response elements | P$ABRE.01 | 0.82 | 1685-1701 | (−) | 1 | 0.855 |
| P$BRRE | Brassinosteroid (BR) response element | P$BZR1.01 | 0.95 | 1696-1712 | (−) | 1 | 0.954 |
| P$GBOX | Plant G-box/C-box bZIP proteins | P$GBF1.01 | 0.94 | 1696-1716 | (−) | 1 | 0.963 |
| P$TEFB | TEF-box | P$TEF1.01 | 0.76 | 1696-1716 | (−) | 0.96 | 0.826 |
| P$OPAQ | Opaque-2 like transcriptional activators | P$O2_GCN4.01 | 0.81 | 1698-1714 | (−) | 0.95 | 0.824 |
| P$DPBF | Dc3 promoter binding factors | P$DPBF.01 | 0.89 | 1700-1710 | (+) | 1 | 0.943 |
| P$LEGB | Legumin Box family | P$RY.01 | 0.87 | 1701-1727 | (−) | 1 | 0.887 |
| P$LEGB | Legumin Box family | P$IDE1.01 | 0.77 | 1708-1734 | (+) | 1 | 0.871 |
| P$MYBS | MYB proteins with single DNA binding repeat | P$TAMYB80.01 | 0.83 | 1727-1743 | (+) | 1 | 0.85 |
| P$ROOT | Root hair-specific cis-elements in angiosperms | P$RHE.02 | 0.77 | 1740-1764 | (+) | 1 | 0.786 |
| P$GBOX | Plant G-box/C-box bZIP proteins | P$EMBP1.01 | 0.84 | 1747-1767 | (−) | 1 | 0.84 |
| P$ABRE | ABA response elements | P$ABRE.01 | 0.82 | 1750-1766 | (−) | 1 | 0.831 |
| O$VTBP | Vertebrate TATA binding protein factor | O$VTATA.01 | 0.90 | 1756-1772 | (+) | 1 | 0.963 |
| P$MYBL | MYB-like proteins | P$MYBPH3.02 | 0.76 | 1765-1781 | (−) | 1 | 0.781 |

TABLE 4

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.
p-VfSBP_perm

| Family | Further Family Information | Matrix | Opt. | Position from-to | Strand | Core sim. | Matrix sim. |
|---|---|---|---|---|---|---|---|
| P$MYBS | MYB proteins with single DNA binding repeat | P$MYBST1.01 | 0.90 | 12-28 | (+) | 1 | 0.918 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.
p-VfSBP_perm

| Family | Further Family Information | Matrix | Opt. | Position from-to | Strand | Core sim. | Matrix sim. |
|---|---|---|---|---|---|---|---|
| P$AGP1 | Plant GATA-type zinc finger protein | P$AGP1.01 | 0.91 | 25-35 | (−) | 1 | 0.914 |
| P$GAGA | GAGA elements | P$BPC.01 | 1.00 | 25-49 | (−) | 1 | 1 |
| P$AGP1 | Plant GATA-type zinc finger protein | P$AGP1.01 | 0.91 | 26-36 | (+) | 1 | 0.914 |
| P$LEGB | Legumin Box family | P$IDE1.01 | 0.77 | 80-106 | (−) | 1 | 0.805 |
| P$GTBX | GT-box elements | P$GT3A.01 | 0.83 | 85-101 | (−) | 1 | 0.843 |
| P$PSRE | Pollen-specific regulatory elements | P$GAAA.01 | 0.83 | 101-117 | (−) | 1 | 0.883 |
| P$GBOX | Plant G-box/C-box bZIP proteins | P$HBP1B.01 | 0.83 | 138-158 | (+) | 1 | 0.834 |
| P$WBXF | W Box family | P$ERE.01 | 0.89 | 154-170 | (−) | 1 | 0.935 |
| P$MYBL | MYB-like proteins | P$MYBPH3.02 | 0.76 | 165-181 | (−) | 0.78 | 0.788 |
| P$NACF | Plant specific NAC [NAM (no apical meristem), ATAF172, CUC2 (cup-shaped cotyledons 2)] transcription factors | P$TANAC69.01 | 0.68 | 173-195 | (−) | 0.81 | 0.728 |
| P$MADS | MADS box proteins | P$AGL1.01 | 0.84 | 174-194 | (−) | 0.98 | 0.856 |
| P$MADS | MADS box proteins | P$AGL1.01 | 0.84 | 175-195 | (+) | 0.98 | 0.844 |
| P$TCPF | DNA-binding proteins with the plant specific TCP-domain | P$ATTCP20.01 | 0.94 | 189-201 | (+) | 1 | 0.968 |
| P$L1BX | L1 box, motif for L1 layer-specific expression | P$ATML1.02 | 0.76 | 194-210 | (−) | 0.89 | 0.795 |
| P$AHBP | *Arabidopsis* homeobox protein | P$BLR.01 | 0.90 | 198-208 | (+) | 0.83 | 0.936 |
| P$EINL | Ethylen insensitive 3 like factors | P$TEIL.01 | 0.92 | 215-223 | (−) | 0.96 | 0.924 |
| P$GBOX | Plant G-box/C-box bZIP proteins | P$HBP1A.01 | 0.88 | 217-237 | (−) | 1 | 0.908 |
| P$GBOX | Plant G-box/C-box bZIP proteins | P$GBF1.01 | 0.94 | 218-238 | (+) | 1 | 0.963 |
| P$GTBX | GT-box elements | P$S1F.01 | 0.79 | 218-234 | (+) | 1 | 0.821 |
| P$ABRE | ABA response elements | P$ABF1.03 | 0.82 | 219-235 | (+) | 1 | 0.825 |
| P$ROOT | Root hair-specific cis-elements in angiosperms | P$RHE.01 | 0.77 | 221-245 | (−) | 1 | 0.803 |
| P$CE1F | Coupling element 1 binding factors | P$SBOX.01 | 0.87 | 222-234 | (−) | 0.78 | 0.916 |
| O$VTBP | Vertebrate TA-TA binding protein factor | O$VTATA.01 | 0.90 | 233-249 | (−) | 1 | 0.939 |
| P$IBOX | Plant I-Box sites | P$GATA.01 | 0.93 | 245-261 | (−) | 1 | 0.963 |
| P$MYBS | MYB proteins with single DNA binding repeat | P$HVMCB1.01 | 0.93 | 248-264 | (+) | 1 | 0.957 |
| P$AHBP | *Arabidopsis* homeobox protein | P$ATHB5.01 | 0.89 | 256-266 | (+) | 0.94 | 0.896 |
| P$NCS1 | Nodulin consensus sequence 1 | P$NCS1.01 | 0.85 | 256-266 | (−) | 0.88 | 0.871 |
| O$VTBP | Vertebrate TA-TA binding protein factor | O$ATATA.01 | 0.78 | 260-276 | (+) | 1 | 0.819 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$LREM | Light responsive element motif, not modulated by different light qualities | P$RAP22.01 | 0.85 | 290-300 | (−) | 1 | 0.931 |
| P$AGP1 | Plant GATA-type zinc finger protein | P$AGP1.01 | 0.91 | 292-302 | (−) | 1 | 0.984 |
| P$AGP1 | Plant GATA-type zinc finger protein | P$AGP1.01 | 0.91 | 293-303 | (+) | 1 | 0.915 |
| P$LREM | Light responsive element motif, not modulated by different light qualities | P$RAP22.01 | 0.85 | 306-316 | (+) | 1 | 0.938 |
| P$MYBL | MYB-like proteins | P$CARE.01 | 0.83 | 308-324 | (−) | 1 | 0.854 |
| P$MYBL | MYB-like proteins | P$ATMYB77.01 | 0.87 | 319-335 | (+) | 1 | 0.87 |
| O$INRE | Core promoter initiator elements | O$DINR.01 | 0.94 | 322-332 | (+) | 1 | 0.969 |
| P$MADS | MADS box proteins | P$AGL15.01 | 0.79 | 345-365 | (+) | 0.85 | 0.825 |
| P$CCAF | Circadian control factors | P$CCA1.01 | 0.85 | 354-368 | (+) | 1 | 0.895 |
| P$HEAT | Heat shock factors | P$HSE.01 | 0.81 | 375-389 | (−) | 1 | 0.861 |
| P$MYBL | MYB-like proteins | P$WER.01 | 0.87 | 392-408 | (−) | 1 | 0.87 |
| P$MYBL | MYB-like proteins | P$WER.01 | 0.87 | 394-410 | (+) | 1 | 0.95 |
| P$MSAE | M-phase-specific activator elements | P$MSA.01 | 0.80 | 395-409 | (−) | 0.75 | 0.808 |
| P$HMGF | High mobility group factors | P$HMG_IY.01 | 0.89 | 402-416 | (−) | 1 | 0.929 |
| P$CCAF | Circadian control factors | P$CCA1.01 | 0.85 | 404-418 | (+) | 1 | 0.871 |
| P$AHBP | *Arabidopsis* homeobox protein | P$BLR.01 | 0.90 | 407-417 | (−) | 1 | 0.901 |
| P$LREM | Light responsive element motif, not modulated by different light qualities | P$RAP22.01 | 0.85 | 411-421 | (+) | 1 | 0.916 |
| P$HEAT | Heat shock factors | P$HSE.01 | 0.81 | 415-429 | (+) | 1 | 0.811 |
| P$SUCB | Sucrose box | P$SUCROSE.01 | 0.81 | 421-439 | (−) | 0.75 | 0.849 |
| P$DOFF | DNA binding with one finger (DOF) | P$PBOX.01 | 0.75 | 431-447 | (−) | 0.76 | 0.782 |
| P$WBXF | W Box family | P$WRKY.01 | 0.92 | 453-469 | (+) | 1 | 0.958 |
| P$MYBL | MYB-like proteins | P$MYBPH3.02 | 0.76 | 468-484 | (−) | 0.82 | 0.849 |
| P$OPAQ | Opaque-2 like transcriptional activators | P$O2_GCN4.01 | 0.81 | 486-502 | (+) | 1 | 0.818 |
| P$OPAQ | Opaque-2 like transcriptional activators | P$O2.01 | 0.87 | 498-514 | (−) | 1 | 0.919 |
| P$HEAT | Heat shock factors | P$HSE.01 | 0.81 | 512-526 | (−) | 1 | 0.824 |
| P$NCS2 | Nodulin consensus sequence 2 | P$NCS2.01 | 0.79 | 525-539 | (−) | 0.75 | 0.815 |
| P$WBXF | W Box family | P$WRKY.01 | 0.92 | 533-549 | (−) | 1 | 0.966 |
| P$WBXF | W Box family | P$WRKY.01 | 0.92 | 543-559 | (+) | 1 | 0.966 |
| P$WBXF | W Box family | P$ERE.01 | 0.89 | 562-578 | (+) | 1 | 0.972 |
| P$DOFF | DNA binding with one finger (DOF) | P$PBOX.01 | 0.75 | 614-630 | (+) | 0.76 | 0.766 |
| P$GTBX | GT-box elements | P$S1F.01 | 0.79 | 630-646 | (+) | 1 | 0.819 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$AGP1 | Plant GATA-type zinc finger protein | P$AGP1.01 | 0.91 | 636-646 | (−) | 1 | 0.913 |
| P$AGP1 | Plant GATA-type zinc finger protein | P$AGP1.01 | 0.91 | 637-647 | (+) | 1 | 0.921 |
| P$MYBL | MYB-like proteins | P$GAMYB.01 | 0.91 | 640-656 | (−) | 1 | 0.918 |
| P$HEAT | Heat shock factors | P$HSE.01 | 0.81 | 649-663 | (+) | 0.78 | 0.87 |
| P$HEAT | Heat shock factors | P$HSE.01 | 0.81 | 654-668 | (−) | 1 | 0.815 |
| O$INRE | Core promoter initiator elements | O$DINR.01 | 0.94 | 660-670 | (−) | 1 | 0.944 |
| P$PREM | Motifs of plastid response elements | P$MGPROTORE.01 | 0.77 | 691-721 | (−) | 1 | 0.789 |
| P$GAPB | GAP-Box (light response elements) | P$GAP.01 | 0.88 | 702-716 | (−) | 1 | 0.897 |
| P$GTBX | GT-box elements | P$GT1.01 | 0.85 | 723-739 | (−) | 1 | 0.925 |
| P$AHBP | *Arabidopsis* homeobox protein | P$WUS.01 | 0.94 | 726-736 | (−) | 1 | 1 |
| P$CARM | CA-rich motif | P$CARICH.01 | 0.78 | 731-749 | (+) | 1 | 0.855 |
| P$MYCL | Myc-like basic helix-loop-helix binding factors | P$ICE.01 | 0.95 | 734-752 | (+) | 0.95 | 0.961 |
| P$MYBL | MYB-like proteins | P$GAMYB.01 | 0.91 | 773-789 | (+) | 1 | 0.951 |
| P$GTBX | GT-box elements | P$GT3A.01 | 0.83 | 775-791 | (+) | 1 | 0.899 |
| P$MYBL | MYB-like proteins | P$CARE.01 | 0.83 | 801-817 | (−) | 1 | 0.837 |
| O$VTBP | Vertebrate TA-TA binding protein factor | O$ATATA.01 | 0.78 | 803-819 | (−) | 1 | 0.811 |
| P$L1BX | L1 box, motif for L1 layer-specific expression | P$PDF2.01 | 0.85 | 814-830 | (−) | 1 | 0.869 |
| P$GTBX | GT-box elements | P$GT1.01 | 0.85 | 815-831 | (−) | 0.97 | 0.854 |
| O$VTBP | Vertebrate TA-TA binding protein factor | O$ATATA.01 | 0.78 | 819-835 | (−) | 0.75 | 0.874 |
| P$MADS | MADS box proteins | P$AGL15.01 | 0.79 | 828-848 | (+) | 1 | 0.857 |
| P$CCAF | Circadian control factors | P$CCA1.01 | 0.85 | 843-857 | (−) | 1 | 0.883 |
| P$GTBX | GT-box elements | P$SBF1.01 | 0.87 | 844-860 | (−) | 1 | 0.948 |
| P$CARM | CA-rich motif | P$CARICH.01 | 0.78 | 845-863 | (+) | 1 | 0.806 |
| P$MYBL | MYB-like proteins | P$CARE.01 | 0.83 | 849-865 | (−) | 1 | 0.876 |
| P$GTBX | GT-box elements | P$SBF1.01 | 0.87 | 869-885 | (+) | 1 | 0.883 |
| P$RAV5 | 5'-part of bipartite RAV1 binding site | P$RAV1-5.01 | 0.96 | 882-892 | (+) | 1 | 0.96 |
| P$L1BX | L1 box, motif for L1 layer-specific expression | P$PDF2.01 | 0.85 | 884-900 | (−) | 0.85 | 0.853 |
| P$AHBP | *Arabidopsis* homeobox protein | P$WUS.01 | 0.94 | 888-898 | (−) | 1 | 1 |
| P$MYBL | MYB-like proteins | P$ATMYB77.01 | 0.87 | 895-911 | (+) | 1 | 0.962 |
| P$GTBX | GT-box elements | P$SBF1.01 | 0.87 | 897-913 | (+) | 1 | 0.883 |
| P$AHBP | *Arabidopsis* homeobox protein | P$BLR.01 | 0.90 | 906-916 | (+) | 1 | 1 |
| P$AHBP | *Arabidopsis* homeobox protein | P$BLR.01 | 0.90 | 907-917 | (−) | 1 | 0.903 |
| P$CARM | CA-rich motif | P$CARICH.01 | 0.78 | 908-926 | (−) | 1 | 0.826 |
| P$MYBL | MYB-like proteins | P$NTMYBAS1.01 | 0.96 | 916-932 | (−) | 1 | 0.962 |
| P$MIIG | MYB IIG-type binding sites | P$PALBOXP.01 | 0.81 | 918-932 | (−) | 0.94 | 0.817 |
| P$SPF1 | Sweet potato DNA-binding factor with two WRKY-domains | P$SP8BF.01 | 0.87 | 931-943 | (−) | 1 | 0.889 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$L1BX | L1 box, motif for L1 layer-specific expression | P$ATML1.01 | 0.82 | 948-964 | (+) | 1 | 0.908 |
| P$AHBP | Arabidopsis homeobox protein | P$ATHB9.01 | 0.77 | 959-969 | (+) | 0.75 | 0.816 |
| P$AHBP | Arabidopsis homeobox protein | P$ATHB9.01 | 0.77 | 959-969 | (−) | 1 | 0.909 |
| P$AHBP | Arabidopsis homeobox protein | P$HAHB4.01 | 0.87 | 970-980 | (+) | 1 | 0.916 |
| P$AHBP | Arabidopsis homeobox protein | P$ATHB1.01 | 0.90 | 973-983 | (+) | 1 | 0.989 |
| P$AHBP | Arabidopsis homeobox protein | P$HAHB4.01 | 0.87 | 973-983 | (−) | 1 | 0.976 |
| P$IDDF | ID domain factors | P$ID1.01 | 0.92 | 976-988 | (+) | 1 | 0.928 |
| P$AHBP | Arabidopsis homeobox protein | P$HAHB4.01 | 0.87 | 985-995 | (+) | 1 | 0.916 |
| P$GTBX | GT-box elements | P$SBF1.01 | 0.87 | 985-1001 | (+) | 1 | 0.891 |
| P$GTBX | GT-box elements | P$SBF1.01 | 0.87 | 986-1002 | (−) | 1 | 0.877 |
| P$AHBP | Arabidopsis homeobox protein | P$HAHB4.01 | 0.87 | 992-1002 | (−) | 1 | 0.916 |
| P$IBOX | Plant I-Box sites | P$GATA.01 | 0.93 | 995-1011 | (+) | 1 | 0.935 |
| P$LEGB | Legumin Box family | P$LEGB.01 | 0.65 | 998-1024 | (+) | 0.75 | 0.676 |
| P$AHBP | Arabidopsis homeobox protein | P$HAHB4.01 | 0.87 | 1008-1018 | (+) | 1 | 0.937 |
| P$AHBP | Arabidopsis homeobox protein | P$WUS.01 | 0.94 | 1012-1022 | (−) | 1 | 1 |
| P$MYBL | MYB-like proteins | P$GAMYB.01 | 0.91 | 1022-1038 | (−) | 1 | 0.925 |
| P$SPF1 | Sweet potato DNA-binding factor with two WRKY-domains | P$SP8BF.01 | 0.87 | 1029-1041 | (−) | 0.78 | 0.879 |
| P$SUCB | Sucrose box | P$SUCROSE.01 | 0.81 | 1036-1054 | (−) | 1 | 0.83 |
| P$AHBP | Arabidopsis homeobox protein | P$ATHB1.01 | 0.90 | 1054-1064 | (+) | 1 | 0.99 |
| P$AHBP | Arabidopsis homeobox protein | P$ATHB5.01 | 0.89 | 1054-1064 | (−) | 0.83 | 0.94 |
| P$GTBX | GT-box elements | P$GT3A.01 | 0.83 | 1066-1082 | (+) | 1 | 0.889 |
| O$PTBP | Plant TATA binding protein factor | O$PTATA.02 | 0.90 | 1086-1100 | (+) | 1 | 0.94 |
| O$VTBP | Vertebrate TA-TA binding protein factor | O$VTATA.01 | 0.90 | 1087-1103 | (+) | 0.89 | 0.927 |
| O$PTBP | Plant TATA binding protein factor | O$PTATA.01 | 0.88 | 1088-1102 | (+) | 1 | 0.958 |
| O$VTBP | Vertebrate TA-TA binding protein factor | O$VTATA.01 | 0.90 | 1089-1105 | (+) | 1 | 0.971 |
| P$DOFF | DNA binding with one finger (DOF) | P$DOF3.01 | 0.99 | 1098-1114 | (+) | 1 | 0.995 |
| P$E2FF | E2F-homolog cell cycle regulators | P$E2F.01 | 0.82 | 1117-1131 | (−) | 1 | 0.833 |
| P$SPF1 | Sweet potato DNA-binding factor with two WRKY-domains | P$SP8BF.01 | 0.87 | 1130-1142 | (+) | 1 | 0.881 |
| P$PSRE | Pollen-specific regulatory elements | P$GAAA.01 | 0.83 | 1146-1162 | (+) | 1 | 0.873 |
| P$GTBX | GT-box elements | P$S1F.01 | 0.79 | 1170-1186 | (−) | 1 | 0.797 |
| P$SUCB | Sucrose box | P$SUCROSE.01 | 0.81 | 1173-1191 | (+) | 1 | 0.813 |
| P$MADS | MADS box proteins | P$AGL2.01 | 0.82 | 1174-1194 | (+) | 1 | 0.9 |
| P$AHBP | Arabidopsis homeobox protein | P$BLR.01 | 0.90 | 1189-1199 | (+) | 0.83 | 0.919 |
| P$IDDF | ID domain factors | P$ID1.01 | 0.92 | 1205-1217 | (−) | 1 | 0.97 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$DOFF | DNA binding with one finger (DOF) | P$PBOX.01 | 0.75 | 1229-1245 | (−) | 0.76 | 0.763 |
| P$MYBL | MYB-like proteins | P$WER.01 | 0.87 | 1234-1250 | (−) | 0.94 | 0.88 |
| O$PTBP | Plant TATA binding protein factor | O$PTATA.01 | 0.88 | 1241-1255 | (+) | 1 | 0.964 |
| O$VTBP | Vertebrate TA-TA binding protein factor | O$VTATA.01 | 0.90 | 1242-1258 | (+) | 1 | 0.967 |
| P$DOFF | DNA binding with one finger (DOF) | P$PBOX.01 | 0.75 | 1265-1281 | (−) | 0.76 | 0.762 |
| P$GTBX | GT-box elements | P$GT3A.01 | 0.83 | 1265-1281 | (+) | 0.75 | 0.839 |
| P$AHBP | *Arabidopsis* homeobox protein | P$BLR.01 | 0.90 | 1274-1284 | (−) | 1 | 0.928 |
| O$PTBP | Plant TATA binding protein factor | O$PTATA.01 | 0.88 | 1277-1291 | (+) | 1 | 0.908 |
| O$VTBP | Vertebrate TA-TA binding protein factor | O$VTATA.01 | 0.90 | 1278-1294 | (+) | 1 | 0.918 |
| P$OCSE | Enhancer element first identified in the promoter of the octopine synthase gene (OCS) of the *Agrobacterium tumefaciens* T-DNA | P$OCSL.01 | 0.69 | 1278-1298 | (+) | 0.77 | 0.712 |
| P$MYCL | Myc-like basic helix-loop-helix binding factors | P$MYCRS.01 | 0.93 | 1284-1302 | (−) | 0.86 | 0.933 |
| P$TALE | TALE (3-aa acid loop extension) class homeodomain proteins | P$KN1_KIP.01 | 0.88 | 1289-1301 | (−) | 1 | 1 |
| P$AREF | Auxin response element | P$SEBF.01 | 0.96 | 1292-1304 | (+) | 1 | 0.98 |
| P$MSAE | M-phase-specific activator elements | P$MSA.01 | 0.80 | 1295-1309 | (−) | 0.75 | 0.803 |
| P$DOFF | DNA binding with one finger (DOF) | P$PBOX.01 | 0.75 | 1296-1312 | (−) | 1 | 0.797 |
| P$MYBL | MYB-like proteins | P$WER.01 | 0.87 | 1310-1326 | (−) | 0.94 | 0.876 |
| P$AHBP | *Arabidopsis* homeobox protein | P$BLR.01 | 0.90 | 1319-1329 | (+) | 1 | 0.93 |
| O$VTBP | Vertebrate TA-TA binding protein factor | O$ATATA.01 | 0.78 | 1323-1339 | (−) | 1 | 0.833 |
| P$LREM | Light responsive element motif, not modulated by different light qualities | P$RAP22.01 | 0.85 | 1327-1337 | (−) | 1 | 0.936 |
| P$IBOX | Plant I-Box sites | P$GATA.01 | 0.93 | 1328-1344 | (+) | 1 | 0.939 |
| P$SUCB | Sucrose box | P$SUCROSE.01 | 0.81 | 1334-1352 | (+) | 1 | 0.816 |
| P$AHBP | *Arabidopsis* homeobox protein | P$ATHB5.01 | 0.89 | 1335-1345 | (−) | 0.83 | 0.904 |
| P$AHBP | *Arabidopsis* homeobox protein | P$BLR.01 | 0.90 | 1335-1345 | (+) | 1 | 0.998 |
| P$GTBX | GT-box elements | P$SBF1.01 | 0.87 | 1338-1354 | (+) | 1 | 0.896 |
| P$SUCB | Sucrose box | P$SUCROSE.01 | 0.81 | 1338-1356 | (−) | 1 | 0.819 |
| P$AHBP | *Arabidopsis* homeobox protein | P$ATHB5.01 | 0.89 | 1345-1355 | (+) | 0.83 | 0.902 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$AHBP | *Arabidopsis* homeobox protein | P$BLR.01 | 0.90 | 1345-1355 | (−) | 1 | 0.998 |
| P$AGP1 | Plant GATA-type zinc finger protein | P$AGP1.01 | 0.91 | 1354-1364 | (−) | 1 | 0.916 |
| P$AHBP | *Arabidopsis* homeobox protein | P$HAHB4.01 | 0.87 | 1365-1375 | (−) | 1 | 0.896 |
| O$VTBP | Vertebrate TATA binding protein factor | O$VTATA.01 | 0.90 | 1376-1392 | (−) | 1 | 0.949 |
| P$HMGF | High mobility group factors | P$HMG_IY.01 | 0.89 | 1377-1391 | (+) | 1 | 0.952 |
| O$PTBP | Plant TATA binding protein factor | O$PTATA.01 | 0.88 | 1379-1393 | (−) | 1 | 0.883 |
| P$IDDF | ID domain factors | P$ID1.01 | 0.92 | 1387-1399 | (+) | 1 | 0.926 |
| P$MYBL | MYB-like proteins | P$GAMYB.01 | 0.91 | 1389-1405 | (+) | 1 | 0.939 |
| O$INRE | Core promoter initiator elements | O$DINR.01 | 0.94 | 1392-1402 | (+) | 1 | 0.943 |
| P$IBOX | Plant I-Box sites | P$IBOX.01 | 0.81 | 1399-1415 | (−) | 0.75 | 0.822 |
| P$MYBL | MYB-like proteins | P$WER.01 | 0.87 | 1410-1426 | (+) | 1 | 0.875 |
| P$SPF1 | Sweet potato DNA-binding factor with two WRKY-domains | P$SP8BF.01 | 0.87 | 1412-1424 | (+) | 1 | 0.91 |
| O$VTBP | Vertebrate TATA binding protein factor | O$LTATA.01 | 0.82 | 1417-1433 | (−) | 1 | 0.847 |
| P$IBOX | Plant I-Box sites | P$IBOX.01 | 0.81 | 1419-1435 | (−) | 0.75 | 0.824 |
| P$WBXF | W Box family | P$WRKY.01 | 0.92 | 1429-1445 | (−) | 1 | 0.958 |
| P$MYBL | MYB-like proteins | P$MYBPH3.02 | 0.76 | 1457-1473 | (+) | 0.82 | 0.798 |
| P$ROOT | Root hair-specific cis-elements in angiosperms | P$RHE.02 | 0.77 | 1458-1482 | (+) | 0.75 | 0.786 |
| P$LFYB | LFY binding site | P$LFY.01 | 0.93 | 1486-1498 | (−) | 0.91 | 0.987 |
| P$CAAT | CCAAT binding factors | P$CAAT.01 | 0.97 | 1490-1498 | (−) | 1 | 0.982 |
| P$HEAT | Heat shock factors | P$HSE.01 | 0.81 | 1526-1540 | (+) | 1 | 0.833 |
| P$GTBX | GT-box elements | P$GT1.01 | 0.85 | 1536-1552 | (−) | 0.84 | 0.869 |
| P$WBXF | W Box family | P$ERE.01 | 0.89 | 1537-1553 | (+) | 1 | 0.9 |
| P$SPF1 | Sweet potato DNA-binding factor with two WRKY-domains | P$SP8BF.01 | 0.87 | 1546-1558 | (+) | 1 | 0.919 |
| P$AHBP | *Arabidopsis* homeobox protein | P$BLR.01 | 0.90 | 1550-1560 | (−) | 1 | 0.93 |
| P$LREM | Light responsive element motif, not modulated by different light qualities | P$RAP22.01 | 0.85 | 1555-1565 | (−) | 1 | 0.882 |
| P$NCS1 | Nodulin consensus sequence 1 | P$NCS1.01 | 0.85 | 1559-1569 | (−) | 0.8 | 0.855 |
| P$GARP | Myb-related DNA binding proteins (Golden2, ARR, Psr) | P$ARR10.01 | 0.97 | 1560-1568 | (+) | 1 | 0.97 |
| P$IDDF | ID domain factors | P$ID1.01 | 0.92 | 1563-1575 | (+) | 1 | 0.952 |
| P$NCS2 | Nodulin consensus sequence 2 | P$NCS2.01 | 0.79 | 1565-1579 | (+) | 0.75 | 0.845 |
| O$VTBP | Vertebrate TATA binding protein factor | O$MTATA.01 | 0.84 | 1570-1586 | (+) | 1 | 0.846 |

TABLE 4-continued

Boxes and Motifs identified in the permutated sequence of the VfSBP promoter. Preferably associated boxes are annotated in line 8, 14, 26, 56, 58, 59, 66, 121, 144, 148, 158, 185, 200, 201, 211, 215, 218, 219, 220, 225, 226, 228 of tables 3 and 4. Essential boxes are annotated in line 130, 132 and 146 of tables 3 and 4.

p-VfSBP_perm

| Family | Further Family Information | Matrix | Opt. | Position from-to | Strand | Core sim. | Matrix sim. |
|---|---|---|---|---|---|---|---|
| P$DOFF | DNA binding with one finger (DOF) | P$PBF.01 | 0.97 | 1571-1587 | (+) | 1 | 0.988 |
| P$LEGB | Legumin Box family | P$RY.01 | 0.87 | 1572-1598 | (−) | 1 | 0.898 |
| P$NCS2 | Nodulin consensus sequence 2 | P$NCS2.01 | 0.79 | 1610-1624 | (+) | 1 | 0.867 |
| P$MADS | MADS box proteins | P$AGL3.01 | 0.83 | 1637-1657 | (+) | 1 | 0.851 |
| P$GTBX | GT-box elements | P$GT3A.01 | 0.83 | 1652-1668 | (−) | 1 | 0.854 |
| P$MYBL | MYB-like proteins | P$NTMYBAS1.01 | 0.96 | 1654-1670 | (−) | 1 | 0.971 |
| P$AHBP | *Arabidopsis* homeobox protein | P$HAHB4.01 | 0.87 | 1671-1681 | (+) | 1 | 0.934 |
| P$OCSE | Enhancer element first identified in the promoter of the octopine synthase gene (OCS) of the *Agrobacterium tumefaciens* T-DNA | P$OCSL.01 | 0.69 | 1677-1697 | (+) | 1 | 0.763 |
| P$GBOX | Plant G-box/C-box bZIP proteins | P$GBF1.01 | 0.94 | 1682-1702 | (−) | 1 | 0.968 |
| P$ABRE | ABA response elements | P$ABRE.01 | 0.82 | 1685-1701 | (−) | 1 | 0.855 |
| P$BRRE | Brassinosteroid (BR) response element | P$BZR1.01 | 0.95 | 1696-1712 | (−) | 1 | 0.954 |
| P$GBOX | Plant G-box/C-box bZIP proteins | P$GBF1.01 | 0.94 | 1696-1716 | (−) | 1 | 0.963 |
| P$TEFB | TEF-box | P$TEF1.01 | 0.76 | 1696-1716 | (−) | 0.84 | 0.799 |
| P$DPBF | Dc3 promoter binding factors | P$DPBF.01 | 0.89 | 1700-1710 | (+) | 1 | 0.943 |
| P$EREF | Ethylen respone element factors | P$ANT.01 | 0.81 | 1701-1717 | (+) | 1 | 0.862 |
| P$LEGB | Legumin Box family | P$RY.01 | 0.87 | 1701-1727 | (−) | 1 | 0.925 |
| P$LEGB | Legumin Box family | P$RY.01 | 0.87 | 1704-1730 | (+) | 1 | 0.967 |
| P$LEGB | Legumin Box family | P$IDE1.01 | 0.77 | 1708-1734 | (+) | 1 | 0.888 |
| P$MADS | MADS box proteins | P$MADS.01 | 0.75 | 1722-1742 | (+) | 1 | 0.758 |
| P$MYBS | MYB proteins with single DNA binding repeat | P$TAMYB80.01 | 0.83 | 1727-1743 | (+) | 1 | 0.861 |
| P$URNA | Upstream sequence element of U-snRNA genes | P$USE.01 | 0.75 | 1731-1747 | (+) | 1 | 0.77 |
| P$ROOT | Root hair-specific cis-elements in angiosperms | P$RHE.02 | 0.77 | 1740-1764 | (+) | 1 | 0.79 |
| P$GBOX | Plant G-box/C-box bZIP proteins | P$EMBP1.01 | 0.84 | 1747-1767 | (−) | 1 | 0.84 |
| P$ABRE | ABA response elements | P$ABRE.01 | 0.82 | 1750-1766 | (−) | 1 | 0.831 |
| O$VTBP | Vertebrate TATA binding protein factor | O$VTATA.01 | 0.90 | 1756-1772 | (+) | 1 | 0.957 |
| P$MYBL | MYB-like proteins | P$MYBPH3.02 | 0.76 | 1765-1781 | (−) | 1 | 0.781 |

1.2 Vector Construction

Using the Multisite Gateway System (Invitrogen, Carlsbad, Calif., USA), promoter::reporter-gene cassettes were assembled into binary constructs for plant transformation. beta-Glucuronidase (GUS) or uidA gene which encodes an enzyme for which various chromogenic substrates are known, was utilized as reporter protein for determining the expression features of the permutated p-PvArc5_perm (SEQ ID NO2) and p-VfSBP_perm (SEQ ID NO4) promoter sequences.

The DNA fragments representing promoters p-PvArc5_perm (SEQ ID NO2) and p-VfSBP_perm (SEQ ID NO4) were generated by gene synthesis. Endonucleolytic restriction sites suitable for cloning the promoter fragments into beta-Glucuronidase reporter gene cassettes were included in the synthesis. The p-PvArc5_perm (SEQ ID NO2) promoter was cloned into a pENTR/A vector harboring the beta-Glucuronidase reporter gene c-GUS (with the prefix c-denoting coding sequence) followed by the t-PvArc (with the prefix t- denoting terminator) transcription terminafor sequence using restriction endonucleases FseI and NcoI, yielding construct LJB2012. Similarly, the p-VfSBP_perm (SEQ ID NO4) promoter was cloned into a pENTR/B vector harboring the beta-Glucuronidase reporter gene c-GUS followed by the t-StCatpA transcriptional terminator sequence using restriction endonucleases FseI and NcoI, yielding construct LJB2007.

The complementary pENTR vectors without any expression cassettes were constructed by introduction of a multiple cloning site via KpnI and HindIII restriction sites. By performing a site specific recombination (LR-reaction), the created pENTR/A, pENTR/B and pENTR/C were combined with the pSUN destination vector (pSUN derivative) according to the manufacturers (Invitrogen, Carlsbad, Calif., USA) Multisite Gateway manual. The reactions yielded a binary vector with the p-PvArc5_perm (SEQ ID NO2) promoter, the beta-Glucuronidase coding sequence c-GUS and the t-PvArc terminator, for which the full construct sequence is given (SEQ ID NO7). Accordingly, a binary vector with the p-VfSBP_perm (SEQ ID NO4) promoter, the beta-Glucuronidase reporter gene and the t-StCatpA terminator for which the full construct sequence is given (SEQ ID NO8). The resulting plant transformation vectors are summarized in table 5:

TABLE 5

Plant expression vectors for *B. napus* transformation

| plant expression vector | Composition of the expression cassette Promoter::reporter gene::terminator | SEQ ID NO |
|---|---|---|
| LJB2045 | p-PvArc5_perm::c-GUS::t-PvArc | 7 |
| LJB2043 | p-VfSBP_perm::c-GUS::t-StCatpA | 8 |

1.3 Generation of Transgenic Rapeseed Plants (Amended Protocol According to Moloney et al., 1992, Plant Cell Reports, 8: 238-242)

In preparation for the generation of transgenic rapeseed plants, the binary vectors were transformed into *Agrobacterium tumefaciens* C58C1:pGV2260 (Deblaere et al., 1985, Nucl. Acids. Res. 13: 4777-4788). A 1:50 dilution of an overnight culture of *Agrobacteria* harboring the respective binary construct was grown in Murashige-Skoog Medium (Murashige and Skoog, 1962, Physiol. Plant 15, 473) supplemented with 3% saccharose (3MS-Medium). For the transformation of rapeseed plants, petioles or hypocotyledons of sterile plants were incubated with a 1:50 *Agrobacterium* solution for 5-10 minutes followed by a three-day co-incubation in darkness at 25° C. on 3 MS. Medium supplemented with 0.8% bacto-agar. After three days, the explants were transferred to MS-medium containing 500 mg/l Claforan (Cefotaxime-Sodium), 100 nM lmazetapyr, 20 microM Benzylaminopurin (BAP) and 1.6 g/l Glucose in a 16 h light/8 h darkness light regime, which was repeated in weekly periods. Growing shoots were transferred to MS-Medium containing 2% saccharose, 250 mg/l Claforan and 0.8% Bacto-agar. After 3 weeks, the growth hormone 2-Indolbutyl acid was added to the medium to promote root formation. Shoots were transferred to soil following root development, grown for two weeks in a growth chamber and grown to maturity in greenhouse conditions.

Example 2: Expression Profile of the p-PvArc5_perm and p-VfSBP_perm Gene Control Elements To demonstrate and analyze the transcription regulating properties of a promoter, it is useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-β-D-glucuronic acid during corresponding activity assays (Jefferson 1987). For determination of promoter activity and tissue specificity, plant tissue is dissected, stained and analyzed as described (e.g., Bäumlein 1991).

The regenerated transgenic T0 rapeseed plants harboring single or double insertions of the transgene deriving from constructs LJB2043 or LJB2045 were used for reporter gene analysis.

Table 6 summarizes the reporter gene activity observed in plants harboring transgenes containing SEQ ID NO2 and SEQ ID NO4 in constructs LJB2043 and LJB2045, respectively:

TABLE 6 beta-Glucuronidase reporter gene activity in selected rapeseed plants harboring transgenes with SEQ ID NO2 (p-PvARC5-perm) and SEQ ID NO4 (p-VfSBP-perm) compared to the GUS expression derived from the respective starting sequence in rapeseed (p-VfSBP) or *Phaseolus* and *Arabidopsis* plants (p-PvArc5).

| Tissue | LJB2043 p-VfSBP-perm | p-VfSBP | LJB2045 p-PvArc5_perm | p-PvArc5* |
|---|---|---|---|---|
| leaves | negative | negative | negative | negative |
| stem | negative | negative | negative | negative |
| roots | negative | negative | negative | negative |
| flower | negative | negative | negative | negative |
| silique (without seed) | negative | not analyzed | negative | not assayed |
| embryo (early) | weak | weak | strong | strong, no seperate analyses of different stages |
| embryo (young) | weak | weak | strong | |
| embryo (medium) | strong | strong | strong | |
| embryo (mature) | strong | strong | strong | strong |
| seed shell | weak | not analyzed | strong | strong |

*expression in *Phaseolus* and *Arabidopsis* according to Goossens et al.

Figure 2:
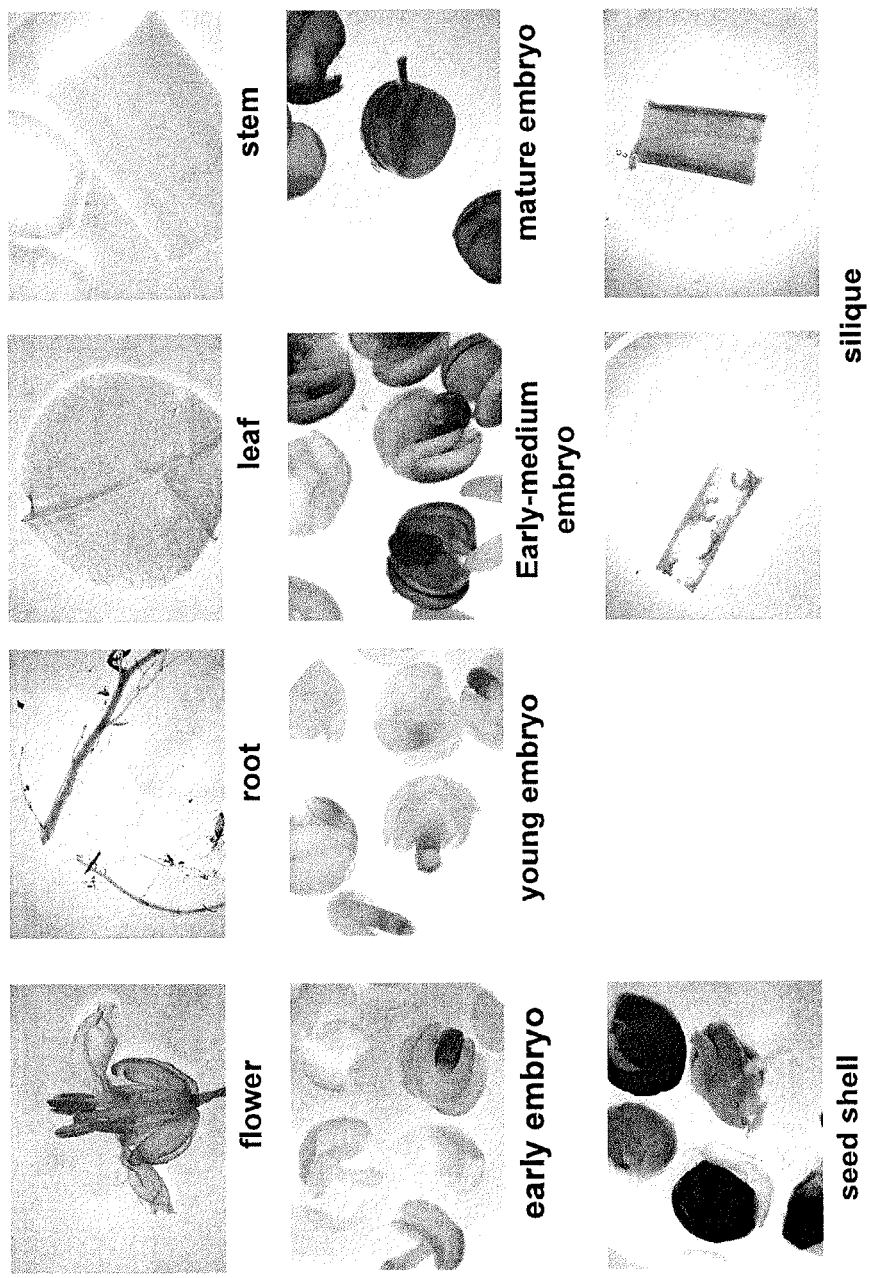

The gene expression activity conferred by p-PvArc5 perm and p-VfSBP_perm is shown exemplary in FIG. 1 (p-PvArc5_perm) and in FIG. 2 (P-VfSBP_perm).

General results for SEQ ID NO2: Strong GUS expression was detected in all stages of embryo development and in seed shells. No activity was found in other tissues analyzed.

General results for SEQ ID NO4: Weak GUS expression was detected in early and young embryo stages, strong GUS expression could be observed in medium and mature embryos. Weak expression was monitored in seed shells. No activity was found in other tissues investigated.

Example 3

3.1 Random Permutation of the Promoter Sequence

Using publicly available data, a promoter showing seed specific expression in plants was selected for analyzing the effects of sequence permutation in periodic intervals throughout the full length of the promoter DNA sequence. The wild type sequences of the Brassica napus p-BnNapin promoter was analyzed and annotated for the occurrence of cis-regulatory elements using available literature data (Ellerström et al., Ericson et al., Ezcurra et al.). In the following, the DNA sequence of the promoter was permutated in the region of −1000 to +1 nucleotides with the following criteria to yield p-BnNapin_perm (SEQ ID NO6): DNA permutation was conducted in a way to not affect cis regulatory elements which have been proven previously to be essential for seed specific gene expression and motives essential for gene expression. The remaining promoter sequence was randomly permutated resulting in a promoter sequence with an overall nucleotide homology of 75% to the initial p-BnNapin sequence 3.2 Vector Construction Using the Multisite Gateway System (Invitrogen, Carlsbad, Calif., USA), promoter::reporter-gene cassettes were assembled into binary constructs for plant transformation. Beta-Glucuronidase (GUS) or uidA gene which encodes an enzyme for which various chromogenic substrates are known, was utilized as reporter protein for determining the expression features of the permutated p-BnNapin_perm (SEQ ID NO6) promoter sequences.

The DNA fragments representing promoter p-BnNapin_perm was generated by gene synthesis. Endonucleolytic restriction sites suitable for cloning the promoter fragment into a beta-Glucuronidase reporter gene cassette was included in the synthesis. p-BnNapin_perm (SEQ ID NO6) promoter was cloned into a pENTR/A vector harboring the beta-Glucuronidase reporter gene c-GUS (with the prefix c-denoting coding sequence) followed by the t-nos transcription terminator sequence using restriction endonucleases BamHI and NcoI, yielding pENTR/A LLL1168.

A 1138 bp DNA fragment representing the native promoter p-BnNapin (SEQ ID NO5) was generated by PCR with the following primers.

```
                           SEQ ID NO 11
Loy963   GATATAGGTACCTCTTCATCGGTGATTGATTCCT

SEQ ID NO 12
Loy964   GATATACCATGGTCGTGTATGTTTTTAATCTTGTTTG
```

Endonucleolytic restriction sites suitable for cloning the promoter fragment into a beta-Glucuronidase reporter gene cassette were included in the primers. p-BnNapin (SEQ ID NO5) promoter was cloned into a pENTR/A vector harboring the beta-Glucuronidase reporter gene c-GUS (with the prefix c- denoting coding sequence) followed by the t-nos transcription terminator sequence using restriction endonucleases KpnI and NcoI, yielding pENTR/A LLL1166.

By performing a site specific recombination (LR-reaction), the newly created pENTRs/A LLL1168 and LLL1166, were combined with pENTR/B and pENTR/C and the pSUN destination vector (pSUN derivative) according to the manufacturers (Invitrogen, Carlsbad, Calif., USA) Multi-site Gateway manual. The reaction yielded binary vector LLL 1184 with the p-BnNapin_perm (SEQ ID NO6) promoter, the beta-Glucuronidase coding sequence c-GUS and the t-nos terminator, and binary vector LLL 1176 with the native p-BnNapin (SEQ ID NO5) promoter, the beta-Glucuronidase coding sequence c-GUS and the t-nos terminator. For both vectors the full construct sequence is given (SEQ ID NO9 and 10). The resulting plant transformation vectors are shown in table 7:

TABLE 7

Plant expression vectors for A. thaliana transformation

| plant expression vector | Composition of the expression cassette Promoter::reporter gene::terminator | SEQ ID NO |
|---|---|---|
| LLL1184 | p-BnNapin_perm::c-GUS::t-nos | 9 |
| LLL1176 | p-BnNapin::c-GUS::t-nos | 10 |

3.3 Generation of Arabidopsis thaliana Plants

A. thaliana plants were grown in soil until they flowered. Agrobacterium tumefaciens (strain C58C1 [pMP90]) transformed with the construct of interest was grown in 500 mL in liquid YEB medium (5 g/L Beef extract, 1 g/L Yeast Extract (Duchefa), 5 g/L Peptone (Duchefa), 5 g/L sucrose (Duchefa), 0.49 g/L MgSO$_4$ (Merck)) until the culture reached an OD$_{600}$ 0.8-1.0. The bacterial cells were harvested by centrifugation (15 minutes, 5,000 rpm) and resuspended in 500 mL infiltration solution (5% sucrose, 0.05% SILWET L-77 [distributed by Lehle seeds, Cat. No. VIS-02]). Flowering plants were dipped for 10-20 seconds into the Agrobacterium solution. Afterwards the plants were kept in the dark for one day and then in the greenhouse until seeds could be harvested. Transgenic seeds were selected on soil by spraying the seeds directly after sowing with a solution of 0.016 g/l Imazamox. After 12 to 14 days surviving plants were transferred to pots and grown in the greenhouse.

Example 4: Expression Profile of the Native p-Bn-Napin and the p-BnNapin_perm Gene Control Elements To demonstrate and analyze the transcription regulating properties of a promoter, it is useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-β-D-glucuronic acid during corresponding activity assays (Jefferson 1987). For determination of promoter activity and tissue specificity, plant tissue is dissected, stained and analyzed as described (e.g., Bäumlein 1991).

The regenerated transgenic T0 Arabidopsis plants harboring single or double insertions of the transgene deriving from constructs LLL1184 (SEQ ID NO9) and constructs LLL1176 (SEQ ID NO10) were used for reporter gene analysis. Table 8 summarizes the reporter gene activity observed in plants harboring transgenes containing SEQ ID NO9 and SEQ ID NO10 in constructs LLL1184 and LLL1176, respectively:

TABLE 8 beta-Glucuronidase reporter gene activity in selected Arabidopsis plants harboring transgenes with SEQ ID NO 9 or 10 respectively.

| Tissue | LLL1176 | LLL1184 |
|---|---|---|
| leaves | negative | negative |
| Stem | negative | negative |
| Roots | negative | negative |
| Flower | negative | negative |
| Silique | weak | weak |
| Embryo (medium) | strong | strong |
| Embryo (mature) | strong | strong |

Figure 3:
Figure 3:
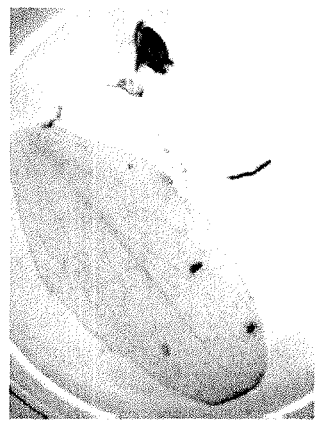
Figure 3:
Figure 3:
Figure 3:
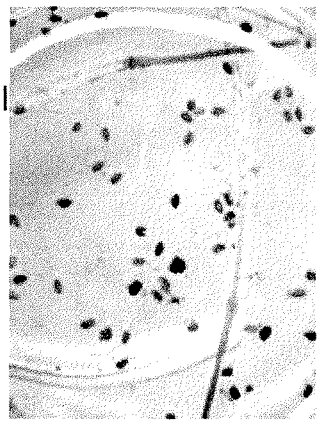
Figure 3:
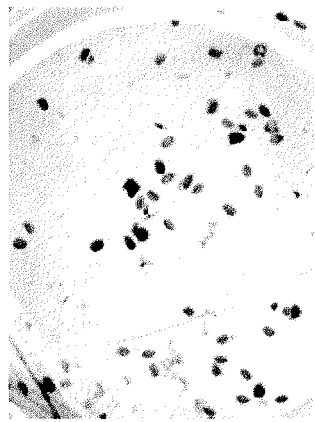

The gene expression activity conferred by pBn-Napin and p-BNapin_perm is shown exemplary in FIG. 3 (p-Bn_napin SEQ ID NO5, p-BnNapin_perm SEQ ID NO6)

General results for SEQ ID NO5 and 6: For both promoters pBn-Napin and p-BNapin_perm strong GUS expression was detected in medium to mature stages of embryo development. Weak expression was monitored in seed shells and in siliques. No activity was found in other tissues analyzed.

Example 5: Directed Permutation of a Constitutive Promoter Sequence

Using publicly available data, one promoters showing constitutive expression in plants was selected (de Pater, B. S., van der Mark, F., Rueb, S., Katagiri, F., Chua, N. H., Schilperoort, R. A. and Hensgens, L. A. (1992) The promoter of the rice gene GOS2 is active in various different monocot tissues and binds rice nuclear factor ASF-1 Plant J. 2 (6)) for analyzing the effects of sequence permutation in periodic intervals throughout the full length of the promoter DNA sequence. The wildtype or starting sequence of the Oryza sativa p-GOS2 (SEQ ID NO 13) (with the prefix p- denoting promoter) promoter was analyzed and annotated for the occurrence of motives, boxes, cis-regulatory elements using e.g. the GEMS Launcher Software (www.genomatix.de) as described above in example 1.

The promoter p-Gos2 encompasses a 5'UTR sequence with an internal intron. To ensure correct splicing of the intron after permutation, splice sites and putative branching point were not altered. No nucleotide exchanges were introduced into sequences 10 bp up- and downstream of the splice site (5' GT; 3' CAG) and "TNA" sequence elements within the last 100 base pairs of the original p-Gos2 were preserved after permutation.

In the following, the DNA sequence of the promoter was permutated according to the method of the invention to yield p-GOS2_perm1 and p-GOS2_perm2 respectively (SEQ ID NO 14 and 15).

The list of motives, boxes, cis regulatory elements in the p-GOS2 promoters before and after the permutation are shown in Table 9 for the starting sequence of p-GOS2, Table 10 for the p-GOS2_perm1 (SEQ ID NO 14) and Table 11 for the p-GOS2_perm2 sequence (SEQ ID NO 15).

Empty lines resemble motives, boxes, cis regulatory elements not found in one sequence but present in the corresponding sequence, hence, motives, boxes, cis regulatory elements that were deleted from the starting sequence or that were introduced into the permutated sequence.

TABLE 9

Boxes and Motifs identified in the starting sequence of the p-GOS2 promoter

| | p-GOS2 | | | Position Position | Core sim. | Matrix sim. |
|---|---|---|---|---|---|---|
| Family | Further Family Information | Matrix | Opt. | from-to | — | — |
| P$NCS1 | Nodulin consensus sequence 1 | P$NCS1.01 | 0.85 | 6  16 | 1 | 0.857 |
| P$MSAE | M-phase-specific activator elements | P$MSA.01 | 0.8 | 15  29 | 1 | 0.832 |
| P$MYBL | MYB-like proteins | P$GAMYB.01 | 0.91 | 29  45 | 1 | 0.927 |
| P$MYBL | MYB-like proteins | P$WER.01 | 0.87 | 33  49 | 1 | 0.897 |
| P$MADS | MADS box proteins | P$AGL2.01 | 0.82 | 35  55 | 0.79 | 0.82 |
| P$NACF | Plant specific NAC [NAM (no apical meristem), ATAF172, CUC2 (cup-shaped cotyledons 2)] transcription factors | P$IDEF2.01 | 0.96 | 48  60 | 1 | 0.96 |
| P$BRRE | Brassinosteroid (BR) response element | P$BZR1.01 | 0.95 | 48  64 | 1 | 0.954 |
| O$PTBP | Plant TATA binding protein factor | O$PTATA.01 | 0.88 | 60  74 | 1 | 0.883 |
| O$VTBP | Vertebrate TATA binding protein factor | O$VTATA.01 | 0.9 | 61  77 | 1 | 0.961 |
| O$INRE | Core promoter initiator elements | O$DINR.01 | 0.94 | 65  75 | 0.97 | 0.94 |
| O$VTBP | Vertebrate TATA binding protein factor | O$LTATA.01 | 0.82 | 69  85 | 1 | 0.842 |
| O$VTBP | Vertebrate TATA binding protein factor | O$VTATA.01 | 0.9 | 71  87 | 0.89 | 0.921 |
| O$YTBP | Yeast TATA binding protein factor | O$SPT15.01 | 0.83 | 74  90 | 1 | 0.832 |
| O$YTBP | Yeast TATA binding protein factor | O$SPT15.01 | 0.83 | 75  91 | 1 | 0.876 |
| O$VTBP | Vertebrate TATA binding protein factor | O$ATATA.01 | 0.78 | 76  92 | 0.75 | 0.781 |

TABLE 9-continued

Boxes and Motifs identified in the starting sequence of the p-GOS2 promoter

| p-GOS2 | | | | Position Position | | Core sim. | Matrix sim. |
|---|---|---|---|---|---|---|---|
| Family | Further Family Information | Matrix | Opt. | from | to | | |
| O$YTBP | Yeast TATA binding protein factor | O$SPT15.01 | 0.83 | 77 | 93 | 0.76 | 0.835 |
| P$MIIG | MYB IIG-type binding sites | P$PALBOXL.01 | 0.8 | 118 | 132 | 0.77 | 0.841 |
| P$DOFF | DNA binding with one finger (DOF) | P$DOF1.01 | 0.98 | 126 | 142 | 1 | 0.99 |
| P$DOFF | DNA binding with one finger (DOF) | P$PBF.01 | 0.97 | 149 | 165 | 1 | 0.989 |
| P$WNAC | Wheat NAC-domain transcription factors | P$TANAC69.01 | 0.68 | 170 | 192 | 0.81 | 0.712 |
| O$VTBP | Vertebrate TATA binding protein factor | O$ATATA.01 | 0.78 | 187 | 203 | 1 | 0.922 |
| P$E2FF | E2F-homolog cell cycle regulators | P$E2F.01 | 0.82 | 193 | 207 | 1 | 0.829 |
| O$INRE | Core promoter initiator elements | O$DINR.01 | 0.94 | 200 | 210 | 0.97 | 0.945 |
| P$AHBP | *Arabidopsis* homeobox protein | P$ATHB5.01 | 0.89 | 207 | 217 | 0.83 | 0.903 |
| P$AHBP | *Arabidopsis* homeobox protein | P$HAHB4.01 | 0.87 | 207 | 217 | 1 | 0.967 |
| P$CNAC | Calcium regulated NAC-factors | P$CBNAC.02 | 0.85 | 215 | 235 | 1 | 0.947 |
| P$MYBS | MYB proteins with single DNA binding repeat | P$PHR1.01 | 0.84 | 217 | 233 | 1 | 0.944 |
| P$OCSE | Enhancer element first identified in the promoter of the octopine synthase gene (OCS) of the *Agrobacterium tumefaciens* T-DNA | P$OCSL.01 | 0.69 | 216 | 236 | 1 | 0.722 |
| P$MYBS | MYB proteins with single DNA binding repeat | P$PHR1.01 | 0.84 | 222 | 238 | 1 | 0.979 |
| P$GTBX | GT-box elements | P$SBF1.01 | 0.87 | 246 | 262 | 1 | 0.901 |
| P$STKM | Storekeeper motif | P$STK.01 | 0.85 | 251 | 265 | 1 | 0.85 |
| P$AHBP | *Arabidopsis* homeobox protein | P$ATHB5.01 | 0.89 | 254 | 264 | 0.83 | 0.904 |
| P$AHBP | *Arabidopsis* homeobox protein | P$BLR.01 | 0.9 | 254 | 264 | 1 | 0.998 |
| P$HEAT | Heat shock factors | P$HSFA1A.01 | 0.75 | 284 | 300 | 1 | 0.757 |
| P$CCAF | Circadian control factors | P$CCA1.01 | 0.85 | 297 | 311 | 1 | 0.953 |
| P$LFYB | LFY binding site | P$LFY.01 | 0.93 | 318 | 330 | 0.91 | 0.945 |
| P$GAGA | GAGA elements | P$BPC.01 | 1 | 329 | 353 | 1 | 1 |
| P$CCAF | Circadian control factors | P$EE.01 | 0.84 | 335 | 349 | 0.75 | 0.865 |
| P$GAGA | GAGA elements | P$BPC.01 | 1 | 331 | 355 | 1 | 1 |
| P$CCAF | Circadian control factors | P$CCA1.01 | 0.85 | 337 | 351 | 1 | 0.968 |
| P$GTBX | GT-box elements | P$SBF1.01 | 0.87 | 341 | 357 | 1 | 0.875 |
| P$MADS | MADS box proteins | P$SQUA.01 | 0.9 | 345 | 365 | 1 | 0.925 |
| P$CCAF | Circadian control factors | P$EE.01 | 0.84 | 363 | 377 | 1 | 0.925 |
| O$VTBP | Vertebrate TATA binding protein factor | O$MTATA.01 | 0.84 | 383 | 399 | 1 | 0.895 |
| P$CARM | CA-rich motif | P$CARICH.01 | 0.78 | 388 | 406 | 1 | 0.785 |
| P$AHBP | *Arabidopsis* homeobox protein | P$HAHB4.01 | 0.87 | 397 | 407 | 1 | 0.902 |
| O$VTBP | Vertebrate TATA binding protein factor | O$LTATA.01 | 0.82 | 395 | 411 | 1 | 0.889 |
| O$VTBP | Vertebrate TATA binding protein factor | O$LTATA.01 | 0.82 | 396 | 412 | 1 | 0.844 |
| O$PTBP | Plant TATA binding protein factor | O$PTATA.01 | 0.88 | 398 | 412 | 1 | 0.892 |
| O$VTBP | Vertebrate TATA binding protein factor | O$ATATA.01 | 0.78 | 397 | 413 | 0.75 | 0.781 |
| P$AHBP | *Arabidopsis* homeobox protein | P$HAHB4.01 | 0.87 | 400 | 410 | 1 | 0.902 |
| O$VTBP | Vertebrate TATA binding protein factor | O$ATATA.01 | 0.78 | 402 | 418 | 0.75 | 0.781 |
| O$VTBP | Vertebrate TATA binding protein factor | O$VTATA.02 | 0.89 | 405 | 421 | 1 | 0.983 |
| O$PTBP | Plant TATA binding protein factor | O$PTATA.02 | 0.9 | 408 | 422 | 1 | 0.917 |
| P$OCSE | Enhancer element first identified in the promoter of the octopine synthase gene (OCS) of the *Agrobacterium tumefaciens* T-DNA | P$OCSTF.01 | 0.73 | 426 | 446 | 1 | 0.784 |
| P$AHBP | *Arabidopsis* homeobox protein | P$HAHB4.01 | 0.87 | 440 | 450 | 1 | 0.926 |

TABLE 9-continued

Boxes and Motifs identified in the starting sequence of the p-GOS2 promoter

| Family | Further Family Information | Matrix | Opt. | Position from-to | | Core sim. | Matrix sim. |
|---|---|---|---|---|---|---|---|
| P$AHBP | *Arabidopsis* homeobox protein | P$WUS.01 | 0.94 | 444 | 454 | 1 | 1 |
| P$OPAQ | Opaque-2 like transcriptional activators | P$O2_GCN4.01 | 0.81 | 447 | 463 | 1 | 0.819 |
| P$SEF4 | Soybean embryo factor 4 | P$SEF4.01 | 0.98 | 472 | 482 | 1 | 0.984 |
| P$GTBX | GT-box elements | P$SBF1.01 | 0.87 | 481 | 497 | 1 | 0.922 |
| P$DOFF | DNA binding with one finger (DOF) | P$DOF1.01 | 0.98 | 482 | 498 | 1 | 0.994 |
| P$GTBX | GT-box elements | P$SBF1.01 | 0.87 | 482 | 498 | 1 | 0.9 |
| P$WBXF | W Box family | P$WRKY11.01 | 0.94 | 493 | 509 | 1 | 0.963 |
| P$SEF4 | Soybean embryo factor 4 | P$SEF4.01 | 0.98 | 504 | 514 | 1 | 0.994 |
| P$IBOX | Plant I-Box sites | P$GATA.01 | 0.93 | 509 | 525 | 1 | 0.961 |
| P$NCS1 | Nodulin consensus sequence 1 | P$NCS1.01 | 0.85 | 515 | 525 | 1 | 0.948 |
| P$GTBX | GT-box elements | P$S1F.01 | 0.79 | 518 | 534 | 0.75 | 0.793 |
| P$LREM | Light responsive element motif, not modulated by different light qualities | P$RAP22.01 | 0.85 | 527 | 537 | 1 | 0.897 |
| P$L1BX | L1 box, motif for L1 layer-specific expression | P$ATML1.01 | 0.82 | 525 | 541 | 0.75 | 0.825 |
| O$VTBP | Vertebrate TATA binding protein factor | O$ATATA.01 | 0.78 | 539 | 555 | 0.75 | 0.782 |
| P$ROOT | Root hair-specific cis-elements in angiosperms | P$RHE.01 | 0.77 | 568 | 592 | 0.75 | 0.772 |
| P$ABRE | ABA response elements | P$ABRE.01 | 0.82 | 591 | 607 | 1 | 0.837 |
| P$ASRC | AS1/AS2 repressor complex | P$AS1_AS2_II.01 | 0.86 | 599 | 607 | 1 | 0.867 |
| P$L1BX | L1 box, motif for L1 layer-specific expression | P$HDG9.01 | 0.77 | 629 | 645 | 1 | 0.89 |
| P$L1BX | L1 box, motif for L1 layer-specific expression | P$HDG9.01 | 0.77 | 631 | 647 | 0.8 | 0.783 |
| P$L1BX | L1 box, motif for L1 layer-specific expression | P$ATML1.01 | 0.82 | 638 | 654 | 1 | 0.877 |
| P$CCAF | Circadian control factors | P$EE.01 | 0.84 | 649 | 663 | 1 | 0.899 |
| P$DOFF | DNA binding with one finger (DOF) | P$PBF.01 | 0.97 | 687 | 703 | 1 | 0.987 |
| P$GTBX | GT-box elements | P$SBF1.01 | 0.87 | 689 | 705 | 1 | 0.888 |
| P$AHBP | *Arabidopsis* homeobox protein | P$BLR.01 | 0.9 | 695 | 705 | 1 | 0.929 |
| P$CCAF | Circadian control factors | P$EE.01 | 0.84 | 694 | 708 | 1 | 0.954 |
| P$LREM | Light responsive element motif, not modulated by different light qualities | P$RAP22.01 | 0.85 | 701 | 711 | 1 | 1 |
| O$VTBP | Vertebrate TATA binding protein factor | O$ATATA.01 | 0.78 | 699 | 715 | 0.75 | 0.822 |
| P$HMGF | High mobility group factors | P$HMG_IY.01 | 0.89 | 711 | 725 | 1 | 0.929 |
| P$AHBP | *Arabidopsis* homeobox protein | P$ATHB1.01 | 0.9 | 716 | 726 | 0.79 | 0.901 |
| P$AHBP | *Arabidopsis* homeobox protein | P$BLR.01 | 0.9 | 716 | 726 | 1 | 0.998 |
| O$VTBP | Vertebrate TATA binding protein factor | O$VTATA.02 | 0.89 | 716 | 732 | 1 | 0.893 |
| P$SUCB | Sucrose box | P$SUCROSE.01 | 0.81 | 715 | 733 | 1 | 0.856 |
| P$DOFF | DNA binding with one finger (DOF) | P$PBOX.01 | 0.75 | 718 | 734 | 0.76 | 0.762 |
| P$HEAT | Heat shock factors | P$HSE.01 | 0.81 | 718 | 734 | 1 | 0.833 |
| P$GAPB | GAP-Box (light response elements) | P$GAP.01 | 0.88 | 733 | 747 | 1 | 0.924 |
| P$MYBL | MYB-like proteins | P$MYBPH3.02 | 0.76 | 744 | 760 | 0.78 | 0.834 |
| O$VTBP | Vertebrate TATA binding protein factor | O$ATATA.01 | 0.78 | 754 | 770 | 0.75 | 0.831 |
| P$TELO | Telo box (plant interstitial telomere motifs) | P$ATPURA.01 | 0.85 | 756 | 770 | 0.75 | 0.869 |
| P$MYCL | Myc-like basic helix-loop-helix binding factors | P$OSBHLH66.01 | 0.85 | 789 | 807 | 1 | 0.851 |
| P$BRRE | Brassinosteroid (BR) response element | P$BZR1.01 | 0.95 | 793 | 809 | 1 | 0.998 |
| P$URNA | Upstream sequence element of U-snRNA genes | P$USE.01 | 0.75 | 812 | 828 | 0.75 | 0.797 |
| P$MADS | MADS box proteins | P$AGL1.01 | 0.84 | 812 | 832 | 1 | 0.895 |
| P$MADS | MADS box proteins | P$AGL1.01 | 0.84 | 813 | 833 | 0.92 | 0.911 |
| P$NCS1 | Nodulin consensus sequence 1 | P$NCS1.01 | 0.85 | 872 | 882 | 0.81 | 0.888 |
| P$LREM | Light responsive element motif, not modulated by different light qualities | P$RAP22.01 | 0.85 | 879 | 889 | 1 | 0.896 |

TABLE 9-continued

Boxes and Motifs identified in the starting sequence of the p-GOS2 promoter

| p-GOS2 | | | | Position Position | | Core sim. | Matrix sim. |
|---|---|---|---|---|---|---|---|
| Family | Further Family Information | Matrix | Opt. | from-to | | — | — |
| P$MSAE | M-phase-specific activator elements | P$MSA.01 | 0.8 | 880 | 894 | 1 | 0.877 |
| P$MYBL | MYB-like proteins | P$NTMYBAS1.01 | 0.96 | 900 | 916 | 0.95 | 0.968 |
| P$GTBX | GT-box elements | P$SBF1.01 | 0.87 | 909 | 925 | 1 | 0.905 |
| P$MYBL | MYB-like proteins | P$AS1__AS2__I.01 | 0.99 | 911 | 927 | 1 | 1 |
| P$LREM | Light responsive element motif, not modulated by different light qualities | P$RAP22.01 | 0.85 | 981 | 991 | 1 | 0.893 |
| O$PTBP | Plant TATA binding protein factor | O$PTATA.02 | 0.9 | 982 | 996 | 1 | 0.951 |
| P$L1BX | L1 box, motif for L1 layer-specific expression | P$PDF2.01 | 0.85 | 982 | 998 | 1 | 0.884 |
| O$VTBP | Vertebrate TATA binding protein factor | O$VTATA.01 | 0.9 | 983 | 999 | 1 | 0.955 |
| P$MADS | MADS box proteins | P$AGL15.01 | 0.79 | 1006 | 1026 | 0.83 | 0.793 |
| P$MYBS | MYB proteins with single DNA binding repeat | P$ZMMRP1.01 | 0.79 | 1008 | 1024 | 0.78 | 0.811 |
| O$PTBP | Plant TATA binding protein factor | O$PTATA.02 | 0.9 | 1010 | 1024 | 1 | 0.91 |
| P$CGCG | Calmodulin binding/ CGCG box binding proteins | P$ATSR1.01 | 0.84 | 1051 | 1067 | 1 | 0.859 |
| P$ABRE | ABA response elements | P$ABF1.01 | 0.79 | 1053 | 1069 | 1 | 0.837 |
| P$CE3S | Coupling element 3 sequence | P$CE3.01 | 0.77 | 1052 | 1070 | 1 | 0.893 |
| P$NACF | Plant specific NAC [NAM (no apical meristem), ATAF172, CUC2 (cup-shaped cotyledons 2)] transcription factors | P$ANAC092.01 | 0.92 | 1055 | 1067 | 1 | 0.927 |
| P$DPBF | Dc3 promoter binding factors | P$DPBF.01 | 0.89 | 1057 | 1067 | 1 | 0.908 |
| P$PREM | Motifs of plastid response elements | P$MGPROTORE.01 | 0.77 | 1059 | 1089 | 1 | 0.806 |
| O$MTEN | Core promoter motif ten elements | O$HMTE.01 | 0.88 | 1072 | 1092 | 0.96 | 0.94 |
| P$DREB | Dehydration responsive element binding factors | P$HVDRF1.01 | 0.89 | 1079 | 1093 | 1 | 0.922 |
| P$PREM | Motifs of plastid response elements | P$MGPROTORE.01 | 0.77 | 1077 | 1107 | 1 | 0.805 |
| O$MTEN | Core promoter motif ten elements | O$DMTE.01 | 0.77 | 1097 | 1117 | 0.84 | 0.805 |
| P$OPAQ | Opaque-2 like transcriptional activators | P$O2.02 | 0.87 | 1135 | 1151 | 1 | 0.915 |
| P$SALT | Salt/drought responsive elements | P$ALFIN1.02 | 0.95 | 1136 | 1150 | 1 | 0.954 |
| P$L1BX | L1 box, motif for L1 layer-specific expression | P$PDF2.01 | 0.85 | 1179 | 1195 | 1 | 0.882 |
| P$SBPD | SBP-domain proteins | P$SBP.01 | 0.88 | 1199 | 1215 | 1 | 0.912 |
| P$PALA | Conserved box A in PAL and 4CL gene promoters | P$PALBOXA.01 | 0.84 | 1201 | 1219 | 1 | 0.863 |
| P$MYBS | MYB proteins with single DNA binding repeat | P$ZMMRP1.01 | 0.79 | 1230 | 1246 | 1 | 0.833 |
| P$AHBP | *Arabidopsis* homeobox protein | P$ATHB9.01 | 0.77 | 1244 | 1254 | 1 | 0.867 |
| P$MADS | MADS box proteins | P$AGL2.01 | 0.82 | 1248 | 1268 | 0.97 | 0.828 |
| P$MYBS | MYB proteins with single DNA binding repeat | P$MYBST1.01 | 0.9 | 1262 | 1278 | 1 | 0.953 |
| P$HEAT | Heat shock factors | P$HSE.01 | 0.81 | 1278 | 1294 | 1 | 0.864 |
| P$LEGB | Legumin Box family | P$RY.01 | 0.87 | 1277 | 1303 | 1 | 0.871 |
| P$MYBS | MYB proteins with single DNA binding repeat | P$OSMYBS.01 | 0.82 | 1343 | 1359 | 0.75 | 0.822 |
| O$INRE | Core promoter initiator elements | O$DINR.01 | 0.94 | 1349 | 1359 | 0.97 | 0.955 |
| P$STKM | Storekeeper motif | P$STK.01 | 0.85 | 1355 | 1369 | 1 | 0.95 |
| P$GTBX | GT-box elements | P$GT.01 | 0.85 | 1403 | 1419 | 0.97 | 0.865 |
| O$VTBP | Vertebrate TATA binding protein factor | O$ATATA.01 | 0.78 | 1439 | 1455 | 0.75 | 0.797 |
| P$OCSE | Enhancer element first identified in the promoter of the octopine synthase gene (OCS) of the *Agrobacterium tumefaciens* T-DNA | P$OCSL.01 | 0.69 | 1437 | 1457 | 0.77 | 0.745 |
| P$HEAT | Heat shock factors | P$HSFA1A.01 | 0.75 | 1478 | 1494 | 1 | 0.764 |
| P$WBXF | W Box family | P$WRKY.01 | 0.92 | 1488 | 1504 | 1 | 0.94 |
| P$TEFB | TEF-box | P$TEF1.01 | 0.76 | 1491 | 1511 | 0.96 | 0.858 |

TABLE 9-continued

Boxes and Motifs identified in the starting sequence of the p-GOS2 promoter

| p-GOS2 | | | | Position Position | | Core sim. | Matrix sim. |
|---|---|---|---|---|---|---|---|
| Family | Further Family Information | Matrix | Opt. | from-to | | — | — |
| P$MYBS | MYB proteins with single DNA binding repeat | P$HVMCB1.01 | 0.93 | 1498 | 1514 | 1 | 0.934 |
| P$MYBS | MYB proteins with single DNA binding repeat | P$TAMYB80.01 | 0.83 | 1509 | 1525 | 0.75 | 0.837 |
| P$MSAE | M-phase-specific activator elements | P$MSA.01 | 0.8 | 1551 | 1565 | 1 | 0.802 |
| P$OPAQ | Opaque-2 like transcriptional activators | P$O2.01 | 0.87 | 1558 | 1574 | 1 | 0.883 |
| P$AHBP | *Arabidopsis* homeobox protein | P$ATHB5.01 | 0.89 | 1569 | 1579 | 0.83 | 0.904 |
| P$AHBP | *Arabidopsis* homeobox protein | P$ATHB5.01 | 0.89 | 1569 | 1579 | 0.94 | 0.978 |
| O$VTBP | Vertebrate TATA binding protein factor | O$ATATA.01 | 0.78 | 1609 | 1625 | 0.75 | 0.781 |
| P$LREM | Light responsive element motif, not modulated by different light qualities | P$RAP22.01 | 0.85 | 1613 | 1623 | 1 | 0.966 |
| P$TEFB | TEF-box | P$TEF1.01 | 0.76 | 1617 | 1637 | 0.84 | 0.812 |
| P$WNAC | Wheat NAC-domain transcription factors | P$TANAC69.01 | 0.68 | 1625 | 1647 | 0.9 | 0.775 |
| P$NACF | Plant specific NAC [NAM (no apical meristem), ATAF172, CUC2 (cup-shaped cotyledons 2)] transcription factors | P$ANAC019.01 | 0.94 | 1632 | 1644 | 0.95 | 0.968 |
| P$GTBX | GT-box elements | P$S1F.01 | 0.79 | 1642 | 1658 | 1 | 0.917 |
| P$PSRE | Pollen-specific regulatory elements | P$GAAA.01 | 0.83 | 1644 | 1660 | 1 | 0.864 |
| P$MYBL | MYB-like proteins | P$MYBPH3.01 | 0.8 | 1647 | 1663 | 1 | 0.938 |
| P$DOFF | DNA binding with one finger (DOF) | P$DOF1.01 | 0.98 | 1694 | 1710 | 1 | 1 |
| P$HEAT | Heat shock factors | P$HSFA1A.01 | 0.75 | 1703 | 1719 | 0.86 | 0.757 |
| P$CCAF | Circadian control factors | P$EE.01 | 0.84 | 1719 | 1733 | 1 | 0.955 |
| P$MADS | MADS box proteins | P$AG.01 | 0.8 | 1717 | 1737 | 0.9 | 0.816 |
| P$GTBX | GT-box elements | P$ASIL1.01 | 0.93 | 1732 | 1748 | 1 | 0.967 |
| O$INRE | Core promoter initiator elements | O$DINR.01 | 0.94 | 1749 | 1759 | 1 | 0.957 |
| P$SUCB | Sucrose box | P$SUCROSE.01 | 0.81 | 1749 | 1767 | 0.75 | 0.837 |
| P$SUCB | Sucrose box | P$SUCROSE.01 | 0.81 | 1754 | 1772 | 0.75 | 0.815 |
| P$L1BX | L1 box, motif for L1 layer-specific expression | P$ATML1.02 | 0.76 | 1757 | 1773 | 0.89 | 0.848 |
| P$AHBP | *Arabidopsis* homeobox protein | P$ATHB9.01 | 0.77 | 1761 | 1771 | 0.75 | 0.815 |
| O$VTBP | Vertebrate TATA binding protein factor | O$VTATA.02 | 0.89 | 1777 | 1793 | 1 | 0.996 |
| P$DOFF | DNA binding with one finger (DOF) | P$DOF3.01 | 0.99 | 1778 | 1794 | 1 | 0.995 |
| O$PTBP | Plant TATA binding protein factor | O$PTATA.02 | 0.9 | 1780 | 1794 | 1 | 0.923 |
| P$IBOX | Plant I-Box sites | P$GATA.01 | 0.93 | 1787 | 1803 | 1 | 0.967 |
| P$MYBS | MYB proteins with single DNA binding repeat | P$MYBST1.01 | 0.9 | 1790 | 1806 | 1 | 0.972 |
| O$VTBP | Vertebrate TATA binding protein factor | O$ATATA.01 | 0.78 | 1803 | 1819 | 0.75 | 0.797 |
| P$IBOX | Plant I-Box sites | P$GATA.01 | 0.93 | 1847 | 1863 | 1 | 0.945 |
| P$MYBS | MYB proteins with single DNA binding repeat | P$MYBST1.01 | 0.9 | 1850 | 1866 | 1 | 0.966 |
| P$MADS | MADS box proteins | P$SQUA.01 | 0.9 | 1866 | 1886 | 1 | 0.916 |
| P$GTBX | GT-box elements | P$SBF1.01 | 0.87 | 1872 | 1888 | 1 | 0.905 |
| O$VTBP | Vertebrate TATA binding protein factor | O$LTATA.01 | 0.82 | 1873 | 1889 | 1 | 0.837 |
| P$AHBP | *Arabidopsis* homeobox protein | P$HAHB4.01 | 0.87 | 1878 | 1888 | 1 | 0.902 |
| P$L1BX | L1 box, motif for L1 layer-specific expression | P$ATML1.01 | 0.82 | 1882 | 1898 | 0.75 | 0.824 |
| O$INRE | Core promoter initiator elements | O$DINR.01 | 0.94 | 1886 | 1896 | 0.97 | 0.949 |
| P$EPFF | EPF-type zinc finger factors, two canonical Cys2/His2 zinc finger motifs separated by spacers of various length | P$ZPT22.01 | 0.75 | 1887 | 1909 | 1 | 0.774 |
| P$GAPB | GAP-Box (light response elements) | P$GAP.01 | 0.88 | 1907 | 1921 | 1 | 0.903 |
| P$SUCB | Sucrose box | P$SUCROSE.01 | 0.81 | 1912 | 1930 | 1 | 0.849 |

TABLE 9-continued

Boxes and Motifs identified in the starting sequence of the p-GOS2 promoter

| | p-GOS2 | | | Position Position | | Core sim. | Matrix sim. |
|---|---|---|---|---|---|---|---|
| Family | Further Family Information | Matrix | Opt. | from-to | | — | — |
| P$HMGF | High mobility group factors | P$HMG_IY.01 | 0.89 | 1920 | 1934 | 1 | 0.892 |
| P$SEF4 | Soybean embryo factor 4 | P$SEF4.01 | 0.98 | 1927 | 1937 | 1 | 0.984 |
| P$MYBL | MYB-like proteins | P$ATMYB77.01 | 0.87 | 1973 | 1989 | 1 | 0.9 |
| P$GTBX | GT-box elements | P$ASIL1.01 | 0.93 | 1998 | 2014 | 1 | 0.971 |
| P$OPAQ | Opaque-2 like transcriptional activators | P$O2_GCN4.01 | 0.81 | 2001 | 2017 | 1 | 0.83 |
| P$IBOX | Plant I-Box sites | P$GATA.01 | 0.93 | 2018 | 2034 | 1 | 0.964 |
| P$MYBS | MYB proteins with single DNA binding repeat | P$MYBST1.01 | 0.9 | 2021 | 2037 | 1 | 0.957 |
| P$LREM | Light responsive element motif, not modulated by different light qualities | P$RAP22.01 | 0.85 | 2035 | 2045 | 1 | 0.858 |
| P$MIIG | MYB IIG-type binding sites | P$MYBC1.01 | 0.92 | 2033 | 2047 | 1 | 0.941 |
| P$HEAT | Heat shock factors | P$HSFA1A.01 | 0.75 | 2041 | 2057 | 1 | 0.792 |
| P$MYBL | MYB-like proteins | P$GAMYB.01 | 0.91 | 2054 | 2070 | 1 | 0.918 |
| P$GTBX | GT-box elements | P$GT1.01 | 0.85 | 2056 | 2072 | 1 | 0.876 |
| P$ASRC | AS1/AS2 repressor complex | P$AS1_AS2_II.01 | 0.86 | 2067 | 2075 | 1 | 0.906 |
| P$EINL | Ethylen insensitive 3 like factors | P$TEIL.01 | 0.92 | 2098 | 2106 | 0.96 | 0.926 |
| O$VTBP | Vertebrate TATA binding protein factor | O$LTATA.01 | 0.82 | 2110 | 2126 | 1 | 0.828 |
| P$MYBL | MYB-like proteins | P$MYBPH3.02 | 0.76 | 2110 | 2126 | 1 | 0.807 |

TABLE 10

Boxes and Motifs identified in the permutated sequence of the p-GOS2_perm1 promoter.

| | p-GOS2_perm1 | | | Position Position | | Core | Matrix |
|---|---|---|---|---|---|---|---|
| Family | Further Family Information | Matrix | Opt. | from-to | | sim. | sim. |
| P$NCS1 | Nodulin consensus sequence 1 | P$NCS1.01 | 0.85 | 6 | 16 | 1 | 0.857 |
| P$MSAE | M-phase-specific activator elements | P$MSA.01 | 0.8 | 15 | 29 | 1 | 0.832 |
| P$MYBL | MYB-like proteins | P$GAMYB.01 | 0.91 | 29 | 45 | 1 | 0.92 |
| P$MYBL | MYB-like proteins | P$WER.01 | 0.87 | 33 | 49 | 1 | 0.897 |
| P$MADS | MADS box proteins | P$AGL2.01 | 0.82 | 35 | 55 | 0.79 | 0.82 |
| P$NACF | Plant specific NAC [NAM (no apical meristem), ATAF172, CUC2 (cup-shaped cotyledons 2)] transcription factors | P$IDEF2.01 | 0.96 | 48 | 60 | 1 | 0.96 |
| P$BRRE | Brassinosteroid (BR) response element | P$BZR1.01 | 0.95 | 48 | 64 | 1 | 0.954 |
| O$PTBP | Plant TATA binding protein factor | O$PTATA.01 | 0.88 | 60 | 74 | 1 | 0.887 |
| O$VTBP | Vertebrate TATA binding protein factor | O$VTATA.01 | 0.9 | 61 | 77 | 1 | 0.961 |
| O$INRE | Core promoter initiator elements | O$DINR.01 | 0.94 | 65 | 75 | 0.97 | 0.94 |
| O$VTBP | Vertebrate TATA binding protein factor | O$LTATA.01 | 0.82 | 69 | 85 | 1 | 0.867 |
| O$VTBP | Vertebrate TATA binding protein factor | O$VTATA.01 | 0.9 | 71 | 87 | 0.89 | 0.92 |
| O$YTBP | Yeast TATA binding protein factor | O$SPT15.01 | 0.83 | 74 | 90 | 1 | 0.832 |
| O$YTBP | Yeast TATA binding protein factor | O$SPT15.01 | 0.83 | 75 | 91 | 1 | 0.877 |
| O$VTBP | Vertebrate TATA binding protein factor | O$ATATA.01 | 0.78 | 76 | 92 | 0.75 | 0.781 |
| O$YTBP | Yeast TATA binding protein factor | O$SPT15.01 | 0.83 | 77 | 93 | 0.76 | 0.835 |
| P$MIIG | MYB IIG-type binding sites | P$PALBOXL.01 | 0.8 | 118 | 132 | 0.77 | 0.841 |
| P$DOFF | DNA binding with one finger (DOF) | P$DOF1.01 | 0.98 | 126 | 142 | 1 | 0.99 |
| P$DOFF | DNA binding with one finger (DOF) | P$PBF.01 | 0.97 | 149 | 165 | 1 | 0.989 |
| P$WNAC | Wheat NAC-domain transcription factors | P$TANAC69.01 | 0.68 | 170 | 192 | 0.81 | 0.712 |
| O$VTBP | Vertebrate TATA binding protein factor | O$ATATA.01 | 0.78 | 187 | 203 | 1 | 0.878 |

TABLE 10-continued

Boxes and Motifs identified in the permutated sequence of the p-GOS2_perm1 promoter.

| | p-GOS2_perm1 | | | Position Position from-to | | Core sim. | Matrix sim. |
|---|---|---|---|---|---|---|---|
| Family | Further Family Information | Matrix | Opt. | | | | |
| P$E2FF | E2F-homolog cell cycle regulators | P$E2F.01 | 0.82 | 193 | 207 | 1 | 0.826 |
| P$AHBP | *Arabidopsis* homeobox protein | P$ATHB5.01 | 0.89 | 207 | 217 | 0.83 | 0.903 |
| P$AHBP | *Arabidopsis* homeobox protein | P$HAHB4.01 | 0.87 | 207 | 217 | 1 | 0.967 |
| P$CNAC | Calcium regulated NAC-factors | P$CBNAC.02 | 0.85 | 215 | 235 | 1 | 0.937 |
| P$MYBS | MYB proteins with single DNA binding repeat | P$PHR1.01 | 0.84 | 217 | 233 | 1 | 0.944 |
| P$OCSE | Enhancer element first identified in the promoter of the octopine synthase gene (OCS) of the *Agrobacterium tumefaciens* T-DNA | P$OCSL.01 | 0.69 | 216 | 236 | 1 | 0.735 |
| P$MYBS | MYB proteins with single DNA binding repeat | P$PHR1.01 | 0.84 | 222 | 238 | 1 | 0.979 |
| P$GTBX | GT-box elements | P$SBF1.01 | 0.87 | 246 | 262 | 1 | 0.901 |
| P$STKM | Storekeeper motif | P$STK.01 | 0.85 | 251 | 265 | 1 | 0.85 |
| P$AHBP | *Arabidopsis* homeobox protein | P$ATHB5.01 | 0.89 | 254 | 264 | 0.83 | 0.904 |
| P$AHBP | *Arabidopsis* homeobox protein | P$BLR.01 | 0.9 | 254 | 264 | 1 | 0.998 |
| P$HEAT | Heat shock factors | P$HSFA1A.01 | 0.75 | 284 | 300 | 1 | 0.757 |
| P$CCAF | Circadian control factors | P$CCA1.01 | 0.85 | 297 | 311 | 1 | 0.94 |
| P$LFYB | LFY binding site | P$LFY.01 | 0.93 | 318 | 330 | 0.91 | 0.945 |
| P$WBXF | W Box family | P$ERE.01 | 0.89 | 322 | 338 | 1 | 0.893 |
| P$GAGA | GAGA elements | P$BPC.01 | 1 | 329 | 353 | 1 | 1 |
| P$CCAF | Circadian control factors | P$EE.01 | 0.84 | 335 | 349 | 0.75 | 0.865 |
| P$GAGA | GAGA elements | P$BPC.01 | 1 | 331 | 355 | 1 | 1 |
| P$CCAF | Circadian control factors | P$CCA1.01 | 0.85 | 337 | 351 | 1 | 0.968 |
| P$GTBX | GT-box elements | P$SBF1.01 | 0.87 | 341 | 357 | 1 | 0.875 |
| P$MADS | MADS box proteins | P$SQUA.01 | 0.9 | 345 | 365 | 1 | 0.925 |
| P$CCAF | Circadian control factors | P$EE.01 | 0.84 | 363 | 377 | 1 | 0.924 |
| O$VTBP | Vertebrate TATA binding protein factor | O$MTATA.01 | 0.84 | 383 | 399 | 1 | 0.895 |
| P$CARM | CA-rich motif | P$CARICH.01 | 0.78 | 388 | 406 | 1 | 0.8 |
| P$AHBP | *Arabidopsis* homeobox protein | P$HAHB4.01 | 0.87 | 397 | 407 | 1 | 0.902 |
| O$VTBP | Vertebrate TATA binding protein factor | O$LTATA.01 | 0.82 | 395 | 411 | 1 | 0.889 |
| O$VTBP | Vertebrate TATA binding protein factor | O$LTATA.01 | 0.82 | 396 | 412 | 1 | 0.844 |
| O$PTBP | Plant TATA binding protein factor | O$PTATA.01 | 0.88 | 398 | 412 | 1 | 0.892 |
| O$VTBP | Vertebrate TATA binding protein factor | O$ATATA.01 | 0.78 | 397 | 413 | 0.75 | 0.781 |
| P$AHBP | *Arabidopsis* homeobox protein | P$HAHB4.01 | 0.87 | 400 | 410 | 1 | 0.902 |
| O$VTBP | Vertebrate TATA binding protein factor | O$ATATA.01 | 0.78 | 402 | 418 | 0.75 | 0.781 |
| O$VTBP | Vertebrate TATA binding protein factor | O$VTATA.02 | 0.89 | 405 | 421 | 1 | 0.983 |
| O$PTBP | Plant TATA binding protein factor | O$PTATA.02 | 0.9 | 408 | 422 | 1 | 0.917 |
| P$OCSE | Enhancer element first identified in the promoter of the octopine synthase gene (OCS) of the *Agrobacterium tumefaciens* T-DNA | P$OCSTF.01 | 0.73 | 426 | 446 | 1 | 0.762 |
| P$AHBP | *Arabidopsis* homeobox protein | P$HAHB4.01 | 0.87 | 440 | 450 | 1 | 0.926 |
| P$AHBP | *Arabidopsis* homeobox protein | P$WUS.01 | 0.94 | 444 | 454 | 1 | 1 |
| P$OPAQ | Opaque-2 like transcriptional activators | P$O2_GCN4.01 | 0.81 | 447 | 463 | 1 | 0.819 |
| P$SEF4 | Soybean embryo factor 4 | P$SEF4.01 | 0.98 | 472 | 482 | 1 | 0.988 |
| P$GTBX | GT-box elements | P$SBF1.01 | 0.87 | 481 | 497 | 1 | 0.922 |
| P$DOFF | DNA binding with one finger (DOF) | P$DOF1.01 | 0.98 | 482 | 498 | 1 | 0.994 |
| P$GTBX | GT-box elements | P$SBF1.01 | 0.87 | 482 | 498 | 1 | 0.9 |
| P$WBXF | W Box family | P$WRKY11.01 | 0.94 | 493 | 509 | 1 | 0.957 |
| P$SEF4 | Soybean embryo factor 4 | P$SEF4.01 | 0.98 | 504 | 514 | 1 | 0.988 |
| P$IBOX | Plant I-Box sites | P$GATA.01 | 0.93 | 509 | 525 | 1 | 0.961 |
| P$NCS1 | Nodulin consensus sequence 1 | P$NCS1.01 | 0.85 | 515 | 525 | 1 | 0.948 |
| P$GTBX | GT-box elements | P$S1F.01 | 0.79 | 518 | 534 | 0.75 | 0.793 |
| P$LREM | Light responsive element motif, not modulated by different light qualities | P$RAP22.01 | 0.85 | 527 | 537 | 1 | 0.897 |
| P$L1BX | L1 box, motif for L1 layer-specific expression | P$HDG9.01 | 0.77 | 525 | 541 | 0.75 | 0.78 |

TABLE 10-continued

Boxes and Motifs identified in the permutated sequence of the p-GOS2_perm1 promoter.

| Family | p-GOS2_perm1 Further Family Information | Matrix | Opt. | Position from-to | | Core sim. | Matrix sim. |
|---|---|---|---|---|---|---|---|
| O$VTBP | Vertebrate TATA binding protein factor | O$ATATA.01 | 0.78 | 539 | 555 | 0.75 | 0.782 |
| P$ROOT | Root hair-specific cis-elements in angiosperms | P$RHE.01 | 0.77 | 568 | 592 | 0.75 | 0.772 |
| P$ABRE | ABA response elements | P$ABRE.01 | 0.82 | 591 | 607 | 1 | 0.837 |
| P$ASRC | AS1/AS2 repressor complex | P$AS1_AS2_II.01 | 0.86 | 599 | 607 | 1 | 0.867 |
| P$L1BX | L1 box, motif for L1 layer-specific expression | P$HDG9.01 | 0.77 | 629 | 645 | 1 | 0.888 |
| O$VTBP | Vertebrate TATA binding protein factor | O$ATATA.01 | 0.78 | 631 | 647 | 0.75 | 0.831 |
| P$L1BX | L1 box, motif for L1 layer-specific expression | P$HDG9.01 | 0.77 | 631 | 647 | 0.8 | 0.783 |
| P$L1BX | L1 box, motif for L1 layer-specific expression | P$PDF2.01 | 0.85 | 638 | 654 | 1 | 0.861 |
| P$CCAF | Circadian control factors | P$EE.01 | 0.84 | 649 | 663 | 1 | 0.899 |
| P$DOFF | DNA binding with one finger (DOF) | P$PBF.01 | 0.97 | 687 | 703 | 1 | 0.987 |
| P$GTBX | GT-box elements | P$SBF1.01 | 0.87 | 689 | 705 | 1 | 0.888 |
| P$AHBP | *Arabidopsis* homeobox protein | P$BLR.01 | 0.9 | 695 | 705 | 1 | 0.929 |
| P$CCAF | Circadian control factors | P$EE.01 | 0.84 | 694 | 708 | 1 | 0.954 |
| P$LREM | Light responsive element motif, not modulated by different light qualities | P$RAP22.01 | 0.85 | 701 | 711 | 1 | 0.98 |
| P$HMGF | High mobility group factors | P$HMG_IY.01 | 0.89 | 711 | 725 | 1 | 0.929 |
| P$AHBP | *Arabidopsis* homeobox protein | P$ATHB1.01 | 0.9 | 716 | 726 | 0.79 | 0.901 |
| P$AHBP | *Arabidopsis* homeobox protein | P$BLR.01 | 0.9 | 716 | 726 | 1 | 0.998 |
| O$VTBP | Vertebrate TATA binding protein factor | O$VTATA.02 | 0.89 | 716 | 732 | 1 | 0.893 |
| P$SUCB | Sucrose box | P$SUCROSE.01 | 0.81 | 715 | 733 | 1 | 0.856 |
| P$DOFF | DNA binding with one finger (DOF) | P$PBOX.01 | 0.75 | 718 | 734 | 0.76 | 0.762 |
| P$HEAT | Heat shock factors | P$HSE.01 | 0.81 | 718 | 734 | 1 | 0.833 |
| P$GAPB | GAP-Box (light response | P$GAP.01 | 0.88 | 733 | 747 | 1 | 0.917 |
| P$MYBL | MYB-like proteins | P$MYBPH3.02 | 0.76 | 744 | 760 | 0.78 | 0.834 |
| O$VTBP | Vertebrate TATA binding protein factor | O$ATATA.01 | 0.78 | 754 | 770 | 0.75 | 0.831 |
| P$TELO | Telo box (plant interstitial telomere motifs) | P$ATPURA.01 | 0.85 | 756 | 770 | 0.75 | 0.869 |
| P$MYCL | Myc-like basic helix-loop-helix binding factors | P$OSBHLH66.01 | 0.85 | 789 | 807 | 1 | 0.851 |
| P$BRRE | Brassinosteroid (BR) response element | P$BZR1.01 | 0.95 | 793 | 809 | 1 | 0.998 |
| P$URNA | Upstream sequence element of U-snRNA genes | P$USE.01 | 0.75 | 812 | 828 | 0.75 | 0.797 |
| P$MADS | MADS box proteins | P$AGL1.01 | 0.84 | 812 | 832 | 1 | 0.895 |
| P$MADS | MADS box proteins | P$AGL1.01 | 0.84 | 813 | 833 | 0.92 | 0.911 |
| P$NCS1 | Nodulin consensus sequence 1 | P$NCS1.01 | 0.85 | 872 | 882 | 0.81 | 0.888 |
| P$LREM | Light responsive element motif, not modulated by different light qualities | P$RAP22.01 | 0.85 | 879 | 889 | 1 | 0.896 |
| P$MSAE | M-phase-specific activator elements | P$MSA.01 | 0.8 | 880 | 894 | 1 | 0.877 |
| P$MYBL | MYB-like proteins | P$NTMYBAS1.01 | 0.96 | 900 | 916 | 0.95 | 0.968 |
| P$GTBX | GT-box elements | P$SBF1.01 | 0.87 | 909 | 925 | 1 | 0.905 |
| P$MYBL | MYB-like proteins | P$AS1_AS2_I.01 | 0.99 | 911 | 927 | 1 | 1 |
| P$LREM | Light responsive element motif, not modulated by different light qualities | P$RAP22.01 | 0.85 | 981 | 991 | 1 | 0.893 |
| O$PTBP | Plant TATA binding protein factor | O$PTATA.02 | 0.9 | 982 | 996 | 1 | 0.951 |
| P$L1BX | L1 box, motif for L1 layer-specific expression | P$PDF2.01 | 0.85 | 982 | 998 | 1 | 0.884 |
| O$VTBP | Vertebrate TATA binding protein factor | O$VTATA.01 | 0.9 | 983 | 999 | 1 | 0.955 |
| P$MADS | MADS box proteins | P$AGL15.01 | 0.79 | 1006 | 1026 | 0.83 | 0.8 |
| P$MYBS | MYB proteins with single DNA binding repeat | P$ZMMRP1.01 | 0.79 | 1008 | 1024 | 0.78 | 0.811 |
| O$PTBP | Plant TATA binding protein factor | O$PTATA.02 | 0.9 | 1010 | 1024 | 1 | 0.91 |
| P$CGCG | Calmodulin binding/CGCG box binding proteins | P$ATSR1.01 | 0.84 | 1051 | 1067 | 1 | 0.859 |
| P$ABRE | ABA response elements | P$ABF1.01 | 0.79 | 1053 | 1069 | 1 | 0.837 |
| P$CE3S | Coupling element 3 sequence | P$CE3.01 | 0.77 | 1052 | 1070 | 1 | 0.863 |

TABLE 10-continued

Boxes and Motifs identified in the permutated sequence of the p-GOS2_perm1 promoter.

| p-GOS2_perm1 | | | | Position Position | | Core | Matrix |
|---|---|---|---|---|---|---|---|
| Family | Further Family Information | Matrix | Opt. | from | to | sim. | sim. |
| P$NACF | Plant specific NAC [NAM (no apical meristem), ATAF172, CUC2 (cup-shaped cotyledons 2)] transcription factors | P$ANAC092.01 | 0.92 | 1055 | 1067 | 1 | 0.927 |
| P$DPBF | Dc3 promoter binding factors | P$DPBF.01 | 0.89 | 1057 | 1067 | 1 | 0.908 |
| P$PREM | Motifs of plastid response elements | P$MGPROTORE.01 | 0.77 | 1059 | 1089 | 1 | 0.806 |
| O$MTEN | Core promoter motif ten elements | O$HMTE.01 | 0.88 | 1072 | 1092 | 0.96 | 0.94 |
| P$DREB | Dehydration responsive element binding factors | P$HVDRF1.01 | 0.89 | 1079 | 1093 | 1 | 0.917 |
| P$PREM | Motifs of plastid response elements | P$MGPROTORE.01 | 0.77 | 1077 | 1107 | 1 | 0.807 |
| O$MTEN | Core promoter motif ten elements | O$DMTE.01 | 0.77 | 1097 | 1117 | 0.84 | 0.805 |
| P$OPAQ | Opaque-2 like transcriptional activators | P$O2.02 | 0.87 | 1135 | 1151 | 1 | 0.915 |
| P$SALT | Salt/drought responsive elements | P$ALFIN1.02 | 0.95 | 1136 | 1150 | 1 | 0.954 |
| P$L1BX | L1 box, motif for L1 layer-specific expression | P$PDF2.01 | 0.85 | 1179 | 1195 | 1 | 0.882 |
| P$SBPD | SBP-domain proteins | P$SBP.01 | 0.88 | 1199 | 1215 | 1 | 0.912 |
| P$PALA | Conserved box A in PAL and 4CL gene promoters | P$PALBOXA.01 | 0.84 | 1201 | 1219 | 1 | 0.863 |
| P$MYBS | MYB proteins with single DNA binding repeat | P$ZMMRP1.01 | 0.79 | 1230 | 1246 | 1 | 0.833 |
| P$AHBP | *Arabidopsis* homeobox protein | P$ATHB9.01 | 0.77 | 1244 | 1254 | 1 | 0.89 |
| P$AHBP | *Arabidopsis* homeobox protein | P$ATHB9.01 | 0.77 | 1244 | 1254 | 0.75 | 0.777 |
| P$MADS | MADS box proteins | P$AGL2.01 | 0.82 | 1248 | 1268 | 0.97 | 0.835 |
| P$MYBS | MYB proteins with single DNA binding repeat | P$MYBST1.01 | 0.9 | 1262 | 1278 | 1 | 0.953 |
| P$HEAT | Heat shock factors | P$HSE.01 | 0.81 | 1278 | 1294 | 1 | 0.864 |
| P$LEGB | Legumin Box family | P$RY.01 | 0.87 | 1277 | 1303 | 1 | 0.871 |
| P$MYBS | MYB proteins with single DNA binding repeat | P$OSMYBS.01 | 0.82 | 1343 | 1359 | 0.75 | 0.822 |
| O$INRE | Core promoter initiator elements | O$DINR.01 | 0.94 | 1349 | 1359 | 0.97 | 0.955 |
| P$STKM | Storekeeper motif | P$STK.01 | 0.85 | 1355 | 1369 | 1 | 0.927 |
| P$GTBX | GT-box elements | P$GT1.01 | 0.85 | 1403 | 1419 | 0.97 | 0.865 |
| P$OCSE | Enhancer element first identified in the promoter of the octopine synthase gene (OCS) of the *Agrobacterium tumefaciens* T-DNA | P$OCSL.01 | 0.69 | 1437 | 1457 | 0.77 | 0.703 |
| P$HEAT | Heat shock factors | P$HSFA1A.01 | 0.75 | 1478 | 1494 | 1 | 0.764 |
| P$WBXF | W Box family | P$ERE.01 | 0.89 | 1488 | 1504 | 1 | 0.968 |
| P$TEFB | TEF-box | P$TEF1.01 | 0.76 | 1491 | 1511 | 0.96 | 0.852 |
| P$MYBS | MYB proteins with single DNA binding repeat | P$HVMCB1.01 | 0.93 | 1498 | 1514 | 1 | 0.934 |
| P$MYBS | MYB proteins with single DNA binding repeat | P$TAMYB80.01 | 0.83 | 1509 | 1525 | 0.75 | 0.837 |
| P$MSAE | M-phase-specific activator elements | P$MSA.01 | 0.8 | 1551 | 1565 | 1 | 0.82 |
| P$OPAQ | Opaque-2 like transcriptional activators | P$O2.01 | 0.87 | 1558 | 1574 | 1 | 0.883 |
| P$AHBP | *Arabidopsis* homeobox protein | P$ATHB5.01 | 0.89 | 1569 | 1579 | 0.83 | 0.904 |
| P$AHBP | *Arabidopsis* homeobox protein | P$ATHB5.01 | 0.89 | 1569 | 1579 | 0.94 | 0.978 |
| O$VTBP | Vertebrate TATA binding protein factor | O$ATATA.01 | 0.78 | 1609 | 1625 | 0.75 | 0.781 |
| P$LREM | Light responsive element motif, not modulated by different light qualities | P$RAP22.01 | 0.85 | 1613 | 1623 | 1 | 0.966 |
| P$TEFB | TEF-box | P$TEF1.01 | 0.76 | 1617 | 1637 | 0.84 | 0.761 |
| P$WNAC | Wheat NAC-domain transcription factors | P$TANAC69.01 | 0.68 | 1625 | 1647 | 0.9 | 0.75 |
| P$NACF | Plant specific NAC [NAM (no apical meristem), ATAF172, CUC2 (cup-shaped cotyledons 2)] transcription factors | P$ANAC019.01 | 0.94 | 1632 | 1644 | 0.95 | 0.968 |
| P$GTBX | GT-box elements | P$S1F.01 | 0.79 | 1642 | 1658 | 1 | 0.882 |
| P$PSRE | Pollen-specific regulatory elements | P$GAAA.01 | 0.83 | 1644 | 1660 | 1 | 0.864 |
| P$MYBL | MYB-like proteins | P$MYBPH3.01 | 0.8 | 1647 | 1663 | 1 | 0.938 |
| P$DOFF | DNA binding with one finger (DOF) | P$DOF1.01 | 0.98 | 1694 | 1710 | 1 | 1 |
| P$HEAT | Heat shock factors | P$HSFA1A.01 | 0.75 | 1703 | 1719 | 0.86 | 0.765 |
| P$CCAF | Circadian control factors | P$EE.01 | 0.84 | 1719 | 1733 | 1 | 0.955 |

TABLE 10-continued

Boxes and Motifs identified in the permutated sequence of the p-GOS2_perm1 promoter.

| | p-GOS2_perm1 | | | Position Position from-to | | Core sim. | Matrix sim. |
|---|---|---|---|---|---|---|---|
| Family | Further Family Information | Matrix | Opt. | | | | |
| P$MADS | MADS box proteins | P$AG.01 | 0.8 | 1717 | 1737 | 0.9 | 0.816 |
| P$GTBX | GT-box elements | P$ASIL1.01 | 0.93 | 1732 | 1748 | 1 | 0.98 |
| O$INRE | Core promoter initiator elements | O$DINR.01 | 0.94 | 1749 | 1759 | 1 | 0.957 |
| P$SUCB | Sucrose box | P$SUCROSE.01 | 0.81 | 1749 | 1767 | 0.75 | 0.837 |
| P$SUCB | Sucrose box | P$SUCROSE.01 | 0.81 | 1754 | 1772 | 0.75 | 0.815 |
| P$L1BX | L1 box, motif for L1 layer-specific expression | P$ATML1.02 | 0.76 | 1757 | 1773 | 0.89 | 0.848 |
| P$AHBP | *Arabidopsis* homeobox protein | P$ATHB9.01 | 0.77 | 1761 | 1771 | 0.75 | 0.815 |
| P$MADS | MADS box proteins | P$AGL3.01 | 0.83 | 1768 | 1788 | 0.97 | 0.838 |
| O$VTBP | Vertebrate TATA binding protein factor | O$VTATA.02 | 0.89 | 1777 | 1793 | 1 | 0.996 |
| P$DOFF | DNA binding with one finger (DOF) | P$DOF3.01 | 0.99 | 1778 | 1794 | 1 | 0.995 |
| O$PTBP | Plant TATA binding protein factor | O$PTATA.02 | 0.9 | 1780 | 1794 | 1 | 0.923 |
| P$IBOX | Plant I-Box sites | P$GATA.01 | 0.93 | 1787 | 1803 | 1 | 0.967 |
| P$MYBS | MYB proteins with single DNA binding repeat | P$MYBST1.01 | 0.9 | 1790 | 1806 | 1 | 0.972 |
| O$VTBP | Vertebrate TATA binding protein factor | O$ATATA.01 | 0.78 | 1803 | 1819 | 0.75 | 0.797 |
| P$IBOX | Plant I-Box sites | P$GATA.01 | 0.93 | 1847 | 1863 | 1 | 0.945 |
| P$MYBS | MYB proteins with single DNA binding repeat | P$MYBST1.01 | 0.9 | 1850 | 1866 | 1 | 0.966 |
| P$MADS | MADS box proteins | P$SQUA.01 | 0.9 | 1866 | 1886 | 1 | 0.916 |
| P$GTBX | GT-box elements | P$SBF1.01 | 0.87 | 1872 | 1888 | 1 | 0.905 |
| O$VTBP | Vertebrate TATA binding protein factor | O$LTATA.01 | 0.82 | 1873 | 1889 | 1 | 0.837 |
| P$AHBP | *Arabidopsis* homeobox protein | P$HAHB4.01 | 0.87 | 1878 | 1888 | 1 | 0.902 |
| P$L1BX | L1 box, motif for L1 layer-specific expression | P$ATML1.01 | 0.82 | 1882 | 1898 | 0.75 | 0.824 |
| O$INRE | Core promoter initiator elements | O$DINR.01 | 0.94 | 1886 | 1896 | 0.97 | 0.949 |
| P$EPFF | EPF-type zinc finger factors, two canonical Cys2/His2 zinc finger motifs separated by spacers of various length | P$ZPT22.01 | 0.75 | 1887 | 1909 | 1 | 0.752 |
| P$GAPB | GAP-Box (light response elements) | P$GAP.01 | 0.88 | 1907 | 1921 | 1 | 0.903 |
| P$SUCB | Sucrose box | P$SUCROSE.01 | 0.81 | 1912 | 1930 | 1 | 0.849 |
| P$HMGF | High mobility group factors | P$HMG_IY.01 | 0.89 | 1920 | 1934 | 1 | 0.892 |
| P$SEF4 | Soybean embryo factor 4 | P$SEF4.01 | 0.98 | 1927 | 1937 | 1 | 0.984 |
| P$MYBL | MYB-like proteins | P$ATMYB77.01 | 0.87 | 1973 | 1989 | 1 | 0.9 |
| P$GTBX | GT-box elements | P$ASIL1.01 | 0.93 | 1998 | 2014 | 1 | 0.958 |
| P$OPAQ | Opaque-2 like transcriptional activators | P$O_GCN4.01 | 0.81 | 2001 | 2017 | 1 | 0.875 |
| P$IBOX | Plant I-Box sites | P$GATA.01 | 0.93 | 2018 | 2034 | 1 | 0.964 |
| P$MYBS | MYB proteins with single DNA binding repeat | P$MYBST1.01 | 0.9 | 2021 | 2037 | 1 | 0.957 |
| P$LREM | Light responsive element motif, not modulated by different light qualities | P$RAP22.01 | 0.85 | 2035 | 2045 | 1 | 0.868 |
| P$MIIG | MYB IIG-type binding sites | P$MYBC1.01 | 0.92 | 2033 | 2047 | 1 | 0.938 |
| P$HEAT | Heat shock factors | P$HSFA1A.01 | 0.75 | 2041 | 2057 | 1 | 0.792 |
| P$MYBL | MYB-like proteins | P$GAMYB.01 | 0.91 | 2054 | 2070 | 1 | 0.918 |
| P$GTBX | GT-box elements | P$GT1.01 | 0.85 | 2056 | 2072 | 1 | 0.876 |
| P$ASRC | AS1/AS2 repressor complex | P$AS1_AS2_II.01 | 0.86 | 2067 | 2075 | 1 | 0.906 |
| P$ASRC | AS1/AS2 repressor complex | P$AS1_AS2_II.01 | 0.86 | 2075 | 2083 | 1 | 0.906 |
| P$EINL | Ethylen insensitive 3 like factors | P$TEIL.01 | 0.92 | 2098 | 2106 | 0.96 | 0.926 |
| O$VTBP | Vertebrate TATA binding protein factor | O$LTATA.01 | 0.82 | 2110 | 2126 | 1 | 0.828 |
| P$MYBL | MYB-like proteins | P$MYBPH3.02 | 0.76 | 2110 | 2126 | 1 | 0.807 |

TABLE 11

Boxes and Motifs identified in the permutated sequence of the p-GOS2_perm2 promoter.

| p-GOS2_perm2 | | | | Position Position | | Core | Matrix |
|---|---|---|---|---|---|---|---|
| Family | Further Family Information | Matrix | Opt. | from | to | sim. | sim. |
| P$NCS1 | Nodulin consensus sequence 1 | P$NCS1.01 | 0.85 | 6 | 16 | 1 | 0.857 |
| P$MSAE | M-phase-specific activator elements | P$MSA.01 | 0.8 | 15 | 29 | 1 | 0.832 |
| P$MYBL | MYB-like proteins | P$GAMYB.01 | 0.91 | 29 | 45 | 1 | 0.95 |
| P$MYBL | MYB-like proteins | P$WER.01 | 0.87 | 33 | 49 | 1 | 0.897 |
| P$MADS | MADS box proteins | P$AGL2.01 | 0.82 | 35 | 55 | 0.789 | 0.82 |
| P$NACF | Plant specific NAC [NAM (no apical meristem), ATAF172, CUC2 (cup-shaped cotyledons 2)] transcription factors | P$IDEF2.01 | 0.96 | 48 | 60 | 1 | 0.96 |
| P$BRRE | Brassinosteroid (BR) response element | P$BZR1.01 | 0.95 | 48 | 64 | 1 | 0.954 |
| O$PTBP | Plant TATA binding protein factor | O$PTATA.01 | 0.88 | 60 | 74 | 1 | 0.883 |
| O$VTBP | Vertebrate TATA binding protein factor | O$VTATA.01 | 0.9 | 61 | 77 | 1 | 0.961 |
| O$INRE | Core promoter initiator elements | O$DINR.01 | 0.94 | 65 | 75 | 0.969 | 0.94 |
| O$VTBP | Vertebrate TATA binding protein factor | O$LTATA.01 | 0.82 | 69 | 85 | 1 | 0.867 |
| O$VTBP | Vertebrate TATA binding protein factor | O$VTATA.01 | 0.9 | 71 | 87 | 0.892 | 0.92 |
| O$YTBP | Yeast TATA binding protein factor | O$SPT15.01 | 0.83 | 74 | 90 | 1 | 0.832 |
| O$YTBP | Yeast TATA binding protein factor | O$SPT15.01 | 0.83 | 75 | 91 | 1 | 0.877 |
| O$VTBP | Vertebrate TATA binding protein factor | O$ATATA.01 | 0.78 | 76 | 92 | 0.75 | 0.781 |
| O$YTBP | Yeast TATA binding protein factor | O$SPT15.01 | 0.83 | 77 | 93 | 0.755 | 0.835 |
| P$MIIG | MYB IIG-type binding sites | P$PALBOXL.01 | 0.8 | 118 | 132 | 0.768 | 0.841 |
| P$DOFF | DNA binding with one finger (DOF) | P$DOF1.01 | 0.98 | 126 | 142 | 1 | 0.99 |
| P$DOFF | DNA binding with one finger (DOF) | P$PBF.01 | 0.97 | 149 | 165 | 1 | 0.989 |
| P$WNAC | Wheat NAC-domain transcription factors | P$TANAC69.01 | 0.68 | 170 | 192 | 0.812 | 0.713 |
| O$VTBP | Vertebrate TATA binding protein factor | O$ATATA.01 | 0.78 | 187 | 203 | 1 | 0.869 |
| P$E2FF | E2F-homolog cell cycle regulators | P$E2F.01 | 0.82 | 193 | 207 | 1 | 0.829 |
| O$INRE | Core promoter initiator elements | O$DINR.01 | 0.94 | 200 | 210 | 0.969 | 0.945 |
| P$AHBP | *Arabidopsis* homeobox protein | P$ATHB5.01 | 0.89 | 207 | 217 | 0.83 | 0.903 |
| P$AHBP | *Arabidopsis* homeobox protein | P$HAHB4.01 | 0.87 | 207 | 217 | 1 | 0.967 |
| P$CNAC | Calcium regulated NAC-factors | P$CBNAC.02 | 0.85 | 215 | 235 | 1 | 0.95 |
| P$MYBS | MYB proteins with single DNA binding repeat | P$PHR1.01 | 0.84 | 217 | 233 | 1 | 0.975 |
| P$OCSE | Enhancer element first identified in the promoter of the octopine synthase gene (OCS) of the *Agrobacterium tumefaciens* T-DNA | P$OCSL.01 | 0.69 | 216 | 236 | 1 | 0.71 |
| P$MYBS | MYB proteins with single DNA binding repeat | P$PHR1.01 | 0.84 | 222 | 238 | 1 | 0.922 |
| P$GTBX | GT-box elements | P$SBF1.01 | 0.87 | 246 | 262 | 1 | 0.901 |
| P$STKM | Storekeeper motif | P$STK.01 | 0.85 | 251 | 265 | 1 | 0.85 |
| P$AHBP | *Arabidopsis* homeobox protein | P$ATHB5.01 | 0.89 | 254 | 264 | 0.83 | 0.904 |
| P$AHBP | *Arabidopsis* homeobox protein | P$BLR.01 | 0.9 | 254 | 264 | 1 | 0.998 |
| P$HEAT | Heat shock factors | P$HSFA1A.01 | 0.75 | 284 | 300 | 1 | 0.784 |
| P$CCAF | Circadian control factors | P$CCA1.01 | 0.85 | 297 | 311 | 1 | 0.947 |
| P$LFYB | LFY binding site | P$LFY.01 | 0.93 | 318 | 330 | 0.914 | 0.945 |
| P$GAGA | GAGA elements | P$BPC.01 | 1 | 329 | 353 | 1 | 1 |
| P$CCAF | Circadian control factors | P$EE.01 | 0.84 | 335 | 349 | 0.75 | 0.865 |
| P$GAGA | GAGA elements | P$BPC.01 | 1 | 331 | 355 | 1 | 1 |
| P$CCAF | Circadian control factors | P$CCA1.01 | 0.85 | 337 | 351 | 1 | 0.968 |
| P$GTBX | GT-box elements | P$SBF1.01 | 0.87 | 341 | 357 | 1 | 0.875 |
| P$MADS | MADS box proteins | P$SQUA.01 | 0.9 | 345 | 365 | 1 | 0.925 |
| P$CCAF | Circadian control factors | P$EE.01 | 0.84 | 363 | 377 | 1 | 0.925 |

TABLE 11-continued

Boxes and Motifs identified in the permutated sequence of the p-GOS2_perm2 promoter.

| p-GOS2_perm2 | | | | Position Position from-to | | Core sim. | Matrix sim. |
|---|---|---|---|---|---|---|---|
| Family | Further Family Information | Matrix | Opt. | | | | |
| O$VTBP | Vertebrate TATA binding protein factor | O$MTATA.01 | 0.84 | 383 | 399 | 1 | 0.91 |
| P$CARM | CA-rich motif | P$CARICH.01 | 0.78 | 388 | 406 | 1 | 0.785 |
| P$AHBP | *Arabidopsis* homeobox protein | P$HAHB4.01 | 0.87 | 397 | 407 | 1 | 0.902 |
| O$VTBP | Vertebrate TATA binding protein factor | O$LTATA.01 | 0.82 | 395 | 411 | 1 | 0.889 |
| O$VTBP | Vertebrate TATA binding protein factor | O$LTATA.01 | 0.82 | 396 | 412 | 1 | 0.844 |
| O$PTBP | Plant TATA binding protein factor | O$PTATA.01 | 0.88 | 398 | 412 | 1 | 0.892 |
| O$VTBP | Vertebrate TATA binding protein factor | O$ATATA.01 | 0.78 | 397 | 413 | 0.75 | 0.781 |
| P$NCS2 | *Arabidopsis* homeobox protein | P$HAHB4.01 | 0.87 | 400 | 410 | 1 | 0.902 |
| P$MSAE | Vertebrate TATA binding protein factor | O$ATATA.01 | 0.78 | 402 | 418 | 0.75 | 0.781 |
| P$MYBL | Vertebrate TATA binding protein factor | O$VTATA.02 | 0.89 | 405 | 421 | 1 | 0.983 |
| P$MYBL | Plant TATA binding protein factor | O$PTATA.02 | 0.9 | 408 | 422 | 1 | 0.917 |
| P$OCSE | Enhancer element first identified in the promoter of the octopine synthase gene (OCS) of the *Agrobacterium tumefaciens* T-DNA | P$OCSTF.01 | 0.73 | 426 | 446 | 1 | 0.733 |
| P$AHBP | *Arabidopsis* homeobox protein | P$HAHB4.01 | 0.87 | 440 | 450 | 1 | 0.921 |
| P$AHBP | *Arabidopsis* homeobox protein | P$WUS.01 | 0.94 | 444 | 454 | 1 | 1 |
| P$OPAQ | Opaque-2 like transcriptional activators | P$O2_GCN4.01 | 0.81 | 447 | 463 | 1 | 0.819 |
| P$SEF4 | Soybean embryo factor 4 | P$SEF4.01 | 0.98 | 472 | 482 | 1 | 0.987 |
| P$GTBX | GT-box elements | P$SBF1.01 | 0.87 | 481 | 497 | 1 | 0.922 |
| P$DOFF | DNA binding with one finger (DOF) | P$DOF1.01 | 0.98 | 482 | 498 | 1 | 0.994 |
| P$GTBX | GT-box elements | P$SBF1.01 | 0.87 | 482 | 498 | 1 | 0.9 |
| P$WBXF | W Box family | P$WRKY11.01 | 0.94 | 493 | 509 | 1 | 0.957 |
| P$SEF4 | Soybean embryo factor 4 | P$SEF4.01 | 0.98 | 504 | 514 | 1 | 0.998 |
| P$IBOX | Plant I-Box sites | P$GATA.01 | 0.93 | 509 | 525 | 1 | 0.986 |
| P$NCS1 | Nodulin consensus sequence 1 | P$NCS1.01 | 0.85 | 515 | 525 | 1 | 0.948 |
| P$GTBX | GT-box elements | P$S1F.01 | 0.79 | 518 | 534 | 0.75 | 0.793 |
| P$LREM | Light responsive element motif, not modulated by different light qualities | P$RAP22.01 | 0.85 | 527 | 537 | 1 | 0.897 |
| P$L1BX | L1 box, motif for L1 layer-specific expression | P$ATML1.01 | 0.82 | 525 | 541 | 0.75 | 0.825 |
| O$VTBP | Vertebrate TATA binding protein factor | O$ATATA.01 | 0.78 | 539 | 555 | 0.75 | 0.782 |
| P$ROOT | Root hair-specific cis-elements in angiosperms | P$RHE.01 | 0.77 | 568 | 592 | 0.75 | 0.787 |
| P$ABRE | ABA response elements | P$ABRE.01 | 0.82 | 591 | 607 | 1 | 0.837 |
| P$ASRC | AS1/AS2 repressor complex | P$AS1_AS2_II.01 | 0.86 | 599 | 607 | 1 | 0.867 |
| P$L1BX | L1 box, motif for L1 layer-specific expression | P$HDG9.01 | 0.77 | 629 | 645 | 1 | 0.883 |
| P$L1BX | L1 box, motif for L1 layer-specific expression | P$HDG9.01 | 0.77 | 631 | 647 | 0.797 | 0.776 |
| P$L1BX | L1 box, motif for L1 layer-specific expression | P$ATML1.01 | 0.82 | 638 | 654 | 1 | 0.886 |
| P$CCAF | Circadian control factors | P$EE.01 | 0.84 | 649 | 663 | 1 | 0.891 |
| P$DOFF | DNA binding with one finger (DOF) | P$PBF.01 | 0.97 | 687 | 703 | 1 | 0.987 |
| P$GTBX | GT-box elements | P$SBF1.01 | 0.87 | 689 | 705 | 1 | 0.888 |
| P$AHBP | *Arabidopsis* homeobox protein | P$BLR.01 | 0.9 | 695 | 705 | 1 | 0.929 |
| P$CCAF | Circadian control factors | P$EE.01 | 0.84 | 694 | 708 | 1 | 0.954 |
| P$LREM | Light responsive element motif, not modulated by different light qualities | P$RAP22.01 | 0.85 | 701 | 711 | 1 | 1 |
| P$MADS | MADS box proteins | P$RIN.01 | 0.77 | 699 | 719 | 1 | 0.776 |
| P$HMGF | High mobility group factors | P$HMG_IY.01 | 0.89 | 711 | 725 | 1 | 0.924 |
| P$AHBP | *Arabidopsis* homeobox protein | P$ATHB1.01 | 0.9 | 716 | 726 | 0.789 | 0.901 |

TABLE 11-continued

Boxes and Motifs identified in the permutated sequence of the p-GOS2_perm2 promoter.

| p-GOS2_perm2 | | | | Position | | Core | Matrix |
|---|---|---|---|---|---|---|---|
| Family | Further Family Information | Matrix | Opt. | Position from-to | | sim. | sim. |
| P$AHBP | *Arabidopsis* homeobox protein | P$BLR.01 | 0.9 | 716 | 726 | 1 | 0.998 |
| O$VTBP | Vertebrate TATA binding protein factor | O$VTATA.02 | 0.89 | 716 | 732 | 1 | 0.893 |
| P$SUCB | Sucrose box | P$SUCROSE.01 | 0.81 | 715 | 733 | 1 | 0.856 |
| P$DOFF | DNA binding with one finger (DOF) | P$PBOX.01 | 0.75 | 718 | 734 | 0.761 | 0.762 |
| P$HEAT | Heat shock factors | P$HSE.01 | 0.81 | 718 | 734 | 1 | 0.833 |
| P$GAPB | GAP-Box (light response elements) | P$GAP.01 | 0.88 | 733 | 747 | 1 | 0.885 |
| P$MYBL | MYB-like proteins | P$MYBPH3.02 | 0.76 | 744 | 760 | 0.779 | 0.834 |
| O$VTBP | Vertebrate TATA binding protein factor | O$ATATA.01 | 0.78 | 754 | 770 | 0.75 | 0.831 |
| P$TELO | Telo box (plant interstitial telomere motifs) | P$ATPURA.01 | 0.85 | 756 | 770 | 0.75 | 0.869 |
| P$MYCL | Myc-like basic helix-loop-helix binding factors | P$OSBHLH66.01 | 0.85 | 789 | 807 | 1 | 0.851 |
| P$BRRE | Brassinosteroid (BR) response element | P$BZR1.01 | 0.95 | 793 | 809 | 1 | 0.998 |
| P$URNA | Upstream sequence element of U-snRNA genes | P$USE.01 | 0.75 | 812 | 828 | 0.75 | 0.797 |
| P$MADS | MADS box proteins | P$AGL1.01 | 0.84 | 812 | 832 | 1 | 0.895 |
| P$MADS | MADS box proteins | P$AGL1.01 | 0.84 | 813 | 833 | 0.915 | 0.911 |
| P$NCS1 | Nodulin consensus sequence 1 | P$NCS1.01 | 0.85 | 872 | 882 | 0.805 | 0.888 |
| P$LREM | Light responsive element motif, not modulated by different light qualities | P$RAP22.01 | 0.85 | 879 | 889 | 1 | 0.896 |
| P$MSAE | M-phase-specific activator elements | P$MSA.01 | 0.8 | 880 | 894 | 1 | 0.877 |
| P$MYBL | MYB-like proteins | P$NTMYBAS1.01 | 0.96 | 900 | 916 | 0.949 | 0.968 |
| P$GTBX | GT-box elements | P$SBF1.01 | 0.87 | 909 | 925 | 1 | 0.905 |
| P$MYBL | MYB-like proteins | P$AS1_AS2_I.01 | 0.99 | 911 | 927 | 1 | 1 |
| P$LREM | Light responsive element motif, not modulated by different light qualities | P$RAP22.01 | 0.85 | 981 | 991 | 1 | 0.893 |
| O$PTBP | Plant TATA binding protein factor | O$PTATA.02 | 0.9 | 982 | 996 | 1 | 1 |
| P$L1BX | L1 box, motif for L1 layer-specific expression | P$PDF2.01 | 0.85 | 982 | 998 | 1 | 0.884 |
| O$VTBP | Vertebrate TATA binding protein factor | O$VTATA.01 | 0.9 | 983 | 999 | 1 | 0.973 |
| P$MADS | MADS box proteins | P$AGL15.01 | 0.79 | 1006 | 1026 | 0.825 | 0.793 |
| P$MYBS | MYB proteins with single DNA binding repeat | P$ZMMRP1.01 | 0.79 | 1008 | 1024 | 0.778 | 0.811 |
| O$PTBP | Plant TATA binding protein factor | O$PTATA.02 | 0.9 | 1010 | 1024 | 1 | 0.91 |
| P$CGCG | Calmodulin binding/CGCG box binding proteins | P$ATSR1.01 | 0.84 | 1051 | 1067 | 1 | 0.859 |
| P$ABRE | ABA response elements | P$ABF1.01 | 0.79 | 1053 | 1069 | 1 | 0.797 |
| P$CE3S | Coupling element 3 sequence | P$CE3.01 | 0.77 | 1052 | 1070 | 1 | 0.874 |
| P$NACF | Plant specific NAC [NAM (no apical meristem), ATAF172, CUC2 (cup-shaped cotyledons 2)] transcription factors | P$ANAC092.01 | 0.92 | 1055 | 1067 | 1 | 0.924 |
| P$DPBF | Dc3 promoter binding factors | P$DPBF.01 | 0.89 | 1057 | 1067 | 1 | 0.908 |
| P$PREM | Motifs of plastid response elements | P$MGPROTORE.01 | 0.77 | 1059 | 1089 | 1 | 0.806 |
| O$MTEN | Core promoter motif ten elements | O$HMTE.01 | 0.88 | 1072 | 1092 | 0.961 | 0.94 |
| P$DREB | Dehydration responsive element binding factors | P$HVDRF1.01 | 0.89 | 1079 | 1093 | 1 | 0.922 |
| P$PREM | Motifs of plastid response | P$MGPROTORE.01 | 0.77 | 1077 | 1107 | 1 | 0.784 |
| O$MTEN | Core promoter motif ten elements | O$DMTE.01 | 0.77 | 1097 | 1117 | 0.844 | 0.802 |
| P$OPAQ | Opaque-2 like transcriptional activators | P$O2.02 | 0.87 | 1135 | 1151 | 1 | 0.915 |
| P$SALT | Salt/drought responsive elements | P$ALFIN1.02 | 0.95 | 1136 | 1150 | 1 | 0.954 |
| P$L1BX | L1 box, motif for L1 layer-specific expression | P$PDF2.01 | 0.85 | 1179 | 1195 | 1 | 0.882 |
| P$SBPD | SBP-domain proteins | P$SBP.01 | 0.88 | 1199 | 1215 | 1 | 0.912 |

TABLE 11-continued

Boxes and Motifs identified in the permutated sequence of the p-GOS2_perm2 promoter.

| p-GOS2_perm2 | | | | Position | | Core | Matrix |
|---|---|---|---|---|---|---|---|
| Family | Further Family Information | Matrix | Opt. | Position from-to | | sim. | sim. |
| P$PALA | Conserved box A in PAL and 4CL gene promoters | P$PALBOXA.01 | 0.84 | 1201 | 1219 | 1 | 0.863 |
| P$MYBS | MYB proteins with single DNA binding repeat | P$ZMMRP1.01 | 0.79 | 1230 | 1246 | 1 | 0.838 |
| P$AHBP | *Arabidopsis* homeobox protein | P$ATHB9.01 | 0.77 | 1244 | 1254 | 1 | 0.777 |
| P$MADS | MADS box proteins | P$AGL2.01 | 0.82 | 1248 | 1268 | 0.969 | 0.828 |
| P$MYBS | MYB proteins with single DNA binding repeat | P$MYBST1.01 | 0.9 | 1262 | 1278 | 1 | 0.953 |
| P$HEAT | Heat shock factors | P$HSE.01 | 0.81 | 1278 | 1294 | 1 | 0.864 |
| P$LEGB | Legumin Box family | P$RY.01 | 0.87 | 1277 | 1303 | 1 | 0.871 |
| P$MYBS | MYB proteins with single DNA binding repeat | P$OSMYBS.01 | 0.82 | 1343 | 1359 | 0.75 | 0.822 |
| O$INRE | Core promoter initiator elements | O$DINR.01 | 0.94 | 1349 | 1359 | 0.969 | 0.955 |
| P$STKM | Storekeeper motif | P$STK.01 | 0.85 | 1355 | 1369 | 1 | 0.95 |
| P$GTBX | GT-box elements | P$GT1.01 | 0.85 | 1403 | 1419 | 0.969 | 0.85 |
| O$VTBP | Vertebrate TATA binding protein factor | O$ATATA.01 | 0.78 | 1439 | 1455 | 0.75 | 0.797 |
| P$OCSE | Enhancer element first identified in the promoter of the octopine synthase gene (OCS) of the *Agrobacterium tumefaciens* T-DNA | P$OCSL.01 | 0.69 | 1437 | 1457 | 0.769 | 0.734 |
| P$HEAT | Heat shock factors | P$HSFA1A.01 | 0.75 | 1478 | 1494 | 1 | 0.764 |
| P$WBXF | W Box family | P$WRKY.01 | 0.92 | 1488 | 1504 | 1 | 0.94 |
| P$TEFB | TEF-box | P$TEF1.01 | 0.76 | 1491 | 1511 | 0.957 | 0.859 |
| P$MYBS | MYB proteins with single DNA binding repeat | P$HVMCB1.01 | 0.93 | 1498 | 1514 | 1 | 0.934 |
| P$MYBS | MYB proteins with single DNA binding repeat | P$TAMYB80.01 | 0.83 | 1509 | 1525 | 0.75 | 0.845 |
| P$MSAE | M-phase-specific activator elements | P$MSA.01 | 0.8 | 1551 | 1565 | 1 | 0.807 |
| P$OPAQ | Opaque-2 like transcriptional-activators | P$O2.01 | 0.87 | 1558 | 1574 | 1 | 0.883 |
| P$AHBP | *Arabidopsis* homeobox protein | P$ATHB5.01 | 0.89 | 1569 | 1579 | 0.83 | 0.904 |
| P$AHBP | *Arabidopsis* homeobox protein | P$ATHB5.01 | 0.89 | 1569 | 1579 | 0.936 | 0.978 |
| O$VTBP | Vertebrate TATA binding protein factor | O$ATATA.01 | 0.78 | 1609 | 1625 | 0.75 | 0.781 |
| P$LREM | Light responsive element motif, not modulated by different light qualities | P$RAP22.01 | 0.85 | 1613 | 1623 | 1 | 0.966 |
| P$TEFB | TEF-box | P$TEF1.01 | 0.76 | 1617 | 1637 | 0.839 | 0.812 |
| P$WNAC | Wheat NAC-domain transcription factors | P$TANAC69.01 | 0.68 | 1625 | 1647 | 0.896 | 0.811 |
| P$NACF | Plant specific NAC [NAM (no apical meristem), ATAF172, CUC2 (cup-shaped cotyledons 2)] transcription factors | P$ANAC019.01 | 0.94 | 1632 | 1644 | 0.953 | 0.968 |
| P$GTBX | GT-box elements | P$S1F.01 | 0.79 | 1642 | 1658 | 1 | 0.917 |
| P$PSRE | Pollen-specific regulatory elements | P$GAAA.01 | 0.83 | 1644 | 1660 | 1 | 0.864 |
| P$MYBL | MYB-like proteins | P$MYBPH3.01 | 0.8 | 1647 | 1663 | 1 | 0.938 |
| P$DOFF | DNA binding with one finger (DOF) | P$DOF1.01 | 0.98 | 1694 | 1710 | 1 | 1 |
| P$HEAT | Heat shock factors | P$HSFA1A.01 | 0.75 | 1703 | 1719 | 0.857 | 0.757 |
| P$CCAF | Circadian control factors | P$EE.01 | 0.84 | 1719 | 1733 | 1 | 0.953 |
| P$MADS | MADS box proteins | P$AG.01 | 0.8 | 1717 | 1737 | 0.902 | 0.813 |
| P$GTBX | GT-box elements | P$ASIL1.01 | 0.93 | 1732 | 1748 | 1 | 0.967 |
| O$INRE | Core promoter initiator elements | O$DINR.01 | 0.94 | 1749 | 1759 | 1 | 0.965 |
| P$SUCB | Sucrose box | P$SUCROSE.01 | 0.81 | 1749 | 1767 | 0.75 | 0.83 |
| P$SUCB | Sucrose box | P$SUCROSE.01 | 0.81 | 1754 | 1772 | 0.75 | 0.822 |
| P$L1BX | L1 box, motif for L1 layer-specific expression | P$ATML1.02 | 0.76 | 1757 | 1773 | 0.89 | 0.848 |
| P$AHBP | *Arabidopsis* homeobox protein | P$ATHB9.01 | 0.77 | 1761 | 1771 | 0.75 | 0.815 |
| O$VTBP | Vertebrate TATA binding protein factor | O$VTATA.02 | 0.89 | 1777 | 1793 | 1 | 0.996 |
| P$DOFF | DNA binding with one finger (DOF) | P$DOF3.01 | 0.99 | 1778 | 1794 | 1 | 0.995 |

TABLE 11-continued

Boxes and Motifs identified in the permutated sequence of the p-GOS2_perm2 promoter.

| p-GOS2_perm2 | | | Position Opt. | Position from-to | | Core sim. | Matrix sim. |
|---|---|---|---|---|---|---|---|
| Family | Further Family Information | Matrix | | | | | |
| O$PTBP | Plant TATA binding protein factor | O$PTATA.02 | 0.9 | 1780 | 1794 | 1 | 0.923 |
| P$IBOX | Plant I-Box sites | P$GATA.01 | 0.93 | 1787 | 1803 | 1 | 0.967 |
| P$MYBS | MYB proteins with single DNA binding repeat | P$MYBST1.01 | 0.9 | 1790 | 1806 | 1 | 0.972 |
| O$VTBP | Vertebrate TATA binding protein factor | O$ATATA.01 | 0.78 | 1803 | 1819 | 0.75 | 0.812 |
| P$IBOX | Plant I-Box sites | P$GATA.01 | 0.93 | 1847 | 1863 | 1 | 0.945 |
| P$MYBS | MYB proteins with single DNA binding repeat | P$MYBST1.01 | 0.9 | 1850 | 1866 | 1 | 0.966 |
| P$MADS | MADS box proteins | P$SQUA.01 | 0.9 | 1866 | 1886 | 1 | 0.916 |
| P$GTBX | GT-box elements | P$SBF1.01 | 0.87 | 1872 | 1888 | 1 | 0.905 |
| O$VTBP | Vertebrate TATA binding protein factor | O$LTATA.01 | 0.82 | 1873 | 1889 | 1 | 0.837 |
| P$AHBP | *Arabidopsis* homeobox protein | P$HAHB4.01 | 0.87 | 1878 | 1888 | 1 | 0.902 |
| P$L1BX | L1 box, motif for L1 layer-specific expression | P$ATML1.01 | 0.82 | 1882 | 1898 | 0.75 | 0.824 |
| O$INRE | Core promoter initiator elements | O$DINR.01 | 0.94 | 1886 | 1896 | 0.969 | 0.949 |
| P$EPFF | EPF-type zinc finger factors, two canonical Cys2/His2 zinc finger motifs separated by spacers of various length | P$ZPT22.01 | 0.75 | 1887 | 1909 | 1 | 0.755 |
| P$GAPB | GAP-Box (light response elements) | P$GAP.01 | 0.88 | 1907 | 1921 | 1 | 0.903 |
| P$SUCB | Sucrose box | P$SUCROSE.01 | 0.81 | 1912 | 1930 | 1 | 0.849 |
| P$HMGF | High mobility group factors | P$HMG_IY.01 | 0.89 | 1920 | 1934 | 1 | 0.892 |
| P$SEF4 | Soybean embryo factor 4 | P$SEF4.01 | 0.98 | 1927 | 1937 | 1 | 0.984 |
| P$MYBL | MYB-like proteins | P$ATMYB77.01 | 0.87 | 1973 | 1989 | 1 | 0.894 |
| P$GTBX | GT-box elements | P$ASIL1.01 | 0.93 | 1998 | 2014 | 1 | 0.971 |
| P$OPAQ | Opaque-2 like transcriptional activators | P$O2_GCN4.01 | 0.81 | 2001 | 2017 | 1 | 0.83 |
| P$IBOX | Plant I-Box sites | P$GATA.01 | 0.93 | 2018 | 2034 | 1 | 0.964 |
| P$MYBS | MYB proteins with single DNA binding repeat | P$MYBST1.01 | 0.9 | 2021 | 2037 | 1 | 0.957 |
| P$LREM | Light responsive element motif, not modulated by different light qualities | P$RAP22.01 | 0.85 | 2035 | 2045 | 1 | 0.858 |
| P$MIIG | MYB IIG-type binding sites | P$MYBC1.01 | 0.92 | 2033 | 2047 | 1 | 0.941 |
| P$HEAT | Heat shock factors | P$HSFA1A.01 | 0.75 | 2041 | 2057 | 1 | 0.801 |
| P$MYBL | MYB-like proteins | P$GAMYB.01 | 0.91 | 2054 | 2070 | 1 | 0.918 |
| P$GTBX | GT-box elements | P$GT1.01 | 0.85 | 2056 | 2072 | 1 | 0.876 |
| P$ASRC | AS1/AS2 repressor complex | P$AS1_AS2_II.01 | 0.86 | 2067 | 2075 | 1 | 0.906 |
| P$EINL | Ethylen insensitive 3 like factors | P$TEIL.01 | 0.92 | 2098 | 2106 | 0.964 | 0.926 |
| O$VTBP | Vertebrate TATA binding protein factor | O$LTATA.01 | 0.82 | 2110 | 2126 | 1 | 0.828 |
| P$MYBL | MYB-like proteins | P$MYBPH3.02 | 0.76 | 2110 | 2126 | 1 | 0.807 |

5.2 Vector Construction

The DNA fragments representing promoter p-GOS2_perm1 (SEQ ID NO14) and p-GOS2_perm2 (SEQ ID NO15), respectively, were generated by gene synthesis. Endonucleolytic restriction sites suitable for cloning the promoter fragments were included in the synthesis. The p-GOS2_perm1 (SEQ ID NO14) and p-GOS2_perm2 (SEQ ID NO15) promoters are cloned into destination vectors compatible with the Multisite Gateway System upstream of an attachment site and a terminator using Swa1 restriction endonuclease.

beta-Glucuronidase (GUS) or uidA gene which encodes an enzyme for which various chromogenic substrates are known, is utilized as reporter protein for determining the expression features of the permutated p-GOS2_perm (SEQ ID NO14) and p-GOS2_perm2 (SEQ ID NO15) promoter sequences.

A pENTR/A vector harboring the beta-Glucuronidase reporter gene c-GUS (with the prefix c-denoting coding sequence) is constructed using site specific recombination (BP-reaction).

By performing a site specific recombination (LR-reaction), the created pENTR/A is combined with the destination vector according to the manufacturers (Invitrogen, Carlsbad, Calif., USA) Multisite Gateway manual. The reaction yields a binary vector with the p-GOS2_perm1 promoter (SEQ ID NO14) or the p-Gos2_perm2 promoter (SEQ ID NO 15), respectively, the beta-Glucuronidase coding sequence c-GUS and a terminator.

5.3 Generation of Transgenic Rice Plants

The *Agrobacterium* containing the respective expression vector is used to transform *Oryza sativa* plants. Mature dry seeds of the rice japonica cultivar Nipponbare are dehusked.

Sterilization is carried out by incubating for one minute in 70% ethanol, followed by 30 minutes in 0.2% HgCl$_2$, followed by a 6 times 15 minutes wash with sterile distilled water. The sterile seeds are then germinated on a medium containing 2.4-D (callus induction medium). After incubation in the dark for four weeks, embryogenic, scutellum-derived calli are excised and propagated on the same medium. After two weeks, the calli are multiplied or propagated by subculture on the same medium for another 2 weeks. Embryogenic callus pieces are sub-cultured on fresh medium 3 days before co-cultivation (to boost cell division activity).

Agrobacterium strain LBA4404 containing the respective expression vector is used for co-cultivation. Agrobacterium is inoculated on AB medium with the appropriate antibiotics and cultured for 3 days at 28° C. The bacteria are then collected and suspended in liquid co-cultivation medium to a density (OD$_{600}$) of about 1. The suspension is then transferred to a Petri dish and the calli immersed in the suspension for 15 minutes. The callus tissues are then blotted dry on a filter paper and transferred to solidified, co-cultivation medium and incubated for 3 days in the dark at 25° C. Co-cultivated calli are grown on 2.4-D-containing medium for 4 weeks in the dark at 28° C. in the presence of a selection agent. During this period, rapidly growing resistant callus islands developed. After transfer of this material to a regeneration medium and incubation in the light, the embryogenic potential is released and shoots developed in the next four to five weeks. Shoots are excised from the calli and incubated for 2 to 3 weeks on an auxin-containing medium from which they are transferred to soil. Hardened shoots are grown under high humidity and short days in a greenhouse.

The primary transformants are transferred from a tissue culture chamber to a greenhouse. After a quantitative PCR analysis to verify copy number of the T-DNA insert, only single copy transgenic plants that exhibit tolerance to the selection agent are kept for harvest of T1 seed. Seeds are then harvested three to five months after transplanting. The method yields single locus transformants at a rate of over 50% (Aldemita and Hodges1996, Chan et al. 1993, Hiei et al. 1994).

Example 6: Expression Profile of the p-GOS2_perm1 (SEQ ID NO14) and p-GOS2_perm2 (SEQ ID NO15) Control Elements To demonstrate and analyze the transcription regulating properties of a promoter, it is useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-β-D-glucuronic acid during corresponding activity assays (Jefferson 1987). For determination of promoter activity and tissue specificity, plant tissue is dissected, stained and analyzed as described (e.g., Bäumlein 1991).

The regenerated transgenic T0 rice plants are used for reporter gene analysis.

General results for SEQ ID NO14: Medium-strong GUS expression is detected in all plant tissues analyzed.

General results for SEQ ID NO15: Medium-strong GUS expression is detected in all plant tissues analyzed.

General results for SEQ ID NO13: Medium-strong GUS expression is detected in all plant tissues analyzed.

The invention claimed is:

1. A synthetic promoter comprising SEQ ID NO: 2.

2. An expression construct comprising the synthetic promoter of claim 1 operably linked to a nucleotide sequence of interest.

3. A vector comprising the expression construct of claim 2.

4. A host cell comprising the synthetic promoter of claim 1.

5. The host cell of claim 4, wherein said host cell is a plant cell.

6. A plant or plant part comprising the synthetic promoter of claim 1.

7. A plant seed comprising the synthetic promoter of claim 1.

8. A method of making a transgenic plant or plant cell, the method comprising
   a) transforming a plant or plant cell with a construct comprising SEQ ID NO: 2 operably linked to a sequence of interest to produce a transgenic plant or plant cell; and optionally,
   b) regenerating a transgenic plant from said transformed plant cell.

9. The method of claim 8 further comprising producing seed from said transgenic plant and collecting said seed.

* * * * *